(12) United States Patent
Galemmo et al.

(10) Patent No.: US 8,445,503 B2
(45) Date of Patent: *May 21, 2013

(54) INHIBITORS OF POLO-LIKE KINASE

(75) Inventors: Robert A. Galemmo, San Francisco, CA (US); Dean R. Artis, Kensington, CA (US); Xiaocong Michael Ye, Palo Alto, CA (US); Danielle Aubele, Burlingame, CA (US); Anh Truong, Burlingame, CA (US); Simeon Bowers, Oakland, CA (US); Roy K. Hom, San Francisco, CA (US); Yong-Liang Zhu, Fremont, CA (US); R. Jeffrey Neitz, San Francisco, CA (US); Jennifer Sealy, Oakland, CA (US); Marc Adler, Orinda, CA (US); Paul Beroza, Belmont, CA (US); John P. Anderson, San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/974,401

(22) Filed: Dec. 21, 2010

(65) Prior Publication Data

US 2011/0212942 A1    Sep. 1, 2011

Related U.S. Application Data

(60) Provisional application No. 61/289,980, filed on Dec. 23, 2009, provisional application No. 61/404,797, filed on Oct. 8, 2010.

(51) Int. Cl.
*A01N 43/54* (2006.01)
*A61K 31/505* (2006.01)
*C07D 491/00* (2006.01)

(52) U.S. Cl.
USPC .......................................... 514/267; 544/251

(58) Field of Classification Search ....................... None
See application file for complete search history.

(56) References Cited

U.S. PATENT DOCUMENTS

| | | | |
|---|---|---|---|
| 6,025,489 | A | 2/2000 | Davey et al. |
| 6,806,272 | B2 | 10/2004 | Bauer et al. |
| 8,129,387 | B2 | 3/2012 | Charrier et al. |
| 2010/0143301 | A1 | 6/2010 | Desai et al. |

FOREIGN PATENT DOCUMENTS

| | | |
|---|---|---|
| CA | 2 774 731 | 3/2011 |
| EP | 1 312 365 A1 | 5/2003 |
| WO | WO 03/020722 | 3/2003 |
| WO | WO 2007/120752 | 10/2007 |
| WO | WO 2007/135374 | 11/2007 |
| WO | WO 2008/051494 | 5/2008 |
| WO | WO 2008/076392 A2 | 6/2008 |
| WO | WO 2008/146914 A1 | 12/2008 |
| WO | WO 2009/023269 | 2/2009 |
| WO | WO 2009/042806 | 4/2009 |
| WO | WO 2009/071480 | 6/2009 |
| WO | WO 2009/103010 A2 | 8/2009 |
| WO | WO 2009/130016 | 10/2009 |
| WO | WO 2009/130453 A1 | 10/2009 |
| WO | WO 2011/025889 | 3/2011 |
| WO | WO 2011/035534 | 3/2011 |
| WO | WO 2011/101369 | 8/2011 |

OTHER PUBLICATIONS

Vippagunta et. al. Advanced Drug Delivery Reviews 48 (2001) 3-26.*
International Search Report for related International Application No. PCT/US2010/061535 mailed Feb. 15, 2011.
U.S. Appl. No. 12/974,622, filed Dec. 21, 2012.
Office Action dated Apr. 11, 2012, in U.S. Appl. No. 12/974,622.

* cited by examiner

*Primary Examiner* — Jeffrey Murray
(74) *Attorney, Agent, or Firm* — Finnegan, Henderson, Farabow, Garrett & Dunner

(57) ABSTRACT

The present invention provides compounds having a structure according to Formula (I):

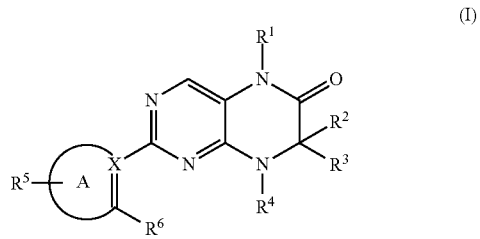

or a salt or solvate thereof, wherein ring A, X, $R^1$, $R^2$, $R^3$, $R^4$, $R^5$ and $R^6$ are defined herein. The invention further provides pharmaceutical compositions including the compounds of the invention and methods of making and using the compounds and compositions of the invention, e.g., in the treatment and prevention of various disorders, such as Parkinson's disease.

9 Claims, No Drawings

INHIBITORS OF POLO-LIKE KINASE

CROSS REFERENCE TO RELATED APPLICATIONS

This application claims priority to U.S. Provisional Application Ser. No. 61/289,980 entitled "Inhibitors of Polo-Like Kinase" filed Dec. 23, 2009 and U.S. Provisional Application Ser. No. 61/404,797 entitled "Inhibitors of Polo-Like Kinase" filed Oct. 8, 2010, which are incorporated herein by reference in their entirety.

BACKGROUND OF THE INVENTION

Lewy body diseases (LBDs) are characterized by degeneration of the dopaminergic system, motor alterations, cognitive impairment, and formation of Lewy bodies (LBs) (see, e.g., McKeith et al, *Neurology* 1996, 47:1113-1124). LBDs include Parkinson's disease (PD), Diffuse Lewy body disease (DLBD), Lewy body variant of Alzheimer's disease (LBV), combined Parkinson's disease (PD) and Alzheimer's disease (AD), as well as the syndromes identified as multiple system atrophy (MSA). Dementia with Lewy bodies (DLB) is a term coined to reconcile differences in the terminology of LBDs. Disorders with LBs continue to be a common cause for movement disorders and cognitive deterioration in the aging population (see e.g., Galasko et al., *Arch. Neurol.* 1994, 51:888-895).

In recent years, new hope for understanding the pathogenesis of LBDs has emerged. Several studies suggest that the synaptic protein alpha-synuclein plays a central role in PD pathogenesis. For example, alpha-synuclein accumulates in LBs (see e.g., Spillantini et al., *Nature* 1997, 388:839-840; Takeda et al., *J. Pathol.* 1998, 152:367-372; and Wakabayashi et al., *Neurosci. Lett.* 1997, 239:45-48). Further, mutations in the alpha-synuclein gene co-segregate with rare familial forms of parkinsonism (see e.g., Kruger et al., *Nature Gen.* 1998, 18:106-8; and Polymeropoulos, et al., *Science* 1997, 276:2045-2047). In addition, overexpression of alpha-synuclein in transgenic mice (e.g., Masliah et al., *Science* 2000, 287:1265-1269) and Drosophila (see e.g., Feany et al, *Nature* 2000, 404:394-398) mimics several pathological aspects of PD.

Many scientists believe that PD is a relatively late development in a systemic synucleinopathy and that "parkinsonism is just the tip of the iceberg" (Langston, Annals of Neurology (2006) 59:591-596). For example, Lewy bodies have been described in sympathetic ganglia and in the myenteric plexus of the gut (Herzog E., Dtch Z Nervenheilk (1928) 107:75-80; Kupsky et al., Neurology (1987) 37:1253-1255). Various disorders have been associated with the presence of Lewy bodies. For example, Lewy bodies have been found in the brain stem of a patient with rapid eye movement sleep behavioral disorder (Uchiyama et al., Neurology (1995) 45:709-712). Olfactory dysfunction has been reported in many PD patients long before the development of parkinsonism. Examination of cardiac tissue from patients with incidental Lewy body disease and typical PD revealed synuclein-positive neuritis in the myocardium (Iwanaga et al., Neurology (1999) 52:1269-1271). There is also evidence that esophageal, lower bowel and bladder dysfunction are early manifestations of PD-related pathology in the peripheral autonomic system (Qualman et al., Gastroenterology (1984) 87:848-856; Castell et al., Neurogasdtroenterol Motil (2001) 13:361-364; Hague et al., Acta Neuropathol (Berl) (1997) 94:192-196). Thus, the fact that accumulation of alpha-synuclein in the brain and other tissues is associated with similar morphological and neurological alterations in species as diverse as humans, mice, and flies suggests that this molecule contributes to the development of PD.

Although the incidence of LBDs continues to increase, creating a serious public health problem, these disorders lack approved treatments.

SUMMARY OF THE INVENTION

Compounds are provided that are inhibitors of polo-like kinases (PLKs), in particular PLK1 or PLK2, preferably wherein the compound selectively inhibits PLK2 relative to PLK1. PLK2 is a kinase that has been shown to phosphorylate alpha-synuclein, a protein involved in the formation of Lewy bodies. Inhibitors of PLK2 are thus useful for the treatment of neurodegenerative diseases, and especially those implicating the formation of Lewy bodies (e.g., Parkinson's disease). Also provided are pharmaceutical compositions comprising inhibitors of PLK2 and methods of utilizing those compositions in the treatment and prevention of various neurodegenerative disorders associated with activation of polo-like kinases, such as Lewy body and Lewy body-type diseases.

Certain PLK inhibitors are known (see, e.g., WO 2003/020722 and U.S. Pat. No. 6,806,272). Typically, those inhibitors are designed to inhibit PLK1, a kinase which is involved in cell proliferation. Consequently those inhibitors are useful for the treatment of various cancers. Thus, compounds described herein that are inhibitors of PLK1 are useful in the treatment of various cancers. PLK inhibitors that are characterized by selectivity for PLK2 over other polo-like kinases, such as PLK1 have not yet been described. Compounds are described herein that are inhibitors of PLK2, preferebly those that are selective relative to PLK1, and are useful in the treatment of neurodegenerative disorders, such as Parkinson's disease and other Lewy body diseases.

In various aspects, compounds are provided having a structure according to Formula (I):

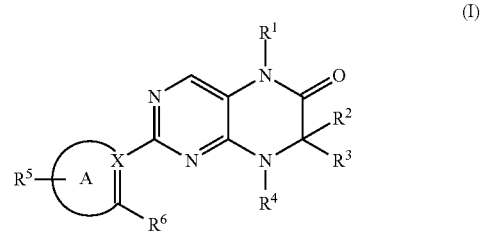

or a salt or solvate thereof, wherein:

X is C or N and the dashed line represents a single or double bond;

A is a ring selected from the group consisting of phenyl, pyridine, pyrimidine, pyrazine, pyridazine, pyrrole, pyrazole, imidazole, thiazole, isothiazole, isoxazole, triazole, thiadiazole, benzimidazole, indole, pyrrolo[2,3-b]pyridine, quinoline, pyrrolidine, piperidine, piperazine, and dihydro-imidazole;

$R^1$ is methyl (e.g. —$CD_3$ or —$CH_3$, more preferably —$CH_3$);

$R^2$ is hydrogen, methyl (e.g. —$CD_3$ or —$CH_3$), ethyl (e.g. —$CD_2CD_3$ or —$CH_2CH_3$), —$CH_2$-cyclopropyl, or —$CH_2CF_3$;

$R^3$ is methyl (e.g. —$CD_3$ or —$CH_3$), ethyl (e.g. —$CD_2CD_3$ or —$CH_2CH_3$), —$CH_2$-cyclopropyl, or —$CH_2CF_3$;

or $R^2$ and $R^3$, together with the carbon atom to which they are attached, are optionally joined to form cyclobutyl;

R[4] is selected from the group consisting of —NH$_2$, —NHCH$_3$, —NHcyclopropyl, pyrrolidine, —CH$_2$-cyclopropyl, —CH(CH$_3$)-cyclopropyl, cyclopropyl, cyclobutyl optionally substituted with 1 or 2 fluoro, cyclopentyl optionally substituted with 1 or 2 fluoro, isopropyl (e.g. —CH(CH$_3$)$_2$ or —CD(CD$_3$)$_2$), —CH$_2$CH$_2$CF$_3$, tetrahydropyran, tetrahydrofuran, oxetane, phenyl optionally substituted with 1 or 2 substituents R[7], pyrazole optionally substituted with 1 substituent R[8], and pyrimidine;

or R[4] and R[3], together with the atoms to which they are attached, are optionally joined to form a substituted or unsubstituted 5- to 7-membered heterocyclic ring selected from the group consisting of

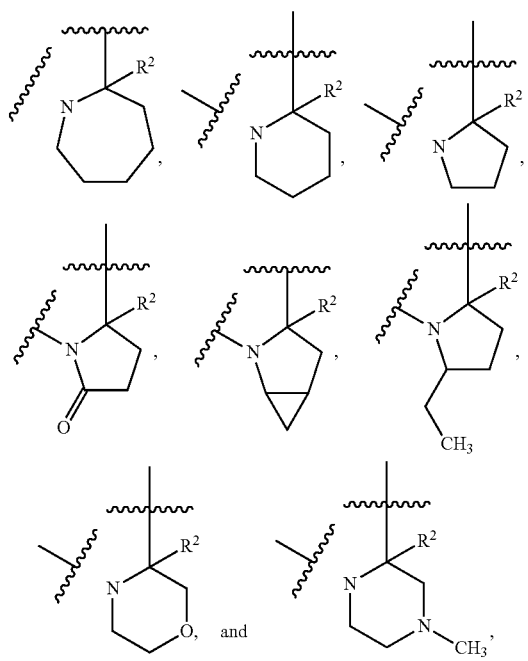

wherein

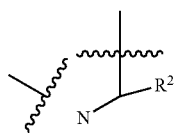

represents the core ring of Formula I, i.e. the N attached to R[4] and the C attached to R[3];

or R[4], R[2] and R[3], together with the atoms to which they are attached, are optionally joined to form a substituted or unsubstituted 7-membered heterocyclic ring selected from the group consisting of

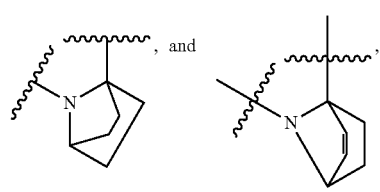 [SMILES: *N1C2CCC1(*)CC2 ; *N1C2C=CC1(*)CC2]

wherein

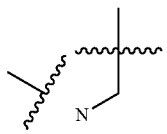

represents the core ring of Formula I, i.e. the N attached to R[4] and the C attached to R[3]/R[2];

R[5] is hydrogen, —Br, —CN, —CH$_3$, —CH$_2$CN, —CH$_2$CH$_2$NH$_2$, —OH, —O$^-$, =O, —OCH$_3$, —Obenzyl, —C(O)OH, —C(O)OCH$_3$, —C(O)OCH$_2$CH$_3$, —C(O)NH$_2$, —C(O)NHCH$_3$, —C(O)N(CH$_3$)$_2$,

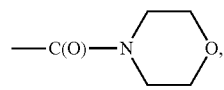

—NH$_2$, =NH, —NHCH$_3$, —N(CH$_3$)$_2$, —NHS(O)$_2$CH$_3$, —S(O)$_2$CH$_3$, phenyl, thiazole, pyridine or pyrazine;

R[6] is hydrogen, —Cl, —Br, —CH$_3$, —CF$_3$, —CH$_2$NH$_2$, —NH$_2$, —CH$_2$NHC(O)OCH$_3$, —CH$_2$NHC(O)CH$_3$, —CH$_2$NHC(O)phenyl, —CH$_2$NHS(O)$_2$CH$_3$, —CH$_2$NHS(O)$_2$phenyl, —NHC(O)CH$_3$, —NHC(O)OCH$_3$, —NHC(O)phenyl, —NHS(O)$_2$CH$_3$, —NHS(O)$_2$-phenyl, —C≡CHphenyl, cyclopropyl, cyclopentenyl, benzyl, phenyl optionally sub with 1, 2 or 3 substituents R[9], pyridine optionally substituted with 1 fluoro, pyrimidine, pyrazine, pyridazine, pyrazole, thiazole, oxazole, thiophene optionally substituted with 1 chloro, pyrrolidine, oxazolidinone, pyrrolidinone, dihydropyran, tetrahydropyran, morpholine, 4-methyl-piperazine, pyrrolidine-dione, pyridinone, isoquinoline, or quinoline;

R[7] at each occurrence is independently —C(O)NH$_2$, fluoro, chloro, cyano, pyrazole, triazole, pyridine or pyrimidine;

R[8] is methyl or 2-(trimethylsilyl)ethoxy)methyl, cyclopropyl, or —CH$_2$-cyclopropyl; and R[9] at each occurrence is independently selected from the group consisting of fluoro, chloro, bromo, —S(O)$_2$CH$_3$, —OCF$_3$, —CF$_3$, —CN, pyridine, triazole, and pyrazole.

In one embodiment, compounds are provided having a structure according to Formula (I), or a salt or solvate thereof, wherein:

A is a ring selected from the group consisting of phenyl, pyridin-2-yl, pyridin-3-yl, pyridin-4-yl, pyrimidin-5-yl, pyrazin-2-yl, pyridazin-4-yl, pyridin-2-on-4-yl, pyridin-4-imine, pyrrol-2-yl, pyrazol-1-yl, pyrazol-3-yl, pyrazol-4-yl, imidazol-1-yl, thiazol-5-yl, isothiazol-4-yl, isoxazol-4-yl, 1,2,3-triazol-5-yl, 1,2,4-triazol-1-yl, 1,2,3-thiadiazol-5-yl, benzimidazol-1-yl, indol-1-yl, indol-2-yl, indol-7-yl, pyrrolo[2,3-b]pyridin-5-yl, quinolin-8-yl, pyrrolidin-1-yl, piperidin-1-yl, piperazin-1-yl, and 4,5-dihydro-1H-imidazol-1-yl (A orientation is preferably structurally as follows:

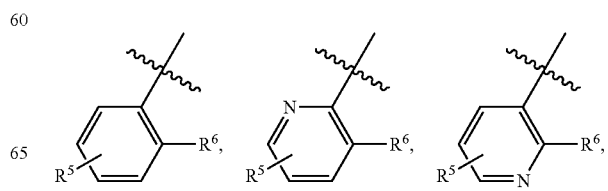

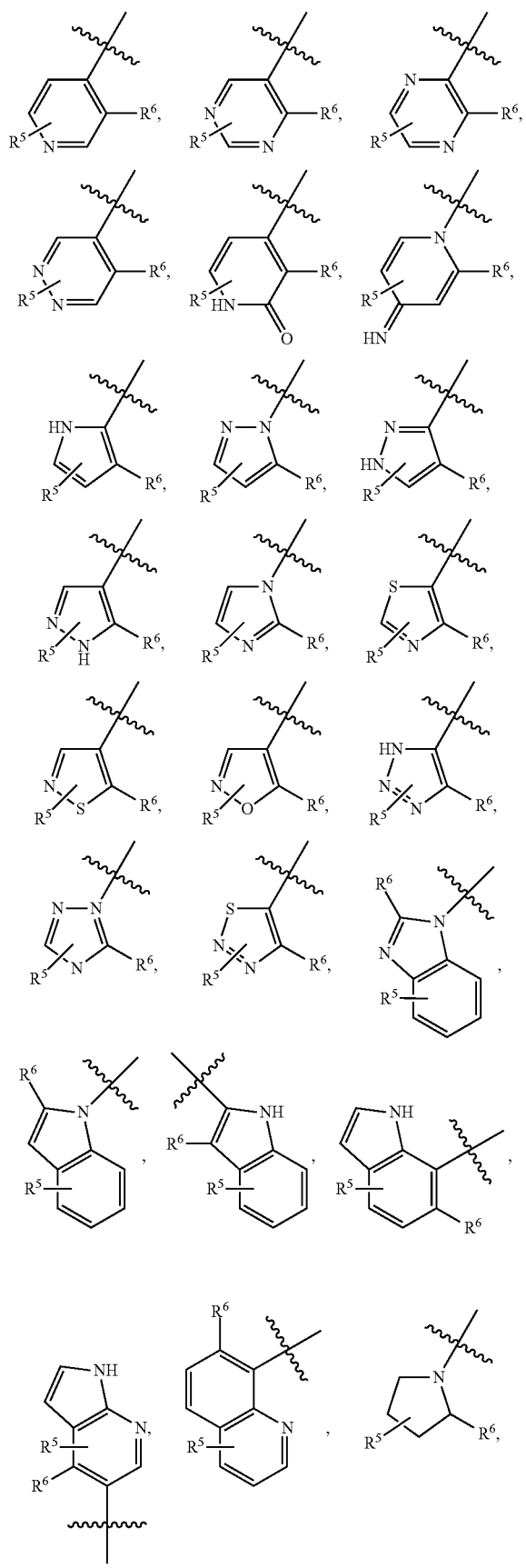

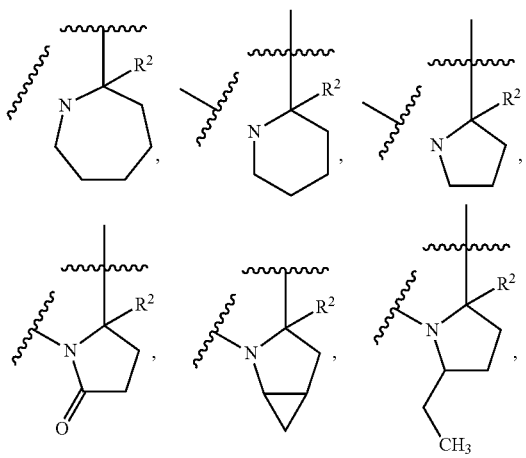

wherein

[wavy bond symbol] represents the attachment of X to the 2-position of the 7,8-dihydropteridin-6(5H)-one core;

R$^1$ is —CD$_3$ or —CH$_3$;

R$^2$ is hydrogen, —CD$_3$, —CH$_3$, —CD$_2$CD$_3$, —CH$_2$CH$_3$, —CH$_2$-cyclopropyl, or —CH$_2$CF$_3$;

R$^3$ is —CD$_3$, —CH$_3$, —CD$_2$CD$_3$, —CH$_2$CH$_3$, —CH$_2$-cyclopropyl, or —CH$_2$CF$_3$; or R$^2$ and R$^3$, together with the carbon atom to which they are attached, are optionally joined to form cyclobutyl;

R$^4$ is selected from the group consisting of —NH$_2$, —NHCH$_3$, —NHcyclopropyl, pyrrolidin-1-yl, —CH$_2$-cyclopropyl, —CH(CH$_3$)-cyclopropyl, cyclopropyl, cyclobutyl, 3-fluorocyclobutyl, 3,3-difluorocyclobutyl, cyclopentyl, 3,3-difluorocyclopentyl, —CH(CH$_3$)$_2$, —CD(CD$_3$)$_2$, —CH$_2$CH$_2$CF$_3$, tetrahydro-2H-pyran-4-yl, tetrahydrofuran-3-yl, oxetan-3-yl, phenyl, 4-fluoro-phenyl, 4-chloro-phenyl, 3-cyano-phenyl, 4-cyano-phenyl, 3-pyrimidin-5-yl-phenyl, 3-pyrazol-1-yl-phenyl, 3-pyridin-3-yl-phenyl, 3-1,2,4-triazol-1-yl-phenyl, pyrazol-3-yl, pyrazol-4-yl, 1-methyl-pyrazol-4-yl, 1-cyclopropyl-pyrazol-4-yl, 1-cyclopropylmethyl-pyrazol-4-yl, 1-(2-(trimethylsilyl)ethoxy)methyl)-pyrazol-4-yl, and pyrimidin-5-yl;

or R$^4$ and R$^3$, together with the atoms to which they are attached, are optionally joined to form a substituted or unsubstituted 5- to 7-membered heterocyclic ring selected from the group consisting of

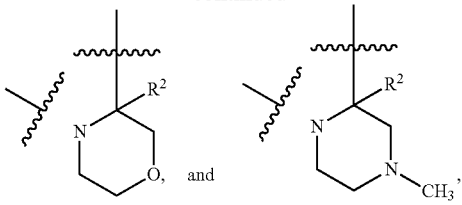

wherein

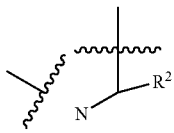

represents the core ring of Formula I, i.e. the N attached to $R^4$ and the C attached to $R^3$;

or $R^4$, $R^2$ and $R^3$, together with the atoms to which they are attached, are optionally joined to form a substituted or unsubstituted 7-membered heterocyclic ring selected from the group consisting of

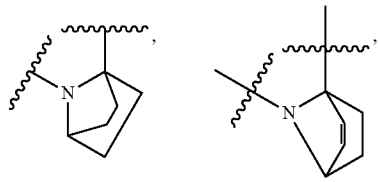 [SMILES: *N1C2CCC1(*)CC2 ; *N1C2C=CC1(*)CC2]

wherein

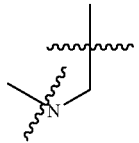

represents the core ring of Formula I, i.e. the N attached to $R^4$ and the C attached to $R^3/R^2$;

$R^5$ is hydrogen, —Br, —CN, —CH$_3$, —CH$_2$CN, —CH$_2$CH$_2$NH$_2$, —OH, =O, —O$^-$, —OCH$_3$, —Obenzyl, —C(O)OH, —C(O)OCH$_3$, —C(O)OCH$_2$CH$_3$, —C(O)NH$_2$, —C(O)NHCH$_3$, —C(O)N(CH$_3$)$_2$,

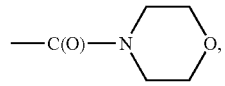

—NH$_2$, —NHCH$_3$, —N(CH$_3$)$_2$, —NHS(O)$_2$CH$_3$, —S(O)$_2$CH$_3$, phenyl, thiazol-2-yl, thiazol-4-yl, pyridin-3-yl, and pyrazin-2-yl;

$R^6$ is hydrogen, —Cl, —Br, —CH$_3$, —CF$_3$, —CH$_2$NH$_2$, —NH$_2$, —CH$_2$NHC(O)OCH$_3$, —CH$_2$NHC(O)CH$_3$, —CH$_2$NHC(O)phenyl, —CH$_2$NHS(O)$_2$CH$_3$, —CH$_2$NHS(O)$_2$-phenyl, —NHC(O)CH$_3$, —NHC(O)OCH$_3$, —NHC(O)phenyl, —NHS(O)$_2$CH$_3$, —NHS(O)$_2$-phenyl, —CH=CHphenyl, cyclopropyl, cyclopent-1-enyl, benzyl, phenyl optionally substituted with 1, 2, or 3 substituents $R^9$, pyridin-2-yl, 5-fluoro-pyridin-2-yl, pyridin-3-yl, 5-fluoro-pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, 5-Cl-thiophen-2-yl, pyrrolidin-1-yl, oxazolidin-2-on-3-yl, 2-oxopyrrolidin-1-yl, 3,6-dihydro-2H-pyran-4-yl, tetrahydro-2H-pyran-4-yl, morpholin-4-yl, 4-methyl-piperazin-1-yl, pyrrolidine-2,5-dion-1-yl, pyridin-2-on-1-yl, isoquinolin-1-yl, quinolin-5-yl, and quinolin-3-yl; and $R^9$ gives substitution of the phenyl ring selected from the group consisting of 4-S(O)$_2$CH$_3$, 3-OCF$_3$, 4-OCF$_3$, 3-CF$_3$, 4-CF$_3$, 2-F, 3-F, 3-Cl, 3-Br, 4-F, 2,3-diF, 2,4-diF, 2-Cl-4-F, 3,4-diF, 3,5-diCl, 3,5-diF, 3-F-5-CF$_3$, 3-Cl-4-F, 3-CN, 4-CN, 3,4,5-triF, 3-pyridin-3-yl, 3-1,2,4-triazol-1-yl, and 3-pyrazol-1-yl.

In one embodiment, compounds are provided having a structure according to Formula (I), or a salt or solvate thereof, wherein:

A is a ring selected from the group consisting of phenyl, pyridin-2-yl, pyridin-3-yl, pyridin-4-yl, pyrimidin-5-yl, pyrazin-2-yl, pyridin-2-one, pyridin-4-imine, pyrazol-1-yl, pyrazol-4-yl, imidazol-1-yl, thiazol-5-yl, 1,2,3-triazol-5-yl, 1,2,4-triazol-1-yl, 1,2,3-thiadiazol-5-yl, indol-1-yl, indol-2-yl, indol-7-yl, piperazin-1-yl, 4,5-dihydro-1H-imidazol-1-yl;

$R^1$ is —CD$_3$ or —CH$_3$;

$R^2$ is hydrogen, —CD$_3$, —CH$_3$, —CD$_2$CD$_3$, —CH$_2$CH$_3$ or —CH$_2$CF$_3$;

$R^3$ is —CD$_3$, —CH$_3$, —CD$_2$CD$_3$, —CH$_2$CH$_3$, or —CH$_2$CF$_3$; or $R^2$ and $R^3$, together with the carbon atom to which they are attached, are optionally joined to form cyclobutyl;

$R^4$ is selected from the group consisting of —NH$_2$, cyclopropyl, cyclobutyl, 3,3-difluorocyclobutyl, cyclopentyl, —CH(CH$_3$)$_2$, —CD(CD$_3$)$_2$, —CH$_2$CH$_2$CF$_3$, tetrahydro-2H-pyran-4-yl, tetrahydrofuran-3-yl, oxetan-3-yl, phenyl, 4-fluoro-phenyl, 4-chloro-phenyl, 3-cyano-phenyl, 4-cyano-phenyl, pyrazol-3-yl, pyrazol-4-yl, 1-methyl-pyrazol-4-yl, and pyrimidin-5-yl;

or $R^4$ and $R^3$, together with the atoms to which they are attached, are optionally joined to form a substituted or unsubstituted 5- to 6-membered heterocyclic ring selected from the group consisting of

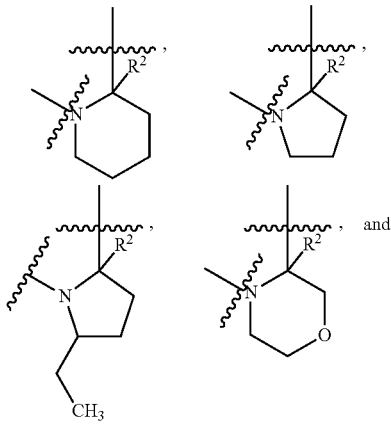

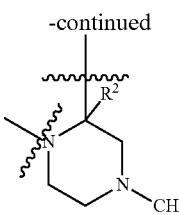

wherein

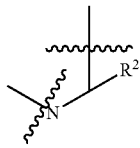

represents the core ring of Formula I, i.e. the N attached to $R^4$ and the C attached to $R^3$;

$R^5$ is hydrogen, —CN, —Br, —CH$_3$, —CH$_2$CN, —CH$_2$CH$_2$NH$_2$, —OH, =O, —O$^-$, —C(O)OH, —C(O)OCH$_3$, —C(O)OCH$_2$CH$_3$, —C(O)NH$_2$, —C(O)NHCH$_3$, —C(O)N(CH$_3$)$_2$,

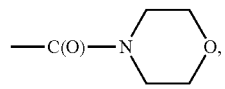

—NH$_2$, —N(CH$_3$)$_2$, —NHS(O)$_2$CH$_3$, phenyl, thiazol-2-yl, thiazol-4-yl, or pyridin-3-yl;

$R^6$ is hydrogen, —Cl, —CH$_3$, —NH$_2$, —CH$_2$NHC(O)OCH$_3$, —CH$_2$NHC(O)CH$_3$, —CH$_2$NHS(O)$_2$CH$_3$, —NHC(O)CH$_3$, —NHC(O)OCH$_3$, —NHS(O)$_2$CH$_3$, cyclopropyl, cyclopent-1-enyl, phenyl optionally substituted with 1, 2, or 3 substituents $R^9$, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, pyrrolidin-1-yl, oxazolidin-2-on-3-yl, 2-oxopyrrolidin-1-yl, tetrahydro-2H-pyran-4-yl, morpholin-4-yl, 4-methyl-piperazin-1-yl, quinolin-5-yl, or quinolin-3-yl; and $R^9$ gives substitution of the phenyl ring selected from the group consisting of 4-S(O)$_2$CH$_3$, 4-CF$_3$, 3-F, 3-Cl, 3-Br, 4-F, 2,4-diF, 3,4-diF, 3,5-diF, 3-C$_{1-4}$-F, 4-CN, 3-1,2,4-triazol-1-yl, and 3-pyrazol-1-yl.

In one embodiment, compounds are provided having a structure according to Formula (I), or a salt or solvate thereof, wherein:

A is a ring selected from the group consisting of pyridin-3-yl, pyridin-4-yl, pyridin-2-one, pyridin-4-imine, pyrazol-1-yl, pyrazol-4-yl, imidazol-1-yl, thiazol-5-yl, 1,2,4-triazol-1-yl, and 1,2,3-thiadiazol-5-yl,;

$R^1$ is —CD$_3$ or —CH$_3$;

$R^2$ is hydrogen, —CD$_3$, —CH$_3$, —CD$_2$CD$_3$, or —CH$_2$CH$_{13}$;

$R^3$ is —CD$_3$, —CH$_3$, —CD$_2$CD$_3$, or —CH$_2$CH$_{13}$;

$R^4$ is selected from the group consisting of —NH$_2$, cyclopropyl, cyclobutyl, cyclopentyl, —CH(CH$_3$)$_2$, —CD(CD$_3$)$_2$, tetrahydro-2H-pyran-4-yl, tetrahydrofuran-3-yl, oxetan-3-yl, 4-chloro-phenyl, 4-cyano-phenyl, pyrazol-3-yl, pyrazol-4-yl, 1-methyl-pyrazol-4-yl, and pyrimidin-5-yl;

or $R^4$ and $R^3$, together with the atoms to which they are attached, are optionally joined to form a substituted or unsubstituted 5- to 6-membered heterocyclic ring selected from the group consisting of

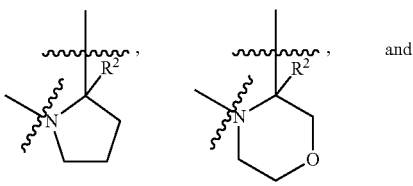

wherein

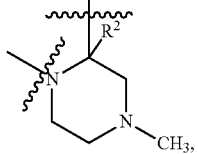

represents the core ring of Formula I, i.e. the N attached to $R^4$ and the C attached to $R^3$;

$R^5$ is hydrogen, —CH$_3$, —CH$_2$CH$_2$NH$_2$, —OH, —O$^-$, —C(O)OH, —C(O)OCH$_2$CH$_3$, —C(O)NH$_2$, —C(O)NHCH$_3$, —C(O)N(CH$_3$)$_2$,

—C(O)—N⟨O⟩,

—NHCH$_3$, or pyridin-3-yl; and $R^6$ is hydrogen, phenyl, 4-methylsulfonyl-phenyl, 4-fluoro-phenyl, 2,3-difluoro-phenyl, 2,4-difluoro-phenyl, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-5-yl, pyrazol-4-yl, thiazol-2-yl, oxazol-2-yl, or oxazolidin-2-on-3-yl.

In one embodiment, the compound is any one or more compounds, or a salt or solvate thereof, as described in the Examples herein. Preferably the compound is any one or more compounds, or a salt or solvate thereof, selected from the group consisting of:

(S)-6a-ethyl-5-methyl-2-(2-phenyl-1H-imidazol-1-yl)-6a,7,9,10-tetrahydro-[1,4]oxazino[3,4-h]pteridin-6(5H)-one (Example 314), (S)-6a-ethyl-5-methyl-2-(5-(thiazol-2-yl)-1H-pyrazol-4-yl)-6a,7,9,10-tetrahydro-[1,4]oxazino[3,4-h]pteridin-6(5H)-one (Example 344), (7R)-7-ethyl-5-methyl-8-(tetrahydrofuran-3-yl)-2-(5-(thiazol-2-yl)-1H-pyrazol-4-yl)-7,8-dihydropteridin-6(5H)-one (Example 365), (S)-6a-ethyl-5,8-dimethyl-2-(2-phenyl-1H-imidazol-1-yl)-'7,8,9,10-tetrahydro-5H-pyrazino[2,1-h]pteridin-6(6aH)-one (Example 374), (S)-2-(2-(2,4-difluorophenyl)-1H-imidazol-1-yl)-6a-ethyl-5-methyl-6a,7,9,10-tetrahydro-[1,4]oxazino[3,4-h]pteridin-6(5H)-one (Example 376), (S)-6a-ethyl-2-(2-(5-fluoropyridin-2-yl)-1H-imidazol-1-yl)-5-methyl-6a,7,9,10-tetrahydro-[1,4]oxazino[3,4-h]pteridin-6(5H)-one (Example 380), (S)-6a-ethyl-5-methyl-2-(2-(thiazol-2-yl)-1H-imidazol-1-yl)-6a,7,9,10-tetrahydro-[1,4]oxazino[3,4-h]pteridin-6(5H)-one (Example 387), (R)-7-ethyl-2-(2-(4-fluorophenyl)-1H-imidazol-1-yl)-5-methyl-8-(1-methyl-1H-pyrazol-4-yl)-7,8-dihydropteridin-6(5H)-one (Example 389), (S)-6a-ethyl-5-methyl-2-(3-phenylpyridin-4-yl)-6a,7,9,10-tetrahydro-[1,4]oxazino[3,4-h]pteridin-6(5H)-one (Example 394), (S)-6a-ethyl-5-methyl-2-(2-phenylpyridin-3-yl)-6a,7,9,10-tetrahydro-[1,4]oxazino[3,4-h]pteridin-6(5H)-one (Example 403), (R)-7-ethyl-2-(2-(4-fluorophenyl)-1H-imidazol-1-yl)-5-methyl-8-(1-methyl-1H-pyrazol-3-yl)-7,8-dihydropteridin-6(5H)-one (Example 407), (R)-7-ethyl-5-methyl-8-(1-methyl-1H-pyrazol-4-yl)-2-(2-phenyl-1H-imidazol-1-yl)-7,8-dihydropteridin-6(5H)-one (Example 409), (S)-2-(5-(2,4-difluorophenyl)-1H-pyrazol-4-yl)-6a-ethyl-5-methyl-6a,7,9,10-tetrahydro-[1,4]oxazino[3,4-h]pteridin-6(5H)-one (Example 411), (R)-7-ethyl-5-methyl-8-(1-methyl-1H-pyrazol-4-yl)-2-(1-methyl-3-(thiazol-2-yl)-1H-pyrazol-4-yl)-7,8-dihydropteridin-6(5H)-one (Example 417), (R)-2-(3-(2,4-difluorophenyl)-1H-pyrazol-4-yl)-7-ethyl-5-methyl-8-(1-methyl-1H-pyrazol-4-yl)-7,8-dihydropteridin-6(5H)-one (Example 419), (R)-7-ethyl-5-methyl-8-(1-methyl-1H-pyrazol-3-yl)-2-(1-methyl-3-(thiazol-2-yl)-1H-pyrazol-4-yl)-7,8-dihydropteridin-6(5H)-one (Example 421), (R)-7-ethyl-5-methyl-8-(1-methyl-1H-pyrazol-3-yl)-2-(1-methyl-5-(thiazol-2-yl)-1H-pyrazol-4-yl)-7,8-dihydropteridin-6(5H)-one (Example 422), (R)-7-ethyl-5-methyl-8-(1-methyl-1H-pyrazol-3-yl)-2-(3-phenylpyridin-4-yl)-7,8-dihydropteridin-6(5H)-one (Example 424), (R)-7-ethyl-5-methyl-8-(1-methyl-1H-pyrazol-3-yl)-2-(2-phenylpyridin-3-yl)-7,8-dihydropteridin-6(5H)-one (Example 425), (R)-7-ethyl-5-methyl-8-(1-methyl-1H-pyrazol-4-yl)-2-(2-phenylpyridin-3-yl)-7,8-dihydropteridin-6(5H)-one (Example 426), (R)-7-ethyl-5-methyl-8-(1-methyl-1H-pyrazol-4-yl)-2-(3-phenylpyridin-4-yl)-7,8-dihydropteridin-6(5H)-one (Example 427), (R)-7-ethyl-5-methyl-8-(1-methyl-1H-pyrazol-3-yl)-2-(2-phenyl-1H-imidazol-1-yl)-7,8-dihydropteridin-6(5H)-one (Example 428), (S)-2-(2-(2,3-difluorophenyl)-1H-imidazol-1-yl)-6a-ethyl-5-methyl-6a,7,9,10-tetrahydro-[1,4]oxazino[3,4-h]pteridin-6(5H)-one (Example 431), (7R)-7-ethyl-5-methyl-2-(1-methyl-3-(thiazol-2-yl)-1H-pyrazol-4-yl)-8-(tetrahydrofuran-3-yl)-7,8-dihydropteridin-6(5H)-one (Example 434), and (7R)-7-ethyl-5-methyl-2-(1-methyl-5-(thiazol-2-yl)-1H-pyrazol-4-yl)-8-(tetrahydrofuran-3-yl)-7,8-dihydropteridin-6(5H)-one (Example 435).

In one embodiment, for compounds of Formula (I), $R^2$, $R^3$, and $R^4$ are selected to give a structure selected from the group consisting of Formula (Ia), Formula (Ib), Formula (Ic), Formula (Id), and Formula (Ie), as follows:

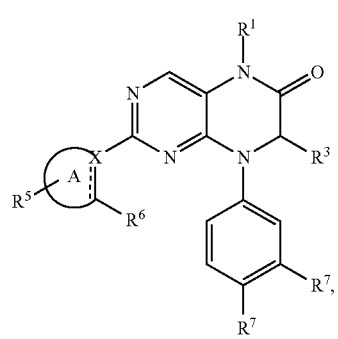
(Ia)

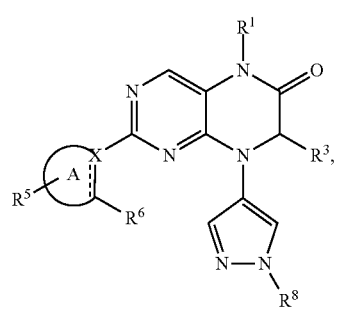
(Ib)

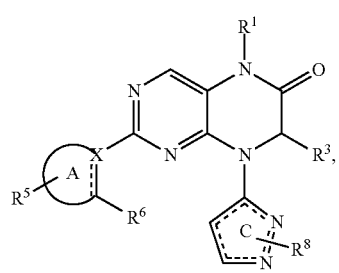
(Ic)

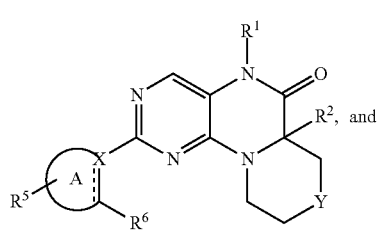
(Id)

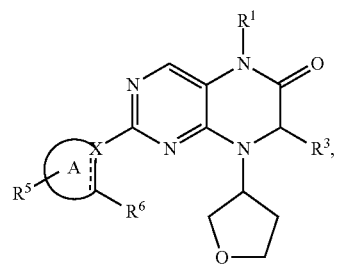
(Ie)

or a salt or solvate thereof, wherein:

C is pyrazole, wherein $R^8$ is bound to either of the nitrogens in the pyrazole ring;

Y is O or N—$CH_3$; and

X, A, $R^1$, $R^2$, $R^3$, $R^5$, $R^6$, $R^7$ and $R^8$ are as defined for Formula I.

In one embodiment, the preferred stereoisomer at the carbon bound to $R^2$ and $R^3$ is as follows:

when $R^2$ is H and $R^3$ is —$CD_3$, —$CH_3$, —$CD_2CD_3$, —$CH_2CH_3$, —$CH_2$-cyclopropyl, or —$CH_2CF_3$, preferably, —$CD_2CD_3$, —$CH_2CH_3$, or —$CH_2CF_3$, the preferred isomer is represented by the following structure of Formula (If):

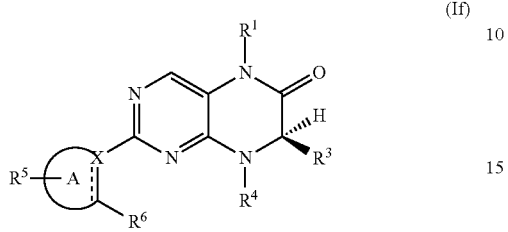

(If)

and when $R^2$ is —$CD_2CD_3$, —$CH_2CH_3$, or —$CH_2CF_3$, and $R^3$ and $R^4$, together with the atoms to which they are attached, combine to form a substituted or unsubstituted 3- to 8-membered heterocyclic ring, the preferred isomer is represented by the following structure of Formula (Ig), where the dotted line connecting $R^3$ and $R^4$ represents one of the rings as provided in Formula (I) above:

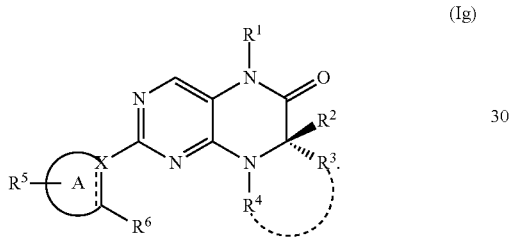

(Ig)

In one embodiment, compounds are provided having a structure selected from the group consisting of Formula (Ih), Formula (Ii), Formula (Ij), Formula (Ik), and Formula (Im), as follows:

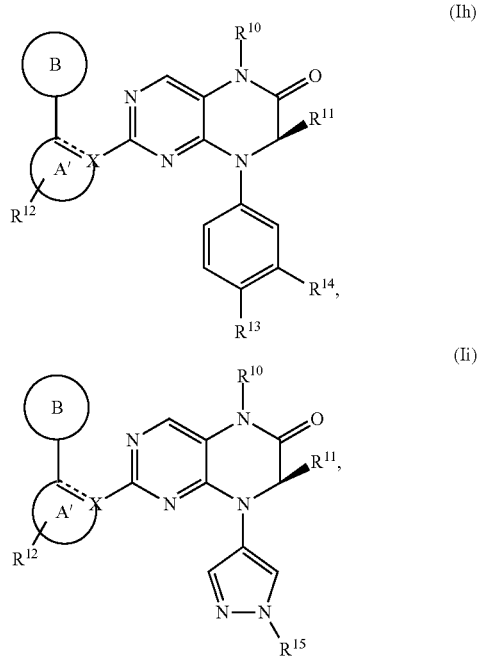

(Ih)

(Ii)

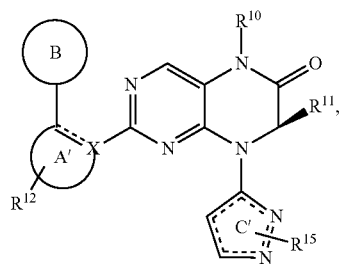

(Ij)

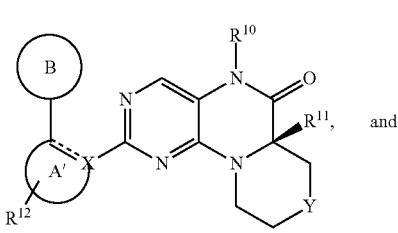

(Ik)

and

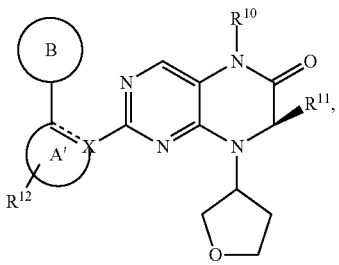

(Im)

or a salt or solvate thereof, wherein:

X is C or N and the dashed line represents a single or double bond;

Y is O or N—$CH_3$;

A' is selected from the group consisting of phenyl, pyridin-2-yl, pyridin-3-yl, pyridin-4-yl, pyrimidin-5-yl, pyrazin-2-yl, pyridin-2-one, pyridin-4-imine, pyrazol-1-yl, pyrazol-4-yl, imidazol-1-yl, thiazol-5-yl, isothiazol-4-yl, isoxazol-4-yl, 1,2,3-triazol-5-yl, 1,2,4-triazol-1-yl, 1,2,3-thiadiazol-5-yl, indol-1-yl, indol-2-yl, indol-7-yl, piperazin-1-yl, 4,5-dihydro-1H-imidazol-1-yl;

B is selected from the group consisting of phenyl optionally substituted with 1, 2, or 3 substituents $R^{16}$, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, pyrrolidin-1-yl, oxazolidin-2-on-3-yl, 2-oxopyrrolidin-1-yl, tetrahydro-2H-pyran-4-yl, morpholin-4-yl, 4-methyl-piperazin-1-yl, quinolin-5-yl, and quinolin-3-yl;

C' is pyrazole, wherein $R^{15}$ is bound to either of the nitrogens in the pyrazole ring;

$R^{10}$ is —$CD_3$ or —$CH_3$;

$R^{11}$ is —$CD_2CD_3$ or —$CH_2CH_3$;

$R^{12}$ is hydrogen, —$CH_3$, —Br, —CN, or —$NH_2$;

$R^{13}$ is hydrogen, —F, —Cl, —C(O)$NH_2$, or —CN;

$R^{14}$ is hydrogen, —F, —Cl, —C(O)$NH_2$, or —CN;

$R^{15}$ is hydrogen, methyl, cyclopropyl, or —$CH_2$-cyclopropyl; and $R^{16}$ at each occurrence is independently selected from the group consisting of fluoro, chloro, bromo, —S(O)$_2CH_3$, —$OCF_3$, —$CF_3$, —CN, pyridine, triazole, and pyrazole.

In one embodiment, compounds are provided having a structure selected from the group consisting of Formula (Ih), Formula (II), Formula (Ij), Formula (Ik), and Formula (Im), or a salt or solvate thereof, wherein:

X is C or N and the dashed line represents a single or double bond;

Y is O or N—CH$_3$;

A' is selected from the group consisting of pyridin-3-yl, pyridin-4-yl, pyridin-2-one, pyridin-4-imine, pyrazol-1-yl, pyrazol-4-yl, imidazol-1-yl, thiazol-5-yl, 1,2,4-triazol-1-yl, and 1,2,3-thiadiazol-5-yl;

B is selected from the group consisting of phenyl, 4-methylsulfonyl-phenyl, 4-fluoro-phenyl, 2,3-difluoro-phenyl, 2,4-difluoro-phenyl, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-5-yl, pyrazol-4-yl, thiazol-2-yl, oxazol-2-yl, or oxazolidin-2-on-3-yl;

$R^{10}$ is —CD$_3$ or —CH$_3$;

$R^{11}$ is —CD$_2$CD$_3$ or —CH$_2$CH$_3$;

$R^{12}$ is hydrogen, —CH$_3$, —Br, —CN, or —NH$_2$;

$R^{13}$ is hydrogen, —F, —Cl, —C(O)NH$_2$, or —CN;

$R^{14}$ is hydrogen, —F, —Cl, —C(O)NH$_2$, or —CN; and $R^{15}$ is —CH$_3$, cyclopropyl, or —CH$_2$-cyclopropyl.

In one embodiment, compounds are provided having a structure selected from the group consisting of Formula (Ii), Formula (Ij), Formula (Ik), and Formula (Im), or a salt or solvate thereof, wherein:

X is C or N and the dashed line represents a single or double bond;

Y is O or N—CH$_3$;

A' is selected from the group consisting of pyridin-3-yl, pyridin-4-yl, pyrazol-4-yl, and imidazol-1-yl;

B is selected from the group consisting of phenyl, 4-fluoro-phenyl, 2,3-difluoro-phenyl, 2,4-difluoro-phenyl, 5-fluoro-pyridin-2-yl, and thiazol-2-yl;

$R^{10}$ is —CD$_3$ or —CH$_3$;

$R^{11}$ is —CD$_2$CD$_3$ or —CH$_2$CH$_3$;

$R^{12}$ is hydrogen or —CH$_3$; and $R^{15}$ is —CH$_3$.

DETAILED DESCRIPTION OF THE INVENTION

Definitions

The definitions and explanations below are for the terms as used throughout this entire document including both the specification and the claims. Throughout the specification and the appended claims, a given formula or name shall encompass all isomers thereof, such as stereoisomers (e.g. diastereomers, enantiomers), geometrical isomers, tautomers, and mixtures thereof where such isomers exist, as well as pharmaceutically acceptable salts and solvates (e.g., hydrates) thereof. In one example, a given formula or name shall encompass all stereoisomers thereof, and pharmaceutically acceptable salts and solvates thereof. In one example, a given formula or name shall encompass all stereoisomers thereof, and pharmaceutically acceptable solvates thereof. In one example, a given formula or name shall encompass all stereoisomers thereof, and pharmaceutically acceptable salts thereof. In one example, a given formula or name shall encompass all pharmaceutically acceptable salts and solvates thereof. In one example, a given formula or name shall encompass all isomers thereof. In one example, a given formula or name shall encompass all stereoisomers thereof. In one example, a given formula or name shall encompass all enantiomers thereof. In one example, a given formula or name shall encompass all diastereomers thereof. In one example, a given formula or name shall encompass all pharmaceutically acceptable salts thereof. In one example, a given formula or name shall encompass all solvates thereof.

Reference to compounds as described herein (e.g. compounds of Formula (I)), or reference to compounds of Formula (I) includes reference to Formula (I) including any sub-generic embodiments thereof, e.g. Formula (Ia), (Ib), (Ic), (Id), (Ie), (If), (Ig), (Ih), (Ii), (Ij), (Ik), or (Im) (including all sub-generic embodiments thereof).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where substituents are indicated as being attached to a structure, those substituents are independently selected and any such substitution results in a stable molecule.

Compounds were named using Autonom 2000 4.01.305, which is available from Beilstein Information Systems, Inc, Englewood, Colo.; ChemDraw v.10.0 or ChemDraw Ultra v. 10.0.4, (available from Cambridgesoft at 100 Cambridge Park Drive, Cambridge, Mass. 02140), or ACD Name pro, which is available from Advanced Chemistry Development, Inc., at 110 Yonge Street, 14$^{th}$ floor, Toronto, Ontario, Canada MSc 1T4. Alternatively, the names were generated based on the IUPAC rules or were derived from names originally generated using the aforementioned nomenclature programs. In any instance where there may be any ambiguity between a name given to a compound structure, or if no name is provided for a given structure, the provided structure is intended to clearly define the compound, and for those compounds only described by the given structure can be readily named using any of the above methods, or other methods known to one skilled in the art.

The terms used in describing substituents within Formula I are well known in the art. For example, "methyl" generically means a group —CH$_3$, or analogous structure in which any atoms can include any isotopes thereof, for example methyl includes —CD$_3$, -$^{14}$CH$_3$, the like.

The term "substituted" in connection with cyclobutyl, cyclopentyl, phenyl, pyrazole, pyridine and thiophene refers to one or more substituents as indicated within the definitions of Formula I.

By "oxo" is meant the group =O.

The phrase "therapeutically effective amount" as used herein means that amount of a compound, material, or composition of the present invention, which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

The terms "treatment" or "treating" when referring to a disease or condition, means producing a desired therapeutic effect. Exemplary therapeutic effects include delaying onset or reducing at least one symptom associated with the disease, positively affecting (e.g., reducing or delaying onset) of a clinical marker associated with the disease and slowing or reversing disease progression.

The term "pharmaceutically acceptable" refers to those properties and/or substances that are acceptable to a patient (e.g., human patient) from a toxicological and/or safety point of view.

The term "pharmaceutically acceptable salts" means salts of the compounds as described herein, e.g. compounds of Formula (I), which are prepared with relatively nontoxic acids or bases, depending on the particular substituents found on the compounds described herein. When compounds of the present invention contain relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino, magnesium and aluminum salts and the like. When compounds of the present invention contain relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, diphosphoric, monohydrogenphosphoric, dihydrogenphosphoric, sulfuric, monohydrogensulfuric, hydriodic and the like, as well as the salts derived from relatively nontoxic organic acids like formic, acetic, propionic, isobutyric, malic, maleic, malonic, benzoic, succinic, suberic, fumaric, lactic, mandelic, phthalic, benzenesulfonic, p-tolylsulfonic, citric, tartaric, methanesulfonic, 2-hydroxyethylsulfonic, salicylic, stearic and the like. Also included are salts of amino acids such as arginate and the like, and salts of organic acids like glucuronic or galactunoric acids and the like (see, for example, Berge et al., *Journal of Pharmaceutical Science*, 1977, 66: 1-19). Certain specific compounds of the present invention contain both basic and acidic functionalities that allow the compounds to be converted into either base or acid addition salts.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

When a substituent includes a negatively charged oxygen atom "O$^-$", e.g., in "—COO$^-$", then the formula is meant to optionally include a proton or an organic or inorganic cationic counterion. In one example, the resulting salt form of the compound is pharmaceutically acceptable. Further, when a compound of Formula (I) includes an acidic group, such as a carboxylic acid group, e.g., written as the substituent "—COOH", "—CO$_2$H" or "—C(O)$_2$H", then the formula is meant to optionally include the corresponding "de-protonated" form of that acidic group, e.g., "—COO$^-$", "—CO$_2^-$" or "—C(O)$_2^-$", respectively.

In addition to salt forms, the present invention provides compounds, which are in a prodrug form. Prodrugs of the compounds described herein are those compounds that readily undergo chemical changes under physiological conditions to provide the compounds of the present invention. Non-limiting examples of "pharmaceutically acceptable derivative" or "prodrug" include pharmaceutically acceptable esters, phosphate esters or sulfonate esters thereof as well as other derivatives of a compound of this invention which, upon administration to a recipient, is capable of providing, either directly or indirectly, a compound of this invention. Particularly favored derivatives or prodrugs are those that increase the bioavailability of the compounds of this invention when such compounds are administered to a mammal (e.g., by allowing an orally administered compound to be more readily absorbed into the blood stream) or which enhance delivery of the parent compound to a biological compartment (e.g., the brain or lymphatic system) relative to the parent species.

Prodrugs include a variety of esters (i.e., carboxylic acid ester). Ester groups, which are suitable as prodrug groups are generally known in the art and include benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$)alkoxy esers, optionally substituted by N-morpholino and amide-forming groups such as di($C_1$-$C_6$)alkylamino. Preferred ester prodrug groups include $C_1$-$C_6$ alkoxy esters. Those skilled in the art will recognize various synthetic methodologies that may be employed to form pharmaceutically acceptable prodrugs of the compounds of Formula (I) (e.g., via esterification of a carboxylic acid group).

In an exemplary embodiment, the prodrug is suitable for treatment/prevention of those diseases and conditions that require the drug molecule to cross the blood brain barrier. In a preferred embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention can exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "and/or", in that materials meeting more than one of the stated criteria are included, e.g., a material that is both a salt and a solvate is encompassed.

The compounds of the present invention can contain unnatural proportions of atomic isotopes at one or more of the atoms that constitute such compounds. For example, the compounds can be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention. Compounds described herein, in which one or more of the hydrogen atoms are replaced with another stable isotope of hydrogen (i.e., deuterium) or a radioactive isotope (i.e., tritium), are part of this invention. For example, alkyl groups generically include isotopic variants of hydrogen and carbon, such that methyl, for example, as an option for a variable in any Formula, includes —CH$_3$, or analogous structure in which any atoms can include any isotopes thereof, for example methyl includes —CD$_3$, —$^{14}$CH$_3$, and the like.

Compositions Including Stereoisomers

Compounds as described herein, e.g. compounds of Formula (I), can exist in particular geometric or stereoisomeric forms. The invention contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of compounds of Formula (I). Additional asymmetric carbon atoms can be present in a substituent such as an alkyl group. All such isomers, as well as mixtures thereof, are intended to be included in this invention. When the compounds described herein contain olefinic double bonds or other centers of geometric asymmetry, and unless specified otherwise, it is intended that the compounds include both E and Z geometric isomers. Likewise, all tautomeric forms and mixtures of tautomers are included.

Optically active (R)- and (S)-isomers and d and l isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "chiral", "enantiomerically enriched" or "diastereomerically enriched" refers to a compound having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

The terms "enantiomeric excess" and "diastereomeric excess" are used in their conventional sense. Compounds with a single stereocenter are referred to as being present in "enantiomeric excess", those with at least two stereocenters are referred to as being present in "diastereomeric excess". The value of ee will be a number from 0 to 100, zero being racemic and 100 being enantiomerically pure. For example, a 90% ee reflects the presence of 95% of one enantiomer and 5% of the other(s) in the material in question.

Hence, in one embodiment, compositions are provided including a first stereoisomer and at least one additional stereoisomer of a compound as described herein, e.g. a compound of Formula (I). The first stereoisomer can be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. In another embodiment, the compound of Formula (I) is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

The term "PLK1-mediated condition", "polo-like kinase 1 mediated disorder" or any other variation thereof, as used herein means any disease or other condition in which PLK1 is known to play a role, or a disease state that is associated with elevated activity or expression of PLK1. For example, a "PLK1-mediated condition" may be relieved by inhibiting PLK1 activity. Such conditions include various cancers, including bladder, thyroid, ovarian, pancreatic, breast, endometrial, prostate, colorectal, lung (e.g. non small cell lung cancer), head and neck, gastric, oropharyngeal, and esophageal cancers, glioma, glioblastoma, papillary carcinoma, hepatoma, melanoma, lymphomas (e.g. non-Hodgkins lymphoma, Hodgkin's lymphoma), leukemias (e.g. chronic myeloid leukemia, acute myeloid leukemia), advanced metastatic cancers, and advanced solid tumors.

The term "PLK2-mediated condition", "polo-like kinase 2 mediated disorder" or any other variation thereof, as used herein means any disease or other condition in which PLK2 is known to play a role, or a disease state that is associated with elevated activity or expression of PLK2. For example, a "PLK2-mediated condition" may be relieved by inhibiting PLK2 activity. Such conditions include certain neurodegenerative diseases, such as dementias with Lewy bodies (DLB) or Lewy body diseases (LBDs), such as Parkinson's disease (PD), diffuse Lewy body disease (DLBD), Lewy body variant of Alzheimer's disease (LBV) and Alzheimer's disease (AD), as well as any syndrome identified as multiple system atrophy (MSA).

The term "neurodegenerative diseases" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease, Parkinson's disease, amyotrophic lateral sclerosis (ALS), Down syndrome, dementia, multi-infarct dementia, mild cognitive impairment (MCI), epilepsy, seizures, Huntington's disease, neurodegeneration induced by viral infection (e.g. AIDS, encephalopathies), traumatic brain injuries, as well as ischemia and stroke.

The term "neurological disorder" refers to any undesirable condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilepticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any undesirable condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

Compositions

Certain 2-aryl- or 2-heteroarylpteridinones (e.g., 2-(imidazo)pteridinones) and certain 7-aryl- or 7-heteroaryl dihydropyrido[4,3-b]pyrazinones, e.g. compounds as described herein within the scope of Formula (I), are potent inhibitors of PLK. In addition those compounds exhibit properties conductive to good CNS exposure. Compared to known PLK inhibitors, compounds as described herein are characterized by one or more of the following properties: (i) reduced affinity for the P-glycoprotein (In one example, the compounds exhibit essentially no binding affinity/are no substrate for the P-glycoprotein);
(ii) relatively low molecular weight;
(iii) reduced number of H-bond donors (In one example, the compounds do not incorporate an H-bond donor group);
(iv) reduced total polar surface area (TPSA);
(v) isoform selectivity favoring PLK2 over PLK1; and
(vi) improved solubility.

Furthermore, certain compounds as described herein are characterized by relatively high brain to plasma ratios and good brain exposure as indicated by in vivo experimental results (see, e.g., Example B). The structure of the current PLK inhibitors provides compounds with good CNS exposure properties and isoform selectivity favoring PLK2 over PLK1.

Exemplary compounds as described herein, e.g. compounds of Formula (I), and their in vitro biological activities are listed in the table of Example A.

In Vitro Activities

Certain compounds as described herein, e.g. compounds of Formula (I), exhibit various in vitro biological activities (see, e.g., Example A), such as activity against polo-like kinases (PLKs). In vitro assays for the determination of PLK activities are known in the art and exemplary assay formats are described herein (see e.g., Example A). Many compounds as described herein, e.g. compounds of Formula (I), are especially active against PLK2, but may also inhibit PLK1 and PLK3.

In one example, the compounds as described herein, e.g. compounds of Formula (I), are inhibitors of PLK2 with an $IC_{50}$ of less than about 50 µM, less than about 40 µM, less than about 30 µM, less than about 20 µM or less than about 10 µM. In another example, the compounds of Formula (I) exhibit inhibitory activity against PLK2 with an $IC_{50}$ of less than about 9 µM, less than about 8 µM, less than about 7 µM, less than about 6 µM, less than about 5 µM, less than about 4 µM, less than about 3 µM, less than about 2 µM, or less than about 1 µM. In yet another example, the compounds of Formula (I) exhibit inhibitory activity against PLK2 with an $IC_{50}$ of less than about 0.9 µM, less than about 0.8 µM, less than about 0.7 µM, less than about 0.6 µM, less than about 0.5 µM, less than about 0.4 µM, less than about 0.3 µM, less than about 0.2 µM. In a particular example, the compounds of Formula (I) exhibit inhibitory activity against PLK2 with an $IC_{50}$ of less than about 0.1 µM (100 nM). In another particular example, the compounds of Formula (I) exhibit inhibitory activity against PLK2 with an $IC_{50}$ of less than about 90 nM, less than about 80 nM, less than about 70 nM, less than about 60 nM, less than about 50 nM, less than about 40 nM, less than about 30 nM or less than about 20 nM. In another particular example, the compounds of Formula (I) exhibit inhibitory activity against PLK2 with an $IC_{50}$ of less than about 10 nM.

In one example, the compounds as described herein, e.g. compounds of Formula (I), are also inhibitors of PLK1 with an $IC_{50}$ of less than about 1 µM, less than about 0.9 µM, less than about 0.8 µM, less than about 0.7 µM, less than about 0.6 µM, less than about 0.5 µM, less than about 0.4 µM, less than about 0.3 µM, less than about 0.2 µM. In a particular example, the compounds of Formula (I) exhibit inhibitory activity against PLK1 with an $IC_{50}$ of less than about 0.1 µM (100 nM). In another particular example, the compounds of Formula (I) exhibit inhibitory activity against PLK1 with an $IC_{50}$ of less than about 90 nM, less than about 80 nM, less than about 70 nM, less than about 60 nM, less than about 50 nM, less than about 40 nM, less than about 30 nM or less than about 20 nM. In another particular example, the compounds of Formula (I) exhibit inhibitory activity against PLK1 with an $IC_{50}$ of less than about 10 nM.

In one example, compounds as described herein, e.g. compounds of Formula (I), inhibit PLK2 and are selective against certain other members of the PLK family. Particularly, compounds of Formula (I) inhibit PLK2 and are selective against PLK1 or PLK3. For the purpose of this application the selectivity of the instant compounds for PLK2 over other PLKs is expressed in a ratio of $IC_{50}$ values. Those can be determined using assays known in the art or those described herein (see e.g., Example A).

In one example, compounds as described herein, e.g. compounds of Formula (I), inhibit PLK2 and are selective against other kinases. Particularly, compounds of Formula (I) inhibit PLK2 and are selective against one or more kinases selected from the group consisting of CDK-1, CDK-2, CDK-5, CLK-1, CLK-2, CLK-3, CLK-4, NEK-1, NEK-2, NEK-4, NEK-6, NEK-7, MAP4K4 and STK16. In one example, compounds are selective against other kinases, such as one or more kinases selected from the group consisting of CDK-1, CDK-2, CDK-5, CLK-1, CLK-2, CLK-3, CLK-4, NEK-1, NEK-2, NEK-4, NEK-6, NEK-7, MAP4K4 and STK16, and are selective against other PLK family members, including PLK1 or PLK3. For the purpose of this application the selectivity of the instant compounds for PLK2 over other kinases is expressed in a ratio of $IC_{50}$ values, or in some instances as a ratio of % inhibition at a given concentration of compound, such as at 10 µM, which can be determined using assays known in the art or those described herein (see e.g., Example A).

Certain compounds as described herein are characterized by the following inhibitory activities involving PLK2 and PLK1. In one example, the ratio of $IC_{50}$ (PLK2)/$IC_{50}$ (PLK1) is less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (PLK2)/$IC_{50}$ (PLK1) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (PLK2)/$IC_{50}$ (PLK1) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (PLK2)/$IC_{50}$ (PLK1) is less than about 0.0009, less than about 0.0008, less than about 0.0007, less than about 0.0006, less than about 0.0005, less than about 0.0004, less than about 0.0003, less than about 0.0002 or less than about 0.0001.

Certain compounds as described herein are characterized by the following inhibitory activities involving PLK2 and PLK3. In one example, the ratio of $IC_{50}$ (PLK2)/$IC_{50}$ (PLK3) is less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (PLK2)/$IC_{50}$ (PLK3) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (PLK2)/$IC_{50}$ (PLK3) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (PLK2)/$IC_{50}$ (PLK3) is less than about 0.0009, less than about 0.0008, less than about 0.0007, less than about 0.0006, less than about 0.0005, less than about 0.0004, less than about 0.0003, less than about 0.0002 or less than about 0.0001.

Certain compounds as described herein are characterized by the following inhibitory activities involving PLK2, PLK1 and PLK3. In one example, the ratio of $IC_{50}$ (PLK2)/$IC_{50}$ (PLK1) is less than about 1, less than about 0.9, less than about 0.8, less than about 0.7, less than about 0.6, less than about 0.5, less than about 0.4, less than about 0.3, less than about 0.2 or less than about 0.1 and the ratio of $IC_{50}$ (PLK2)/$IC_{50}$ (PLK3) is each than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (PLK2)/$IC_{50}$ (PLK1) is less than about 0.09, less than about 0.08, less than about 0.07, less than about 0.06, less than about 0.05, less than about 0.04, less than about 0.03, less than about 0.02 or less than about 0.01 and the ratio of $IC_{50}$ (PLK2)/$IC_{50}$ (PLK3) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (PLK2)/$IC_{50}$ (PLK1) is less than about 0.009, less than about 0.008, less than about 0.007, less than about 0.006, less than about 0.005, less than about 0.004, less than about 0.003, less than about 0.002 or less than about 0.001 and the ratio of $IC_{50}$ (PLK2)/$IC_{50}$ (PLK3) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (PLK2)/$IC_{50}$ (PLK1) is less than about 0.0009, less than about 0.0008, less than about 0.0007, less than about 0.0006, less than about 0.0005, less than about 0.0004, less than about 0.0003, less than about 0.0002 or less than about 0.0001 and the ratio of $IC_{50}$ (PLK2)/$IC_{50}$ (PLK3) is less than about 0.0009, less than about 0.0008, less than about 0.0007, less than about 0.0006, less than about 0.0005, less than about 0.0004, less than about 0.0003, less than about 0.0002 or less than about 0.0001.

Certain compounds as described herein are characterized by the following inhibitory activities involving PLK2 and other kinases. In one example, the ratio of $IC_{50}$ (PLK2)/$IC_{50}$ (Kinase) is less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (PLK2)/$IC_{50}$ (Kinase) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (PLK2)/$IC_{50}$ (Kinase) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (PLK2)/$IC_{50}$ (Kinase) is less than about 0.0009, less than about 0.0008, less than about 0.0007, less than about 0.0006, less than about 0.0005, less than about 0.0004, less than about 0.0003, less than about 0.0002 or less than about 0.0001. Where preferably (Kinase) is one or more kinases selected from the group consisting of CDK-1, CDK-2, CDK-5, CLK-1, CLK-2, CLK-3, CLK-4, NEK-1, NEK-2, NEK-4, NEK-6, NEK-7, MAP4K4 and STK16.

Certain compounds as described herein are characterized by the following inhibitory activities involving PLK2 and other kinases. In one example, the ratio of [% inhibition at 10 µM (Kinase)]/[% inhibition at 10 µM (PLK2)] is less than about 1, less than about 0.9, less than about 0.8, less than about 0.7, less than about 0.6, less than about 0.5, less than about 0.4, less than about 0.3, less than about 0.2 or less than about 0.1. In another example, the ratio of [% inhibition at 10 µM (Kinase)]/[% inhibition at 10 µM (PLK2)] is less than about 0.09, less than about 0.08, less than about 0.07, less than about 0.06, less than about 0.05, less than about 0.04, less than about 0.03, or less than about 0.02. Where preferably (Kinase) is one or more kinases selected from the group consisting of CDK-1, CDK-2, CDK-5, CLK-1, CLK-2, CLK-3, CLK-4, NEK-1, NEK-2, NEK-4, NEK-6, NEK-7, MAP4K4 and STK16.

In Vivo Activities

Certain compounds as described herein exhibit in vivo biological activities, such as the reduction of alpha-synuclein phosphorylation in the brain of a test animal. An in vivo model, which can be used to assess the potential in vivo beneficial effect of the compounds as described herein, is described in Example B. For example, mice dosed with the compounds as described herein show reduced levels of phosphorylated alpha-synuclein (e.g., p-Ser-129-alpha-synuclein) in their brain tissue (e.g., cerebral cortex) when compared to mice treated with vehicle.

Certain compounds as described herein are characterized by the following in vivo biological activities involving the concentration of p-Ser-129-alpha-synuclein and total alpha-synuclein in the brain tissue (e.g., cerebral cortex) of a test animal (e.g., rodent, such as mice, rat, rabbit and the like). In one example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 1%, at least about 2%, at least about 3%, at least about 4%, at least about 5%, at least about 6%, at least about 7%, at least about 8%, at least about 9% or at least about 10% relative to the p-Ser-129-alpha-synuclein/total alpha-synuclein ratio found in the brain tissue of a comparable, untreated (vehicle treated) test animal. In another example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 11%, at least about 12%, at least about 13%, at least about 14%, at least about 15%, at least about 16%, at least about 17%, at least about 18%, at least about 19% or at least about 20% relative to the p-Ser-129- alpha-synuclein/total alpha-synuclein ratio found in brain tissue of a comparable, untreated (vehicle treated) test animal.

In yet another example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 21%, at least about 22%, at least about 23%, at least about 24%, at least about 25%, at least about 26%, at least about 27%, at least about 28%, at least about 29% or at least about 30% relative to the p-Ser-129-alpha-synuclein/total alpha-synuclein ratio found in brain tissue of a comparable, untreated (vehicle treated) test animal. In a further example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 31%, at least about 32%, at least about 33%, at least about 34%, at least about 35%, at least about 36%, at least about 37%, at least about 38%, at least about 39% or at least about 40% relative to the p-Ser-129-alpha-synuclein/total alpha-synuclein ratio found in brain tissue of a comparable, untreated (vehicle treated) test animal. In yet another example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 41%, at least about 42%, at least about 43%, at least about 44%, at least about 45%, at least about 46%, at least about 47%, at least about 48%, at least about 49% or at least about 50% relative to the p-Ser-129-alpha-synuclein/total alpha-synuclein ratio found in brain tissue of a comparable, untreated (vehicle treated) test animal. In yet another example, administration of a compound as described herein to a test animal (e.g., at a dose of about 50 mg, about 100 mg, about 200 mg or about 300 mg/kg), results in a reduction of the p-Ser-129-alpha-synuclein/total alpha-synuclein ratio in the brain tissue of the test animal by at least about 51%, at least about 52%, at least about 53%, at least about 54%, at least about 55%, at least about 56%, at least about 57%, at least about 58%, at least about 59% or at least about 60% relative to the p-Ser-129-alpha-synuclein/total alpha-synuclein ratio found in brain tissue of a comparable, untreated (vehicle treated) test animal.

Synthesis of the Compounds of the Invention

In one example, compounds as described herein, e.g. compounds of Formula (I), in which ring A is connected to the remainder of the molecule via a nitrogen atom, (represented as $A^1$), can be prepared using a procedure outlined in Scheme 1, below:

Scheme 1

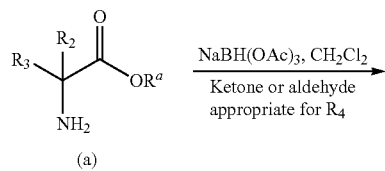

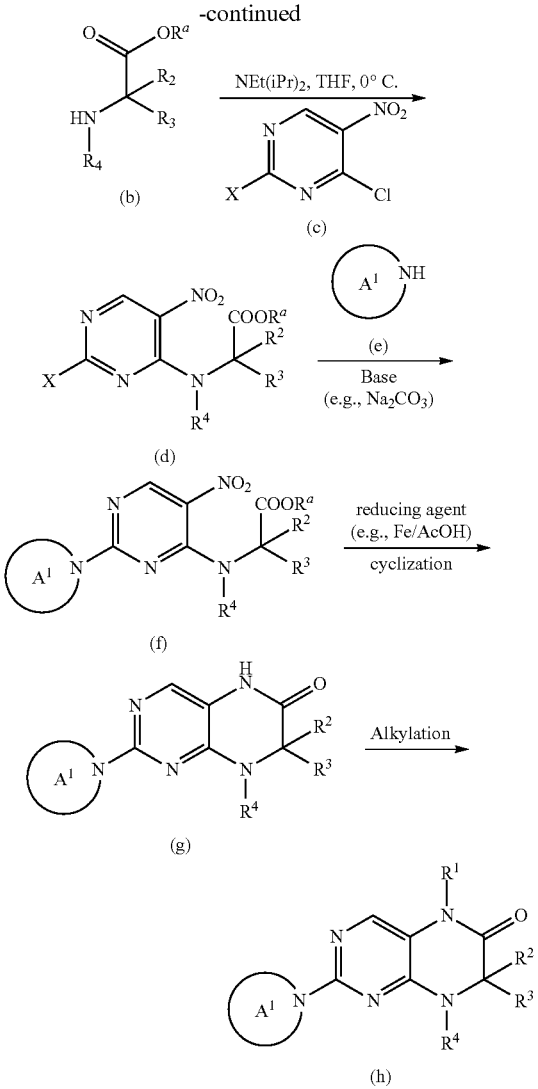

In Scheme 1, $A^1$, $R^1$, $R^2$, $R^3$ and $R^4$ are as defined herein (see, e.g., Formula (I)). In Scheme 1, X is selected from halogen (e.g., Cl, Br or I) and other leaving groups (e.g., mesylate, tosylate and the like). In Scheme 1, $R^a$ is a carboxylic acid protecting group, such as an alkyl group (e.g., methyl, ethyl or propyl).

In Scheme 1, Compound (b) can be prepared from Compound (a) by the reductive amination of amino acid ester followed by coupling with Compound (c) (2,4-dichloro-5-nitropyrimidine, or similar compound where X is a suitable leaving group) to form Compound (d), which can be accomplished by a variety of synthetic methods. To prepare N-substituted amino acid esters, such as Compound (b), from the unsubstituted amino acid Compound (a) and an aldehyde or ketone appropriate for $R^4$, sodium triacetoxy borohydride is especially suitable for reductive animations (A. F. Abdel-Magid, K. G. Carson, B. D. Harris, C. A. Maryanoff, R. D. Shah, *J. Org. Chem.*, 1996, 61, 3849-3862) under a range of temperatures (−78° C. to reflux) in alcoholic or chlorocarbon or other aprotic non-polar solvents with or without catalytic acetic acid. An alternative reagent for reductive amination is sodium cyanoborohydride (Ellen W. Baxter, Allen B. Reitz, Reductive Aminations of Carbonyl Compounds with Borohydride and Borane Reducing Agents in Organic Reactions, 2002, John Wiley and Sons). This reagent can be used effectively in alcoholic or non-polar aprotic solvents at a range of temperatures (−78° C. to reflux) often with a catalytic amount of acetic acid added to enhance the generation of the required imine intermediate in situ. N-arylation of e.g. 2,4-dichloro-5-nitropyrimidine (Compound (b) to Compound (c)) can be accomplished by a variety of methods. The Buchwald-Hartwig amination is a general method that could lead to useful amounts of compound (c) (John P. Wolfe and Stephen L. Buchwald (2004), (Palladium-Catalyzed Amination Of Aryl Halides And Aryl Triflates, *Org. Synth., Coll. Vol.* 10: 423; Frederic Paul, Joe Patt, John F. Hartwig (1994) Palladium-catalyzed formation of carbon-nitrogen bonds. Reaction intermediates and catalyst improvements in the hetero cross-coupling of aryl halides and tin amides *J. Am. Chem. Soc.* 116: 5969-5970). However, the 5-nitro group of this pyrimidine analog activates the 4-Cl towards displacement and often leads to preferential N-arylation at the 4-position over the 2-position using simple base-promoted nucelophilic substitution chemistry. Typical bases used can be alkoxide, NaH, NaOH, $K_2CO_3$, $Na_2CO_3$ or trialkylamines; temperature may range from −78° C. to reflux temperature of the solvent; solvents used may be polar or non-polar aprotic solvents included DMF, acetonitrile, chlorocarbon solvents, THF or DME.

In the reaction of Compound (d), the leaving group X (e.g., Cl) of the nitro analog (d) is replaced with the nitrogen atom of ring $A^1$ (compound (e)) to form compound (f). The nitro group of compound (f) is subsequently reduced to an amine (using a reducing agent), and the ring is closed to form the cyclic amide (g) by reaction of the formed amine with the protected carboxylic acid group (e.g., ester group). Alkylation of the amide nitrogen (e.g., using an alkylhalide) affords compound (h). Exemplary alkylating agents include a base (e.g., NaH) in combination with and alkyl-halide ($R^1$—X, such as $CH_3I$) and a base in combination with a trialkylphosphate.

Alternatively, compound (d) is first cyclized to compound (i), and alkylated to form compound (j), before coupling to the cyclic amine as outlined in Scheme 2, below:

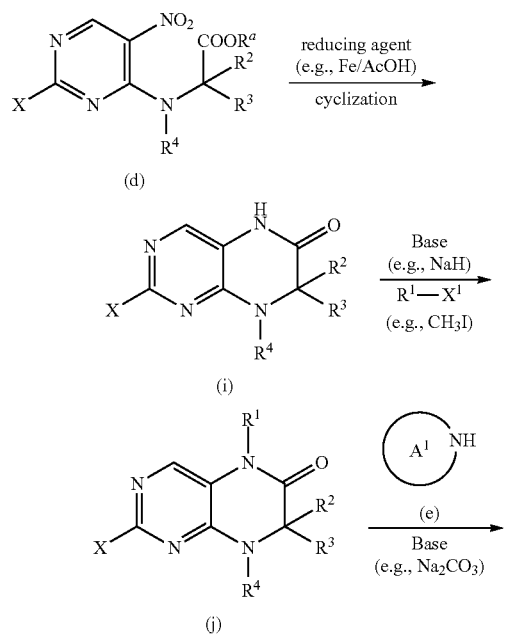

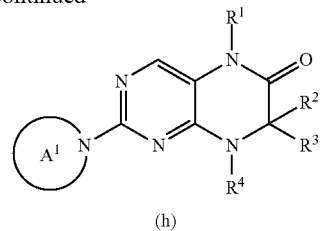

(h)

In Scheme 2, $A^1$, $R^1$, $R^2$, $R^3$ and $R^4$ are as defined herein (see, e.g., Formula (I)). In Scheme 2, X is selected from halogen (e.g., Cl, Br or I) and other leaving groups (e.g., mesylate, tosylate and the like) and $R^a$ is a carboxylic acid protecting group, such as an alkyl group (e.g., methyl, ethyl or propyl).

In another example, compounds as described herein, e.g. compounds of Formula (I), in which ring A is connected to the remainder of the molecule via a carbon atom (represented as $A^2$), can be prepared using a procedure outlined in Scheme 3, below:

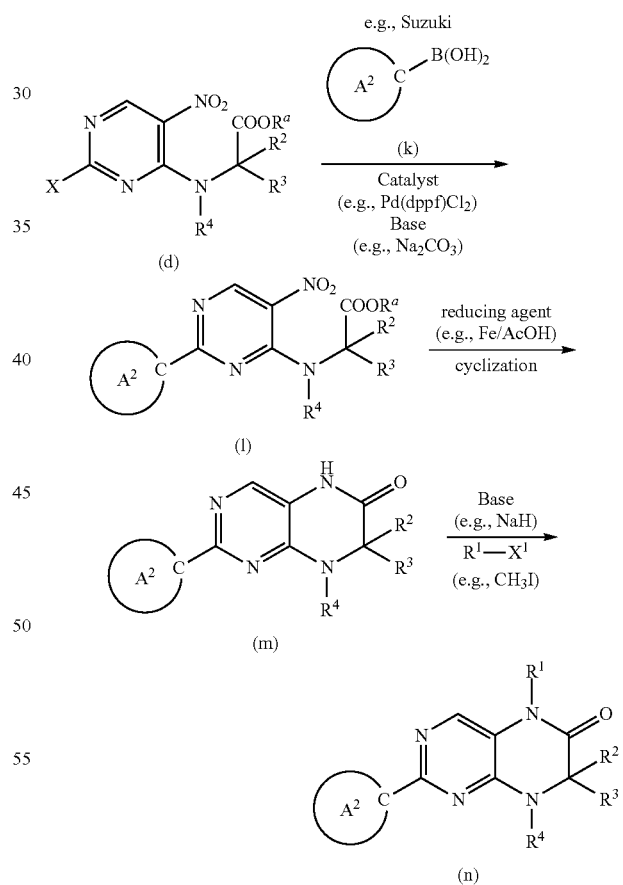

In Scheme 3, $A^2$, $R^1$, $R^2$, $R^3$ and $R^4$ are as defined herein (see, e.g., Formula (I)). In Scheme 3, X is selected from halogen (e.g., Cl, Br or I) and other leaving groups (e.g., mesylate, tosylate and the like) and $R^a$ is a carboxylic acid protecting group, such as an alkyl group (e.g., methyl, ethyl or propyl).

In Scheme 3, compound (d) is reacted with the boronic acid reagent (k) using Suzuki or Suzuki-type reaction conditions, thereby substituting the leaving group X (e.g., Cl) of the nitro analog (d) with the carbon atom of ring $A^2$ to form compound (l). The nitro group of compound (l) is subsequently reduced to an amine (using a reducing agent), and the ring is closed to form the cyclic amide (m) by reaction of the formed amine with the protected carboxylic acid group (e.g., ester group). Alkylation of the amide nitrogen affords compound (n).

Alternatively, compound (d) is first cyclized to compound (i), and alkylated to form compound (j), before reaction with the boronic acid reagent (k) as outlined in Scheme 4, below:

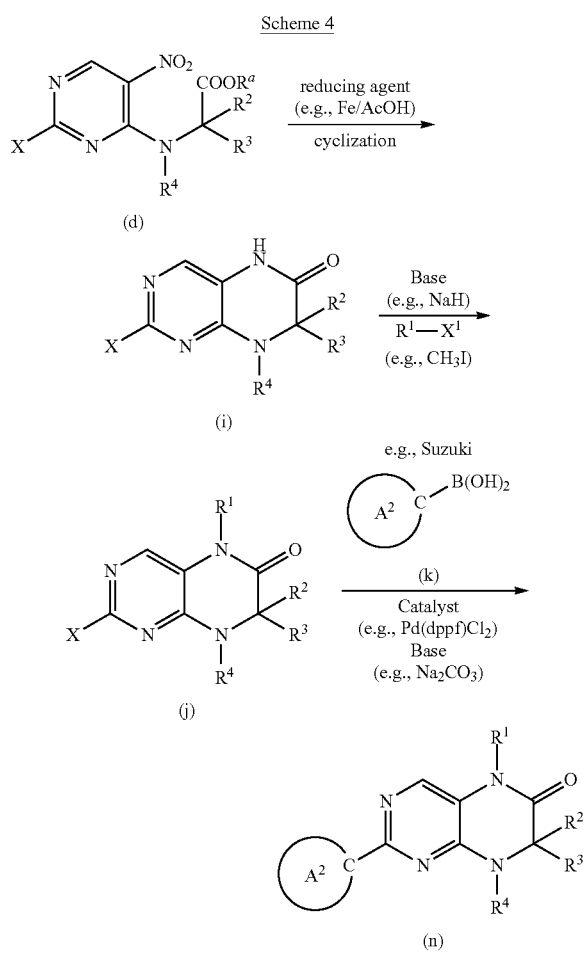

In Scheme 4, $R^1$, $R^2$, $R^3$ and $R^4$ are as defined herein (see, e.g., Formula (I), above). In Scheme 4, X is selected from halogen (e.g., Cl, Br or I) and other leaving groups (e.g., mesylate, tosylate and the like), $A^2$ is selected from aryl and heteroryl as defined herein, and $R^a$ is a carboxylic acid protecting group, such as an alkyl group (e.g., methyl, ethyl or propyl). An exemplary procedure is outlined in Example 5.

Reducing Agent

In Schemes 1 to 4, the reducing agent can be any reagent useful for the reduction of a nitro group to an amino group. Exemplary reducing agents include Fe/AcOH and Raney Ni/$H_2$.

Boronic Acid Reagents

In Schemes 3 and 4, the boronic acid reagent can be any aryl- or heteroaryl boronic acid or ester thereof within the scope of Formula I. Exemplary boronic acid reagents include:

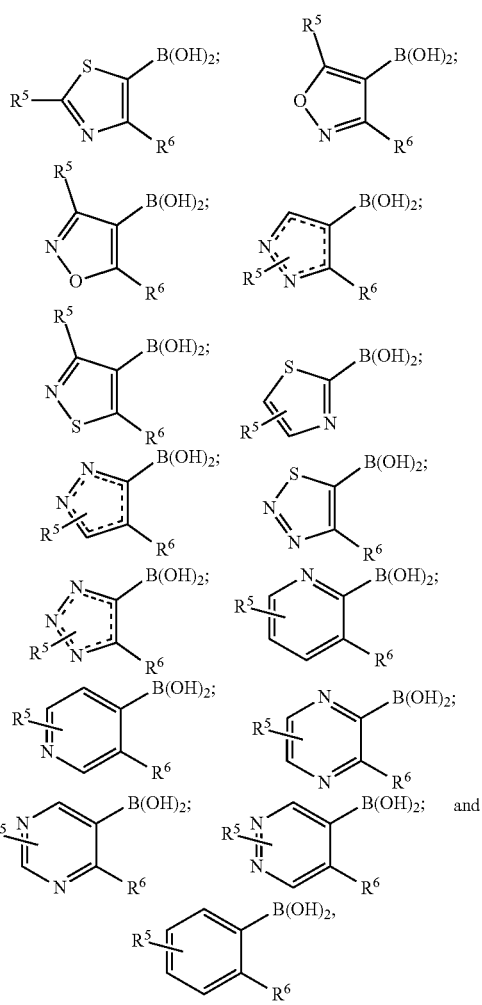

wherein $R^5$ and $R^6$ are as defined for Formula (I).

Catalyst

In Schemes 3 and 4, the catalyst can be any catalyst useful to affect C—C cross coupling reactions, such as Suzuki-type reactions. Such catalysts are known to those of skill in the art and include transition metal catalysts, such as palladium catalysts. Exemplary catalysts include Pd(OAc)$_2$ in combination with a ligand, as well as preformed Pd complexes, such as Pd(dppf)Cl$_2$ and the like.

Pharmaceutical Compositions

The invention further provides pharmaceutical compositions including a compound as described herein, e.g., those of Formulae (I) (or any embodiment thereof), and at least one pharmaceutically acceptable carrier. The term "pharmaceutically acceptable carrier" means all pharmaceutically acceptable ingredients known to those of skill in the art, which are typically considered non-active ingredients. The term "pharmaceutically acceptable carrier" includes solvents, solid or liquid diluents, vehicles, adjuvants, excipients, glidants, binders, granulating agents, dispersing agents, suspending agents, wetting agents, lubricating agents, disintegrants, solubilizers, stabilizers, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., *Handbook of Pharmaceutical Manufacturing Formulations*, Volumes 1-6, Niazi, Sarfaraz K., Taylor & Francis Group 2005, which is incorporated herein by reference in its entirety. A pharmaceutical composition of the invention may include one or more compounds of the invention in association with one or more pharmaceutically acceptable carrier and optionally other active ingredients.

The compounds of the invention may be administered orally, topically, parenterally, by inhalation or spray or rectally in dosage unit formulations containing at least one pharmaceutically acceptable carrier. The term "parenteral" as used herein includes percutaneous, subcutaneous, intravascular (e.g., intravenous), intramuscular, or intrathecal injection or infusion techniques and the like. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the invention may be administered parenterally in a sterile medium. The compound, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a scleral suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.005 mg to about 100 mg per kilogram of body weight per day are useful in the treatment of the diseases and conditions described herein (e.g., about 0.35 mg to about 7 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area one to four times a day.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Methods

Over-activation of PLK2 is believed to be an important mechanism in the formation of Lewy bodies and is thus implicated in diseases, which are characterized by the formation of Lewy bodies. Over-activation of PLK1 is implicated in a variety of cancers. Certain compounds of the invention exhibit inhibitory activity against PLKs (e.g., PLK1, PLK2 and PLK3). Kinase activity can be determined using a kinase assay, which typically employs a kinase substrate and a phosphate group donor, such as ATP (or a derivative thereof). Exemplary kinase substrates for various kinases are described in Example A. The kinase catalyzes the transfer of a phosphate group from the phosphate group donor (e.g., ATP) onto the substrate forming a covalent bond. Compounds of the invention can inhibit the activity of the kinase, slowing the above described reaction and resulting in a smaller number of phosphate groups being transferred. Hence, the current invention provides a method (i.e., an in vitro assay) that includes: (i) contacting a compound of the invention with a kinase (e.g., PLK1, PLK2, PLK3 or other PLK isoform) thereby forming a mixture. The method may further include (ii) contacting the mixture with a kinase substrate (e.g., peptide substrate) and ATP (or a derivative thereof), thereby forming an amount of phosphorylated kinase substrate. The method can further include (iii) measuring the amount of phosphorylated kinase substrate. The amount of phosphorylated substrate may be measured using a detection reagent. Suitable detection reagents can include a metal reagent, such as a lanthanoid (e.g., Eu-63), a radioactive probe, a labeled (e.g., fluorescently labelled) antibody and combinations thereof. In one example, the assay is a fluorescence resonance energy transfer (FRET) assay (e.g., TR-FRET). Examples of such assays are described in Example A. In a particular embodiment, a compound of the invention is used as a reference standard to determine the in vitro activity of other compounds in a kinase assay as described above. Thus, in another example, the compound of the invention is used in an in vitro assay for identifying candidate compounds that are capable of inhibiting PLK (e.g., PLK1, PLK2 and PLK3). In one example, in the above described methods, the kinase is PLK2.

Methods of Treatment

Compounds and compositions of the invention are useful in the treatment and/or prevention of PLK mediated disorders, including PLK1 mediated diseases such as cancers and PLK2 mediated diseases such as neurodegenerative diseases (e.g., Lewy body diseases) described herein. An in vivo model, which can be used to assess the potential in vivo beneficial effect of the compounds of the invention, is described in Example B.

In one example, the invention provides a method of treating a disease. The method includes administering to a mammalian subject (e.g., human) in need thereof a therapeutically effective amount of a compound or salt of the invention, for example those according to any one of Formulae (I) to (XVI) (or any embodiment thereof), or a composition comprising such compounds or salts. Exemplary diseases, which can be treated with the compounds and compositions of the invention include neurodegenerative diseases, and especially alpha-synucleinopathies, e.g., those associated with the formation of Lewy bodies (Lewy body diseases or those associated with the formation of glial cortical inclusions). Lewy body diseases (LBDs) are characterized by the formation of Lewy bodies (LBs) and may further be associated with degeneration of the dopaminergic system, motor alterations and cognitive impairment and include Parkinson's disease and dementia with Lewy bodies (DLB), which is a type of dementia closely allied to Parkinson's disease. It is characterized anatomically by the presence of Lewy bodies—clumps of alpha-synuclein and ubiquitin protein in neurons (e.g., detectable in post-mortem brain biopsies). Multiple system atrophy (MSA) is an exemplary disease associated with the formation of glial cortical inclusions.

Thus, compounds as described herein that are PLK2 inhibitors can be used to treat alpha-synucleinopathies, which include without limitation Lewy body diseases such as Parkinson's disease (PD), Parkinson disease with dementia (PDD), PD at risk syndrome (PARS), dementia with Lewy bodies (DLB) (i.e., diffuse Lewy body disease (DLBD), Lewy body dementia, Lewy body disease, cortical Lewy body disease or senile dementia of Lewy type), Lewy body variant of Alzheimer's disease (LBV) (i.e., diffuse Lewy body type of Alzheimer's disease), combined Parkinson's disease (PD) and Alzheimer's disease (AD), as well as diseases associated with glial cortical inclusions, such as syndromes identified as multiple system atrophy (MSA), including striatonigral degeneration, olivopontocerebellar atrophy, and Shy-Drager syndrome.

Compounds as described herein that are PLK2 inhibitors can also be used to treat disease with Parkinson-like symptoms, such as Hallervorden-Spatz syndrome (also referred to as Hallervorden-Spatz disease), fronto-temporal dementia, Sandhoff disease, progressive supranuclear palsy (PSP), and corticobasal degeneration (CBD).

In a particular example, the neurodegenerative disease is Parkinson's disease, dementia with Lewy bodies (DLB), diffuse Lewy body type of Alzheimer's disease or multiple system atrophy (MSA). Thus, in one example, the invention provides a method of treating Parkinson's disease, dementia with Lewy bodies (DLB), diffuse Lewy body type of Alzheimer's disease or multiple system atrophy (MSA), comprising administering to a mammalian subject (e.g., human) in need of such treatment, a therapeutically effective amount of a compound or composition of any one of Formula (I) (or any embodiment thereof).

Other diseases, which can be treated with the compounds and compositions of the invention also include any conditions associated with the disease, e.g., Parkinsonism, autonomic dysfunctions (e.g., Shy-Drager syndrome, postural or orthostatic hypotension), cerebellar dysfunctions, ataxia, movement disorders, cognitive deterioration, sleep disorders, hearing disorders, tremors, rigidity (e.g., joint stiffness, increased muscle tone), bradykinesia, akinesia and postural instability (failure of postural reflexes, along other disease related factors such as orthostatic hypotension or cognitive and sensory changes, which lead to impaired balance and falls).

Other neurodegenerative diseases which may be treated by the compounds of this invention include, but are not limited to Alzheimer's disease, Down syndrome, dementia, mild cognitive impairment (MCI), amyotrophic lateral sclerosis (ALS) (Lou Gehrig's Disease), traumatic brain injuries, cerebral ischemic brain damage, ischemic or hemorrhaging stroke, hereditary cerebral hemorrhage with amyloidosis of the dutch-type and cerebral amyloid angiopathy. Neurodegenerative diseases also includes epilepsy, seizures, traumatic brain injury, neurodegenerative disease caused by traumatic injury, ischemia/reperfusion in stroke, ischemic and hemorrhaging stroke, cerebral ischemias, acute hypoxia and ischemia or glutamate neurotoxicity.

The association of cancers with polo-like kinases is well known. It has been established that PLK1 over expression inhibits the function of the tumor suppressor p53 (Ando, Kiyohiro, et al., Nichidai Igaku Zasshi (2003), 62(9), 496-501). The presence of PLK1 correlates with the severity of disease and survival in patients with glioma (Duan et al., Xiandai Zhongliu Yixue (2007), 15(7), 912-913). PKL1 gene plays an important regulatory role in the proliferation of human glioma cells, and RNA interference of PLK1 gene inhibits cell proliferation possibly by suppressing the telomerase activity (Fan, Yu et al., Zhonghua Shenjingyixue Zazhi (2009), 8(1), 5-9). In hepatocellular carcinoma levels of PLK1 expression in tumors correlated with poor patient survival (Pellegrino et al., Hepatology (Hoboken, N.J., United States) (2010), 51(3), 857-868; He, Zi-Li et al., World Journal of Gastroenterology (2009), 15(33), 4177-4182). PLK1 expression appears to be tumor specific in human pancreatic carcinoma (Zhu, Yi, et al., Yixianbingxue (2007), 7(1), 9-12). PLK1 is a prognostic marker in ovarian carcinomas whose over expression correlates with shortened survival times for patients (Weichert, W. et al., British Journal of Cancer (2004), 90(4), 815-821). PLK1 is overexpressed in primary colorectal cancers (Takahashi, Takao, et al., Cancer Science (2003), 94(2), 148-152). Evidence suggest that PLK1 does not act as a cell cycle regulator but plays a constitutive role in papillary carcinoma in the early phase, and may contribute to the malignant transformation of this carcinoma (Ito, Y eta al., British Journal of Cancer (2004), 90(2), 414-418). PLK expression is a marker of proliferation and its expression closely correlates with estrogen receptor expression in human breast cancer (Wolf, Georg et al., Pathology, Research and Practice (2000), 196(11), 753-759). Patients with head and neck squamous cell cancer with moderate rather than high expression levels of PLK had longer 5-year survival rates (Knecht, Rainald et al., Cancer Research (1999), 59(12), 2794-2797). In non-small cell lung cancer, patients with moderate expression of PLK had significantly longer 5-year survival rates than patients with high levels of expression (Wolf, Georg et al., Oncogene (1997), 14(5), 543-549). Thus compounds as described herein that are PLK1 inhibitors can be used to treat oncological disorders, including solid tumors, liquid tumors, tumor metastasis, and without limitation, angiogenic disorders, ocular neovasculization, and infantile haemangiomas. Proliferative diseases which may be treated or prevented by the compounds of this invention include, but are not limited to, acute myelogenous leukemia, chronic myelogenous leukemia, metastatic melanoma, hepatocellular carcinoma, pancreatic carcinoma, brain cancer, lung cancer (e.g. non small cell lung cancer), breast cancer, bladder cancer, thyroid cancer, endometrial cancer, prostate cancer, gastric cancer, oropharyngeal cancer, esophageal cancer, head and neck cancer, ovarian carcinomas, papillary carcinomas, colorectal cancers, hepatoma, melanoma, lymphomas (e.g. non-Hodgkins lymphoma, Hodgkin's lymphoma), advanced metastatic cancers, advanced solid tumors, Karposi's sarcoma, multiple myeloma and HTLV-1 mediated tumorigenesis. In one embodiment, the cancer, is glioma, glioblastoma, hepatacellular carcinoma, pancreatic carcinoma, colorectal cancer, papillary carcinoma, ovarian carcinoma, non small cell lung cancer, breast cancer, or squamous cell carcinoma.

In another embodiment, the invention provides a method of treating a disease selected from epilepsy, seizures, Huntington's disease, multiple sclerosis, cancer, age-related macular degeneration, diabetic retinopathy and retinal neurodegeneration related to glaucoma or ocular trauma, the method comprising administering to a mammalian subject (e.g., a human subject) in need thereof a pharmaceutically effective amount of a compound or salt of Formula (I) (or an embodiment thereof) or a pharmaceutical composition comprising at least one compound of Formulae (I) (or an embodiment thereof). Other diseases, which may be treated using the compounds of the invention include alcoholism, Alexander's disease, Alper's disease, ataxia telangiectasia, Batten disease (also known as Spielmeyer-Vogt-Sjogren-Batten disease), prion diseases, bovine spongiform encephalopathy (BSE), Canavan disease, cerebral palsy, Cockayne syndrome, corticobasal degeneration, Creutzfeldt-Jakob disease, frontotemporal lobar degeneration, Huntington's disease, HIV-associated dementia, Kennedy's disease, Krabbe's disease, Lewy body dementia, neuroborreliosis, Machado-Joseph disease (e.g., spinocerebellar ataxia type 3), multiple system atrophy, multiple sclerosis, narcolepsy, Niemann Pick disease, Pelizaeus-Merzbacher disease, Pick's disease, primary lateral sclerosis, progressive supranuclear palsy, Refsum's disease, Sandhoffs disease, Schilder's disease, subacute combined degeneration of spinal cord secondary to pernicious anaemia, spinocerebellar ataxia (multiple types with varying characteristics), spinal muscular atrophy, Steele-Richardson-Olszewski disease and tabes dorsalis.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis and graft versus host disease (GVHD). The compounds and compositions of the invention are also useful to treat pathologic immune responses such as that caused by T cell activation and thrombin-induced platelet aggregation.

Additional specific conditions or diseases that can be treated with the compounds or compositions of the invention include, without limitation, myocardial ischemia, ischemia/reperfusion in heart attacks, organ hypoxia, vascular hyperplasia, cardiac and renal reperfusion injury, thrombosis, cardiac hypertrophy, hepatic ischemia, liver disease, congestive heart failure, thrombin induced platelet aggregation, endotoxemia and/or toxic shock syndrome, and conditions associated with prostaglandin endoperoxidase synthase-2.

Other specific conditions or diseases that can be treated with the compounds or compositions of the invention include, without limitation, acute pancreatitis, chronic pancreatitis, asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, diabetes, thrombocytopenia, atopic dermatitis, chronic active hepatitis, myasthenia gravis, multiple sclerosis, inflammatory bowel disease, ulcerative colitis, Crohn's disease, psoriasis, graft versus host disease (GVHD), inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic beta-cell disease; diseases characterized by massive neutrophil infiltration, rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder.

In addition, PLK inhibitors of the instant invention may be capable of inhibiting the expression of inducible pro-inflammatory proteins. Therefore, other "PLK-mediated conditions" which may be treated by the compounds of this invention include edema, analgesia, fever and pain, such as neuromuscular pain, migrains, cancer pain, dental pain and arthritis pain.

In addition to the compounds of this invention, pharmaceutically acceptable derivatives or prodrugs of the compounds of this invention may also be employed in compositions to treat or prevent the above-identified disorders.

The disclosures in this document of all articles and references, including patents, are incorporated herein by reference in their entirety.

The invention is illustrated further by the following examples, which are not to be construed as limiting the invention in scope or spirit to the specific procedures described in them. Analogous structures and alternative synthetic routes within the scope of the invention will be apparent to those skilled in the art.

EXAMPLES

General

Reagents and solvents obtained from commercial suppliers were used without further purification unless otherwise stated. Thin layer chromatography was performed on pre-coated 0.25 mm silica gel plates (E. Merck, silica gel 60, $F_{254}$). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. $^1$H and $^{13}$C NMR spectra were recorded at 300 or 400 MHz and 75 MHz, respectively, on a Varian Gemini or Bruker Avance spectrometer. Chemical shifts are reported in parts per million (ppm) downfield relative to tetramethylsilane (TMS) or to proton resonances resulting from incomplete deuteration of the NMR solvent (δ scale). Mass spectra (LCMS) were recorded on an Agilent series 1100 mass spectrometer connected to an Agilent series 1100 HPLC.

In several instances the synthetic examples give a racemic mixture of stereoisomers, which are readily separated by chiral HPLC. The absolute configuration of such compounds was typically assigned based on which was the more active compound against PLK2, consistent with the configuration of several analogs and their known configuration from x-ray co-crystal structures.

LCMS was performed on an Agilent 1100 Series HPLC with a Series 1100 MSD with electrospray ionization using a Phenomenex Luna C18 4.6 mm i.d.×30 mm length, 3μ particle size column. Compound purity was typically determined by HPLC/MS analysis using a variety of analytical methods. Exemplary HPLC methods used in the examples below are as follows:

Analytical Method A: The initial solvent composition was 20% $CH_3CN$ with 0.1% Trifluoroacetic Acid (TFA) and water with 0.1% TFA which ramped to 70% $CH_3CN$ over 10 min., held at 70% for 2 min., then ramped to 95% over 1 min. and held at 95% for 2 minutes with a flow rate of 1.5 ml/minute.

Analytical Method B: The same parameters as Method A changed so that the initial solvent composition was 50% $CH_3CN$ which ramped to 95% $CH_3CN$ over 10 minutes with a flow rate of 1.5 mL/minute.

Analytical Method C: The same parameters as Method A changed so that the initial solvent composition was 20% $CH_3CN$ which ramped to 50% $CH_3CN$ over 10 minutes with a flow rate of 1.5 mL/minute.

Analytical Method D: The same parameters as Method A changed so that the initial solvent composition was 5% $CH_3CN$ which ramped to 20% $CH_3CN$ over 10 minutes with a flow rate of 1.5 mL/minute.

Analytical Method E: Solvent A-Water (0.05% TFA), Solvent B-Acetonitrile (0.05% TFA) with a gradient of 5% B to 95% B in 1.4 min, flow rate: 2.3 mL/min, column: SunFire C18, 4.6*50 mm, 3.5 um, oven temperature: 50° C.

The examples are intended to be illustrative and are not limiting or restrictive to the scope of the invention. For example, where additional compounds are prepared similarly to synthetic methods of another example, or in the same manner as another example, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. Reagents, solvents, and other terms used in the following examples may be referred to in abbreviated forms as are known to one skilled in the art, for example terms and abbreviations are used according to the following table.

| Term or abbreviation | Definition |
| --- | --- |
| AcOH or HOAc | Acetic acid |
| AcCl | Acetyl chloride |
| BINAP | 2,2'-bis(diphenylphosphino)-1,1'-binaphthyl |
| BnBr | Benzyl bromide |
| $BrNBu_4$ | Tetrabutylammonium bromide |
| $(Boc)_2O$ | di-tert-butyl dicarbonate |
| tBuOK | Potassium tert-butoxide |
| tBuOH | tert-butanol |
| tBuONO | tert-butyl nitrite |
| mCPBA | meta-Chloroperoxybenzoic acid |
| DAST | Diethylaminosulfur trifluoride |
| DBU | 1,8-dizazbicyclo[5.4.0]undec-7-ene |
| DCM | Dichloromethane ($CH_2Cl_2$) |
| DCE | 1,2-dichloroethane |
| DIB | (Diacetoxyiodo)benzene |
| DIPEA or Hunig's base or $NEt(iPr)_2$ | N,N-diisopropylethylamine |
| DMF | N,N-dimethylformamide |
| DMF-DMA or DMF•DMA | Dimethylformamide dimethylacetal |
| DMAP | 4-Dimethylaminopyridine |
| DME | Dimethyl ether |
| DMSO | Dimethyl sulfoxide |
| DPPP | 1,3-Bis(diphenylphosphino)propane |
| EDCI | 1-Ethyl-3-(3'-dimethylaminopropyl)carbodiimide hydrochloride |
| EtOAc or EA | Ethyl acetate |
| $Et_2O$ | Diethyl ether |
| $Et_2Zn$ | Diethyl Zinc |
| $Et_3N$ | Triethylamine |
| HATU | 2-(1H-7-Azabenzotriazol-1-yl)--1,1,3,3-tetramethyl uronium hexafluorophosphate Methanaminium |
| HOAt | 7-aza-N-hydroxybenzotriazole |
| HMPA | Hexamethylphosphoramide |
| KHMDS | Potassium hexamethyldisilazane |
| LDA | Lithium diisopropylamine |
| $LiBHEt_3$ | Lithium triethylborohydride |
| MPLC | ISCO CombiFlash ® medium pressure liquid chromatography system |
| MeCN | Acetonitrile |
| MeOH | Methanol |
| $Me_3PO_4$ or $(MeO)_3PO$ or $PO(MeO)_3$ | Trimethylphosphate |
| $NaBH(OAc)_3$ | Sodium triacetoxyborohydride |
| NaOAc | Sodium acetate |
| NH(OMe)Me•HCl | N,O-dimethylhydroxylammonium chloride |
| NIS | N-iodosuccinimide |
| NMP | N-methyl-2-pyrrolidone |
| $Pd(OAc)_2$ | Palladium(II) acetate |
| $Pd_2(dba)_3$ | Tris(dibenzylideneacetone)dipalladium(0) |
| $Pd(dppf)Cl_2$ | [1,1'-Bis(diphenylphosphino)ferrocene]dichloropalladium(II), complex with dichloromethane |
| $Pd(PPh_3)_2Cl_2$ | Bis (Triphenylphosphine) Palladium Chloride |

-continued

| Term or abbreviation | Definition |
| --- | --- |
| Pd(PPh₃)₄ | Tetrakis(triphenylphosphine)palladium(0) |
| PE | Petroleum Ether |
| PhMe | Toluene |
| PPA | Polyphosphoric acid |
| iPrOH | isopropanol |
| SnBu₃Cl | Tri-n-butylstannyl chloride |
| TEA | Triethylamine |
| THF | Tetrahydrofuran |
| TFA | Trifluoroacetic acid |
| TFAA | Trifluoroacetic anhydride |
| TMSCl | Trimethylsilyl chloride |
| TMSCN | Trimethylsilyl carbonitrile |

Synthesis of Intermediates (R)-Methyl 2-((2-chloro-5-nitropyrimidin-4-yl)(cyclopentyl)amino)butanoate (Intermediate A)

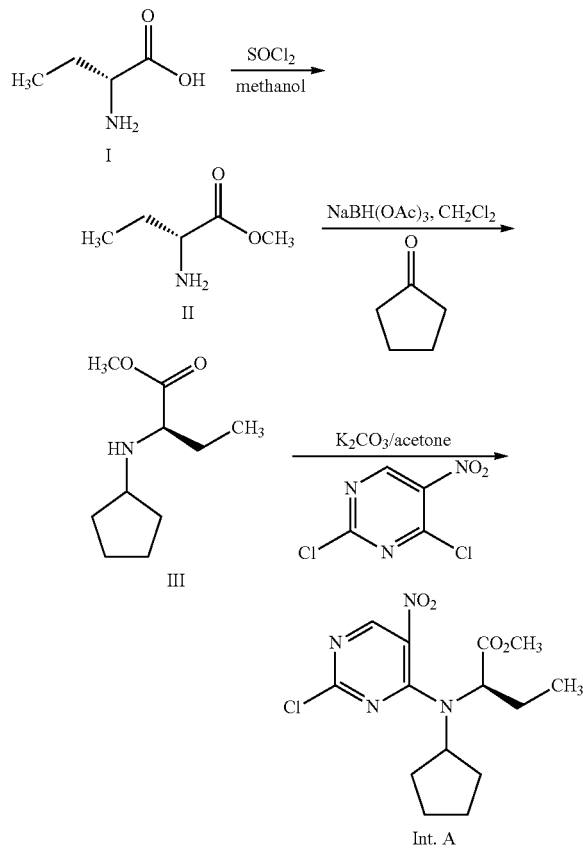

To a suspension of (R)-2-aminobutanoic acid (compound I, 5.0 g, 48 mmol) in MeOH (27 mL) at −10° C. (ice-salt bath) under $N_2$ was added dropwise with stirring $SOCl_2$ (6.4 mL, 86.4 mmol) over 90 min. The flask was fitted with a reflux condenser and heated to 70° C. for 1 hr then cooled to room temperature (rt). The solvent was removed and the residue was dried under high vacuum to afford (R)-methyl 2-aminobutanoate (compound II) as a white powder (7.5 g, 100%).

Compound II (7.4 g) and cyclopentanone (4.1 g, 49 mmol) were dissolved in 80 mL DCM. After the addition of sodium acetate (4.0 g, 4 mmol) and sodium triacetoxyborohydride (15.0 g, 71 mmol) at 0° C., the mixture was stirred for 12 hr at rt and then 50 mL saturated sodium bicarbonate solution were added. The aqueous phase was extracted with dichloromethane. The combined organic phases were washed with water, dried over $MgSO_4$ and evaporated down to give (R)-methyl 2-(cyclopentylamino)butanoate as a light yellow oil (compound III, 8.6 g, 95% yield).

Compound III (8.6 g) and potassium carbonate (6.0 g, 44 mol) were suspended in 120 mL of acetone. To the mixture was added 2,4-dichloro-5-nitropyrimidine (9.0 g) in 40 mL of acetone at 0° C. After 12 hr, another batch of 2,4-dichloro-5-nitropyrimidine (1.0 g) was added and the mixture was stirred for 4 hr. The reaction mixture was evaporated and the residue partitioned between 800 mL ethyl acetate and 600 mL water. The aqueous phase was extracted with ethyl acetate a second time. The combined organic phases were washed with water, dried over $MgSO_4$ and evaporated. The residue was purified by silica column (PE:EtOAc=10:1) to give (R)-methyl 2-((2-chloro-5-nitropyrimidin-4-yl)(cyclopentyl)amino)butanoate as a yellow solid (intermediate A, 8.0 g, 53% yield).

(R)-2-Chloro-8-cyclopentyl-7-ethyl-5-methyl-7,8-dihydropteridin-6(5H)-one (Intermediate B)

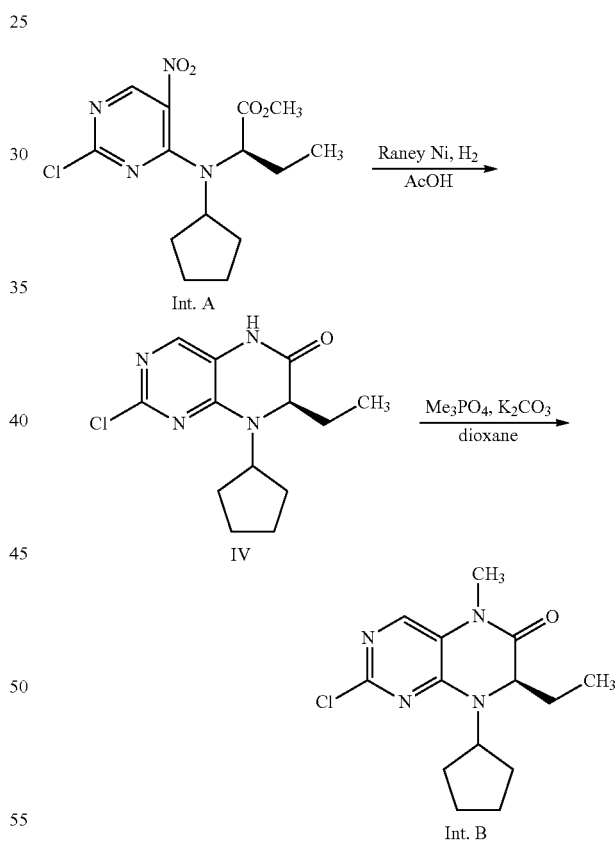

Intermediate A (1 g) was dissolved in AcOH (5 ml), Raney Ni (400 mg) was added, and the mixture was stirred under $H_2$ at 50° C. until intermediate A was consumed. The solvent was removed by evaporation under vacuum, and the residue was purified by flash silica column to give (R)-2-chloro-8-cyclopentyl-7-ethyl-7,8-dihydropteridin-6(5H)-one (compound IV, 530 mg, yield 65%).

Compound IV (260 mg, 0.93 mmol) was dissolved in dioxane (5 ml). Trimethylphosphate (650 mg, 4.6 mmol) and $K_2CO_3$ (192 mg, 1.39 mmol) were added, and the reaction mixture was stirred under N₂ at 90° C. for 6 hr until the starting material was consumed. The reaction mixture was diluted with water and extracted with EtOAc. The solvent was removed, and the residue was purified by silica gel column chromatography (PE:EtOAc=1:1) to give intermediate B as a white solid (270 mg, 86%). $^1$H NMR (CDCl₃) δ: 7.7 (s, 1H), 4.34 (m, 1H), 4.25 (m, 1H), 3.33 (s, 3H), 2.1-1.6 (m, 10H) and 0.86 ppm (t, 3H).

(R)-8-cyclopentyl-7-ethyl-5-methyl-2-(2-oxo-2-phenylethyl)-7,8-dihydropteridin-6(5H)-one (Intermediate B-1)

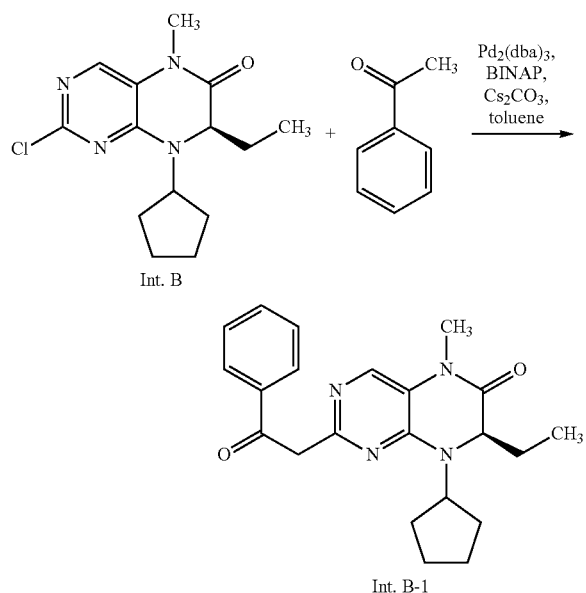

5.0 g of Intermediate B, 2.5 eq of acetophenone, 0.05 eq of Pd₂(dba)₃, 0.1 eq of BINAP and 2.0 eq of Cs₂CO₃ were suspended in a mixture of 50 mL toluene and 10 mL of water, then heated to 120° C. under N₂ for 60 hours. After cooling to rt, added 100 mL of water and washed the organic phase, dried with anhydrous Na₂SO₄, concentrated and purified by silica gel column (PE:EA=3:1) to give the pure Intermediate B-1 (1.2 g, 19%) as yellow solid.

(R)-8-cyclopentyl-7-ethyl-2-hydrazinyl-5-methyl-7,8-dihydropteridin-6(5H)-one (Intermediate B-2)

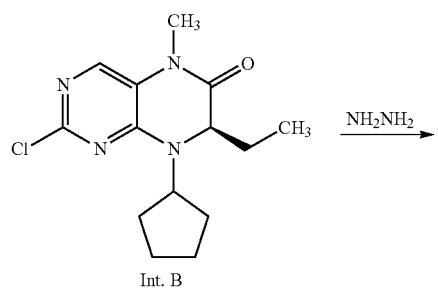

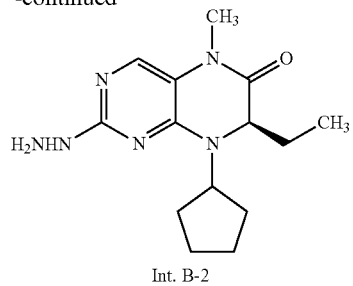

Intermediate B and hydrazine (6 equivalents) in ethanol was heated in a microwave for 1 h at 120° C. The solvent was removed to give Intermediate B-2. This material was used without further purification.

(R)-2-Chloro-7-ethyl-8-isopropyl-5-methyl-7,8-dihydropteridin-6(5H)-one (Intermediate C)

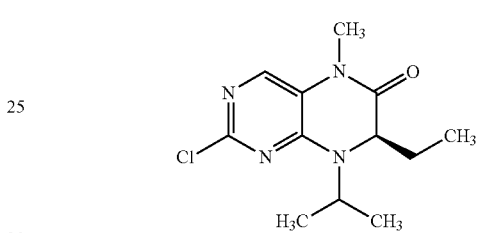

Intermediate C was prepared similarly to the synthetic methods used to prepare intermediate B with the exception that in the reductive amination, acetone was used instead of cyclopentanone. $^1$H NMR (CDCl₃) δ: 7.67 (s, 1H), 4.61 (m, 1H), 4.31 (m, 1H), 3.33 (s, 3H), 1.94 (m, 1H), 1.73 (m, 1H), 1.37 (dd, 6H) and 0.85 ppm (t, 3H).

(R)-methyl 2-((2-chloro-5-nitropyrimidin-4-yl)(isopropyl)amino)butanoate (Intermediate C-1)

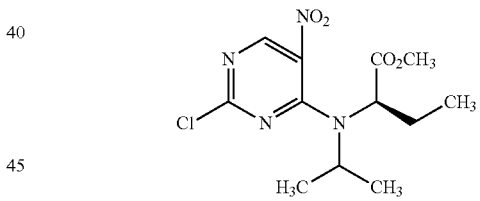

Intermediate C-1 was prepared similarly to the synthetic methods used to prepare Intermediate A with the exception that acetone was used instead of cyclopentanone in the reductive amination step.

(R)-7-ethyl-8-isopropyl-5-methyl-2-(2-oxo-2-phenylethyl)-7,8-dihydropteridin-6(5H)-one (Intermediate C-2)

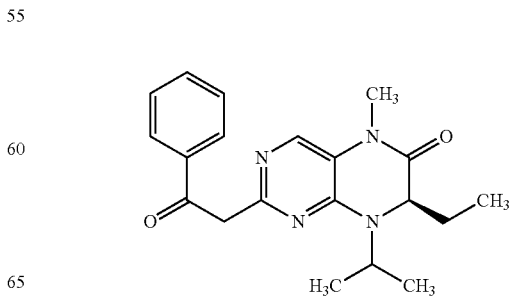

Intermediate C-2 was prepared similarly to the synthetic methods used to prepare Intermediate B-1 with the exception that Intermediate C was used instead of Intermediate B.

(R)-7-ethyl-8-isopropyl-5-methyl-2-(2-oxo-2-(4-(trifluoromethyl)phenyl)ethyl)-7,8-dihydropteridin-6(5H)-one (Intermediate C-3); (R)-7-ethyl-8-isopropyl-5-methyl-2-(2-oxo-2-(4-fluorophenyl)ethyl)-7,8-dihydropteridin-6(5H)-one (Intermediate C-4); and (R)-7-ethyl-8-isopropyl-5-methyl-2-(2-oxo-2-(thiazol-2-yl)ethyl)-7,8-dihydropteridin-6(5H)-one (Intermediate C-5)

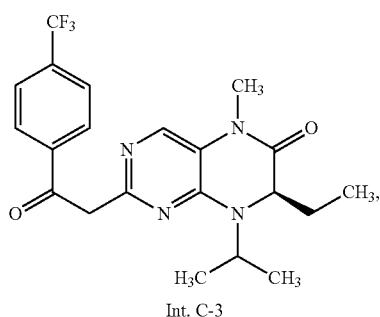

Int. C-3

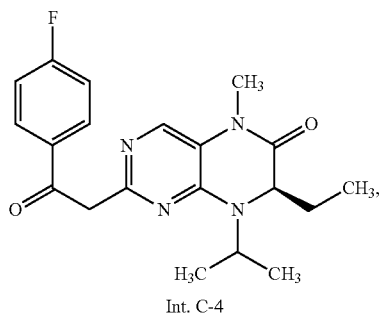

Int. C-4

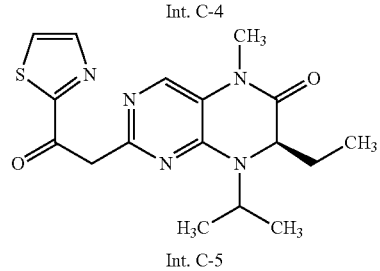

Int. C-5

Intermediates C-3, C-4 and C-5 were prepared similarly to the synthetic methods used to prepare Intermediate B-1 with the exception that Intermediate C was used instead of Intermediate B and 1-(4-(trifluoromethyl)phenyl)ethanone, 1-(4-fluorophenyl)ethanone, and 1-(thiazol-2-yl)ethanone, respectively, were used instead of acetophenone.

(R)-7-ethyl-2-hydrazinyl-8-isopropyl-5-methyl-7,8-dihydropteridin-6(5H)-one (Intermediate C-6)

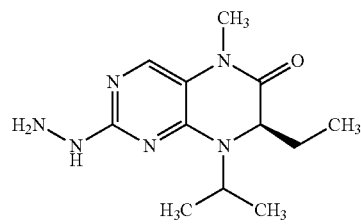 [SMILES: CC[C@@H]1C(=O)N(C)c2cnc(NN)nc2N1C(C)C]

Intermediates C-6 is prepared similarly to the synthetic methods used to prepare intermediate B-2, with Intermediate C instead of Intermediate B.

(R)-7-ethyl-8-isopropyl-5-methyl-2-(2-oxo-2-(1-((2-(trimethylsilyl)ethoxy)methyl)-1H-pyrazol-5-yl)ethyl)-7,8-dihydropteridin-6(5H)-one (Intermediate C-7)

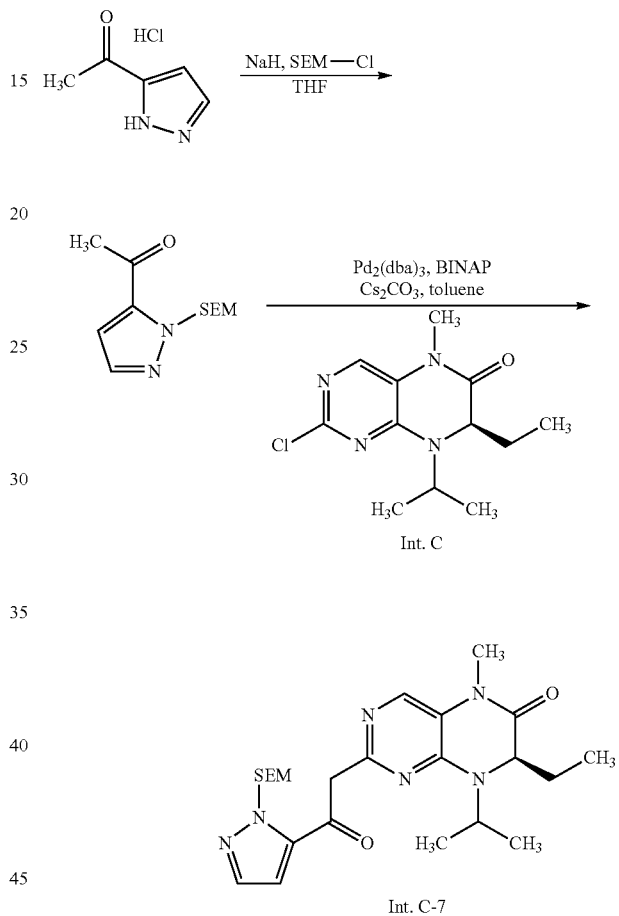

Int. C-7

To a suspension of sodium hydride (3.07 g, 76.75 mmol) in 100 mL of anhydrous THF cooled to 0° C. under $N_2$ (g) inlet was added 1-(1H-pyrazole-5-yl)ethan-1-one hydrochloride (3.09 g, 21.08 mmol). After warming to rt over 1 h, a solution of 2-(trimethylsilyl)ethoxymethyl chloride (4.5 mL, 25.43 mmol) in 100 mL of anhydrous THF was added to the reaction flask via cannulation. The reaction was quenched with water and extracted with EtOAc after 2 h. The organic phase was collected, dried with sodium sulfate, filtered and concentrated under reduced pressure followed by purification by flash chromatography (silica, 50:50 EtOAc/hexane) to give 1-(1-((2-(trimethylsilyl)ethoxy)methyl)-1H-pyrazol-5-yl)ethanone. LCMS; 241.1 m/z $(M+H)^+$.

Intermediates C-7 was prepared similarly to the synthetic methods used to prepare intermediate B-1, with Intermediate C instead of Intermediate B and with 1-(1-((2-(trimethylsilyl)ethoxy)methyl)-1H-pyrazol-5-yl)ethanone instead of acetophenone. LCMS: 473.3 m/z $(M+H)^+$.

7-ethyl-5-methyl-8-(1-methyl-1H-pyrazol-4-yl)-2-(2-oxo-2-(1-((2-(trimethylsilyl)ethoxy)methyl)-1H-pyrazol-5-yl)ethyl)-7,8-dihydropteridin-6(5H)-one (Intermediate KK-5)

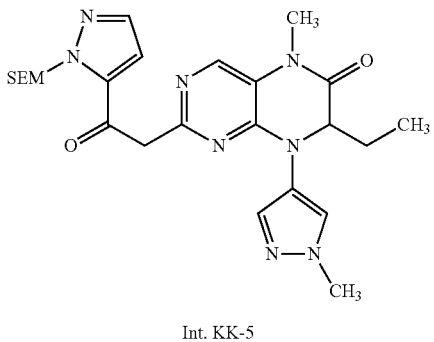 [SMILES: CCC1C(=O)N(C)c2cnc(CC(=O)c3ccnn3COCC[Si](C)(C)C)nc2N1c1cnn(C)c1]

Int. KK-5 is prepared similarly, with Intermediate KK-3 instead of Intermediate C.

(R)-2-Chloro-5-methyl-7,8,9,10-tetrahydro-5H-pyrido[2,1-h]pteridin-6(6aH)-one (Intermediate D)

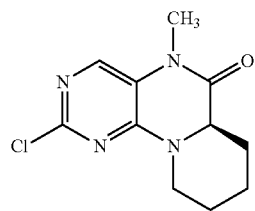 [SMILES: CN1C(=O)[C@H]2CCCCN2c2nc(Cl)ncc21]

Intermediate D was prepared in the same manner as intermediate B, using (R)-piperidine-2-carboxylic acid as the starting material instead of (R)-2-aminobutanoic acid. No reductive amination step, such as that used for the conversion of compound II to compound III, was required. Rather, methylpiperidine-2-carboxylate was reacted directly with 2,4-dichloro-5-nitropyrimidine in the same manner as is described for the conversion of compound III to intermediate A. $^1$H NMR (CDCl$_3$) δ: 7.6 (s, 1H), 4.8 (m, 1H), 4.0 (m, 1H), 3.2 (s, 3H), 2.6 (m, 1H), 2.3 (m, 1H), 1.6 (m, 1H), 1.5 (m, 4H).

(R)-2-Chloro-5-methyl-6a,7,8,9-tetrahydropyrrolo[2,1-h]pteridin-6(5H)-one (Intermediate E)

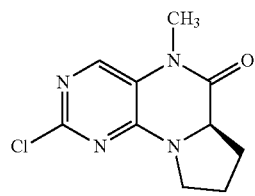 [SMILES: CN1C(=O)[C@H]2CCCN2c2nc(Cl)ncc21]

Intermediate E was prepared in the same manner as intermediate B, using (R)-pyrrolidine-2-carboxylic acid as the starting material instead of (R)-2-aminobutanoic acid. No reductive amination step, such as that used for the conversion of compound II to compound III, was required. Rather, methylpyrrolidine-2-carboxylate was reacted directly with 2,4-dichloro-5-nitropyrimidine in the same manner as is described for the conversion of compound III to intermediate A. $^1$H NMR (CDCl$_3$) δ: 7.65 (s, 1H), 4.19 (m, 1H), 3.81 (m, 1H), 3.68 (m, 1H), 3.32 (s, 3H), 2.51 (m, 1H), 2.08 (m, 3H).

(R)-methyl 1-(2-chloro-5-nitropyrimidin-4-yl)piperidine-2-carboxylate (Intermediate D-1); and (R)-methyl 1-(2-chloro-5-nitropyrimidin-4-yl)pyrrolidine-2-carboxylate (Intermediate E-1)

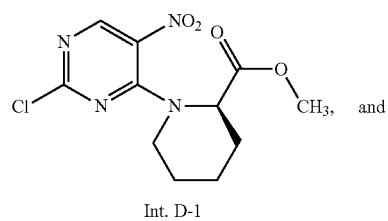

Int. D-1

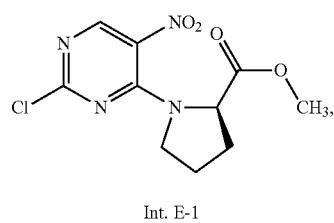

Int. E-1

Intermediates D-1 and E-1 are prepared similarly to the synthetic methods used to prepare intermediate A, with the exception that (R)-piperidine-2-carboxylic acid and (R)-pyrrolidine-2-carboxylic acid, respectively, are used instead of (R)-2-aminobutanoic acid in the first step, with no reductive amination step.

(R)-Methyl 2-((2-chloro-5-nitropyrimidin-4-yl)(cyclobutyl)amino)butanoate (Intermediate F-1) and (R)-2-chloro-8-cyclobutyl-7-ethyl-7,8-dihydropteridin-6(5H)-one (Intermediate F)

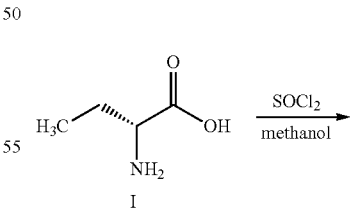

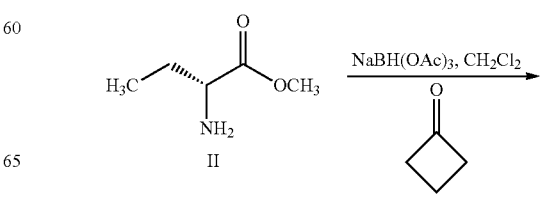

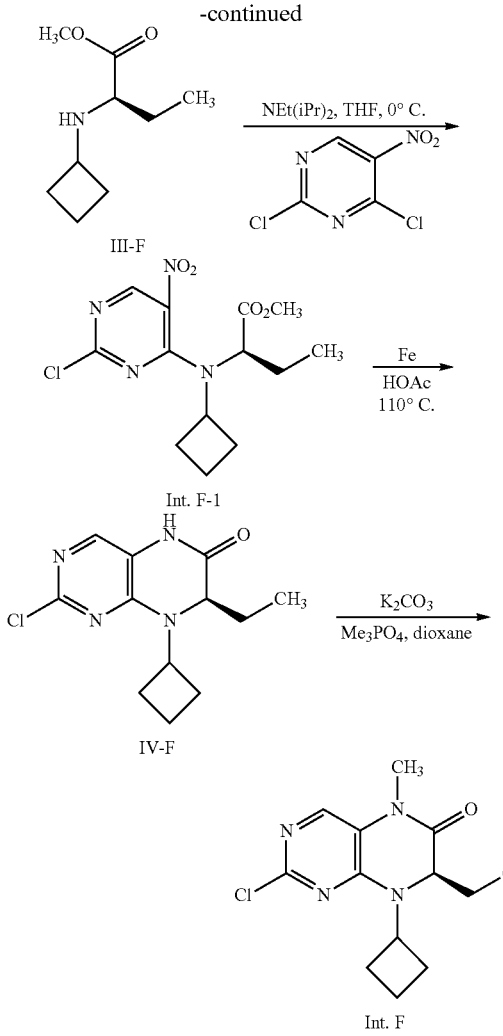

Intermediate F was prepared from compound IV-F similarly to the analogous step in the synthesis of Intermediate B. LCMS: 281.0 m/z (M+H)$^+$.

(R)-2-Chloro-7-ethyl-8-perdeuteroisopropyl-5-methyl-7,8-dihydropteridin-6(5H)-one (Intermediate G)

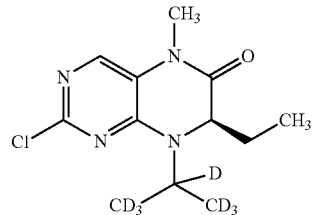

Intermediate G was prepared similarly to the synthetic methods used to prepare Intermediate F with the exception that in the reductive amination used to prepare compound III-F from compound II, (d$_6$)-acetone was used instead of cyclobutanone and sodium triacetoxyborodeuteride was used instead of sodium triacetoxyborohydride. LCMS: 276.1 m/z (M+H)$^+$.

(R)-2-Chloro-7-cyclopropyl-8-isopropyl-5-methyl-7,8-dihydropteridin-6(5H)-one (Intermediate H)

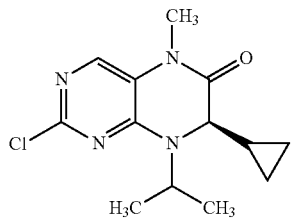 [SMILES: CC(C)N1c2nc(Cl)ncc2N(C)C(=O)[C@H]1C1CC1]

Intermediate H was prepared similarly to the synthetic methods used to prepare Intermediate F with the exception that (R)-2-cyclopropylglycine was used instead of (R)-2-aminobutanoic acid and acetone was used instead of cyclobutanone in the first step. LCMS: 281.1 m/z (M+H)$^+$.

2-Chloro-5-methyl-6a,7,9,10-tetrahydro-[1,4]oxazino[3,4-h]pteridin-6(5H)-one (Intermediate I)

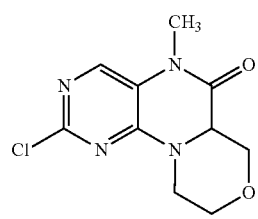 [SMILES: CN1C(=O)C2COCCN2c2nc(Cl)ncc21]

Intermediate I was prepared in the same manner as Intermediate B, using 3-morpholinecarboxylic acid as the starting material instead of (R)-2-aminobutanoic acid. No reductive amination step, such as that used for the conversion of compound II to compound III, was required. Rather, methylmor- Compound II was prepared as described in the synthesis of Intermediate A.

Compound III-F was prepared similarly to the analogous step in the synthesis of Intermediate A, using cyclobutanone instead of cyclopentanone. (LCMS: 172.1 m/z (M+H)$^+$).

To a stirring mixture of III-F and Hunig's Base (1.6 mL, 1.2 eq) in 15 mL of THF at 0° C., a solution of 2,4-dichloro-5-nitropyrimidine (1.55 g, 1.1 eq) in 3 mL of THF at 0° C. was slowly added. After 30 min, the reaction mixture was slowly quenched with brine and diluted with 25 mL of EtOAc. The aqueous phase was separated, followed by a normal aqueous workup with EtOAc. The combined organic layers were washed with brine, dried over MgSO$_4$, and evaporated. The residue was purified by silica column (hexanes:EtOAc=3:1). Yield: 1.1 g (46% in first 3 steps) of Intermediate F-1 (yellow solid). LCMS: 329.0 m/z (M+H)$^+$.

To stirring Intermediate F-1 (1.1 g, 1 eq) in 5 mL of HOAc, iron powder (1.87 g, 6 eq) was added and the reaction was heated at 100° C. for 1 h. The reaction mixture was filtered hot and the cake was further washed with HOAc. The mother liquors were concentrated under reduced pressure. The residue was taken up with 3 N NaOH and EtOAc. The layers were separated and the aqueous layer was extracted with EtOAc. The crude product mixture was further purified by MPLC to give the desired Compound IV-F (680 mg, 76% yield). LCMS: 267.1 m/z (M+H)$^+$.

pholine-3-carboxylate was reacted directly with 2,4-dichloro-5-nitropyrimidine in the same manner as is described for the conversion of compound III to Intermediate A. LCMS: 254.9 m/z (M+H)+.

(R)-Methyl 2((2-chloro-5-nitropyrimidin-4-yl)(tetrahydro-2H-pyran-4-yl)amino)butanoate (Intermediate J-1); and (R)-2-Chloro-7-ethyl-5-methyl-8-(tetrahydro-2H-pyran-4-yl)-7,8-dihydropteridin-6(5H)-one (Intermediate J)

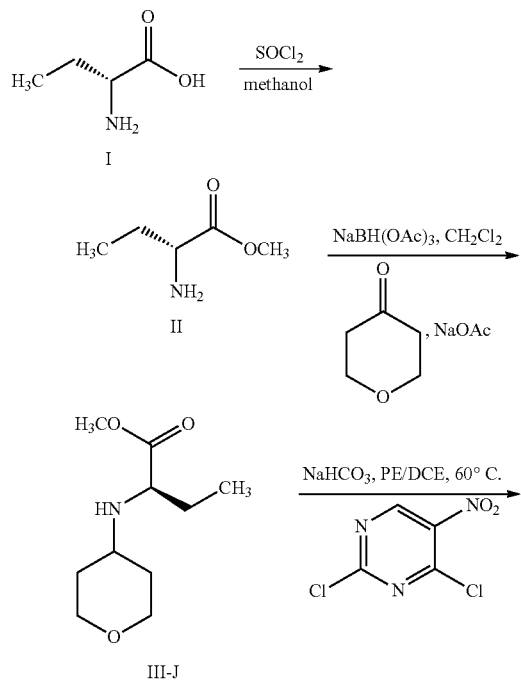

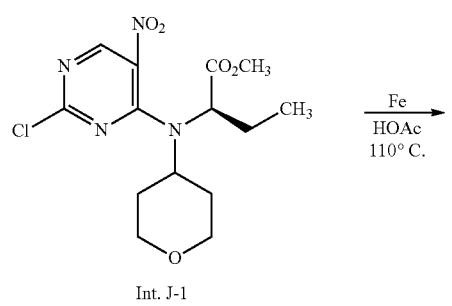

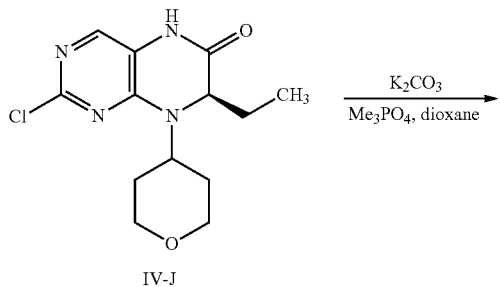

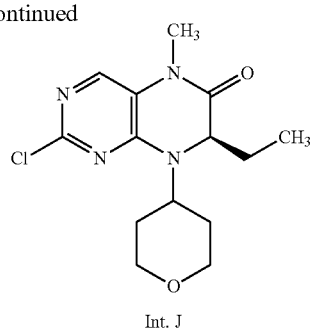

Int. J

Compound II was prepared as described in the synthesis of Intermediate A.

Compound III-J was prepared similarly to the analogous step in the synthesis of Intermediate A, using dihydro-2H-pyran-4(3H)-one instead of cyclopentanone.

To a stirring mixture of compound III-J in petroleum ether:1,2-dichloroethane (2:1, 8 mL total volume), sodium bicarbonate (3.36 g, 4 eq) and 2,4-dichloro-5-nitropyrimidine (2.33 g, 1.2 eq) were added. The resulting mixture was warmed to 60° C. until all the starting material was consumed. This reaction mixture was filtered through a plug of Celite® and the plug was washed several times with dichloromethane. This mixture was concentrated under reduced pressure and further purified via silica gel chromatography to afford Intermediate J-1.

Compound IV-J was prepared from Intermediate J-1 similarly to the analogous step in the synthesis of Intermediate F-1.

Intermediate J was synthesized from compound IV-J similarly to the analogous step in the synthesis of Intermediate F. LCMS: 311.1 m/z (M+H)+.

(S)-2-chloro-6a-ethyl-5-methyl-6a,7,8,9-tetrahydropyrrolo[2,1-h]pteridin-6(5H)-one (Intermediate K) and (S)-methyl 1-(2-chloro-5-nitropyrimidin-4-yl)-2-ethylpyrrolidine-2-carboxylate (Intermediate K-1)

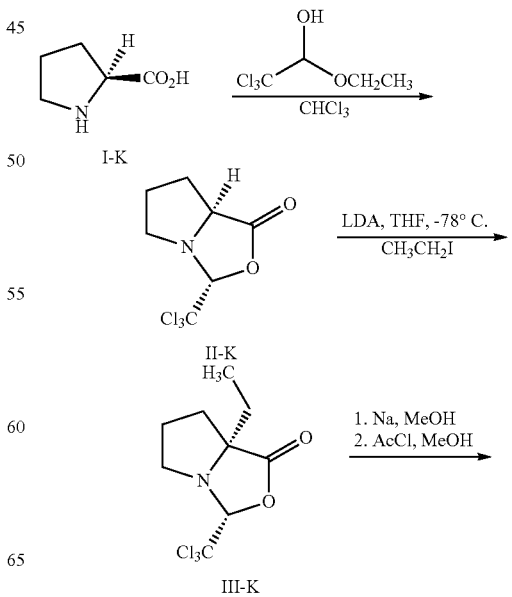

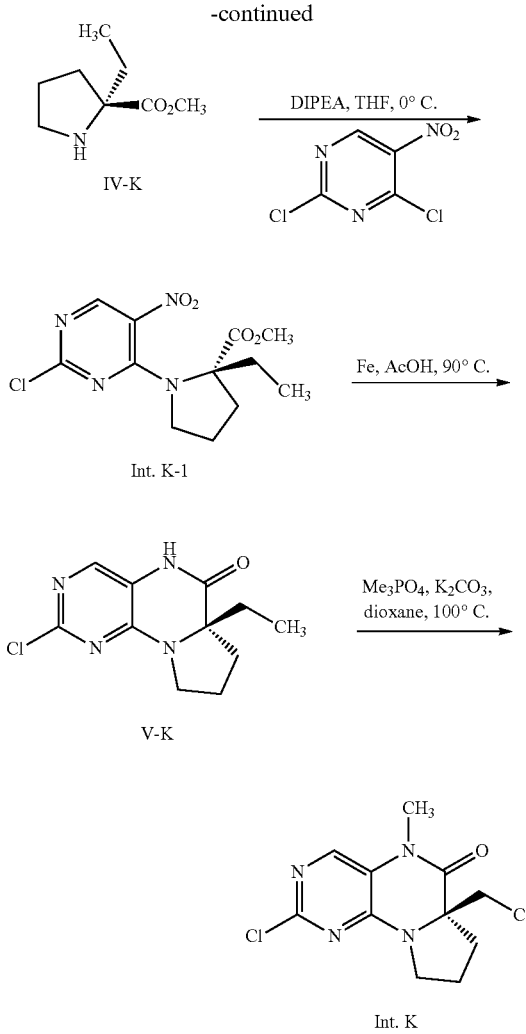

To a suspension of Compound I-K (11.55 g, 100.3 mmol) in 500 mL of chloroform, 2,2,2-trichloro-1-ethoxyethanol (23.27 g, 120.3 mmol) was added. The reaction flask was fitted with a 25-mL Dean-Stark trap and reflux condenser, and the reaction mixture was heated to reflux for 18 h. The reaction mix was cooled to rt and the volatile organics were removed under reduced pressure. The resulting residue was recrystallized from EtOH, by dissolving the residue in 30 mL of boiling EtOH, pouring the hot solution into a 125-mL Erlenmeyer flask, slowly cooling the flask to rt, and then cooling to 0° C. for 1 h. The resulting crystals were isolated by filtration and washed with cold EtOH to provide compound II-K (15.19 g, 62%).

To a solution of N,N-diisopropylamine (7.94 mL, 56.18 mmol) in 25 mL of THF at −78° C., n-butyllitium in hexanes (1.6 M, 37.62 mL, 60.19 mmol) was added. The reaction mixture was stirred for 30 minutes at −78° C., then was warmed to 0° C. for 30 minutes. The reaction was cooled to −78° C. and a solution of compound II-K (9.75 g, 40.13 mmol) in 50 mL of THF was added rapidly via addition funnel. The reaction mixture was stirred for 30 minutes at −78° C. Iodoethane (5.83 mL, 72.23 mmol) was added via syringe in a single portion. The reaction mixture was warmed to −40° C. and was stirred for 1 h. The reaction mixture was poured into a separatory funnel containing 200 mL of water and was extracted with chloroform (3×300 mL). The combined organic extracts were dried with anhydrous $Na_2SO_4$, filtered and concentrated to provide compound III-K (10.94 g, 71%).

Compound III-K (29.0 mmol, 7.90 g) was dissolved in 75 mL of MeOH and sodium (0.420 g, 18.3 mmol) was added in small pieces. The reaction mixture was stirred for 30 minutes at rt until all of the sodium dissolved. The temperature was decreased to 0° C., and acetyl chloride (40 mL, 563 mmol) was added slowly via addition funnel (~1 drop/sec). Upon complete addition of the acetyl chloride, the reaction mixture was warmed to rt and then transferred to a preheated 65° C. oil bath. The reaction mixture was stirred at 65° C. for 12 h, and then was cooled to rt. The reaction mixture was concentrated and the resulting residue was purified by flash chromatography (10% MeOH in $CH_2Cl_2$, stains bright yellow in $KMnO_4$ ($R_f$: 0.29, 10% MeOH in $CH_2Cl_2$)) to provide compound IV-K (3.28 g, 59%).

The conversion of compound IV-K to Intermediate K-1 to compound V-K to Intermediate K was similar to the conversion of compound III-F to Intermediate F-1 to compound IV-F to intermediate F as described above. Intermediate K-1 (6.16 g, 61%). Intermediate K (1.29 g, 49%); $^1$H NMR (300 MHz, $CDCl_3$) δ: 7.63 (s, 1H), 3.85 (m, 1H), 3.71 (m, 1H), 3.33 (s, 3H), 2.28 (m, 2H), 2.04 (m, 2H), 1.78 (m, 1H), 1.62 (m, 1H), 0.80 (t, J=7.5 Hz, 3H); LCMS: 267.0 m/z (M+H)$^+$.

(S)-6a-ethyl-5-methyl-2-(2-oxo-2-phenylethyl)-6a,7, 8,9-tetrahydropyrrolo[2,1-h]pteridin-6(5H)-one (Intermediate K-2)

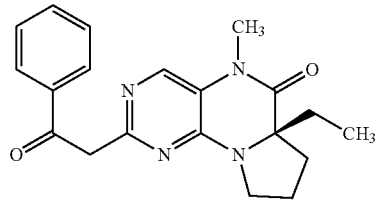 [SMILES: CC[C@@]12CCCN1c1nc(CC(=O)c3ccccc3)ncc1N(C)C2=O]

Intermediates K-2 was prepared similarly to the synthetic methods used to prepare intermediate B-1, with Intermediate K instead of Intermediate B.

(S)-6a-ethyl-5-methyl-2-(2-oxo-2-(thiazol-2-yl) ethyl)-6a,7,8,9-tetrahydropyrrolo[2,1-h]pteridin-6 (5H)-one (Intermediate K-3)

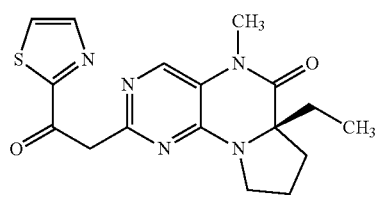 [SMILES: CC[C@@]12CCCN1c1nc(CC(=O)c3nccs3)ncc1N(C)C2=O]

Intermediates K-3 was prepared similarly to the synthetic methods used to prepare intermediate B-1, with Intermediate K instead of Intermediate B and with 1-(thiazol-2-yl)ethanone instead of acetophenone.

(S)-2-chloro-5,6a-dimethyl-6a,7,8,9-tetrahydropyrrolo[2,1-h]pteridin-6(5H)-one (Intermediate L) and (S)-methyl 1-(2-chloro-5-nitropyrimidin-4-yl)-2-methylpyrrolidine-2-carboxylate (Intermediate L-1)

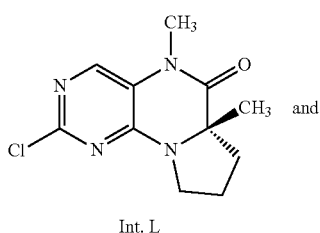

Int. L

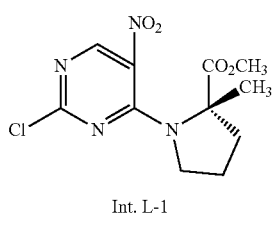

Int. L-1

Intermediates L and L-1 were prepared similarly to the synthetic methods used to prepare Intermediates K and K-1, with the exception that in the alkylation reaction used to prepare compound III-K from compound II-K iodomethane was used instead of iodoethane. Intermediate L: MS (ES): 253.0 m/z (M+H)$^+$.

(R)-tert-butyl 4-(2-chloro-7-ethyl-5-methyl-6-oxo-6,7-dihydropteridin-8(5H)-yl)piperidine-1-carboxylate (Intermediate M)

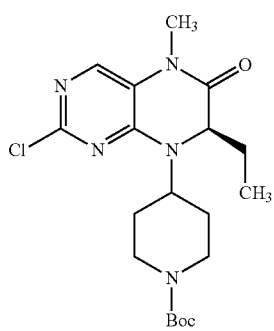 [SMILES: CC[C@@H]1C(=O)N(C)c2cnc(Cl)nc2N1C1CCN(C(=O)OC(C)(C)C)CC1]

Intermediate M was prepared similarly to the synthetic methods used to prepare Intermediate J with the exception that in the reaction used to prepare compound III-J from compound II, tert-butyl 4-oxopiperidine-1-carboxylate was used instead of dihydro-2H-pyran-4(3H)-one. LCMS: 410.1 m/z (M+H)$^+$.

(R)-2-chloro-7-ethyl-5-methyl-8-(tetrahydrofuran-3-yl)-7,8-dihydropteridin-6(5H)-one (Intermediate N) and (R)-methyl 2((2-chloro-5-nitropyrimidin-4-yl) (tetrahydrofuran-3-yl)amino)butanoate (Intermediates N-1 and N-2)

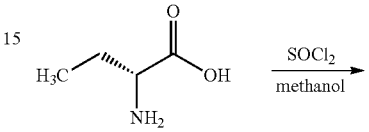

I

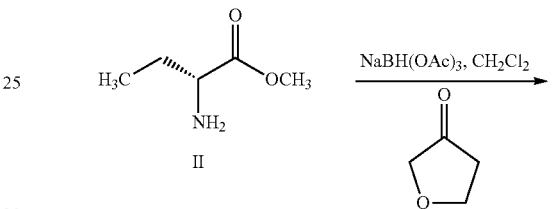

II

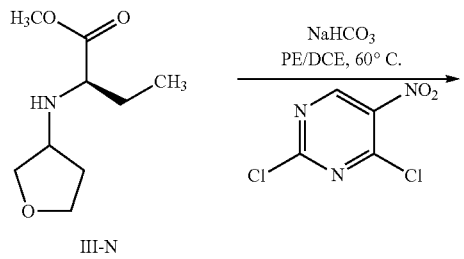

III-N

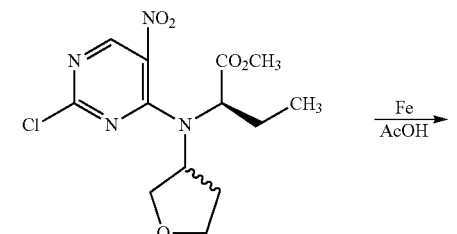

Int. N-1
(separated out Int. N-2)

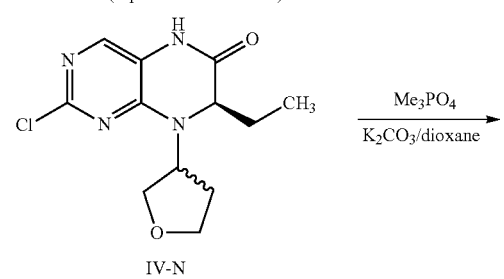

IV-N

-continued

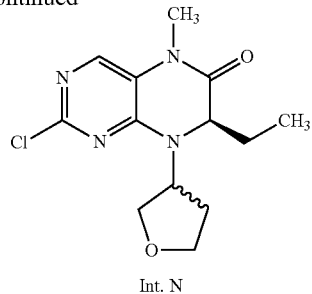

Int. N

Compound II was prepared as described in the synthesis of Intermediate A.

Compound III-N was prepared similarly to the analogous step in the synthesis of Intermediate A, using dihydrofuran-3(2H)-one instead of cyclopentanone. LCMS: 188.1 m/z (M+H)+.

Intermediates N-1 and N-2 were prepared similarly to the analogous step in the synthesis of Intermediate J-1. Intermediate N-1 and N-2 were isolated as the pure diastereomers by silica column (PE:EtOAc=7:3), where Intermediate N-1 elutes later and N-2 elutes earlier. The stereochemistry at the 7-position is known to be the R isomer, while the stereochemistry of the tetrahydrofuran ring for the two diastereomers is not known. Intermediates N-1 or N-2 can be used in the following examples, where the compounds made from Intermediate N-1 are preferred as more active inhibitors of PLK2. Intermediate N-2 (LCMS: 345.1 m/z (M+H)+); ret. Time 5.460 min (Analytical Method A) and the later eluting diastereomer from the silica gel column, Intermediate N-1 (LCMS: 345.1 m/z (M+H)+); ret. Time 5.312 min (Analytical Method A).

Compound IV-N was prepared from Intermediate N-1 similarly to the analogous step in the synthesis of Intermediate F-1. LCMS: 283.2 m/z (M+H)+.

Intermediate N was synthesized from compound IV-N similarly to the analogous step in the synthesis of Intermediate F. LCMS: 297.1 m/z (M+H)+.

(R)-2-chloro-8-cyclopropyl-7-ethyl-5-methyl-7,8-dihydropteridin-6(5H)-one (Intermediate O)

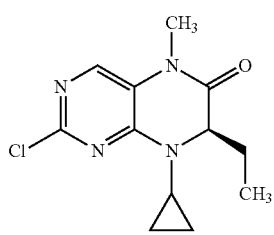 [SMILES: CC[C@@H]1C(=O)N(C)c2cnc(Cl)nc2N1C1CC1]

Intermediate O was prepared similarly to the synthetic methods used to prepare Intermediate J with the exception that in the reductive amination used to prepare compound III-F from compound II, (1-ethoxycyclopropoxy)trimethylsilane was used instead of dihydro-2H-pyran-4(3H)-one. LCMS: 267.1 m/z (M+H)+.

2-Chloro-8-isopropyl-5-methyl-7-(2,2,2-trifluoroethyl)-7,8-dihydropteridin-6(5H)-one (Intermediate P) and ethyl 2-((2-chloro-5-nitropyrimidin-4-yl)(isopropyl)amino)-4,4,4-trifluorobutanoate (Intermediate P-1)

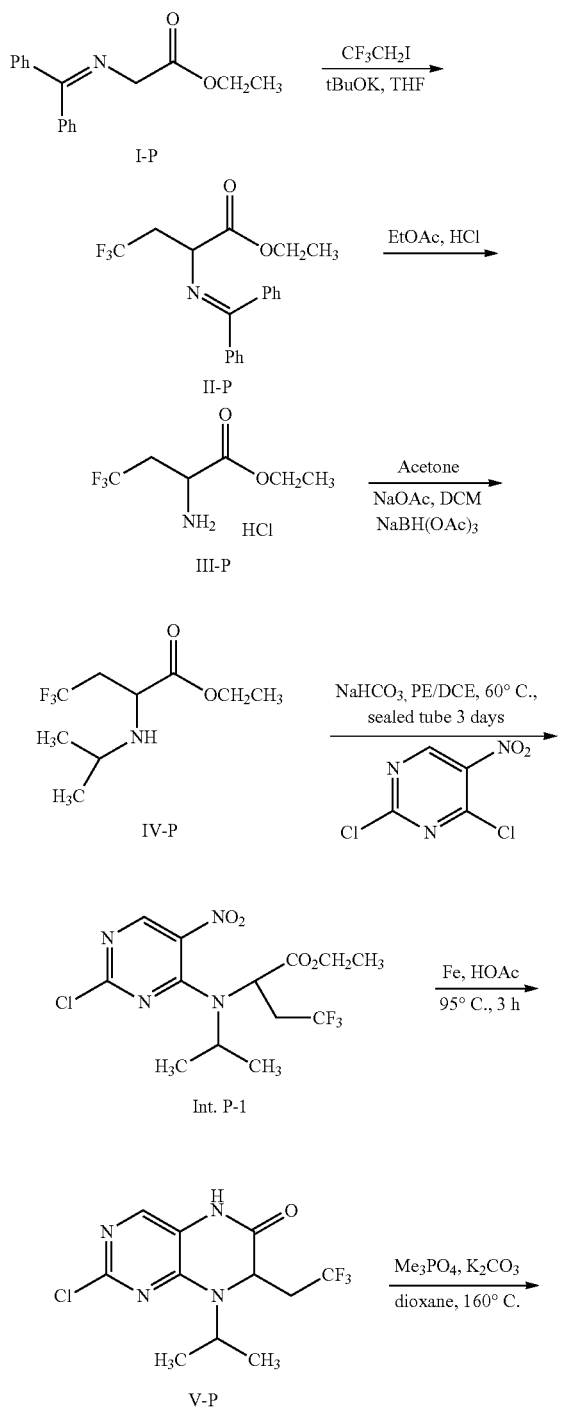

-continued

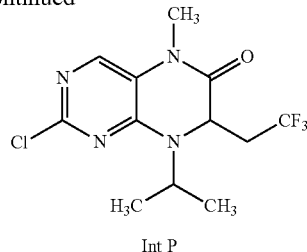

Int P t-BuOK (11.02 g, mmol) was added to 125 mL of DMF and the mixture was stirred at 0° C. for 10 min. Ethyl N-(diphenylmethylene)glycinate (compound I-P, 18 g, 67.34 mmol) was added at this temperature in portions over 5 min. After aging 30 min, 2,2,2-trifluoro-1-iodoethane (14.5 g, 69.07 mmol) was added over 5 min, maintaining the temperature at −5° C. to 5° C. The reaction mixture was stirred at 0° C. for 6 h and then allowed to warm up to rt. After quenching by $NH_4Cl$, the mixture was extracted with EtOAc. The organic phase was washed with water, brine and dried with $MgSO_4$. After evaporation of the solvent, the crude product was purified by MPLC to give a colorless oil as the desired compound II-P (16.75 g, yield 71%). $^1H$ NMR ($CDCl_3$) δ: 7.69 (d, J=3.5 Hz, 2H), 7.54-7.36 (m, 6H), 7.30-7.28 (m, 2H), 4.48 (dd, J=3.5, 8.8 Hz, 1H), 4.30-4.20 (m, 2H), 2.99-2.86 (m, 2H), 1.32 (t, J=7.2 Hz, 3H).

Compound II-P (3.4 g, 9.73 mmol) was dissolved in 30 mL of EtOAc, and 10 mL of 3N HCl was added. The mixture was stirred at rt overnight. Solvent was removed under reduced pressure and the yellow solid was triturated with EtOAc a few times to give a white solid as the pure compound III-P (1.91 g, yield 88%). $^1H$ NMR ($CD_3OD$) δ: 4.72 (dd, J=4.8, 7.1 Hz, 1H), 4.36 (q, J=7.1 Hz, 2H), 3.10-3.02 (m, 1H), 2.96-2.88 (m, 1H), 1.36 (t, J=7.1 Hz, 3H).

Compound IV-P was prepared from compound III-P by the reductive alkylation of the amino acid similarly to the analogous step in the synthesis of intermediate A, with the exception that acetone is used instead of cyclopentanone. $^1H$ NMR ($CDCl_3$) δ: 4.21 (q, J=9.5 Hz, 2H), 3.59 (t, J=8.1 Hz, 1H), 2.75 (p, J=8.2 Hz, 1H), 2.56-2.35 (m, 2H), 1.28 (t, J=9.5 Hz, 3H), 1.01 (t, J=8.6 Hz, 6H).

The conversion of compound IV-P to Intermediate P-1 to compound V-P to Intermediate P was similar to the conversion of compound III-J to Intermediate J-1 to compound IV-J to intermediate J as described above. Intermediate P-1; $^1H$ NMR ($CDCl_3$) δ: 8.67 (s, 1H), 4.31-4.23 (m, 3H), 3.65 (p, J=6.5 Hz, 1H), 3.58-3.50 (m, 1H), 2.80-2.71 (m, 1H), 1.39 (d, J=6.5 Hz, 3H), 1.35 (d, J=6.5 Hz, 3H), 1.29 (t, J=7.1 Hz, 3H). Compound V-P; $^1H$ NMR ($CDCl_3$) δ: 10.12 (s, 1H), 7.89 (s, 1H) 4.69-4.59 (m, 2H), 2.74-2.54 (m, 2H), 1.44 (d, J=6.8 Hz, 3H), 1.41 (d, J=6.8 Hz, 3H); LCMS: 309.0 m/z $(M+H)^+$. Intermediate P; $^1H$ NMR ($CDCl_3$) δ: 7.75 (s, 1H) 4.66-4.57 (m, 2H), 3.31 (s, 3H), 2.69-2.42 (m, 2H), 1.37 (d, J=6.2 Hz, 3H), 1.33 (d, J=6.2 Hz, 3H); LCMS: 323.1 m/z $(M+H)^+$.

2-Chloro-7-perdeuteroethyl-8-perdeuteroisopropyl-5-perdeuteromethyl-7,8-dihydropteridin-6(5H)-one (Intermediate Q) and perdeuteroethyl 2-((2-chloro-5-nitropyrimidin-4-yl)(perdeuteroisopropyl)amino) butanoate (Intermediate Q-1)

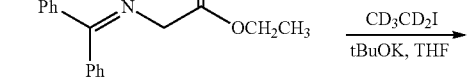

I-Q

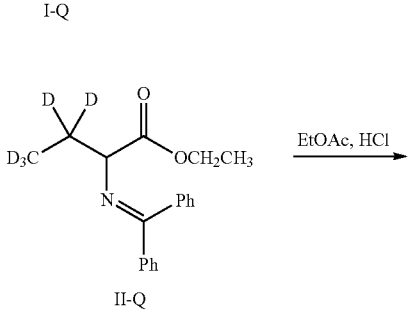

II-Q

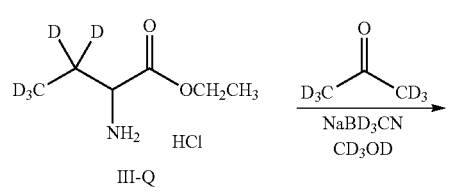

III-Q

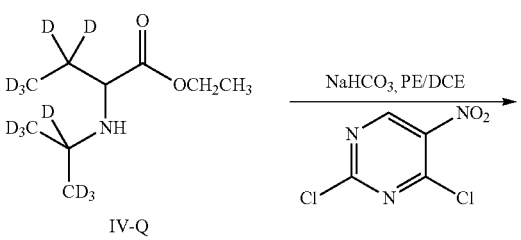

IV-Q

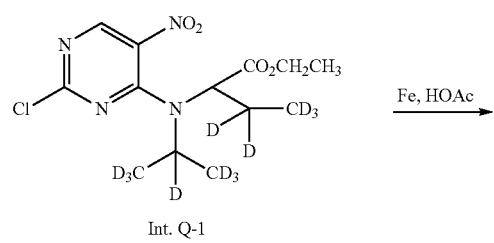

Int. Q-1

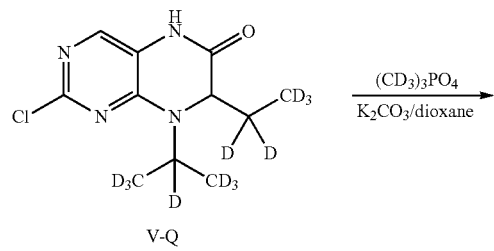

V-Q

-continued

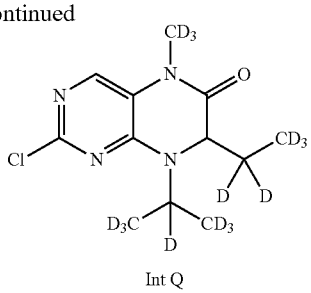

Int Q

Intermediates Q-1 and Q were prepared in the same manner as Intermediates P-1 and P with the exception that in the first step, perdeutero-iodoethane was used instead of 2,2,2-trifluoro-1-iodoethane; in the reductive alkylation of the amino acid, perdeutero-acetone was used instead of acetone and NaBD$_3$CN was used instead of sodium triacetoxyborohydride, and using CD$_3$OD as solvent; and in the last step, using (CD$_3$)$_3$PO$_4$ in the methylation step instead of trimethyl phosphate. The enantiomers may be separated by chiral HPLC. LCMS: 284.3 m/z (M+H)$^+$.

2'-chloro-8'-isopropyl-5'-methyl-5'H-spiro[cyclopropane-1,7'-pteridin]-6'(8'H)-one (Intermediate R)

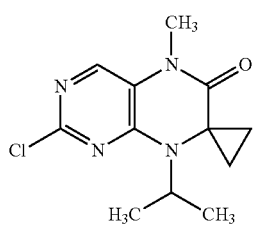 [SMILES: CC(C)N1c2nc(Cl)ncc2N(C)C(=O)C12CC2]

Intermediate R was prepared in the same manner as Intermediate B, using 1-amino-cyclopropanecarboxylic acid instead of (R)-2-aminobutanoic acid in the first step; LCMS: 267.1 m/z (M+H)$^+$.

(S)-2-Chloro-6a-perdeutoreoethyl-5-perdeuteromethyl-6a,7,8,9-tetrahydropyrrolo[2,1-h]pteridin-6 (5H)-one (Intermediate S) and (S)-methyl 1-(2-chloro-5-nitropyrimidin-4-yl)-2-perdeuteroethylpyrrolidine-2-carboxylate (Intermediate S-1)

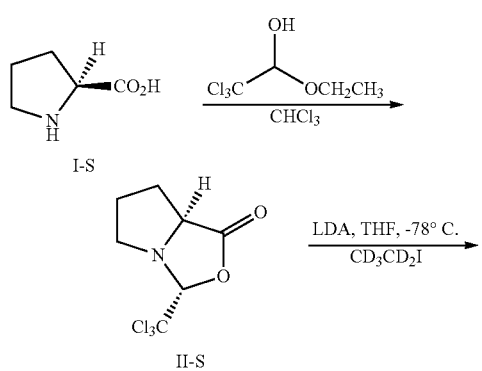

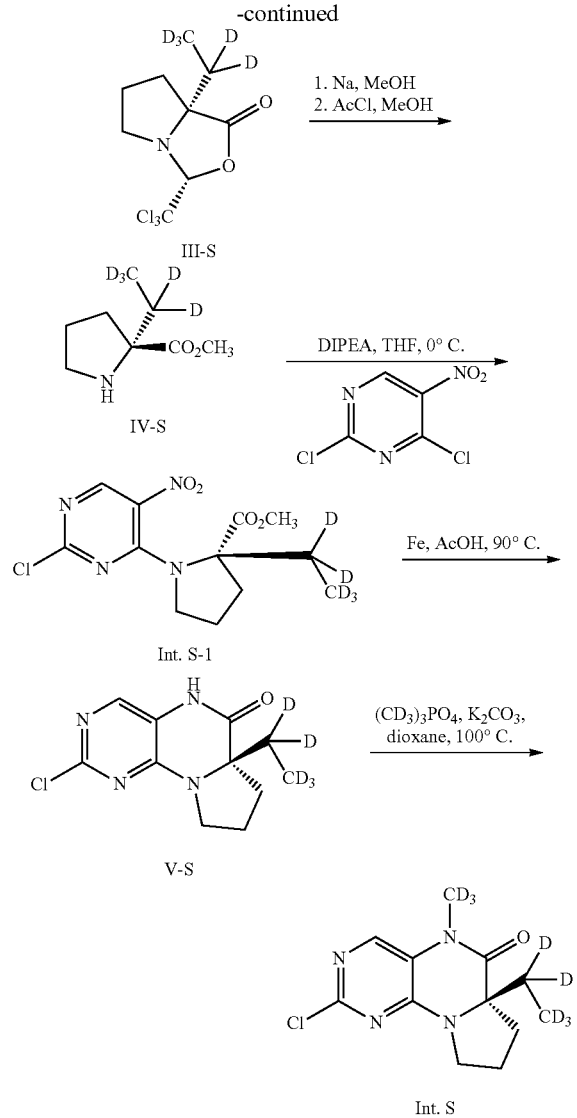

Intermediates S-1 and S were prepared in the same manner as Intermediates K-1 and K with the exception that in the second step, perdeutero-iodoethane was used instead of iodoethane; and in the last step, using (CD$_3$)$_3$PO$_4$ in the methylation step instead of trimethylphosphate. LCMS: 275.2 m/z (M+H)$^+$.

(S)-2-Chloro-6a-ethyl-5-perdeuteromethyl-6a,7,8,9-tetrahydropyrrolo[2,1-h]pteridin-6(5H)-one (Intermediate T)

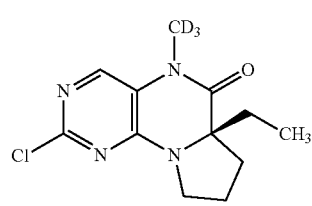 [SMILES: [2H]C([2H])([2H])N1C(=O)[C@]2(CC)CCCN2c2nc(Cl)ncc21]

Intermediate T was prepared in the same manner as Intermediate K with the exception that in the last step (CD$_3$)$_3$PO$_4$ is used instead of trimethyl phosphate.

(R)-2-Chloro-7-ethyl-5-methyl-8-(3,3,3-trifluoropropyl)-7,8-dihydropteridin-6(5H)-one (Intermediate U) and (R)-methyl 2-((2-chloro-5-nitropyrimidin-4-yl) (3,3,3-trifluoropropyl)amino)butanoate (Intermediate U-1)

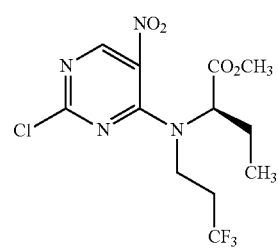

Int. U-1

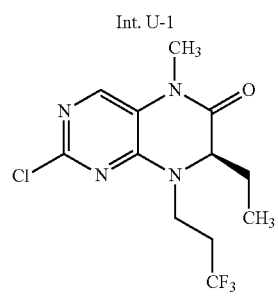

Int. U

Intermediates U-1 and U were prepared in the same manner as Intermediates N-1 and N with the exception that in the reductive alkylation of the amino acid, 3,3,3-trifluoropropanal was used instead of dihydrofuran-3(2H)-one. Intermediate U-1 (1.41 g): LCMS: 371.1 m/z (M+H)$^+$. Intermediate U (254 mg): LCMS: 323.2 m/z (M+H)$^+$.

(R)-2-Chloro-8-(3,3-difluorocyclobutyl)-7-ethyl-5-methyl-7,8-dihydropteridin-6(5H)-one (Intermediate V); (R)-Methyl 2-((3-(benzyloxy)cyclobutyl)(2-chloro-5-nitropyrimidin-4-yl)-amino)butanoate (Intermediate V-1); and (R)-8-(3-(Benzyloxy)cyclobutyl)-2-chloro-7-ethyl-5-methyl-7,8-dihydropteridin-6 (5H)-one (Intermediate V-2)

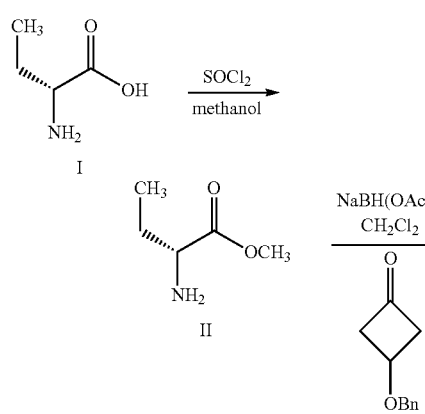

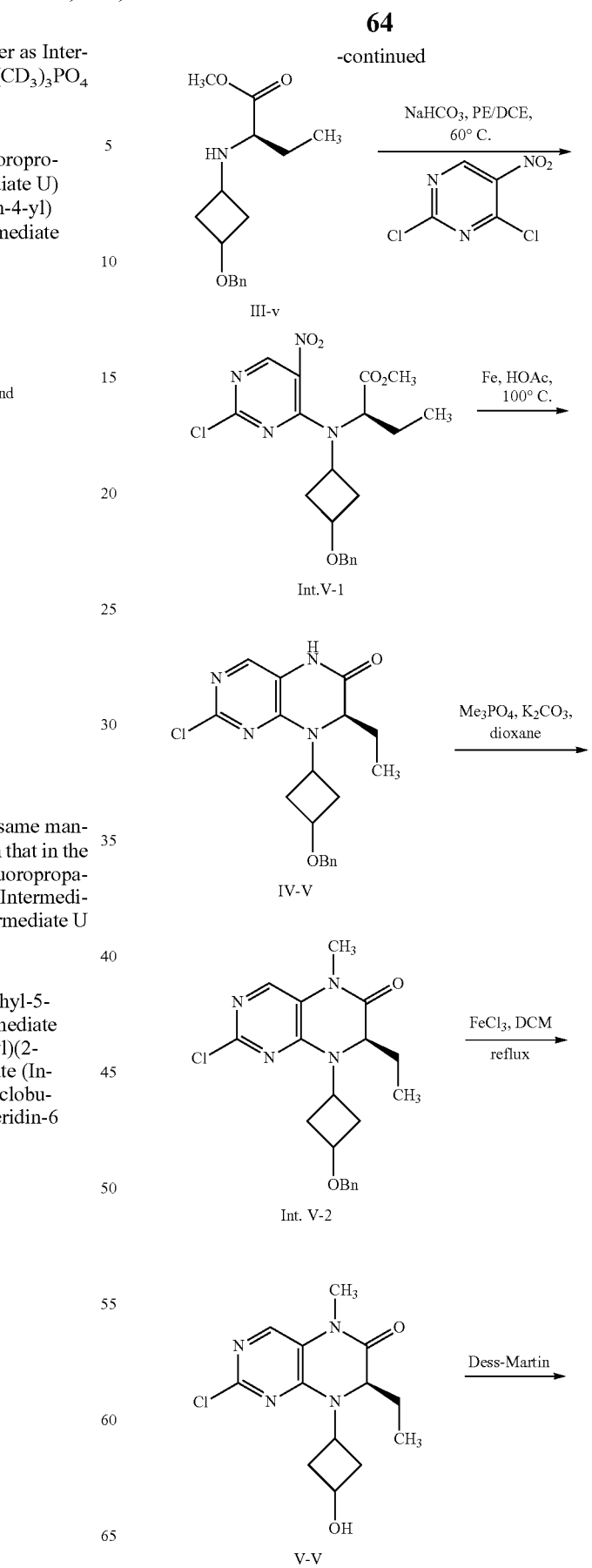

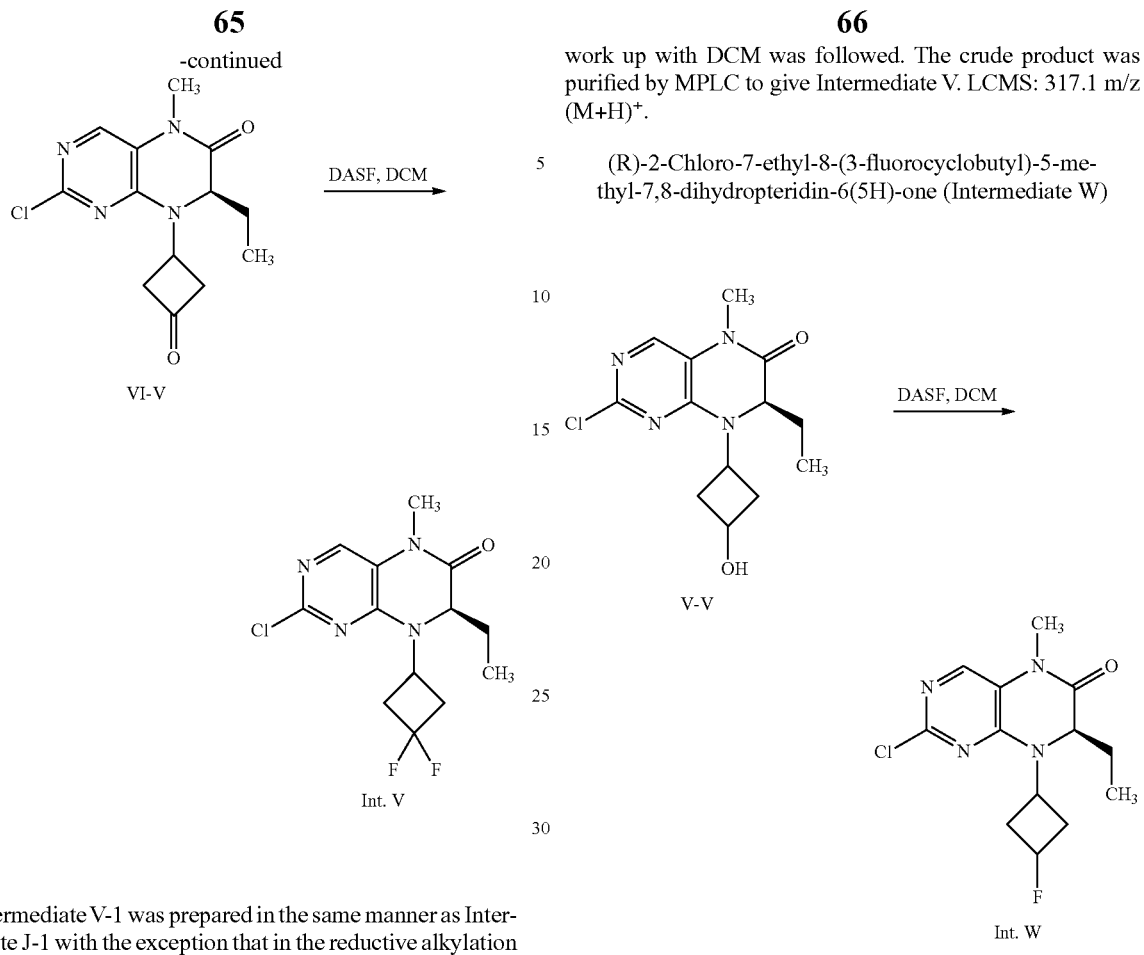

Intermediate V-1 was prepared in the same manner as Intermediate J-1 with the exception that in the reductive alkylation of the amino acid, 3-(benzyloxy)cyclobutanone was used instead of dihydro-2H-pyran-4(3H)-one.

Intermediate V-2 was prepared from Intermediate V-1 in the same manner as Intermediate F was prepared from Intermediate F-1. LCMS: 387.3 m/z (M+H)$^+$.

To a stirring mixture of Intermediate V-2 (1.2 g, 1 eq) in 4 mL of DCM at rt, FeCl$_3$ (500 mg, 10 eq) was added. The reaction mixture was heated at reflux for 1 h, then cooled to rt and slowly diluted with 20 mL of DCM and a solution of 3 N NaOH. The resulting mixture was stirred at rt for 30 min before the layers were separated. The aqueous layer was extracted with DCM (2×25 mL). The organic layers were dried over MgSO$_4$, filtered, and concentrated under reduced pressure. The crude compound V-V was further purified by MPLC. LCMS: 297.2 m/z (M+H)$^+$.

To a stirring mixture of compound V-V (300 mg, 1 eq) in 3 mL of DCM at rt, NaHCO$_3$ (509 mg, 6.0 eq) and Dess-Martin reagent (1.93 g, 4.55 eq) were added. The reaction mixture was stirred at rt until all the alcohol was consumed. The reaction mixture was slowly quenched with a saturated NaHCO$_3$ and Na$_2$S$_2$O$_3$ solution (1:1 in volume). A normal aqueous work up with DCM was followed. The crude product was further purified by MPLC to give the ketone compound VI-V. LCMS: 295.0 m/z (M+H)$^+$.

To a stirring mixture of compound VI-V (210 mg, 1 eq) in 2 mL of DCM at 0° C., DAST (465 μL, 5.0 eq) was added. The reaction mixture was slowly warmed up to rt overnight. The resulting mixture was poured over an ice cold water beaker. The mixture was allowed to stir at rt for 10 min. A normal work up with DCM was followed. The crude product was purified by MPLC to give Intermediate V. LCMS: 317.1 m/z (M+H)$^+$.

(R)-2-Chloro-7-ethyl-8-(3-fluorocyclobutyl)-5-methyl-7,8-dihydropteridin-6(5H)-one (Intermediate W)

To a stirring mixture compound V-V (isolated from synthesis of Intermediate V) (300 mg, 1 eq) in 2 mL of DCM (2 mL) at 0° C., DAST (530 μL, 4.0 eq). The reaction mixture was slowly warmed up to rt for several hours. The resulting mixture was poured over an ice-cold water beaker. The mixture was allowed to stir at rt for 10 min. A normal work up with DCM was followed. The crude product was purified by MPLC to give Intermediate W. LCMS: 299.2 m/z (M+H)$^+$.

(+/−) 2-Chloro-6a-ethyl-5-methyl-6a,7,8,9,10,11-hexahydroazepino[2,1-h]pteridin-6(5H)-one (Intermediate X)

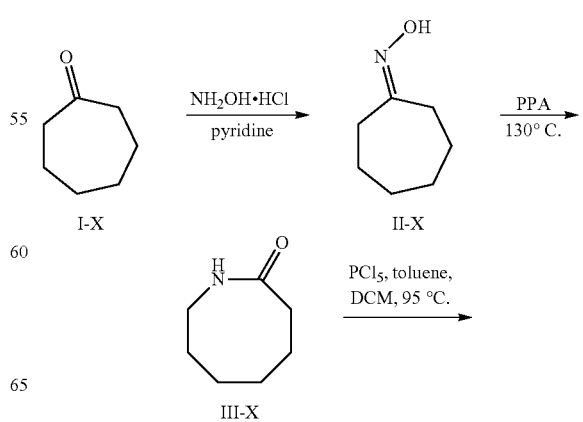

-continued

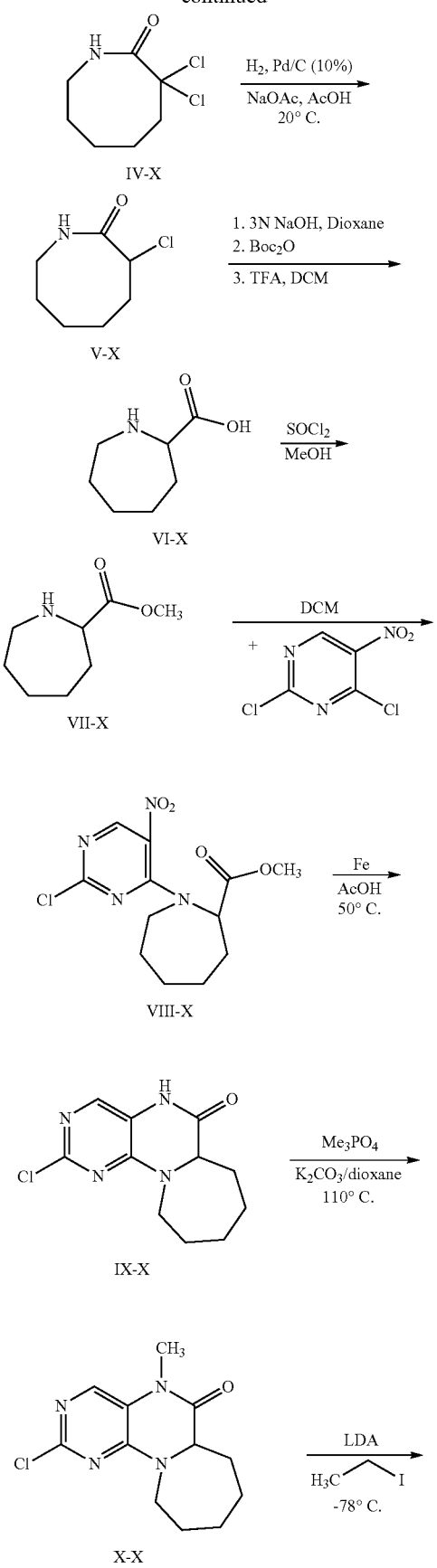

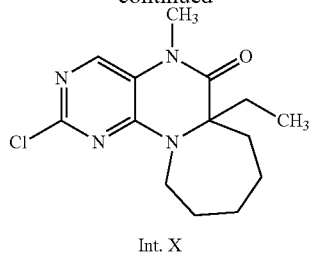

Int. X

To a solution of cycloheptanone (I-X, 1.0 eq) and pyridine (1.5 eq), NH₂OH, HCl salt (1.1 eq) was added at 0° C. After stirring for 10 min at 0° C., the mixture was allowed to warm to rt and stirred 18 h, then solvent was evaporated. The residue was washed with EtOAc, and the filtrate was evaporated to give compound II-X.

Water (6.0 eq) was added to PPA (P₂O₅ 80%, 2.6 eq), then heated to 130° C.; and compound II-X (1.0 eq) was added at such a rate that the temperature was maintained between 130-140° C. The solution was kept at 130° C. for 1 h and slowly cooled to 100° C. The mixture was then stirred with ice water, then extracted with DCM. The organic layer was dried with Na₂SO₄ and concentrated to give compound III-X.

Compound III-X (1.0 eq) in DCM was slowly added to a stirred suspension of PCl₅ (2.0 eq) in toluene. After heating under reflux for 2 h, the brown solution was concentrated. Ice was added to the residue followed by acetone, then aqueous 10% NaHCO₃ solution was added until pH=8. After stirring 16 h, the solution was extracted with DCM, and the extract was dried over Na₂SO₄, filtered, and concentrated under reduced pressure to give an orange oil, which was purified by silica column chromatography (EA/PE=1:5-1:3) to give compound IV-X.

Compound IV-X (1.0 eq) was dissolved in AcOH, 10% Pd/C (0.1 eq) and NaOAc (2.8 eq) were added and the mixture was hydrogenated at 20° C. for 18 h. The catalyst was removed by filtration and the filtrate was evaporated. The residue was neutralized with 10% Na₂CO₃ solution and extracted with DCM several times. The extract was concentrated, and the residue was crystallized from DCM/PE to give compound V-X.

A suspension of compound V-X (1.0 eq) in 3N NaOH (9.0 eq) and dioxane was refluxed for 18 h, then the solution was cooled to rt and Boc₂O (2.0 eq) was added to the mixture followed by dioxane. The reaction mixture was stirred for 4 h, then the mixture was washed with DCM to remove diketopiperazine by-product. The resulting aqueous phase was acidified with concentrated HCl and extracted with DCM. The extract was evaporated to give a colorless oil. The oil was dissolved in DCM, TFA was added and stirred at rt for 30 min. The mixture was evaporated to give an oil, which was washed with DCM/Et₂O to give compound VI-X.

To compound VI-X (1.0 eq) in methanol, SOCl₂ (2.5 eq) was added drop-wise at 0° C. The mixture was stirred at rt for 16 h, then was evaporated and the residue was diluted with DCM and washed with saturated Na₂CO₃ solution. The organic phase was then evaporated to give compound VII-X.

Compound VII-X (1.0 eq) and 2,4-dichloro-5-nitropyrimidine (1.0 eq) were dissolved in DCM, then K₂CO₃ (1.5 eq) was added. The resulting suspension was stirred at rt for 16 h. The mixture was diluted with DCM, then washed with water and brine. The combined organic phases were dried over Na₂SO₄, evaporated and purified by silica column (EtOAc/PE=1:7) to give compound VIII-X.

To compound VIII-X (1.0 eq) in AcOH, Fe (10.0 eq) was added and stirred at 50° C. for 1.5 h. The mixture was filtered and the filtrate was evaporated, the residue was dissolved in DCM, and then washed with saturated NaHCO₃. The aqueous phase was extracted with DCM. The combined organic phase was dried over Na₂SO₄, evaporated and purified by silica column chromatography (EtOAc/PE=1:3 to 1:1) to give compound IX-X.

To compound IX-X (1.0 eq) in dioxane, K₂CO₃ (3.0 eq) and Me₃PO₄ (3.0 eq) were added and this was refluxed at 110° C. for 4 h. The mixture was diluted with EtOAc and washed with water. The organic phase was dried over Na₂SO₄ and concentrated. Compound X-X was crystallized from DCM/PE.

n-BuLi (2.5 M solution in hexane, 1.5 eq) was added dropwise to a stirred solution of diisopropylamine (1.6 eq) in dry THF at −78° C. under Ar. The solution was stirred for 5 min at −78° C., then warmed to 0° C. and stirred for another 20 min. The resulting solution was added dropwise to a solution of compound X-X (1.0 eq) in dry THF at −78° C.; this was stirred for a further 40 min then MeI (3.0 eq) was added and the solution was stirred for 40 min at −78° C. Water was added, the solution was warmed to rt and extracted 3× with EtOAc. The combined organic phases were dried with solid Na₂SO₄, evaporated and purified by silica column chromatography (EtOAc:PE=1:2) to give Intermediate X. MS (ESI): 295 m/z (M+H)⁺; ¹H-NMR (CDCl₃, 500 MHz): δ: 7.57 (s, 1H), 4.64 (d, 1H, J=14 Hz), 3.34 (s, 3H), 3.08 (dd, 1H, J¹=15 Hz, J²=9 Hz), 2.98 (t, 1H, J=14 Hz), 1.94~1.83 (m, 4H), 1.70 (m, 1H), 1.61 (m, 2H), 1.36-1.24 (m, 2H), 0.76 (t, 3H, J=7.5 Hz).

2-Chloro-6a-ethyl-5-methyl-7,8,9,10-tetrahydro-5H-pyrido[2,1-h]pteridin-6(6aH)-one (Intermediate Y) and methyl 1-(2-chloro-5-nitropyrimidin-4-yl)-2-ethylpiperidine-2-carboxylate (Intermediate Y-1)

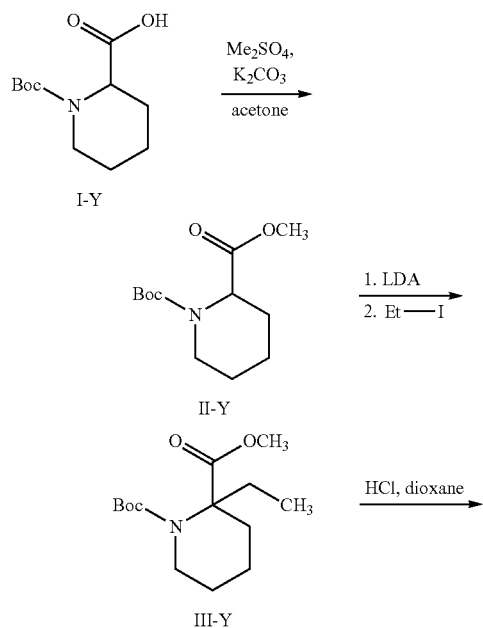

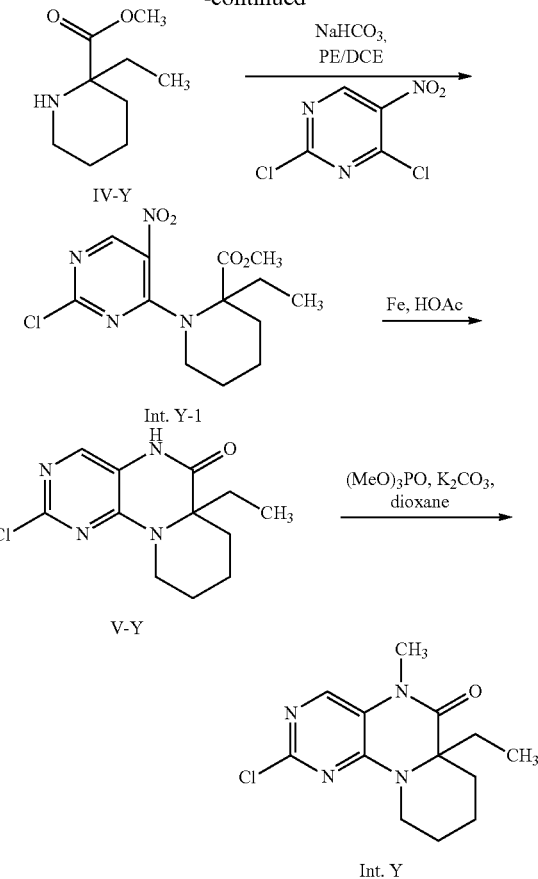

A 100 mL round bottom flask was charged with compound I-Y (5 g, 21.8 mmol), 40 mL of dry acetone, potassium carbonate (9 g, 69 mmol), and dimethylsulfate (3.8 mL, 38 mmol). A condenser was affixed, and the mixture was brought to reflux for 16 h. Upon cooling to 23° C., the reaction mixture was filtered to remove excess base, and the filtrate was concentrated under reduced pressure to give a clear oil as crude compound II-Y (2.25 g). LCMS: 266.1 m/z [M+Na], 144.1 m/z [M-Boc].

Crude compound II-Y (4.5 g, 18.5 mmol) was diluted with 6 mL of THF and slowly added at 0° C. to a preformed mixture of diisopropylamine (2.3 g, 23 mmol) and n-BuLi (10 mL of 2.3 M in THF) at 0° C. After stirring for 40 min at 0° C., a red color was observed, and ethyl iodide (2 mL, 25 mmol) was added by syringe as a neat liquid. After stirring for 0.5 h, the cooling bath was removed and the reaction slowly warmed to 23° C. over 16 h. The reaction mix was quenched by addition of saturated aqueous ammonium chloride and the biphasic mixture was extracted with EtOAc. The organic layer was rinsed with a saturated aqueous sodium bicarbonate solution, dried over sodium sulfate, and decanted before being concentrated under reduced pressure to give the desired compound III-Y. The compound was further purified by MPLC (0 to 100% EtOAc/hexane gradient) to give 3.8 g of compound III-Y.

Deprotection of compound III-Y was achieved by dissolving the pure material in 5 mL of DCM and adding 20 mL of 4N HCl in dioxane. After 1.5 h, LCMS confirmed complete formation of the amine. The reaction mix was concentrated under reduced pressure to give the HCl salt of compound IV-Y as a tan solid.

The conversion of compound IV-Y to Intermediate Y-1 to compound V-Y to Intermediate Y was similar to the conversion of compound III-J to Intermediate J-1 to compound IV-J to intermediate J as described above. Intermediate Y-1 (170 mg); compound V-Y (810 mg). Intermediate Y (700 mg); LCMS: 381.1 m/z (M+H)+; $^1$H-NMR (CDCl$_3$, 400 MHz): δ: 7.56 (s, 1H), 4.73 (dd, 1H, j=11.6, 2.9 Hz), 3.29 (s, 3H), 2.82 (dt, 1H, j=13.5, 2.8 Hz), 2.25 (m, 1H), 1.89 (sex, 1H, j=7.5 Hz), 1.75 (m, 5H), 1.45 (m, 1H), 0.73 (t, 3H, j=7.5 Hz) ppm. $^{13}$C-NMR (CDCl$_3$, 90 MHz): δ: 166.9, 154.2, 152.4, 120.2, 64.4, 38.8, 33.3, 28.2, 26.5, 23.9, 19.7, 8.3 ppm.

Methyl 4-(2-chloro-5-nitropyrimidin-4-yl)-3-ethyl-morpholine-3-carboxylate (Intermediate Z-1) and 2-Chloro-6a-ethyl-5-methyl-6a,7,9,10-tetrahydro-[1,4]oxazino[3,4-h]pteridin-6(5H)-one (Intermediate Z)

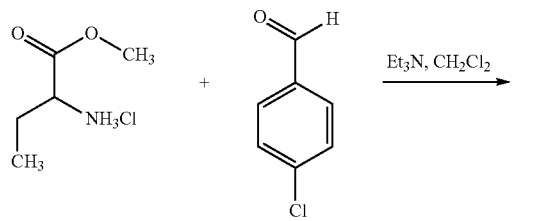

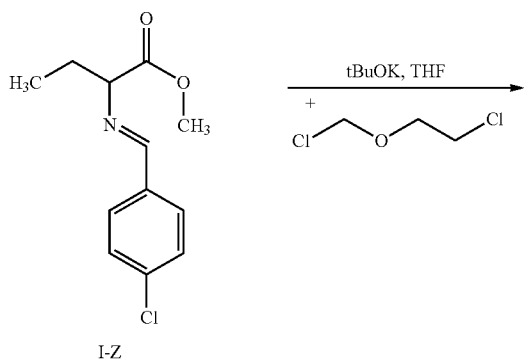

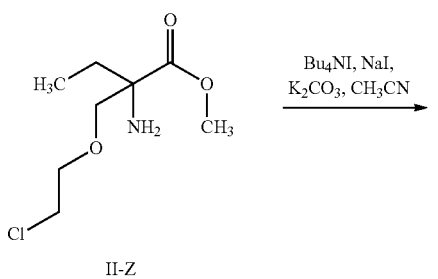

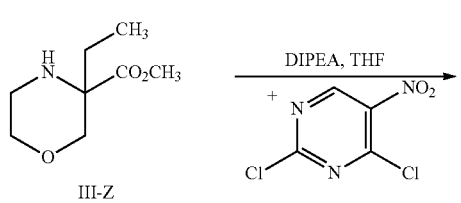

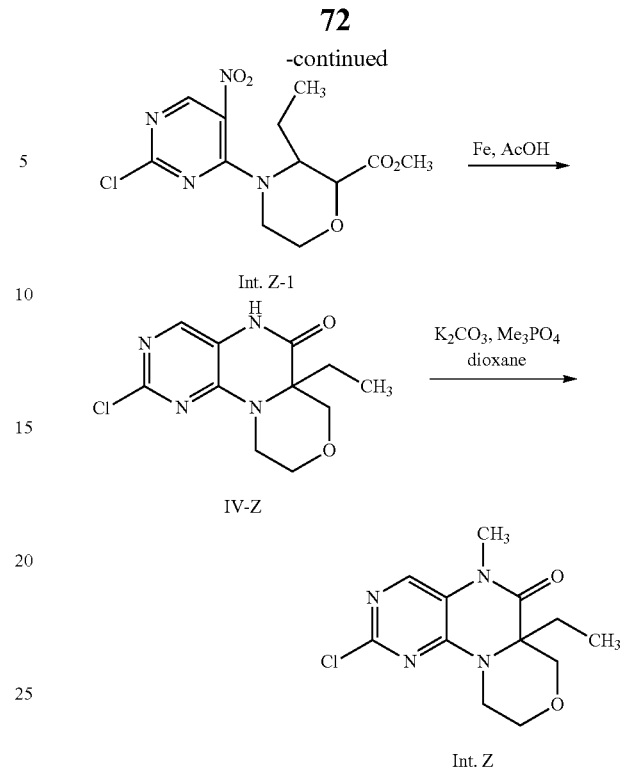

To a suspension of 2-amino-n-butyric acid methyl ester hydrochloride (73.71 mmol, 11.32 g) in 45 mL of DCM, triethylamine (36.85 mmol, 5.13 mL), and MgSO$_4$ (233.1 mmol, 28.06 g) were added. The suspension was stirred for 10 minutes before 4-chlorobenzaldehyde (36.85 mmol, 5.18 g) was added. The reaction mixture was stirred at rt under N$_2$ for 48 h, and then was filtered and concentrated. The resulting residue was dissolved in 50 mL of water and was washed with Et$_2$O (3×50 mL). The combined organic extracts were dried with MgSO$_4$, filtered and concentrated to provide compound I-Z.

The resulting residue (compound I-Z) was added to a −78° C. solution of potassium tert-butoxide (101.64 mmol, 11.41 g) in 50 mL of THF, and was stirred for 10 minutes before 1-chloro-2-(chloromethoxy)ethane (101.64 mmol, 13.11 g) was added. The reaction mixture was stirred for 18 h while slowly warming to rt. The temperature was then decreased to 0° C., and the reaction was quenched with 10 mL of water. The reaction mixture was stirred with 1N HCl at rt for 1.5 hours, and then was washed with 50 mL of Et$_2$O. The pH of the aqueous layer was adjusted to pH=8 with the addition of saturated K$_2$CO$_3$. The reaction mixture was extracted with DCM (3×50 mL). The combined organic extracts were dried with Na$_2$SO$_4$, filtered and concentrated to give compound II-Z.

The resulting residue (compound II-Z) was dissolved in 50 mL of acetonitrile and tetrabutyl ammonium iodide (1.477 mmol, 0.545 g), sodium iodide (73.87 mmol, 11.07 g), and K$_2$CO$_3$ (29.55 mmol, 4.08 g) were added. The reaction mixture was plunged into a preheated 90° C. oil bath and was stirred for 18 h. The reaction mixture was cooled to rt, filtered through a pad of Celite, and concentrated to give compound III-Z.

The conversion of compound III-Z to Intermediate Z-1 to compound IV-Z to Intermediate Z was similar to the conversion of compound III-F to Intermediate F-1 to compound IV-F to intermediate F as described above. Intermediate Z-1

(0.454 g, 4%); ¹H NMR (400 MHz, CDCl₃) δ: 8.78 (s, 1H), 3.91 (m, 5H), 3.72 (s, 3H), 3.56 (m, 1H), 3.04 (m, 1H), 2.50 (m, 1H), 1.97 (m, 1H), 0.86 (t, J=7.3 Hz, 3H), LCMS: 331.1 m/z (M+H)⁺; ret. Time: 1.724 min (Analytical Method A). Intermediate Z (0.280 g, 58%); ¹H NMR (400 MHz, CDCl₃) δ: 7.76 (s, 1H), 4.31 (dd, J=13.9, 2.8 Hz, 1H), 4.18 (d, J=11.7 Hz, 1H), 4.03 (dd, J=11.7, 3.9 Hz, 1H), 3.69 (d, J=11.7 Hz, 1H), 3.58 (dt, J=12.2, 3.1 Hz, 1H), 3.32 (s, 3H), 3.23 (m, 1H), 2.32 (m, 1H), 2.01 (m, 1H), 0.79 (t, J=7.5 Hz, 3H); LCMS: 282.9 m/z (M+H)⁺; ret. Time: 2.717 min (Analytical Method A).

6a-Ethyl-5-methyl-2-(2-oxo-2-phenylethyl)-7,8,9,10-tetrahydro-5H-pyrido[2,1-h]pteridin-6(6aH)-one (Intermediate Z-2)

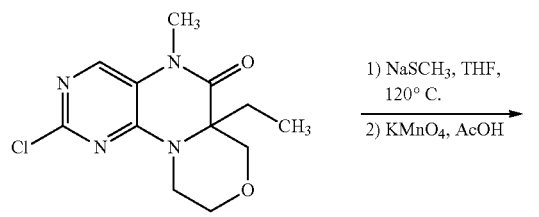

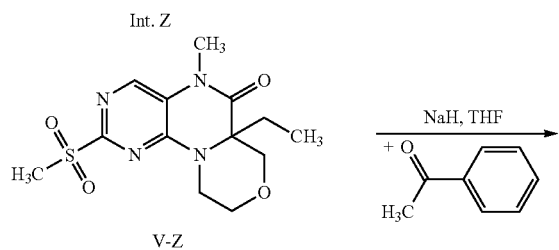

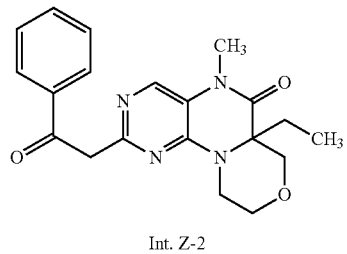

Intermediate Z-1 (0.707 mmol, 0.200 g), sodium methanethiolate (2.12 mmol, 0.148 g) and 2 mL of THF were combined in a sealed tube and heated to 120° C. for 18 h. The reaction mixture was cooled to rt, diluted with 15 mL of EtOAc, washed with water, dried with Na₂SO₄, filtered and concentrated.

The resulting residue was dissolved in 2 mL of AcOH, the temperature was decreased to 0° C., and a solution of KMnO₄ (0.848 mmol, 0.134 g) in 2 mL of water was added. The reaction mixture was stirred for 2 h at 0° C., then was quenched with saturated Na₂SO₃ and warmed to rt and extracted into EtOAc (3×15 mL). The combined organic layers were dried with Na₂SO₄, filtered and concentrated. The resulting residue was purified by flash chromatography (50% EtOAc in hexanes) to give compound V-Z.

Compound V-Z was added to a suspension of NaH (1.81 mmol, 0.07 g) and acetophenone (1.64 mmol, 0.191 g) in 3 mL of THF with stirring at 0° C. The reaction mixture was stirred for 18 h while slowly warming to rt. The reaction mixture was quenched with 10 mL of saturated NH₄Cl, diluted with 20 mL of EtOAc, and the two layers were separated. The organic layer was dried with Na₂SO₄, filtered and concentrated. The resulting residue was purified by flash chromatography (50% EtOAc in hexanes) to provide Intermediate Z-2 as a white solid (0.07 g, 62%). ¹H NMR (400 MHz, CDCl₃) δ: 8.01 (m, 1H), 7.81 (m, 2H), 7.39 (m, 3H), 4.39 (1H), 4.17 (2H), 3.95 (1H), 3.64 (m, 1H), 3.50 (m, 1H), 3.32 (s, 3H), 2.21 (m, 1H), 1.95 (m, 1H), 0.78 (t, J=7.5 Hz, 3H); LCMS: 367.2 m/z (M+H)⁺; ret. Time: 2.308 min (Analytical Method A).

6a-ethyl-5-methyl-2-(2-oxo-2-(thiazol-2-yl)ethyl)-6a,7,9,10-tetrahydro-[1,4]oxazino[3,4-h]pteridin-6(5H)-one (Intermediate Z-3)

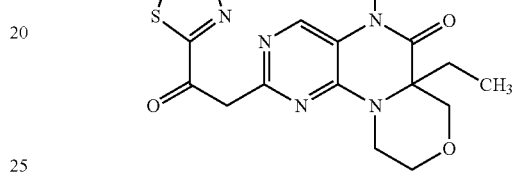

Intermediate Z-3 was prepared from Intermediate Z similarly to the method used for Intermediate Z-2 with 1-(thiazol-2-yl)ethanone instead of acetophenone.

2-(2-(2,4-Difluorophenyl)-2-oxoethyl)-6a-ethyl-5-methyl-6a,7,9,10-tetrahydro-[1,4]oxazino[3,4-h]pteridin-6(5H)-one (Intermediate Z-4)

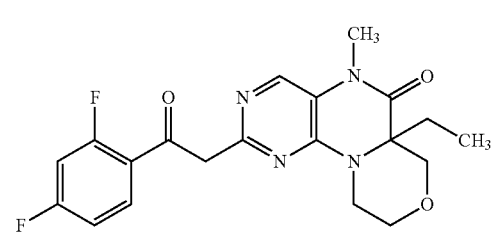

Intermediate Z-4 was prepared from Intermediate Z similarly to the method used for Intermediate Z-2 with 2,4-difluorophenylmethylketone instead of acetophenone.

6a-Ethyl-2-(2-(5-fluoropyridin-2-yl)-2-oxoethyl)-5-methyl-6a,7,9,10-tetrahydro-[1,4]oxazino[3,4-h]pteridin-6(5H)-one (Intermediate Z-5)

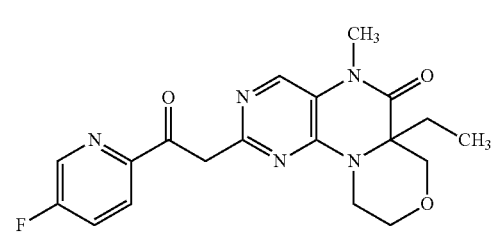

Intermediate Z-5 was prepared from Intermediate Z similarly to the method used for Intermediate Z-2 with 1-(5-fluoropyridin-2-yl)ethanone instead of acetophenone.

(3R)-ethyl 2-(2-chloro-5-nitropyrimidin-4-yl)-2-azabicyclo[3.1.0]hexane-3-carboxylate (Intermediate AA)

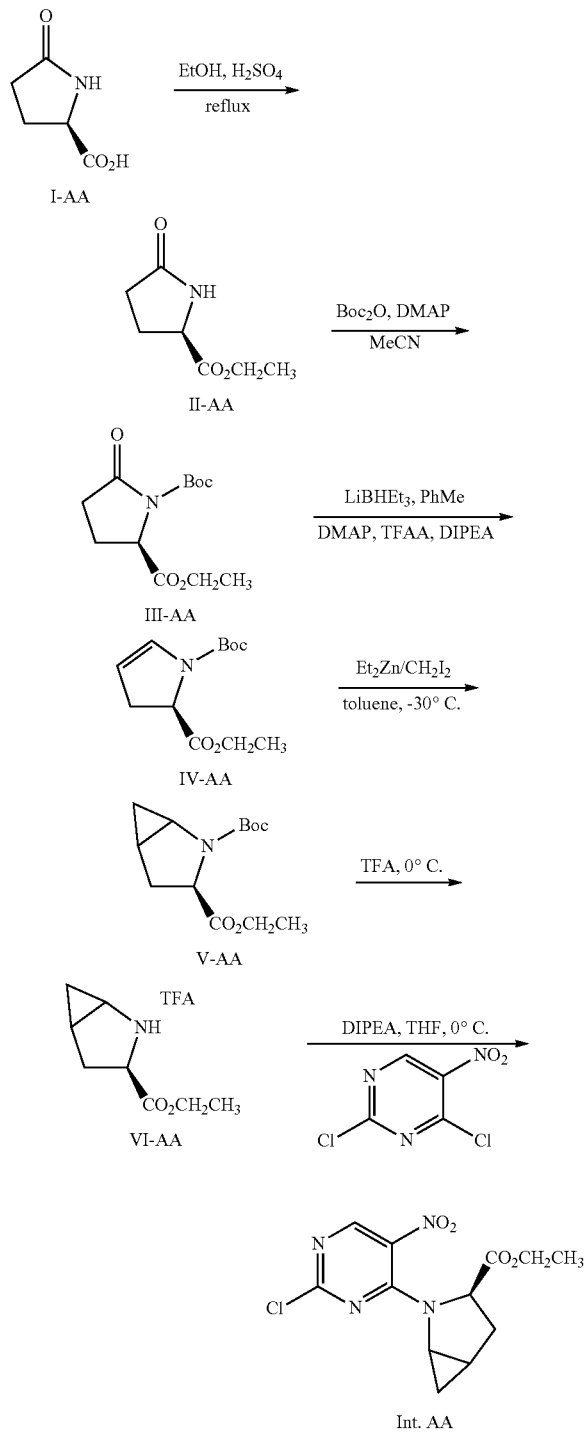

To a solution of D-pyroglutamic acid (compound I-AA, 20.4 g, 0.16 mol) in 100 mL of EtOH, 1.2 mL of conc. sulfuric acid was added. The mixture was heated under reflux overnight. Solvent was removed under reduced pressure to give (R)-ethyl 5-oxopyrrolidine-2-carboxylate (compound II-AA).

To a solution of compound II-AA in 400 mL of acetonitrile cooled in an ice-bath, DMAP (2.65 g) and (Boc)$_2$O (51.8 g, 1.5 eq) were added. The mixture was stirred at rt overnight. Solvent was removed under reduced pressure and the resulting yellow oil was purified by MPLC to give 31 g of (R)-1-tert-butyl 2-ethyl 5-oxopyrrolidine-1,2-dicarboxylate (compound III-AA).

To a solution of compound III-AA (19.3 g, 75.2 mmol) in 162 mL of toluene at −78° C., LiBHEt$_3$ (82.7 mL, 1.0 M in THF) was added dropwise via syringe. The reaction mixture was stirred between −30 and −78° C. for 8 hours, followed by addition of DIPEA (73.3 mL), DMAP (915 mg) and TFAA (14.8 mL). The cooling bath was removed and the mixture was stirred at rt overnight. The reaction was quenched by water and diluted with 200 mL of EtOAc. The organic layer was separated and washed with water, brine and dried over MgSO$_4$. After evaporation of the solvent, the yellow oil was purified by MPLC to give 20.4 g of (R)-1-tert-butyl 2-ethyl 5-oxopyrrolidine-1,2-dicarboxylate (compound IV-AA). $^1$H NMR (CDCl$_3$) δ: 6.53-6.65 (m, 1H), 4.96-4.91 (m, 1H), 4.67-4.55 (m, 1H), 4.24-4.17 (m, 2H), 3.13-3.01 (m, 1H), 2.71-2.61 (m, 1H), 1.74-1.49 (m, 9H), 1.31-1.26 (m, 3H). LCMS: 264.2 m/z (M+Na).

An oven-dried flask equipped with magnetic stirring bar was charged with 2.07 g (8.58 mmol) of compound IV-AA and 21 mL of dry toluene. The resulting solution was cooled to −30° C. and 15.6 mL of ZnEt$_2$ (1.1 M in toluene, 17.2 mmol) was added dropwise. A solution of 2.67 mL of diiodomethane (34.4 mmol) in 2.1 mL of toluene was then added to the mixture and the mixture was stirred between −25 and −30° C. for 6 hours. The reaction was quenched by adding 42 mL of 50% diluted sat. NaHCO$_3$. The organic layer was separated and the aqueous layer was extracted with EtOAc. The organic phases were combined and washed with water, brine and dried with MgSO$_4$. After evaporation of the solvent, the resulting yellow oil was purified by MPLC to give 2-tert-butyl 3-ethyl 2-azabicyclo[3.1.0]hexane-2,3-dicarboxylate (compound V-AA). LCMS: 278.1 m/z (M+Na); ret. Time 6.149 min (Analytical Method A).

Compound V-AA (515 mg, 2.02 mmol) was mixed with 1.5 mL of TFA and stirred at 0° C. for 30 min. TFA was removed under reduced pressure to give (3R)-ethyl 2-azabicyclo[3.1.0]hexane-3-carboxylate (compound VI-AA).

Compound VI-AA (2.17 mmol) was dissolved in 6 mL of THF and cooled to 0° C. DIPEA (1.05 mL, 3 eq) and 2,4-dichloro-4-nitropyrimidine (460 mg, 1.1 eq) were added sequentially. The mixture was stirred at 0° C. for 30 min. Thirty mL of EtOAc was added and the mixture was washed with sat NaHCO$_3$, water, brine and dried with MgSO$_4$. After evaporation of the solvent, the crude product was purified by MPLC to give pure (3R)-ethyl 2-(2-chloro-5-nitropyrimidin-4-yl)-2-azabicyclo[3.1.0]hexane-3-carboxylate (Intermediate AA). $^1$H NMR (CDCl$_3$) δ: 8.60-8.54 (m, 1H), 5.23-5.20 (m, 0.67H), 4.68-4.66 (m, 0.33H), 4.21-4.09 (m, 2H), 3.30 (bs, 0.33H), 3.03 (bs, 0.33H), 2.83 (bs, 0.67H), 2.70-2.65 (m, 0.67H), 2.11-2.07 (m, 1H), 1.79-1.75 (m, 1H), 1.34-1.21 (m, 3H), 1.01 (bs, 1H), 0.82-0.79 (m, 1H).

Methyl 2-((2-chloro-5-nitropyrimidin-4-yl)(3,3,3-trifluoropropyl)amino)-4,4,4-trifluorobutanoate (Intermediate BB-1) and 2-chloro-5-methyl-7-(2,2,2-trifluoroethyl)-8-(3,3,3-trifluoropropyl)-7,8-dihydropteridin-6(5H)-one (Intermediate BB)

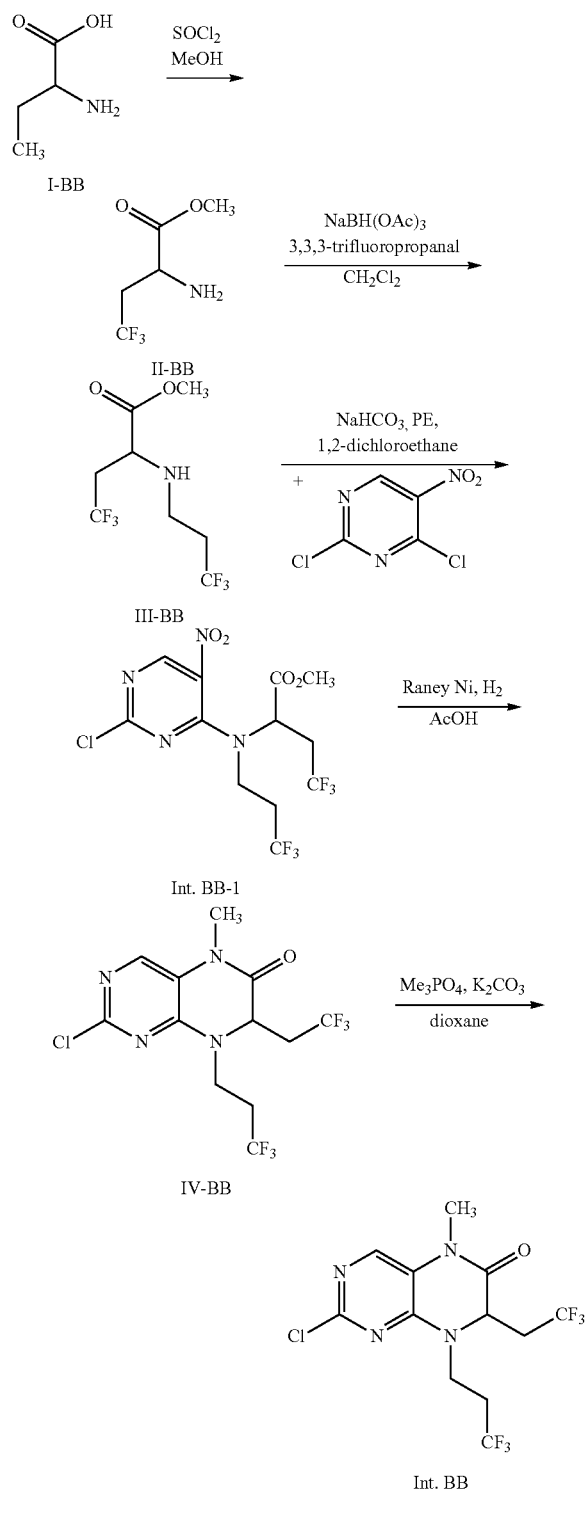

Compound I-BB (2 g, 12.73 mmol) was dissolved in 80 mL of methanol and cooled to 0° C. Thionyl chloride (1.66 mL, 22.91 mmol) was added dropwise over 20 minutes after which the reaction mixture was stirred at 70° C. for 3 h. The resulting solution was concentrated and dried under vacuum to give compound II-BB (2.14 g, 81%); LCMS: 172.0 m/z $(M+H)^+$.

Compound II-BB (1.5 g, 7.22 mmol) and 3,3,3-trifluoropropanal (0.64 g, 5.79 mmol) were dissolved in 20 mL of DCM. After the addition of sodium acetate (0.59 g, 7.23 mmol) and sodium triacetoxyborohydride (2.0 g, 9.39 mmol), the mixture was stirred for 24 hr at rt and then saturated sodium bicarbonate solution was added. The aqueous phase was extracted with DCM. The combined organic phases were washed with water, dried over $MgSO_4$ and evaporated to give compound III-BB. LCMS: 268.1 m/z $(M+H)^+$.

The conversion of compound III-BB to Intermediate BB-1 was similar to the conversion of compound III-J to Intermediate J-1 as described above. Intermediate BB-1 (2.14 g, 69%); LCMS: 425.0 m/z $(M+H)^+$.

Intermediate BB-1 was reacted similarly to the methods used in the synthesis of Intermediate B from Intermediate A to give Intermediate BB.

2-Chloro-7-ethyl-5-methyl-8-phenyl-7,8-dihydropteridin-6(5H)-one (Intermediate CC)

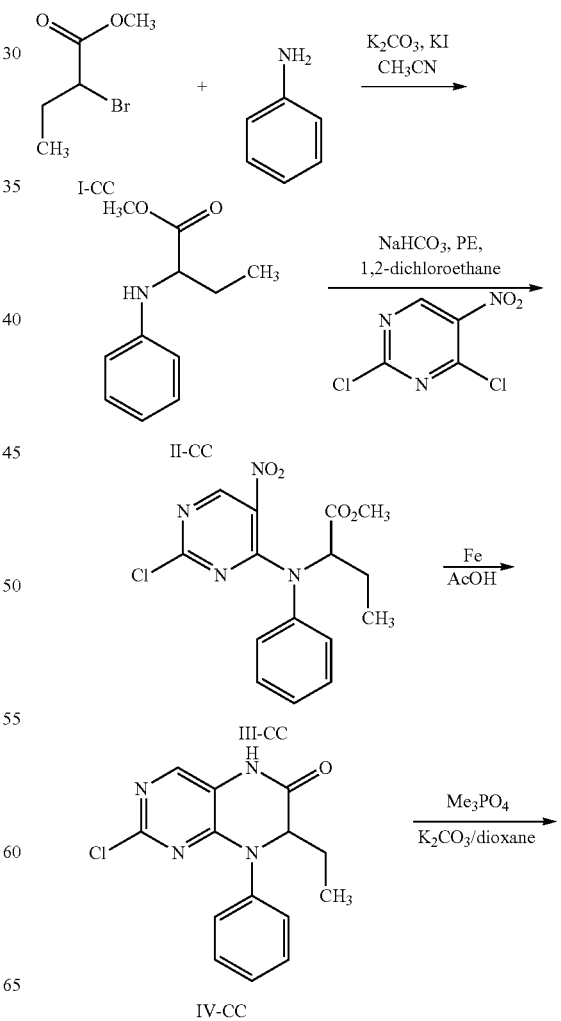

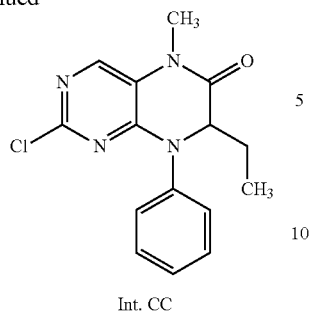

Int. CC

Compound I-CC (3.1 g, 17.1 mmol) and aniline (1.59 g, 17.1 mmol) were dissolved in 30 mL of acetonitrile in a glass pressure tube. After the addition of potassium carbonate (4.71 g, 34.2 mmol) and potassium iodide (0.283 g, 1.71 mmol), the tube was sealed and mixture was stirred for 18 hr at 100° C. The reaction mixture was diluted with ethyl acetate and washed with saturated sodium bicarbonate solution. The organic phase was dried over $Na_2SO_4$, filtered, evaporated down and purified by silica column (hexane:EtOAc) to give Compound II-CC (1.97 g, 59%); LCMS: 194.12 m/z $(M+H)^+$.

The conversion of compound II-CC to compound III-CC to compound IV-CC to Intermediate CC was similar to the conversion of compound III-J to Intermediate J-1 to compound IV-J to intermediate J as described above. Compound III-CC (2.21 g, 62%); LCMS: 351.1 m/z $(M+H)^+$. Compound IV-CC; LCMS: 289.1 m/z $(M+H)^+$. Intermediate CC (754 mg, 50%); LCMS: 303.1 m/z $(M+H)^+$.

(R)-2-chloro-8-(cyclopropylmethyl)-7-ethyl-5-methyl-7,8-dihydropteridin-6(5H)-one (Intermediate DD)

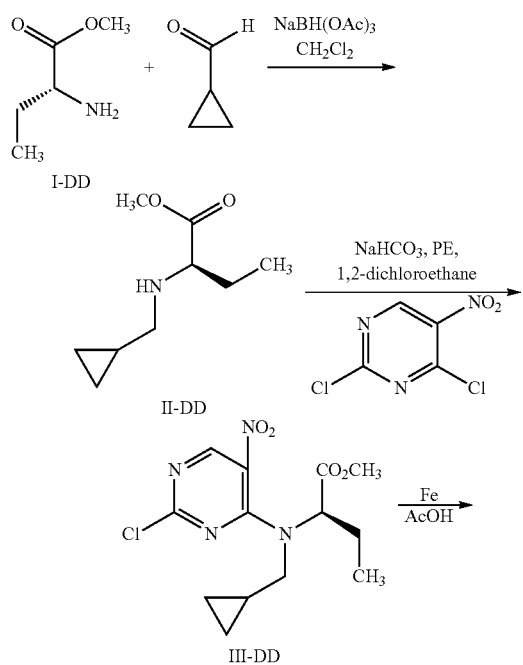

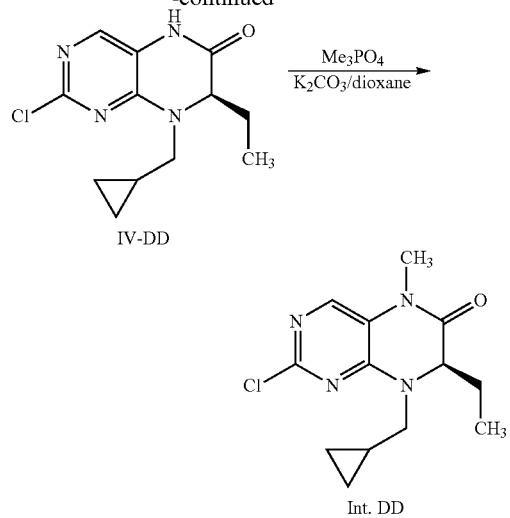

Int. DD

Compound I-DD (1.02 g, 6.70 mmol) and cyclopropanecarbaldehyde (0.375 g, 5.36 mmol) were dissolved in 10 mL of DCM. After the addition of sodium acetate (0.55 g, 5.36 mmol) and sodium triacetoxyborohydride (1.84 g, 8.71 mmol), the mixture was stirred for 18 hr at rt and then saturated sodium bicarbonate solution was added. The aqueous phase was extracted with DCM. The combined organic phases were washed with water, dried over $MgSO_4$ and evaporated down to give Compound II-DD; LCMS: 172.1 m/z $(M+H)^+$.

The conversion of compound II-DD to compound III-DD to compound IV-DD to Intermediate DD was similar to the conversion of compound III-J to Intermediate J-1 to compound IV-J to intermediate J as described above. Compound III-DD (1.42 g, 65%); LCMS: 329.1 m/z $(M+H)^+$. Compound IV-DD; LCMS: 267.1 m/z $(M+H)^+$. Intermediate DD (551 mg, 53%); LCMS: 281.1 m/z $(M+H)^+$.

2-Chloro-7-ethyl-8-(4-fluorophenyl)-5-methyl-7,8-dihydropteridin-6(5H)-one (Intermediate EE)

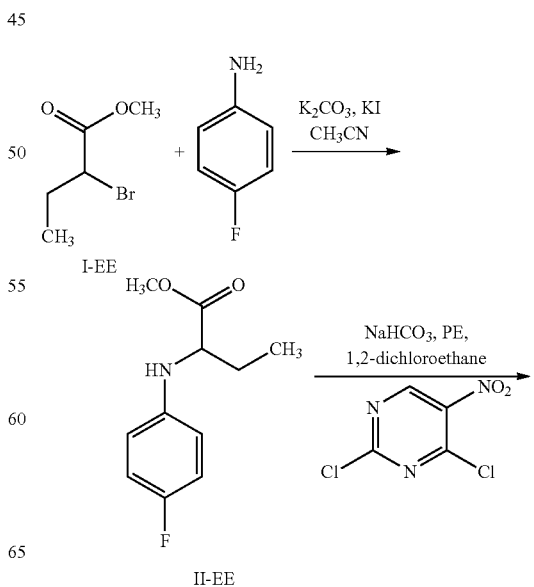

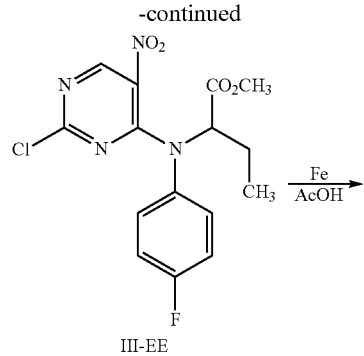

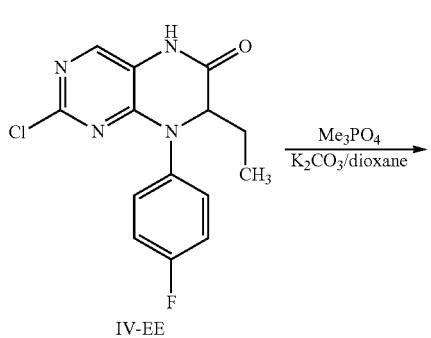

(7R)-2-Chloro-8-(3,3-difluorocyclopentyl)-7-ethyl-5-methyl-7,8-dihydropteridin-6(5H)-one (Intermediate FF)

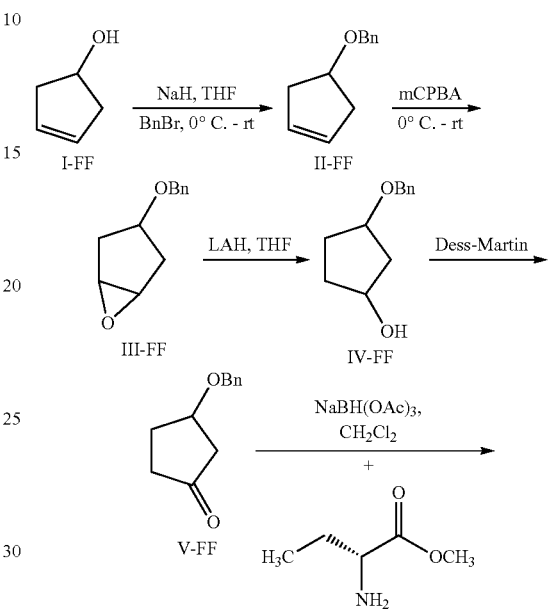

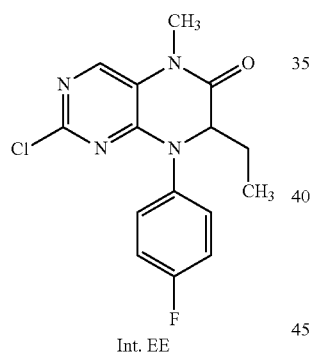

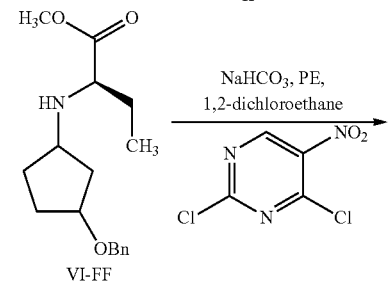

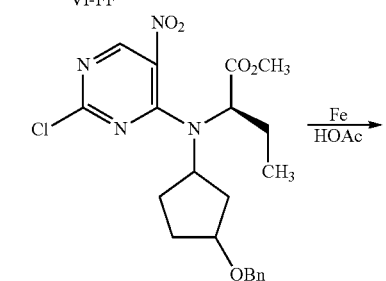

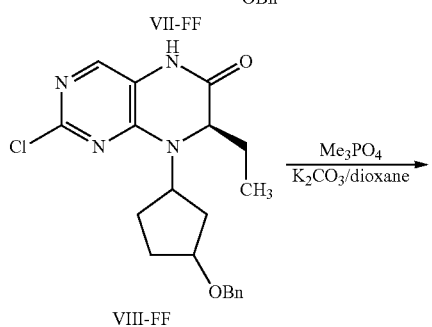

Compound I-EE (3.1 g, 17.1 mmol) and 4-fluoroaniline (1.90 g, 17.1 mmol) were dissolved in 30 mL of acetonitrile in a glass pressure tube. After the addition of potassium carconate (4.71 g, 34.2 mmol) and potassium iodide (0.283 g, 1.71 mmol), the tube was sealed and mixture was stirred for 18 hr at 100° C. The reaction mixture was diluted with ethyl acetate and washed with saturated sodium bicarbonate solution. The organic phase was dried over $Na_2SO_4$, filtered, evaporated down and purified by silica column (hexane:EtOAc) to give Compound II-EE (1.41 g, 39%); LCMS: 212.1 m/z $(M+H)^+$.

The conversion of compound II-EE to compound III-EE to compound IV-EE to Intermediate EE was similar to the conversion of compound III-J to Intermediate J-1 to compound IV-J to intermediate J as described above. Compound III-EE (1.851 g, 79%); LCMS: 369.1 m/z $(M+H)^+$. Compound IV-EE; LCMS: 307.1 m/z $(M+H)^+$. Intermediate EE (841 mg, 78%); LCMS: 321.1 m/z $(M+H)^+$.

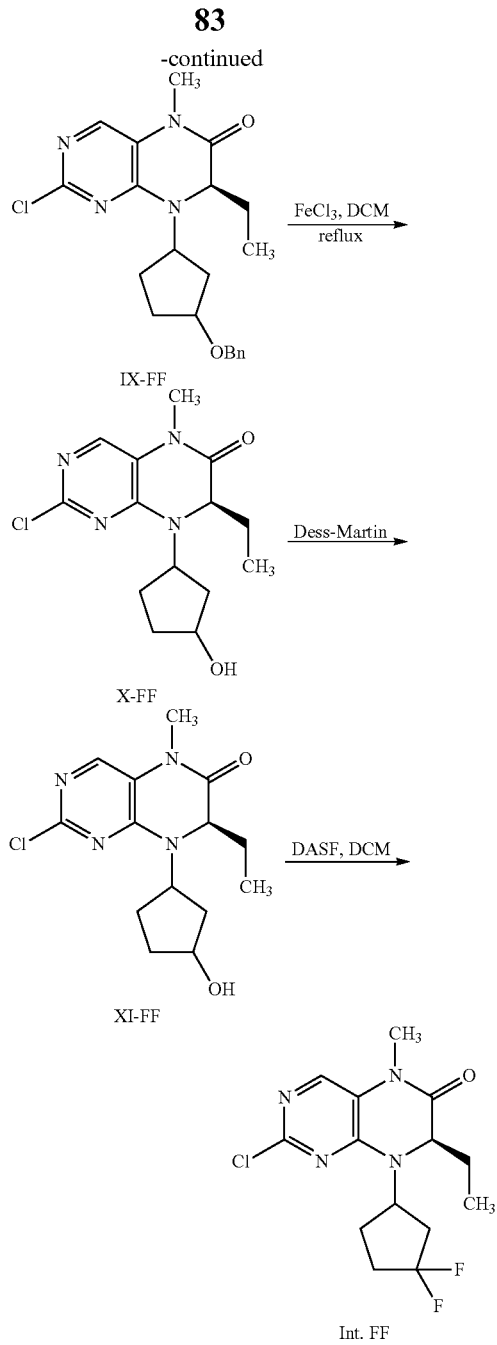

To a stirring mixture of cyclopent-3-enol (1-FF, 2.4 g, 28.5 mmol) in 41 mL of THF at 0° C., NaH (1.6 g, 39.9 mmole, 60% in mineral oil) was added portion wise. The reaction mixture was warmed to rt for 15 min. The reaction mixture was cooled to 0° C. before BnBr was added. The reaction mixture was stirred for 4 h before it was slowly quenched with water and the resulting mixture was diluted with 100 mL of EtOAc. The layers were separated. The aqueous layer was extracted with EtOAc (2×50 mL). The combined organic layers were dried over MgSO$_4$, filtered, and concentrated under reduced pressure. The crude product was purified by MPLC, using EtOAc/Hex to give compound II-FF (1.2 g). LCMS: 175.1 m/z (M+H)$^+$.

To a stirring mixture of ((cyclopent-3-enyloxy)methyl)benzene (II-FF, 1.2 g, 6.85 mmol) in DCM at 0° C., mCPBA (0.13 g, 7.58 mmol) was added in one portion. The reaction mixture was stirred at 0° C. for 2 h before it was slowly warmed to rt. The reaction mixture was slowly quenched with a saturated NaHSO$_3$ and NaHCO$_3$ solution (1:1, 10 mL). The reaction was diluted with EtOAc. The layers were separated. The aqueous layer was extracted with EtOAc (2×50 mL). The combined organic layers were dried over MgSO$_4$, filtered, and concentrated under reduced pressure. The crude product was purified by MPLC, using EtOAc/Hex to give compound III-FF (1.1 g). LCMS: 191.1 m/z (M+H)$^+$.

To a stirring mixture of the epoxide (III-FF, 1.1 g, 5.75 mmol) in 10 mL of THF at 0° C., a solution of LiAlH (6.4 mL, 6.36 mmol, 1.0 M in THF) was added dropwise. The reaction mixture was stirred for 2 h at 0° C. and quickly warmed to rt for 5 min. To this a mixture of Celite/Na$_2$SO$_4$.10H$_2$O (1:1, 5 g total) was added until all the gas was evolved. The solid mixture was dissolved in ether and filtered through a plug of Celite to give the desired compound IV-FF. LCMS: 193.2 m/z (M+H)$^+$.

To a stirring mixture of 3-(benzyloxy)cyclopentanol (IV-FF, 1.7 g) in 30 mL of DCM, NaHCO$_3$ (3.7 g, 44 mmole), and Dess Martin reagent (11.2 g, 26.42 mmol) were added. The resulting mixture was stirred at rt until all the alcohols were consumed. The reaction mixture was slowly quenched with a saturated NaHSO$_3$ and NaHCO$_3$ solution (1:1, 20 mL total volume). The reaction mixture was diluted with EtOAc. The layers were separated and the aqueous layer was extracted with EtOAc (2×50 mL). The combined organic layers were dried over MgSO$_4$, filtered, and concentrated under reduced pressure. The crude product was purified by MPLC, using EtOAc/Hex, to give compound V-F (1.4 g). LCMS: 191.2 m/z (M+H)$^+$.

To a stirring mixture of compound II (500 mg, 3.26 mmol, prepared as in synthesis of Intermediate A) and 3-(benzyloxy)cyclopentanone (V-F, 622 mg, 3.26 mmol) in 7 mL of DCM, sodium acetate (350 mg, 4.3 mmol) and sodium triacetoxyborohydride (1.0 g, 4.56 mmol) were added at 0° C. The resulting mixture was stirred for 12 hr at rt and 50 mL of a saturated sodium bicarbonate solution was added. The layers were separated and the aqueous phase was extracted with DCM (2×25 mL). The combined organic phases were washed with water, dried over MgSO$_4$ and evaporated under reduced pressure to give compound VI-F. LCMS: 292.3 m/z (M+H)$^+$.

The conversion of compound VI-FF to compound VII-FF to compound VIII-FF to compound IX-FF to compound X-FF to compound XI-FF to Intermediate FF was similar to the conversion of compound III-V to Intermediate V-1 to compound IV-V to intermediate V-2 to compound V-V to compound VI-V to Intermediate V as described above. Compound VII-FF; 449.3 m/z (M+H)$^+$. Compound VIII-FF; 387.3 m/z (M+H)$^+$. Compound IX-FF; 401.1 m/z (M+H)$^+$. Compound X-FF; 311.2 m/z (M+H)$^+$. Compound XI-FF; LCMS: 309.2 m/z (M+H)$^+$. Intermediate FF; LCMS: 331.0 m/z (M+H)$^+$.

2'-Chloro-8'-isopropyl-5'-methyl-5'H-spiro[cyclobutane-1,7'-pteridin]-6'(8'H)-one (Intermediate GG)

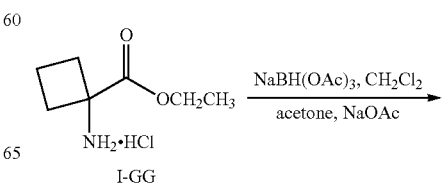

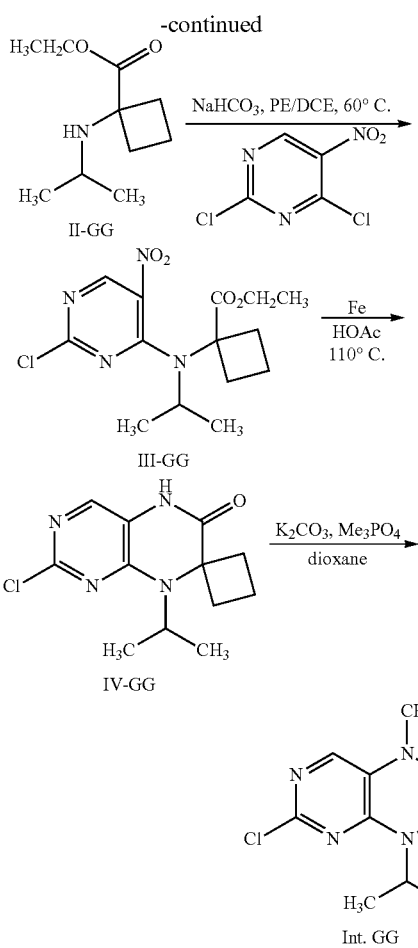

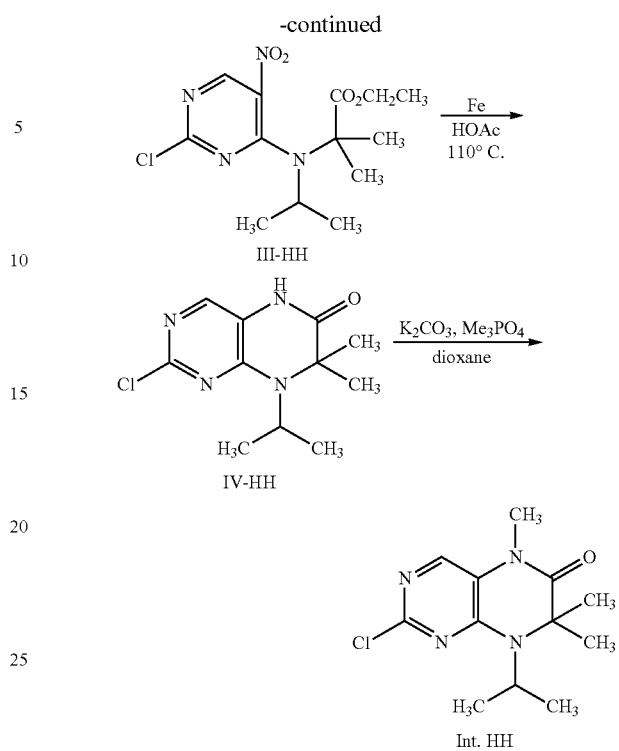

Intermediate HH was prepared similarly to the methods used to prepare Intermediate GG, with methyl 2-amino-2-methylpropanoate hydrochloride instead of ethyl 1-aminocyclobutanecarboxylate hydrochloride Intermediate GG was prepared similarly to the synthesis of Intermediate J, with ethyl 1-aminocyclobutanecarboxylate hydrochloride used instead of (R)-methyl 2-aminobutanoate and with acetone used instead of dihydro-2H-pyran-4(3H)-one. Compound II-GG; LCMS: 186.1 m/z (M+H)$^+$. Compound III-GG; LCMS: 343.1 m/z (M+H)$^+$. Compound IV-GG; LCMS: 267.1 m/z (M+H)$^+$. Intermediate GG; LCMS: 281.1 m/z (M+H)$^+$.

2-chloro-8-isopropyl-5,7,7-trimethyl-7,8-dihydropteridin-6(5H)-one (Intermediate HH)

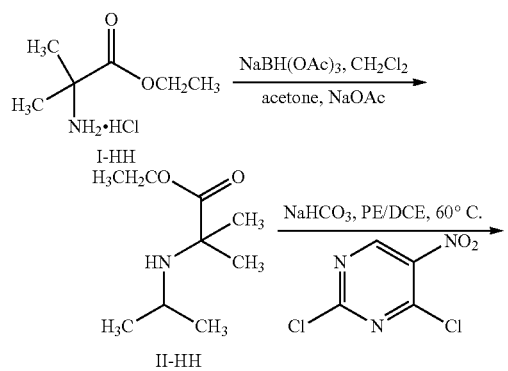

(+/−)Ethyl 1-(2-chloro-5-nitropyrimidin-4-yl)-2-(2,2,2-trifluoroethyl)pyrrolidine-2-carboxylate (Intermediate II)

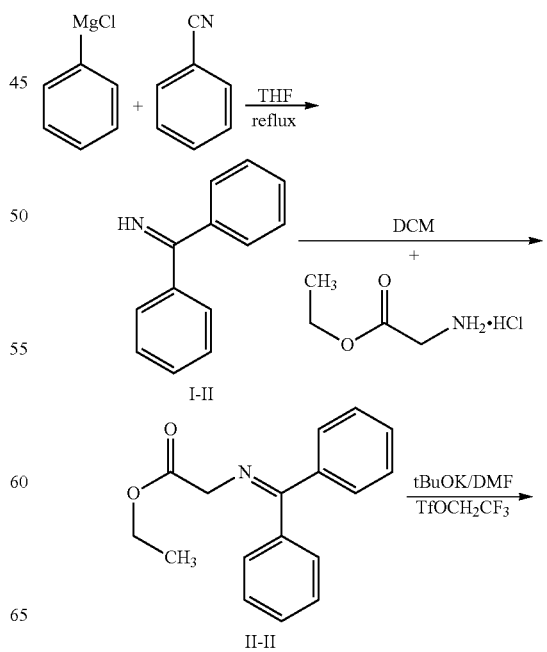

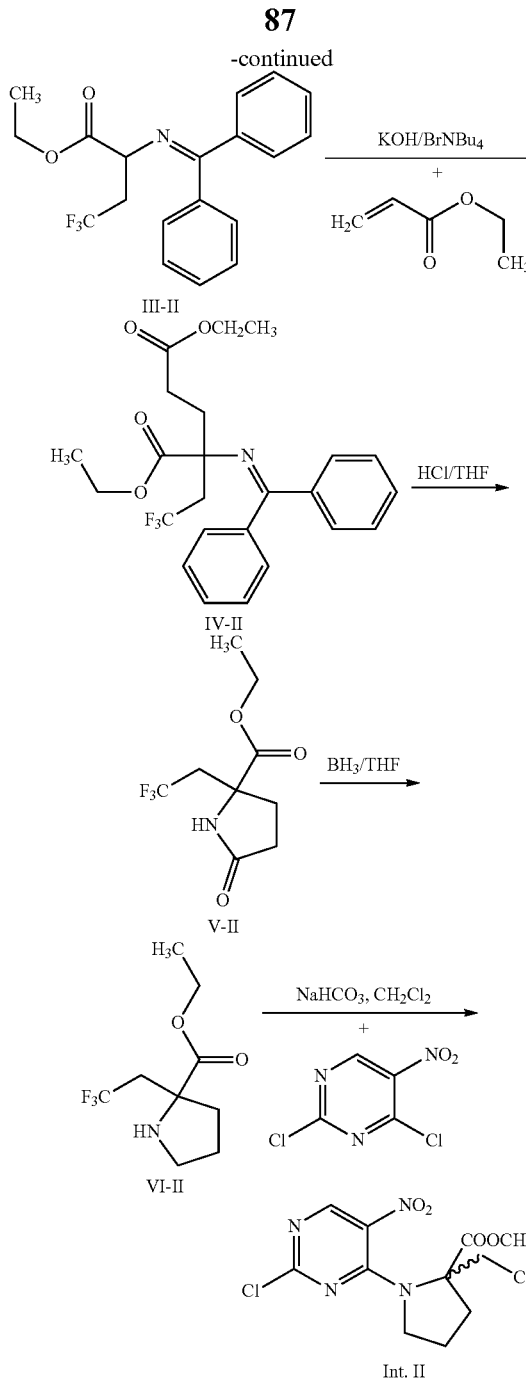

TfOCH$_2$CF$_3$ (10.1 g, 43.4 mmol) was added at 0° C. over 10 min, then the mixture was stirred at rt 18 h. The mixture was partitioned between 5% aqueous NH$_4$Cl and EtOAc, and the organic layer was washed by saturated aqueous NaCl, dried over Na$_2$SO$_4$, concentrated under reduced pressure, and purified by chromatography (PE:EtOAc=15:1) to give compound III-II. LCMS: 350.1 m/z (M+H)$^+$.

To a solution of KOH (5.0 g, 88.5 mmol) and BrNBu$_4$ (0.95 g, 2.95 mmol) in 60 mL of CH$_3$CN, a solution of compound III-II (10.3 g, 29.5 mmol) and ethyl acrylate (14.8 g, 147.6 mmol) in 60 mL of CH$_3$CN was added dropwise at rt. The mixture was stirred 18 h and then the solvent was removed under vacuum. The residue was dissolved in 200 mL of diethyl ether, and washed with water (3×200 mL), dried over Na$_2$SO$_4$, evaporated and purified by chromatography (PE:EtOAc=10:1) to give compound IV-II. LCMS: 450.1 m/z (M+H)$^+$.

A mixture of compound IV-II (7.33 g, 16.3 mmol), 3 mL of concentrated HCl and 50 mL of THF was heated at 40° C. overnight. The solvent was removed and the residue was partitioned between water and EtOAc. The organic layer was washed with water (2×100 mL), dried over Na$_2$SO$_4$, evaporated and purified by flash silica column (PE:EtOAc=75%:25%) to give compound V-II. LCMS: 240.1 m/z (M+H)$^+$.

To compound V-II (1.21 g, 5.06 mmol) in 15 mL of THF, BH$_3$ (1M in THF, 10.1 ml, 10.1 mmol) was carefully added at 0° C. and the mixture was stirred overnight at rt. Ten mL of 1N HCl was added to quench the reaction, then adjusted to pH 7 with aqueous NH$_4$OH. The mixture was concentrated and extracted with 75 mL of EtOAc and the organic layer was washed with water (2×50 mL), dried over Na$_2$SO$_4$ and evaporated to give compound VI-II. LCMS: 226.1 m/z (M+H)$^+$.

Compound VI-II (595 mg, 2.64 mmol), 2,4-dichloro-5-nitropyrimidine (615 mg, 3.17 mmol), NaHCO$_3$ (444 mg, 5.29 mmol) and 20 mL of DCM were stirred at rt for 18 h. The reaction was filtered and the filtrate was washed with water (2×25 mL), dried over Na$_2$SO$_4$ and evaporated, then purified by flash silica column (PE:EtOAc=60%:40%) to give Intermediate II. LCMS: 383.1 m/z (M+H)$^+$.

tert-butyl 2-chloro-6a-ethyl-5-methyl-6-oxo-6a,7,9,10-tetrahydro-5H-pyrazino[2,1-h]pteridine-8(6H)-carboxylate (Intermediate JJ)

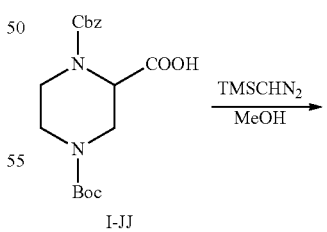

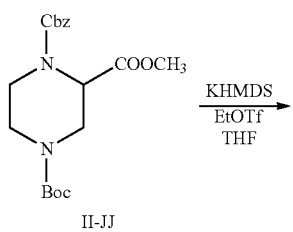

To a solution of phenylmagnesium chloride (100 ml, 200 mmol) in 100 mL of THF, benzonitrile (20.6 g, 200 mmol) was added at 0° C. The mixture was refluxed for 4 h, and then cooled to 0° C. Dry methanol (200 ml) was added carefully, and the solvent was evaporated to give compound I-II. LCMS: 182.1 m/z (M+H)$^+$.

A mixture of compound I-II (36.2 g, 200 mmol), ethyl 2-aminoacetate (28 g, 200 mmol) and 500 mL of DCM was stirred overnight at rt, filtered and the filtrate was washed with water (2×400 mL), dried with Na$_2$SO$_4$, concentrated and the residue was crystallized from PE to give compound II-II. LCMS: 268.1 m/z (M+H)$^+$.

To a solution of t-BuOK (4.41 g, 39.3 mmol) in 30 mL of dry, compound II-II (10 g, 37.4 mmol, dissolved in 20 mL dry DMF) was added at 0° C. over 10 min. After 30 min,

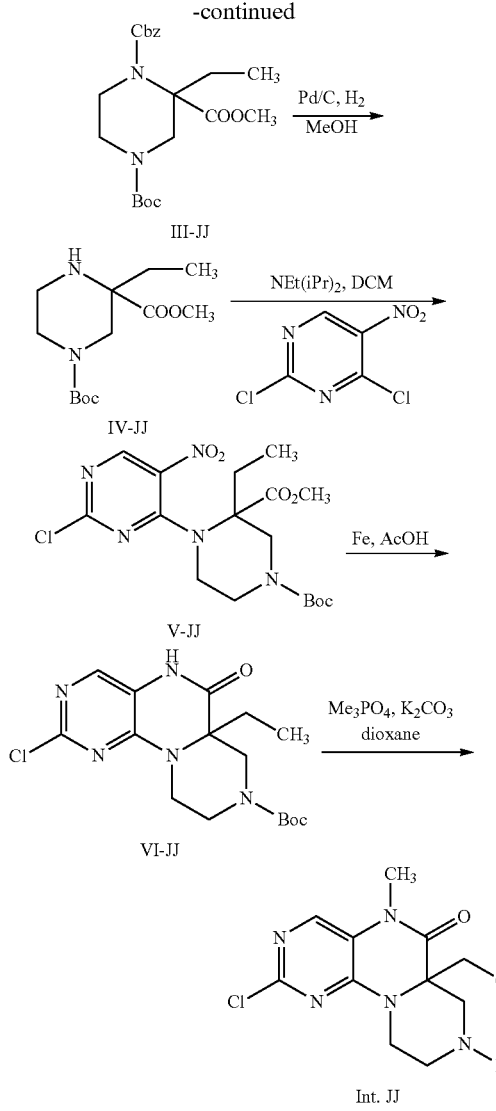

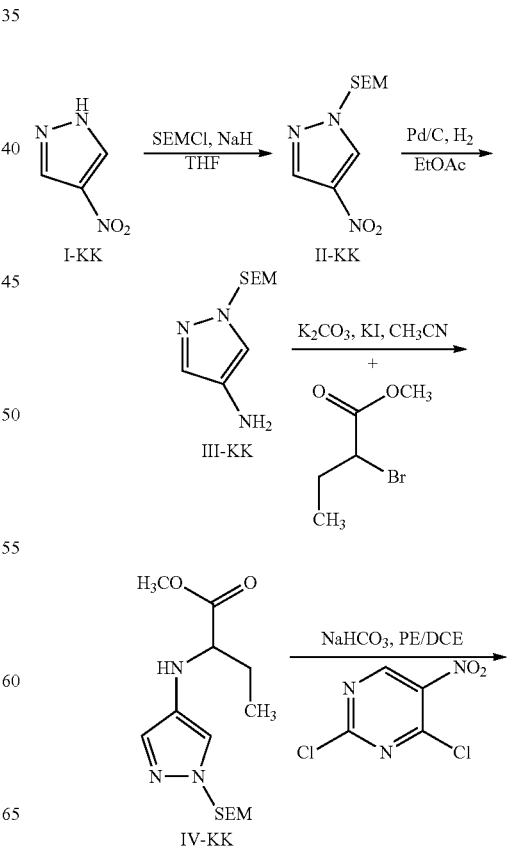

extracted twice with ethyl acetate. The combined organics were dried with MgSO$_4$, filtered and concentrated under reduced pressure. Flash chromatography (0-10% methanol/DCM gradient elution) gave 1-Benzyl 4-tert-butyl 2-methyl 2-ethylpiperazine-1,2,4-tricarboxylate (compound III-JJ) as a yellow oil, approximately 5:1 ratio of methyl and ethyl esters (1.06 g): LCMS: [M+Na]$^+$=429.2 (60%); [M-Boc+H]$^+$=307.1 (100%).

1-Benzyl 4-tert-butyl 2-methyl 2-ethylpiperazine-1,2,4-tricarboxylate (1.1 g, 2.7 mmol) was dissolved in 10 mL of methanol and glacial acetic acid (2 drops) was added. Palladium on carbon (5%, 410 mg) was added, and the reaction mixture was stirred under a H$_2$ atmosphere for 17 h at rt. The mixture was filtered through diatomaceous earth and the filter cake washed with MeOH. The combined filtrates were concentrated under reduced pressure to give 1-tert-butyl 3-methyl 3-ethylpiperazine-1,3-dicarboxylate (compound IV-JJ) as an oil. LCMS: 273.1 m/z (M+H)$^+$.

The conversion of compound IV-JJ to compound V-JJ to compound VI-JJ to Intermediate JJ was similar to the conversion of compound III-F to Intermediate F-1 to compound IV-F to intermediate F as described above. Compound V-JJ; LCMS: 430.1 m/z (M+H)$^+$. Intermediate JJ; LCMS: 382.1 m/z (M+H)$^+$.

Methyl 2-((2-chloro-5-nitropyrimidin-4-yl)(1-((2-(trimethylsilyl)ethoxy)methyl)-1H-pyrazol-4-yl)-amino)butanoate (Intermediate KK-1) and 2-chloro-7-ethyl-5-methyl-8-(1-((2-(trimethylsilyl)ethoxy)methyl)-1H-pyrazol-4-yl)-7,8-dihydropteridin-6(5H)-one (Intermediate KK)

1-(Benzyloxycarbonyl)-4-(tert-butoxycarbonyl)piperazine-2-carboxylic acid (1-JJ, 1.07 g, 2.9 mmol, Small Molecules, Inc., Hoboken, N.J. USA) was dissolved in 10 mL of dry methanol and trimethylsilyl diazomethane (2.0 M in diethyl ether, Aldrich) was added dropwise with stirring at rt until a slight yellow color persisted. The solution was then concentrated under reduced pressure, and flash chromatography (0-50% EtOAc/hexanes elution) gave 1-benzyl 4-tert-butyl 2-methyl piperazine-1,2,4-tricarboxylate (compound II-JJ) as a colorless oil: [M+Na]$^+$=401.2 (35%); [M-Boc+H]$^+$=279.1 (100%).

Following the procedure according to WO 2005/079799 (the disclosure of which is hereby incorporated by reference with respect to this synthesis), 1-benzyl 4-tert-butyl 2-methyl piperazine-1,2,4-tricarboxylate (II-JJ, 1.1 g, 2.9 mmol) was dissolved in 6 mL of dry THF and cooled to −78° C. Potassium hexamethyldisilazane (0.5M solution in toluene, Aldrich, 10 mL, 5.0 mmol) was added by syringe, and the reaction mixture stirred at −78° C. for 75 min. Ethyl trifluoromethanesulfonate (0.65 mL, 5.0 mmol) was added dropwise by syringe to this mixture, and then the reaction was allowed to warm to rt for 5 h. The reaction was quenched with saturated sodium bicarbonate solution, and the mixture was -continued

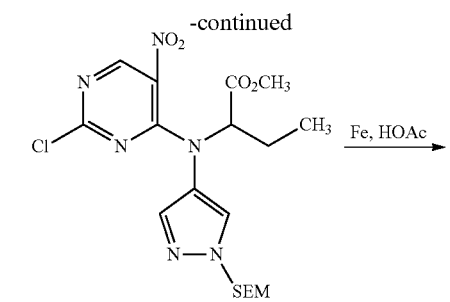

Int. KK-1

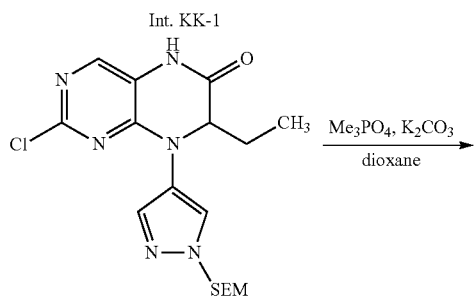

V-KK

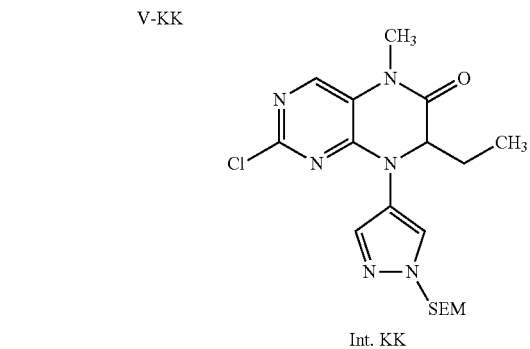

Int. KK

Sodium hydride (849 mg of a 60% dispersion in mineral oil, 21.2 mmol) was added to a solution of compound I-KK (2 g, 17.7 mmol) in 80 mL of THF at 0° C. and the resulting mixture was stirred for 10 minutes. SEM-Cl (3.43 mL, 19.5 mmol) was added dropwise and the resulting mixture was stirred at rt for 1 h. The reaction mixture was diluted with ethyl acetate and washed with brine. The organic phase was dried over $Na_2SO_4$ and evaporated. The residue was purified by silica column (hexane:EtOAc) to give compound II-KK (4.01 g, 93%); LCMS: 243.8 m/z $(M+H)^+$.

Palladium on carbon (10%, 0.5 g) was added to a solution of compound II-KK (4.01 g, 16.4 mmol) in 50 mL of ethyl acetate and the resulting suspension was stirred under 1 atm of hydrogen for 2 hr. The mixture was filtered through a pad of Celite and the filtrate was concentrated under vacuum to give compound III-KK (3.24 g, 93%); LCMS: 214.1 m/z $(M+H)^+$.

Compound III-KK (1.21 g, 5.67 mmol) and methyl 2-bromobutanoate (1.54 g, 8.51 mmol) were dissolved in 15 mL of acetonitrile in a glass pressure tube. Potassium carbonate (1.56 g, 11.342 mmol) and potassium iodide (94 mg, 0.567 mmol) were added and the tube was sealed and the mixture was stirred for 18 hr at 100° C. The reaction mixture was diluted with ethyl acetate and washed with saturated sodium bicarbonate solution. The organic phase was dried over $Na_2SO_4$, filtered, concentrated and purified by silica column (hexane:EtOAc) to give compound IV-KK (1.42 g, 79%); LCMS: 314.1 m/z $(M+H)^+$.

The conversion of compound IV-KK to Intermediate KK-1 to compound V-KK to Intermediate KK was similar to the conversion of compound III-J to Intermediate J-1 to compound IV-J to intermediate J as described above. Intermediate KK-1 (1.83 g, 86%); LCMS: 471.2 m/z $(M+H)^+$. Compound V-KK; LCMS: 409.2 m/z $(M+H)^+$. Intermediate KK (716 mg, 70%); LCMS: 423.2 m/z $(M+H)^+$.

(R)-2-chloro-7-ethyl-5-methyl-8-(1-methyl-1H-pyrazol-4-yl)-7,8-dihydropteridin-6(5H)-one (Intermediate KK-2)

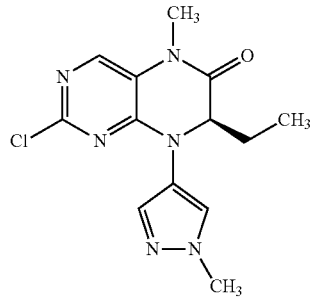

was prepared similarly, where Intermediate KK-1 is separated by chiral chromatography, and the appropriate isomer is carried through and reacted similarly to the method below for Intermediate KK-3 to give Intermediate KK-2.

2-Chloro-7-ethyl-5-methyl-8-(1-methyl-1H-pyrazol-4-yl)-7,8-dihydropteridin-6(5H)-one (Intermediate KK-3)

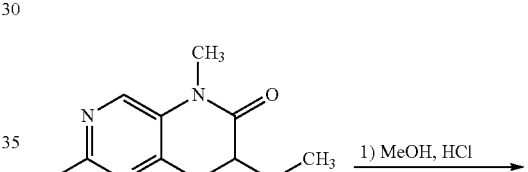

Int. KK

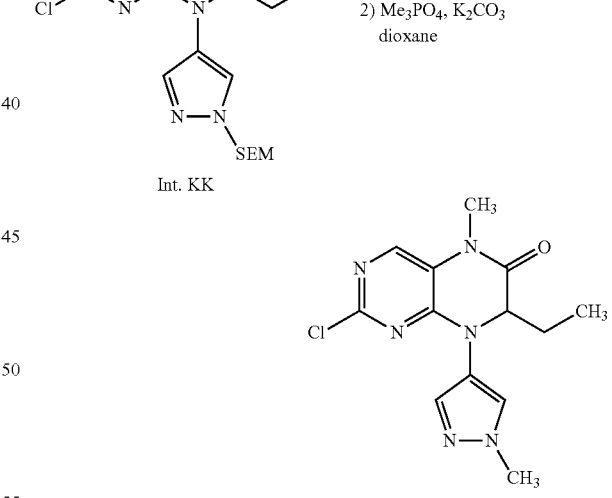

Int. KK-3

To a stirring mixture of Intermediate KK (300 mg, 0.71 mmol) in 5 mL of MeOH, 10 mL of HCl (4N in dioxane) was added. The resulting mixture was warmed to reflux until all the starting material was consumed. The reaction mixture was cooled to rt and concentrated. The crude residue was diluted with EtOAc and neutralized with a saturated $NaHCO_3$ solution. The layers were separated and the aqueous layer was extracted with EtOAc (2×25 mL). The organic layers were dried over $MgSO_4$, filtered, and concentrated under reduced pressure. The crude material was purified by MPLC to give the compound with nitrogen protecting group removed (180 mg); LCMS: 293.0 m/z $(M+H)^+$. This was dissolved in 2 mL of dioxane and K₂CO₃ (189 mg) and Me₃PO₄ (143 mg) were added. The resulting mixture was stirred at 100° C. overnight. The reaction mixture was cooled to rt and diluted with water and EtOAc. The layers were separated and the aqueous layer was extracted with EtOAc (2×25 mL). The organic layers were dried over MgSO₄, filtered, and concentrated. The crude material was purified by MPLC to give the desired Intermediate KK-3. LCMS: 307.1 m/z (M+H)⁺.

2-Chloro-8-(1-(cyclopropylmethyl)-1H-pyrazol-4-yl)-7-ethyl-5-methyl-7,8-dihydropteridin-6(5H)-one (Intermediate KK-4)

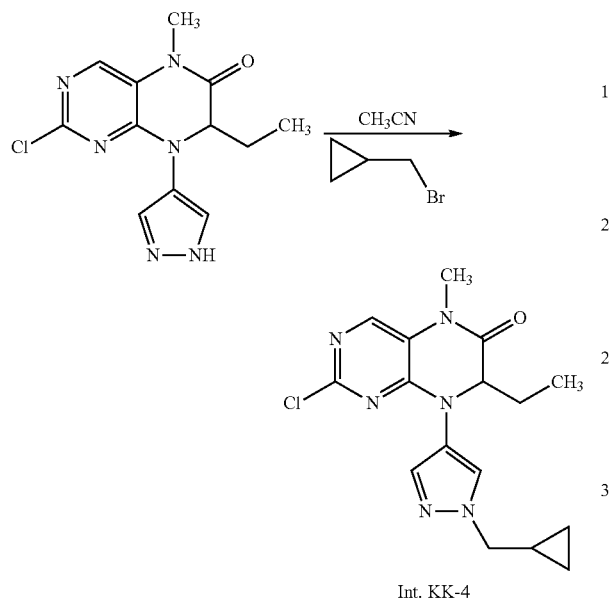

Int. KK-4

To the Intermediate KK with deprotected nitrogen (as prepared in the method of making Intermediate KK-3, 174 mg, 0.59 mmol) in 0.6 mL of acetonitrile, cyclopropyl methyl bromide (242 mg, 1.78 mmol), KI (2 mg) and K₂CO₃ (250 mg, 1.81 mmol) were added. The reaction mixture was stirred at 90° C. overnight. The resulting mixture was cooled to rt and slowly quenched with a saturated NaHCO₃ solution. The reaction mixture was diluted with 25 mL of EtOAc. The layers were separated and the aqueous layer was extracted with EtOAc (2×25 mL). The layers were dried over MgSO₄, filtered, and concentrated, and the resulting material was purified by MPLC to give Intermediate KK-4. LCMS: 347.1 m/z (M+H)⁺.

2-chloro-7-ethyl-5-methyl-8-(3-(pyrimidin-5-yl)phenyl)-7,8-dihydropteridin-6(5H)-one (Intermediate MM)

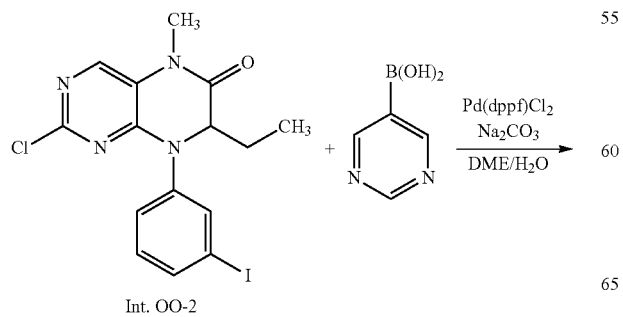

Int. OO-2

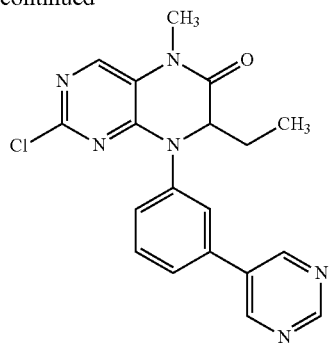

Int. MM

Intermediate OO-2 (50 mg, 0.116 mmol), pyrimidin-5-ylboronic acid (22 mg, 0.174 mmol), sodium carbonate (25 mg, 0.232 mmol) and Pd(dppf)Cl₂ (8 mg, 0.0116 mmol) were dissolved in DME/H₂O (4/1, v/v, 0.7 mL) and a stream of nitrogen was bubbled through the mixture for 5 minutes. The resulting solution was stirred at 70° C. for 2 h. The reaction mixture was diluted with brine, extracted with EtOAc, dried with Na₂SO₄ and concentrated to give Intermediate MM. LCMS: 381.1 m/z (M+H)⁺.

8-(3-(1H-pyrazol-1-yl)phenyl)-2-chloro-7-ethyl-5-methyl-7,8-dihydropteridin-6(5H)-one (Intermediate NN)

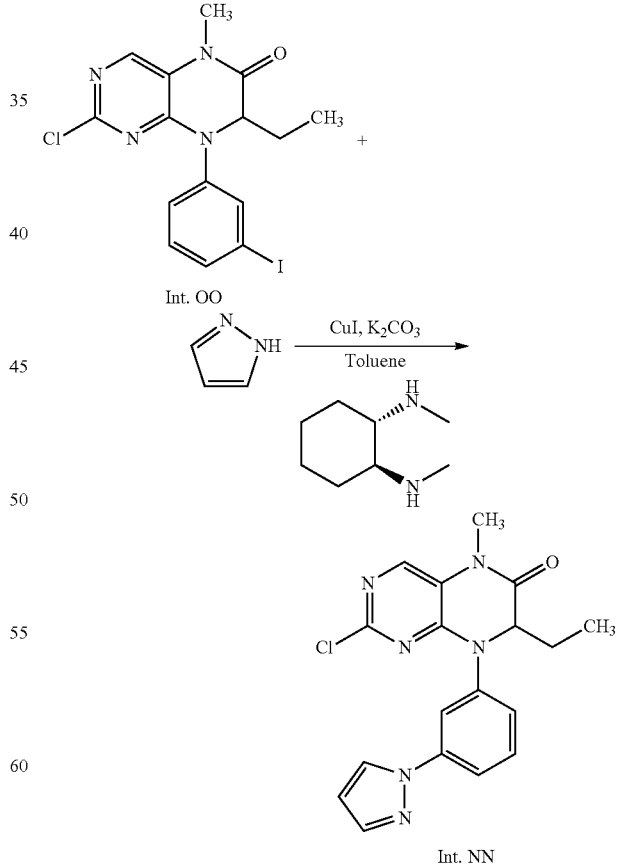

Int. NN

Intermediate OO-2 (50 mg, 0.116 mmol), pyrazole (11 mg, 0.174 mmol), CuI (2.2 mg, 0.0116 mmol), trans-1,2-bis(methylamino)cyclohexane (3.3 mg, 0.0232) and K₂CO₃ (32 mg, 0.232 mmol) were dissolved in toluene (0.5 mL) in a screw cap vial and a stream of nitrogen was bubbled through the mixture for 2 minutes. The resulting solution was stirred at 80° C. for 8 h. The reaction mixture was diluted with brine, extracted with EtOAc, dried with Na₂SO₄ and purified by silica column (hexane:EtOAc) to give Intermediate NN (25 mg, 0.067 mmol). LCMS: 369.1 m/z (M+H)⁺.

3-(2-chloro-7-ethyl-5-methyl-6-oxo-6,7-dihydropteridin-8(5H)-yl)benzonitrile (Intermediate OO) and 2-chloro-7-ethyl-8-(3-iodophenyl)-5-methyl-7,8-dihydropteridin-6(5H)-one (Intermediate OO-2)

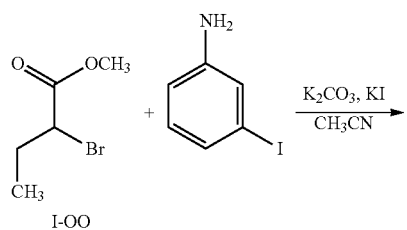

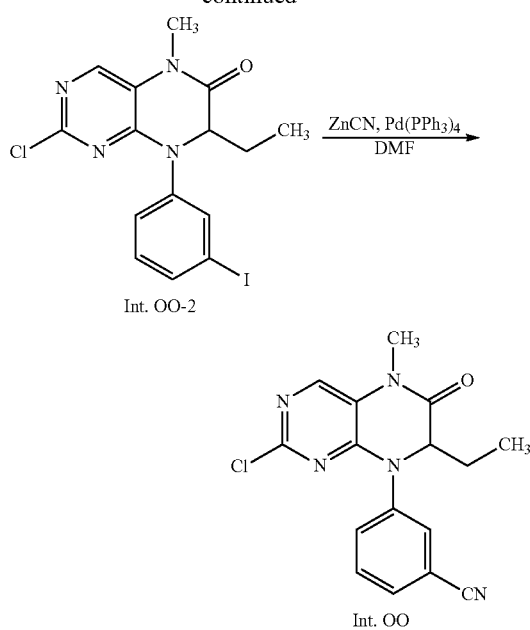

Intermediate OO-2 was prepared similarly to the methods used to prepare Intermediate CC with 3-iodoaniline instead of aniline in the first step.

Intermediate OO-2 (110 mg, 0.256 mmol), zinc cyanide (33 mg, 0.282 mmol) and Pd(PPh₃)₄ (29 mg, 0.0256 mmol) were dissolved in 1 mL of DMF in a screw cap vial and a stream of nitrogen was bubbled through the solution for 5 minutes. The vial was sealed and the reaction mixture was stirred at 100° C. for 18 h. The reaction mixture was purified by silica column (hexane:EtOAc) to give Intermediate OO (75 mg, 89%); LCMS: 328.1 m/z (M+H)⁺.

3-(7-ethyl-2-(2-(4-fluorophenyl)-2-oxoethyl)-5-methyl-6-oxo-6,7-dihydropteridin-8(5H)-yl)benzonitrile (Intermediate OO-1)

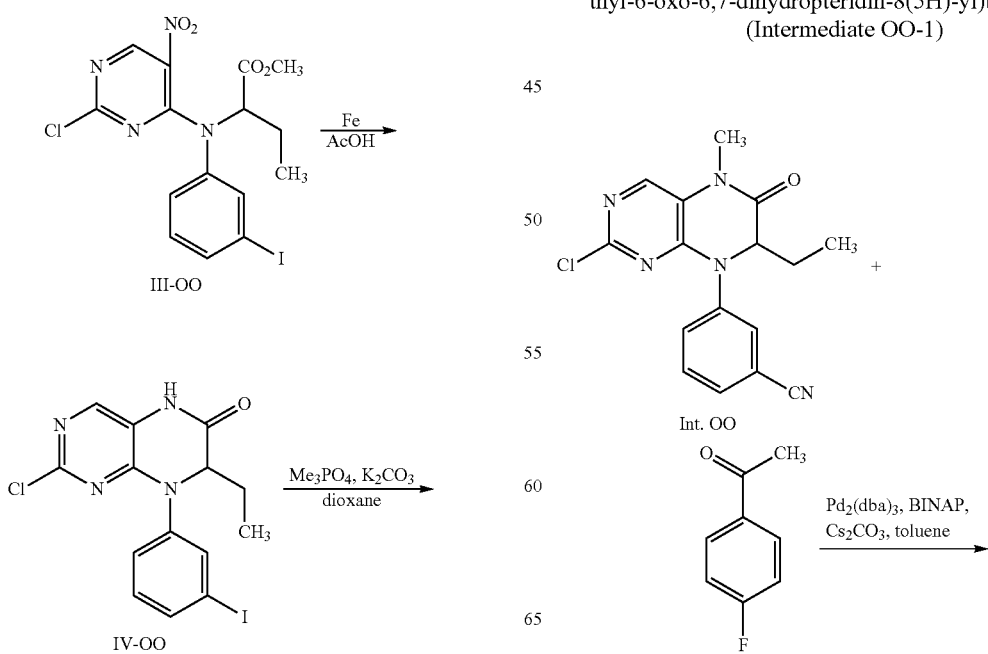

-continued

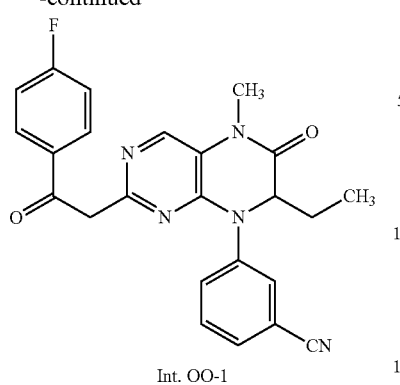
Int. OO-1

Intermediate OO-1 was prepared from Intermediate OO similarly to the method used for synthesis of Intermediate B-1 with 4-fluorophenylmethyl ketone instead of acetophenone.

4-(2-Chloro-7-ethyl-5-methyl-6-oxo-6,7-dihydropteridin-8(5H)-yl)benzonitrile (Intermediate PP)

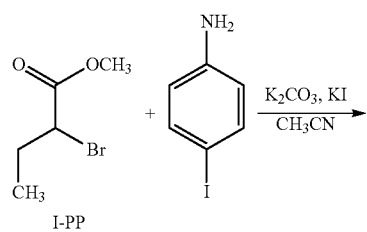
I-PP

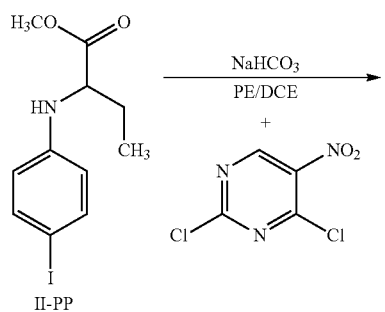
II-PP

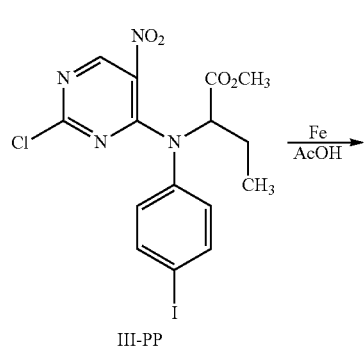
III-PP

-continued

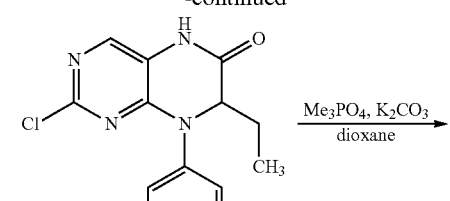
IV-PP

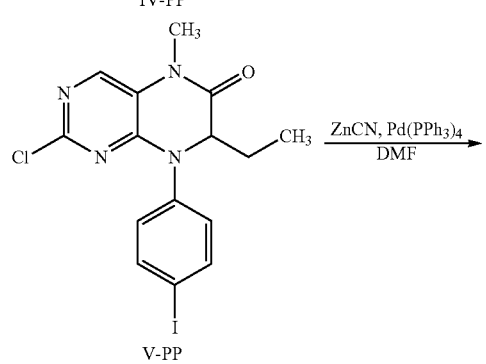
V-PP

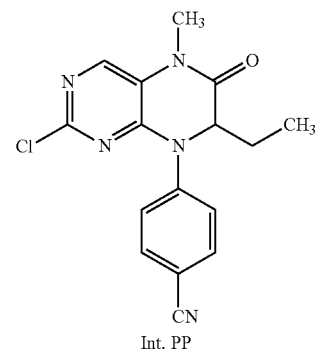
Int. PP

Intermediate PP was prepared similarly to the synthetic methods used to prepare Intermediate OO with 4-iodoaniline instead of 3-iodoaniline. LCMS: 328.1 m/z (M+H)$^+$.

4-(7-ethyl-2-(2-(4-fluorophenyl)-2-oxoethyl)-5-methyl-6-oxo-6,7-dihydropteridin-8(5H)-yl)benzonitrile (Intermediate PP-1)

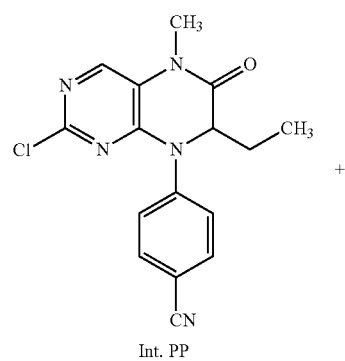
Int. PP

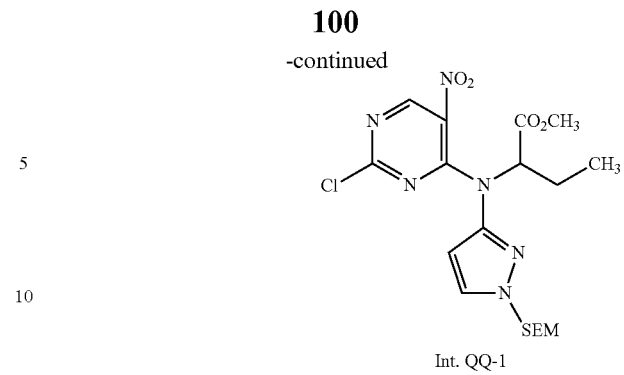

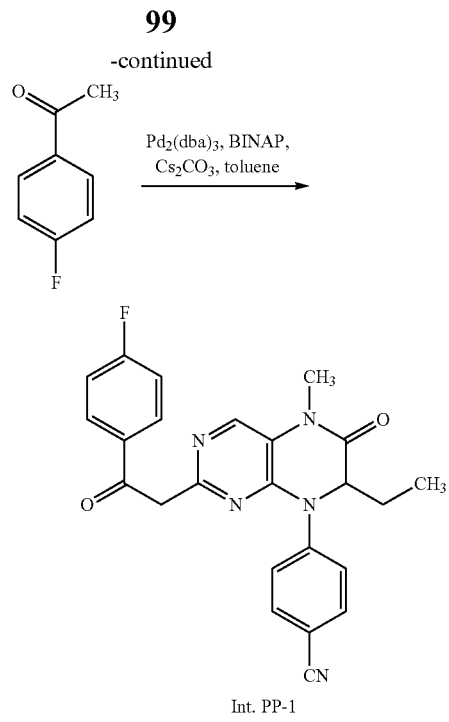

Intermediate PP-1 was prepared from Intermediate PP similarly to the method used for synthesis of Intermediate B-1 with 4-fluorophenylmethyl ketone instead of acetophenone.

Methyl 2-((2-chloro-5-nitropyrimidin-4-yl)(1-((2-(trimethylsilyl)ethoxy)methyl)-1H-pyrazol-3-yl)-amino)butanoate (Intermediate QQ-1)

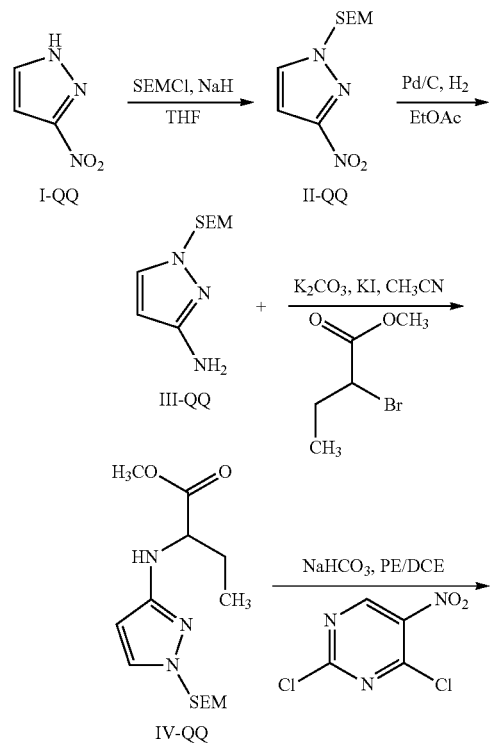

Intermediate QQ-1 was prepared similarly to the synthetic methods used to prepare Intermediate KK-1 with 3-nitro-1H-pyrazole instead of 4-nitro-1H-pyrazole. Compound II-QQ (3.94 g, 92%); LCMS: 266.1 m/z (M+23)$^+$. Compound III-QQ (1.81 g, 95%); LCMS: 214.1 m/z (M+H)$^+$. Compound IV-QQ (1.62 g, 68%); LCMS: 314.1 m/z (M+H)$^+$. Intermediate QQ-1 (0.624 g, 26%); LCMS: 471.2 m/z (M+H)$^+$.

2-chloro-7-ethyl-5-methyl-8-(1-((2-(trimethylsilyl)ethoxy)methyl)-1H-pyrazol-3-yl)-7,8-dihydropteridin-6(5H)-one (Intermediate QQ) and 2-chloro-7-ethyl-5-methyl-8-(1-methyl-1H-pyrazol-3-yl)-7,8-dihydropteridin-6(5H)-one (Intermediate QQ-2)

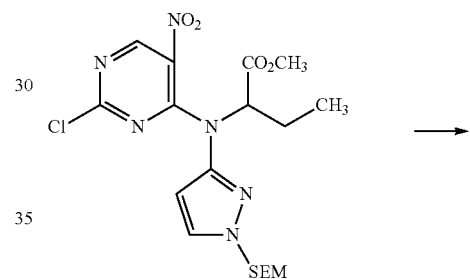

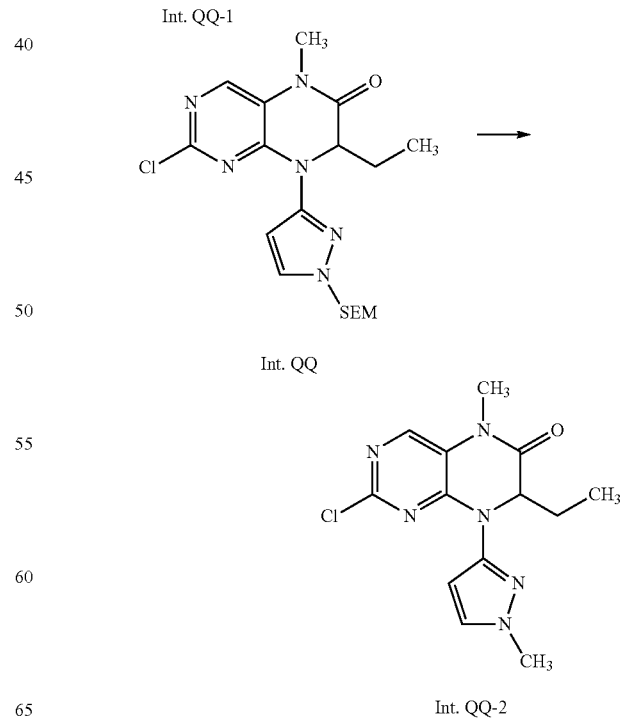

(R)-Methyl 2-((2-chloro-5-nitropyrimidin-4-yl)(oxetan-3-yl)amino)butanoate (Intermediate RR-1)

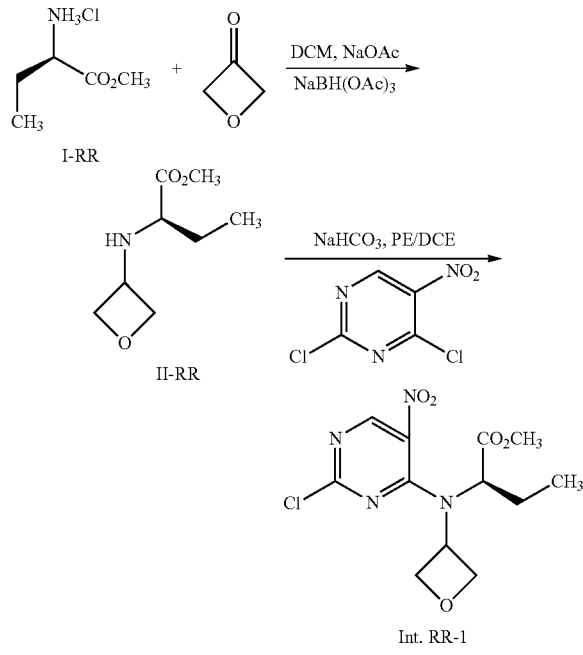

Intermediate RR-1 is prepared from compound I-RR via compound II-RR similarly to the methods used in preparing compound III-J and Intermediate J-1 as described above, with (R)-methyl 2-aminobutanoate hydrochloride used instead of (R)-methyl 2-aminobutanoate and with oxetan-3-one instead of dihydro-2H-pyran-4(3H)-one in the first step. Compound II-RR; LCMS: 174.1 m/z (M+H)+. Intermediate RR-1. LCMS: 331.1 m/z (M+H)+.

(7R)-2-chloro-8-(1-cyclopropylethyl)-7-ethyl-5-methyl-7,8-dihydropteridin-6(5H)-one (Intermediate SS)

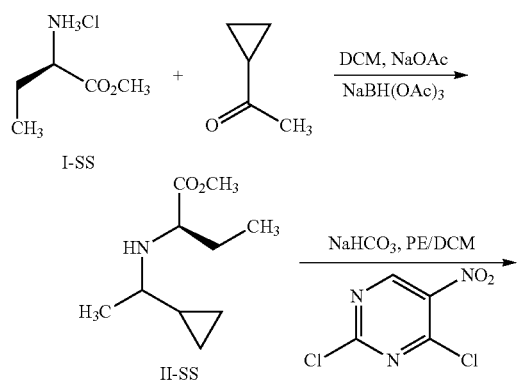

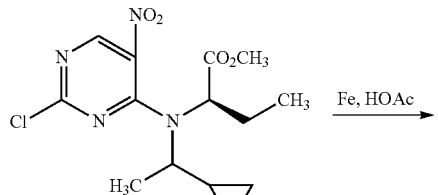

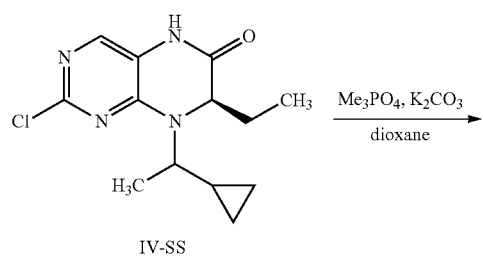

Intermediate SS is prepared from compound I-SS via compound II-SS, III-SS and IV-SS similarly to the methods used in preparing compound III-J, Intermediate J-1, compound IV-J and Intermediate J as described above, with (R)-methyl 2-aminobutanoate hydrochloride used instead of (R)-methyl 2-aminobutanoate and with cyclopropylethanone instead of dihydro-2H-pyran-4(3H)-one in the first step, and with PE/dichloromethane instead of PE/1,2-dichloroethane as solvent in the coupling of 2,4-dichloro-5-nitropyrimidine with compound II-SS. Compound III-SS; LCMS: 343.1 m/z (M+H)+. Compound IV-SS; LCMS: 281.1 m/z (M+H)+. Intermediate SS. LCMS: 295 m/z (M+H)+.

2-Chloro-8-(4-chlorophenyl)-7-ethyl-5-methyl-7,8-dihydropteridin-6(5H)-one (Intermediate TT)

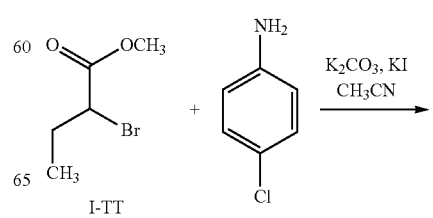

-continued
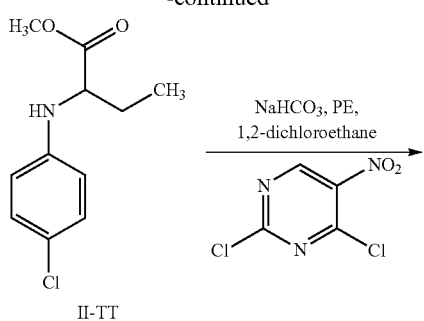
II-TT
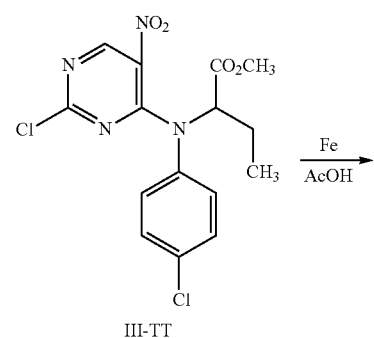
III-TT
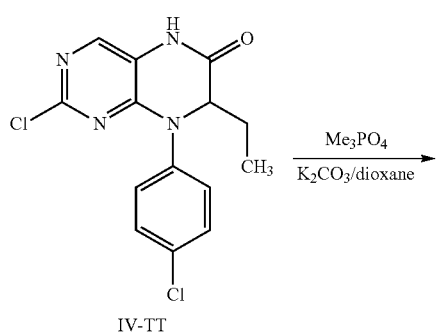
IV-TT
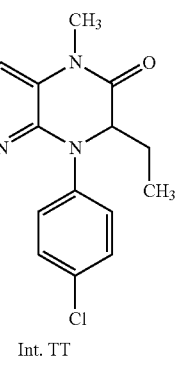
Int. TT
Intermediate TT was prepared by the same method used to prepare Intermediate EE with 4-chloroaniline instead of 4-fluoroaniline.
2-Chloro-8-(3,4-difluorophenyl)-7-ethyl-5-methyl-7,8-dihydropteridin-6(5H)-one (Intermediate UU)
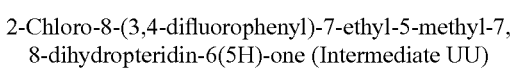
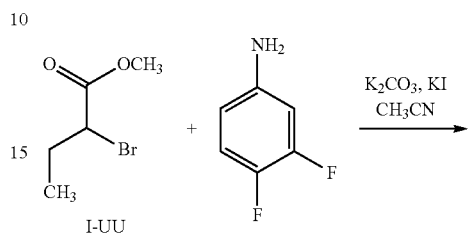
I-UU
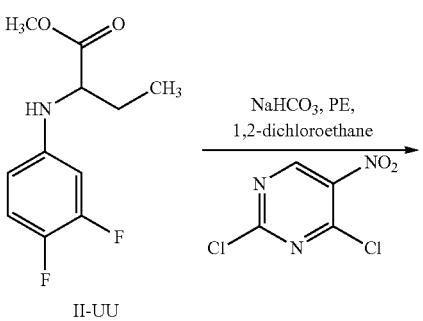
II-UU
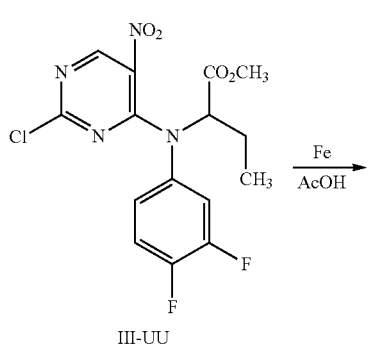
III-UU
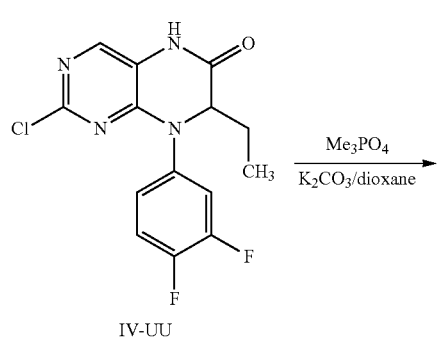
IV-UU -continued

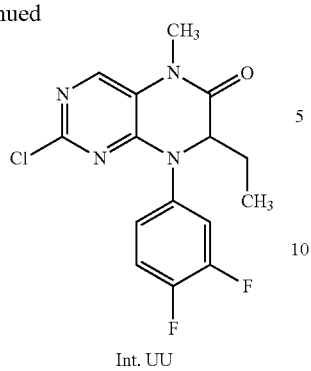

Int. UU

Intermediate UU was prepared similarly to the method used to prepare Intermediate EE with 3,4-difluoroaniline instead of 4-fluoroaniline.

2-Chloro-7-ethyl-5,7-dimethyl-8-(3,3,3-trifluoropropyl)-7,8-dihydropteridin-6(5H)-one (Intermediate VV)

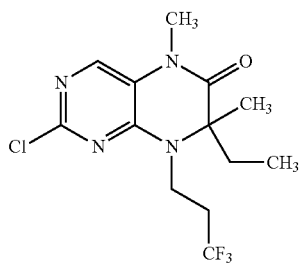

Int. VV

Intermediate VV was prepared similarly to the method used to prepare Intermediate U with methyl 2-amino-2-methylbutanoate substituted for R-methyl 2-aminobutanoate.

Synthesis of Imidazole Intermediates

A number of methods exist in the literature that describe the synthesis of the required imidazole analogs used in the examples herein. For methods that access imidazoles from aldehydes via the dihydroimidazoles followed by oxidation to the imidazole see: Fujioka et al., Tetrahedron Letters 46 (2005) 2197-2199; Gogoi, Konwar, Tetrahedron Letters 47 (2006) 79-82; Nicolaou et al, J. Am. Chem. Soc. 2004, 126, 5192-5201; or Ishihara, Togo, Synlett. 2006, 227-230. For a one-pot method from aryl and heteroaryl nitriles see: Voss et al. Tetrahedron 2008, 64, 645-51. These references are hereby incorporated by reference herein as they relate to the synthesis of such imidazoles.

Synthesis of 2-(4-(methylsulfonyl)phenyl)-1H-imidazole (Imidazole 1)

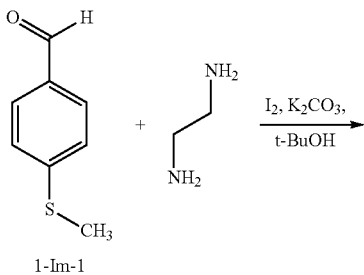

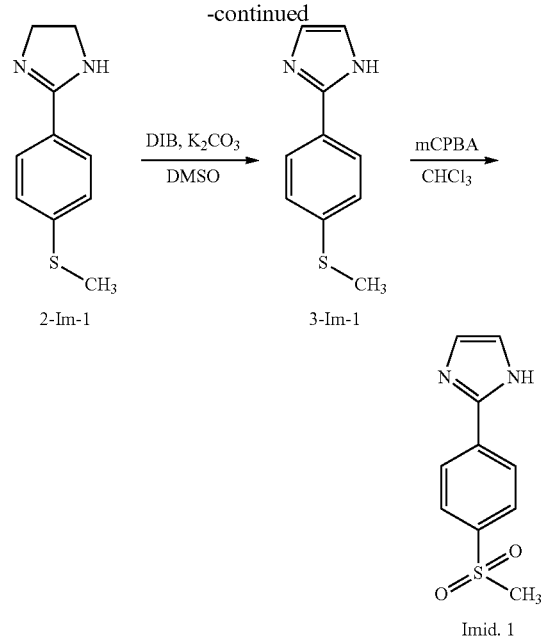

To a solution of 4-(methylthio)benzaldehyde (1-Im-1, 10 g, 1.0 eq) in 1000 mL of t-BuOH, ethylene diamine (1.1 eq) was added. The mixture was stirred at rt under Ar for 30 min, then $K_2CO_3$ (3.0 eq) and $I_2$ (1.25 eq) were added to the mixture. This mixture was stirred at 70° C. for 3 h, then was quenched with aqueous $Na_2SO_3$ until the color of iodine disappeared, then extracted with $CHCl_3$. The organic layer was washed with $NaHCO_3$ and brine and dried with $Na_2SO_4$. The solvent was removed to give 2-(4-(methylthio)phenyl)-4,5-dihydro-1H-imidazole (compound 2-Im-1).

To a solution of 2-(4-(methylthio)phenyl)-4,5-dihydro-1H-imidazole (2-Im-1, 9.6 g, 1.0 eq) in 100 mL of DMSO, DIB (1.1 eq) and $K_2CO_3$ (1.1 eq) were added. The mixture was heated to 70° C. overnight, then extracted with EtOAc and the organic layer was concentrated to provide 2-(4-(methylthio)phenyl)-1H-imidazole (compound 3-Im-1).

To a stirred solution of 2-(4-(methylthio)phenyl)-1H-imidazole (3-Im-1, 5 g, 1.0 eq) in 50 mL of $CHCl_3$, m-CPBA (2.0 eq) was added and the reaction was stirred at rt for 1 h, then washed with 5% aqueous $Na_2SO_3$ and aqueous $Na_2CO_3$ and extracted with EtOAc. The organic layer was dried over $Na_2SO_4$, concentrated and the residue was purified by silica column (80% EtOAc: 20% MeOH) to give Imidazole 1. LCMS (0.01% Ammonia): 223.1 m/z $(M+H)^+$; $^1$H-NMR (DMSO-d6, 500 MHz): δ: 12.87 (s, 1H), 8.17 (d, 2H, J=8.5 Hz), 8.00 (d, 2H, J=8.5 Hz), 7.38 (s, 1H), 7.13 (s, 1H), 3.25 (s, 3H).

Synthesis of 2-(1H-imidazol-2-yl)thiazole (Imidazole 2)

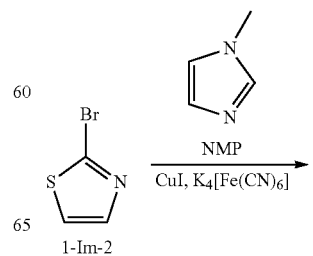

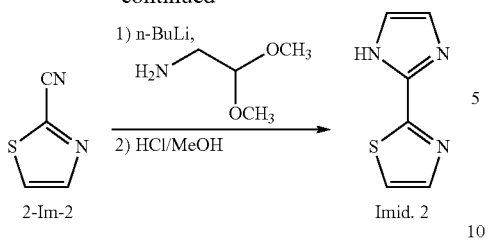

2-Bromothiazole (13.0 g, 1.0 eq), 1-methyl-imidazole (2.0 eq), CuI (0.05 eq) and K[Fe(CN)$_6$] (0.1 eq) were combined in 80 mL of dry NMP and heated in a sealed tube at 140° C. for 16 h. This mixture was extracted with EtOAc and solvent was removed from the organic fraction to give thiazole-2-carbonitrile (compound 2-Im-2).

A 2.5 M solution of nBuLi (2.0 eq) in hexane was added under argon to a solution of 2,2-dimethoxyethanamine (2.0 eq) in THF at −78° C. After stirring for 30 min, thiazole-2-carbonitrile (2-Im-2, 3.0 g, 1.0 eq) was added and the resulting solution was stirred at 0° C. for 2 h, then quenched with 20 mL of 5% MeOH in water. The volatiles were removed and 6N HCl was added to adjust to pH=1. The acidic solution was refluxed overnight, cooled to rt then poured into a mixture of ice and aqueous Na$_2$CO$_3$. This was extracted with EtOAc and the organic layer was concentrated to give Imadazole 2. LCMS (0.01% Ammonia): 152.1 m/z (M+H)$^+$; $^1$H-NMR (DMSO-d6, 500 MHz): δ: 13.19 (bs, 1H), 7.98 (d, 1H, J=3.0 Hz), 7.82 (d, 1H, J=3.0 Hz), 7.36 (s, 1H), 7.14 (s, 1H).

Synthesis of 2-(1H-imidazol-2-yl)pyrimidine (Imidazole 3)

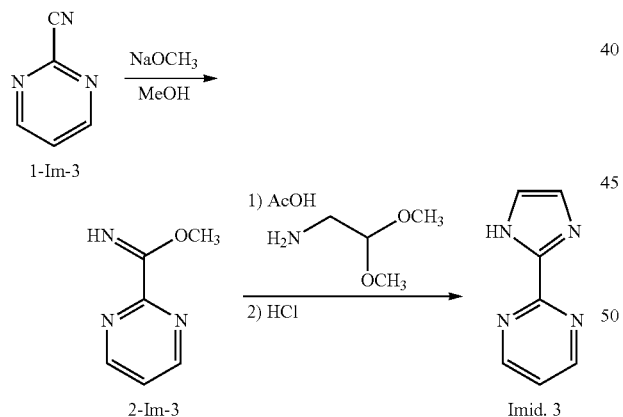

To a solution of NaOCH$_3$ (270 mg) in 50 mL of MeOH, pyrimidine-2-carbonitrile (1-Im-3, 50 mmol) was added. The mixture was stirred at rt for 1 h, then 2,2-dimethoxyethanamine (50 mmol) was added followed by 2 mL of AcOH. This mixture was stirred for 1 h, then 6N HCl was added to adjust pH=1. The resulting acidic solution was heated at reflux for 18 h. After cooling to rt, the reaction was poured into a mixture of ice and aqueous Na$_2$CO$_3$ solution, then extracted with EtOAc and the organic layer was concentrated to give 2-(1H-imidazol-2-yl)pyrimidine (Imidazole 3). LCMS (0.01% Ammonia): 147.2 m/z (M+H)$^+$; $^1$H-NMR (DMSO-d6, 500 MHz): δ: 13.04 (bs, 1H), 8.87 (d, 2H, J=5.0 Hz), 7.44 (t, 1H, J=5.0 Hz), 7.24 (s, 2H).

2-(4-(trifluoromethyl)phenyl)-1H-imidazole (Imidazole 4), 2-(4-(trifluoromethoxy)phenyl)-1H-imidazole (Imidazole 5), 2-(3-(trifluoromethoxy)phenyl)-1H-imidazole (Imidazole 6, and) 2-(1H-imidazol-2-yl)pyrazine (Imidazole 7)

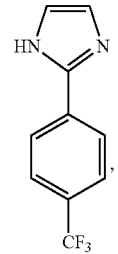

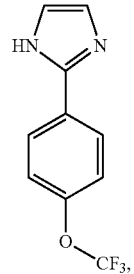

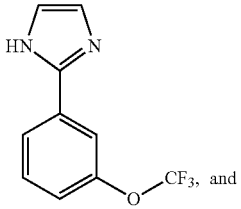

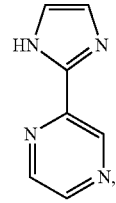

The Imidazoles 4, 5, 6 and 7 were prepared similarly to the methods used for the synthesis of Imidazole 3, with 4-(trifluoromethyl)benzonitrile, 4-(trifluoromethoxy)benzonitrile, 3-(trifluoromethoxy)benzonitrile, and pyrazine-2-carbonitrile, respectively, instead of pyrimidine-2-carbonitrile in the first step. Imidazole 4; LCMS (0.05% TFA): 213.1 m/z (M+H)$^+$; $^1$H-NMR (DMSO-d6, 500 MHz): δ:12.82 (bs, 1H), 8.15 (d, 2H, J=8.5 Hz), 7.82 (d, 2H, J=8.5 Hz), 7.35 (s, 1H), 7.12 (s, 1H). Imidazole 5; LCMS (0.01% Ammonia): 229.1 m/z (M+H)$^+$; $^1$H-NMR (DMSO-d6, 500 MHz): δ: 12.68 (bs, 1H), 8.07 (m, 2H), 7.46 (d, 2H, J=8.5 Hz), 7.19 (bs, 2H). Imidazole 6; LCMS (0.01% Ammonia): 229.1 m/z (M+H)$^+$; $^1$H-NMR (DMSO-d6, 500 MHz): δ: 12.73 (bs, 1H), 7.97 (d, 1H, J=8.0 Hz), 7.90 (s, 1H), 7.59 (t, 1H, J=8.0 Hz), 7.33 (d, 2H, J=8.0 Hz), 7.07 (s, 1H). Imidazole 7; LCMS (0.01% Ammonia): 147.2 m/z (M+H)$^+$; $^1$H-NMR (DMSO-d6, 500 MHz): δ: 13.19 (bs, 1H), 9.34 (d, 1H, J=1.5 Hz), 8.70 (dd, 1H, J$^1$=3 Hz, J$^2$=1.5 Hz), 8.65 (d, 1H, J=3 Hz), 7.34 (bs, 2H).

Synthesis of 3-(1H-imidazol-2-yl)pyridazine
(Imidazole 8)

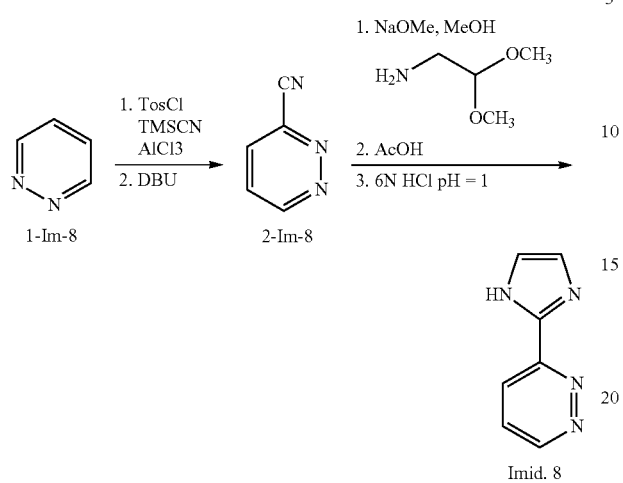

The mixture of pyridazine (1-Im-8, 1 eq), TMSCN (1.8 eq) and AlCl₃ (0.01 eq) in dry DCM was stirred for 1 h under Ar at 0° C., then TosCl (1.72 eq) was added. The resulting mixture was stirred for 48 h under Ar at rt. The solvent was removed under reduced pressure, then the residue was treated with EtOH and the reaction was filtered give a solid. The solid was added to dry THF, then DBU (1.2 eq) was added to the mixture. The mixture was stirred for 2 h under Ar at rt, then aqueous NH₄Cl was added and the mixture was extracted with EtOAc, the organic layer was dried with Na₂SO₄, concentrated and the residue was purified by silica column chromatography to give pyridazine-3-carbonitrile (compound 2-Im-8).

pyridazine-3-carbonitrile (compound 2-Im-8, 1 eq) was added to NaOMe (0.5 eq) in MeOH and stirred for 3 h at rt, then 2,2-dimethoxyethanamine (1 eq) and AcOH (2 eq) were added to the mixture and stirred for 2 h under Ar at 50° C. After this time, 6N HCl was added to the mixture to adjust to pH=1; the mixture was heated to reflux for 18 h, then cooled to rt. The solvent was removed and the residue was treated with aqueous Na₂CO₃ to give a mixture at pH=10. The resulting solid was collected by filtration and washed with PE to give Imidazole 8. LCMS (0.01% Ammonia): 147.1 m/z (M+H)⁺; ¹H-NMR (DMSO-d6, 500 MHz): δ: 13.37 (bs, 1H), 9.21 (d, 1H, J=5.0 Hz), 8.24 (d, 1H, J=8.5 Hz), 7.79 (dd, 1H, J¹=8.5 Hz, J²=5.0 Hz), 7.37 (s, 1H), 7.19 (s, 1H).

Synthesis of 1-(1H-imidazol-2-yl)isoquinoline
(Imidazole 9)

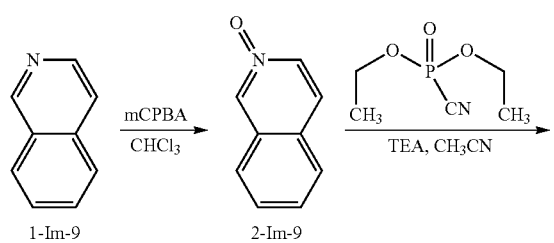

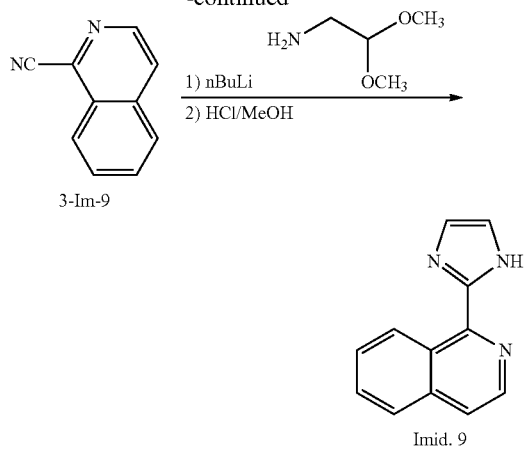

To a stirred solution of isoquinoline (1-Im-9, 5 g, 1.0 eq) in 50 mL of CHCl₃, mCPBA (2.0 eq) was added. The mixture was stirred at rt for 1 h. The reaction was washed with 5% aqueous Na₂SO₃ and aqueous Na₂CO₃, then concentrated and the residue was purified by silica column chromatography to give isoquinoline 2-oxide (2-Im-9).

To a stirred solution of isoquinoline 2-oxide (2-Im-9, 5.8 g) in 140 mL of acetonitrile, diethyl phosphoro-cyanidate (1.5 eq) was added under argon followed by slow addition of TEA (3.0 eq). The mixture was refluxed for 18 h and then extracted with DCM. The organic layer was concentrated and purified by silica column chromatography to give isoquinoline-1-carbonitrile (3-Im-9).

nBuLi (2.5 M in hexane, 2.0 eq) was added under argon to a solution of 2,2-dimethoxyethanamine (2.0 eq) in THF at −78° C. After stirring for 30 min, isoquinoline-1-carbonitrile (3-Im-9, 3.0 g, 1.0 eq) was added. The resulting solution was stirred at 0° C. for 2 h. The reaction was quenched with 20 mL of 5% MeOH in water, the volatiles were removed, then 6N HCl was added to adjust to pH=1. The acidified solution was refluxed 18 h, then cooled to rt and poured into ice/Na₂CO₃ solution. This was extracted with EtOAc and concentrated to provide Imidazole 9. LCMS (0.01% Ammonia): 196.1 m/z (M+H)⁺; ¹H-NMR (DMSO-d6, 500 MHz): δ: 12.93 (bs, 1H), 9.92 (d, 1H, J=8.0 Hz), 8.51 (d, 1H, J=5.5 Hz), 7.96 (d, 1H, J=8.0 Hz), 7.79 (d, 1H, J=5.5 Hz), 7.76 (t, 1H, J=8.0 Hz), 7.70 (t, 1H, J=8.0 Hz), 7.30 (s, 1H), 7.21 (s, 1H).

Synthesis of 3-(1H-imidazol-2-yl)quinoline
(Imidazole 10)

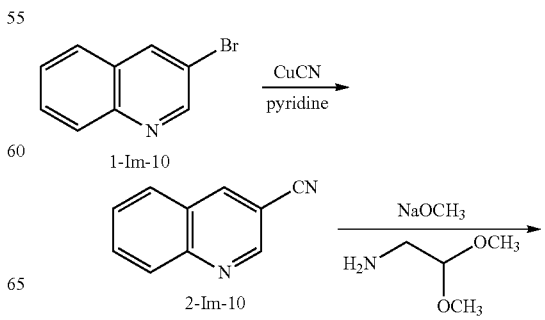

-continued

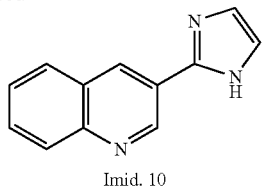

Imid. 10

A suspension of 3-bromoquinoline (1-Im-10, 1.5 g) and CuCN (3 eq) in 10 mL of pyridine in a 25 mL microwave tube was heated at 250° C. for 30 min in a microwave. This was repeated 10 times and the reactions were combined and diluted with 200 mL of EtOAc. The solids were removed by filtration and the EtOAc solution concentrated. The residue was taken up in a solution prepared from 80 mL of 30% aqueous $NH_3$ and 800 mL of water. This was extracted with EtOAc (4×800 mL) then the combined extracts were dried with anhydrous $Na_2SO_4$, concentrated and purified by silica gel chromatography (PE:EtOAc=3:1) to give quinoline-3-carbonitrile (2-Im-10).

Quinoline-3-carbonitrile (2-Im-10, 10 g) was suspended in 65 mL of MeOH, then $NaOCH_3$ (0.1 eq) was added and the reaction was stirred at 25° C. for 15 h. 2,2-Dimethoxyethanamine (1 eq) was added, followed by acetic acid (2 eq) and the mixture was heated at 50° C. for 1 h. The reaction was cooled to rt and 30 mL of 6N HCl was added to give a pH=1 and this mixture was heated at reflux for 5 h. The reaction was diluted with 200 mL of water and extracted with EtOAc (2×200 mL). The aqueous phase was made basic (pH=10) with solid sodium carbonate and the desired compound precipitated out and was isolated by filtration and washed with water to give Imidazole 10. LCMS (0.01% Ammonia): 196.2 m/z $(M+H)^+$; $^1$H-NMR (DMSO-d6, 500 MHz): δ: 12.92 (bs, 1H), 9.51 (d, 1H, J=2.0 Hz), 8.78 (d, 1H, J=2.0 Hz), 8.03 (dd, 2H, J=8.5 Hz), 7.77 (t, 1H, J=8.0 Hz), 7.65 (t, 1H, J=8.0 Hz), 7.28 (bs, 2H).

Synthesis of 2-(4-isopropylphenyl)-1H-imidazole (Imidazole 11)

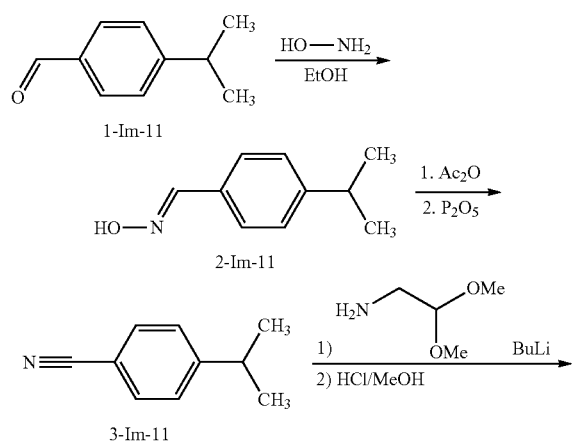

To a solution of compound 1-Im-11 (14.8 g, 1.0 eq) in 148 mL of EtOH, hydroxylamine hydrochloride (1.0 eq) was added. The reaction mixture was stirred at rt for 1 h and concentrated to give compound 2-Im-11.

Compound 2-Im-11 (13.04 g, 1.0 eq) was dissolved in 40 mL of $Ac_2O$ and refluxed for 3 h, then cooled to room temperature and $P_2O_5$ (800 mg) was added; the resulting mixture was refluxed for another 30 min. This was extracted with a mixture of 9:1 PE:EtOAc and purified by silica column chromatography to give compound 3-Im-11.

n-BuLi (2.5M in hexane, 2.0 eq) was added under argon to a solution of dimethoxyethanamine (2.0 eq) in THF at −78° C. This was stirred for 30 min at −78° C., then compound 3-Im-11 (3.0 g, 1.0 eq) was added. The resulting solution was stirred at 0° C. for 2 h, then quenched with 5% $MeOH/H_2O$. The solvent was removed and then HCl (6N) was added until pH=1; this mixture was refluxed for 18 h, then the reaction was cooled to room temperature and poured into ice/aq. $Na_2CO_3$ mixture, extracted with EtOAc and purified by silica column chromatography to provide Imidazole 11. LCMS (0.05% TFA): 187.2 m/z $(M+H)^+$; $^1$H-NMR (DMSO-d6, 500 MHz): δ: 12.41 (bs, 1H), 7.85 (d, 2H, J=8.0 Hz), 7.30 (d, 2H, J=8.0 Hz), 7.10 (bs, 2H), 2.91 (m, 1H), 1.19 (d, 6H, J=18.5 Hz).

2-(3-isopropylphenyl)-1H-imidazole (Imidazole 12)

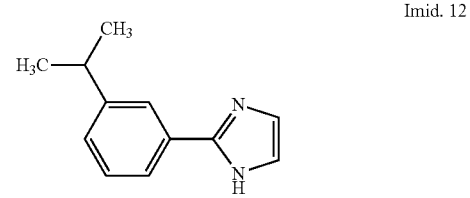

Imidazole 12 was prepared similarly to the method used for Imidazole 11 with 3-isopropylbenzaldehyde instead of 4-isopropylbenzaldehyde. LCMS (0.05% TFA): 187.2 m/z $(M+H)^+$; $^1$H-NMR ($CDCl_3$, 500 MHz): δ: 13.21 (bs, 1H), 7.85 (s, 1H), 7.77 (d, 1H, J=8.0 Hz), 7.21 (t, 1H, J=8.0 Hz), 7.16 (s, 2H), 7.14 (t, 1H, J=8.0 Hz), 2.72 (m, 1H), 1.05 (d, 6H, J=7.0 Hz).

Preparation of Boronic Acids 5-(thiazol-2-yl)-1-((2-(trimethylsilyl)ethoxy)methyl)-1H-pyrazol-4-ylboronic acid (Boronic Acid 1)

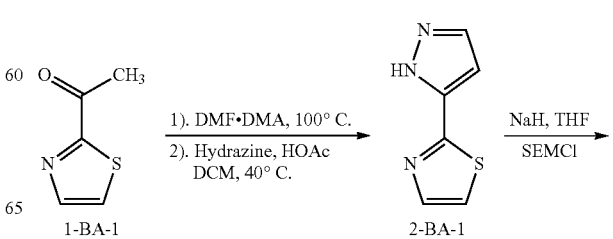

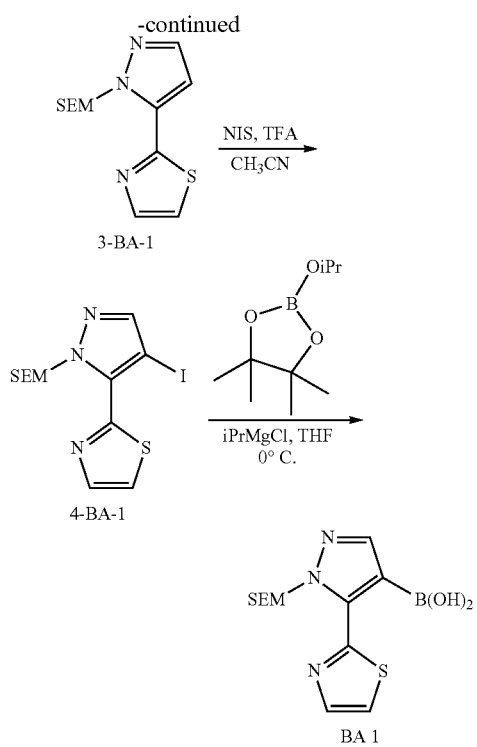

Dissolved 1-(thiazol-2-yl)ethanone (1-BA-1, 5 g, 39.7 mmole) in DMF DMA (9.5 g, 2 eq). The resulting mixture was warmed to 100° C. until all the ketone starting material was consumed. This material was concentrated under reduced pressure to give 6.5 g of crude intermediate. This material was dissolved in 25 mL of DCM and 5 mL of HOAc was added, followed by hydrazine (5 g, 4 eq) at 0° C. The resulting mixture was heated at reflux until all the starting material was consumed. The reaction mixture was cooled to rt and neutralized with 30 mL of a saturated NaHCO$_3$ solution. The layers were separated and the aqueous layer was extracted with DCM (2×50 mL). The organic layers were dried over MgSO$_4$, filtered, and concentrated under reduced pressure. The crude material was purified by MPLC (eluted with 0-20% MeOH/DCM) to give 2-(1H-pyrazol-5-yl)thiazole (Compound 2-BA-1, ~6 g). LC/MS: 152.0 m/z (M+H)$^+$.

To a stirring mixture of 2-(1H-pyrazol-5-yl)thiazole (Compound I-BA-1, 6.5 g) in 50 mL of THF, NaH (1.8 g, 43 mmole, 60% by weight) was added in portions. The reaction mixture was stirred at rt for 20 min before SEM-Cl (7.8 g, 47.3 mmole) was added dropwise. The reaction mixture was stirred at rt until all the starting material was consumed. The crude reaction mixture was slowly quenched with 50 mL of water, 50 mL of brine, and diluted with 50 mL of EtOAc. The layers were separated and the aqueous layer was extracted with EtOAc (2×50 mL). The organic layer was concentrated and purified by MPLC [0-50% EtOAc/hex] to give 2-(1-((2-(trimethylsilyl)ethoxy)methyl)-1H-pyrazol-5-yl)thiazole (Compound 3-BA-1, 11.3 g). LCMS: 282.1 m/z (M+H)$^+$.

To a stirring mixture of 2-(1-((2-(trimethylsilyl)ethoxy)methyl)-1H-pyrazol-5-yl)thiazole (Compound 2-BA-1) in 50 mL of acetonitrile at rt under nitrogen were added TFA (1 mL) and NIS (10.8 g). The reaction mixture was stirred at rt overnight and an additional amount of NIS (0.5 eq to 1.0 eq) was added as needed. The crude reaction mixture was slowly quenched with ~30 mL of a saturated aqueous Na$_2$S$_2$O$_3$ solution, and ~30 mL of a saturated aqueous NaHCO$_3$ solution.

The reaction mixture was diluted with 50 mL of EtOAc, the layers were separated and the aqueous layer was extracted with EtOAc (2×50 mL). The organic layer was purified by MPLC (eluted with 0-50% EtOAc/hex) to give 2-(4-iodo-1-((2-(trimethylsilyl)ethoxy)methyl)-1H-pyrazol-5-yl)thiazole (Compound 4-BA-1). LCMS: 408.0 m/z (M+H)$^+$.

To stirring mixture of 2-(4-iodo-1-((2-(trimethylsilyl)ethoxy)methyl)-1H-pyrazol-5-yl)thiazole (Compound 4-BA-1, 11.3 g) in THF (0.35 M) at 0° C., a solution of iPrMgCl (16 mL, 1.2 eq) in THF was added dropwise. The reaction mixture was stirred for 30 min before 2-isopropoxy-4,4,5,5-tetramethyl-1,3,2-dioxaborolane (9.1 mL, 1.6 eq) was added over 10 min. The cold bath was removed and the resulting mixture was stirred at rt for 1 hr. The mixture was diluted with 50 mL of EtOAc and quenched with 25 mL of a saturated aqueous NH$_4$Cl solution. The layers were separated and the aqueous layer was extracted with EtOAc. The organic portion was purified by MPLC (eluted with 0-100% EtOAc/Hex) to give Boronic Acid 1. LCMS: 326.1 m/z (M+H)$^+$.

5-(pyridin-2-yl)-1-((2-(trimethylsilyl)ethoxy)methyl)-1H-pyrazol-4-ylboronic acid (Boronic Acid 3) and 5-(2,4-difluorophenyl)-4-(4,4,5,5-tetramethyl-1,3,2-dioxaborolan-2-yl)-1-((2-(trimethylsilyl)ethoxy)methyl)-1H-pyrazole (Boronic Acid 4)

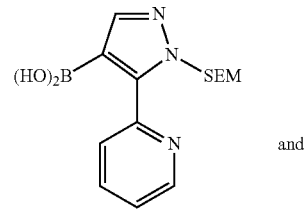

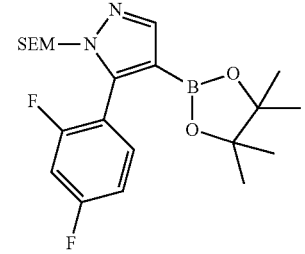

are prepared similarly with 1-(pyridin-2-yl)ethanone and 1-(2,4-difluorophenyl)ethanone, respectively, instead of 1-(thiazol-2-yl)ethanone in the first step. Boronic Acid 4 is isolated and used as the dioxaborolane ester.

Preparation of 3-phenyl-4-(4,4,5,5-tetramethyl-1,3,2-dioxaborolan-2-yl)pyridine (Boronic Acid 2)

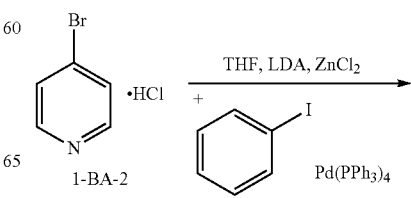

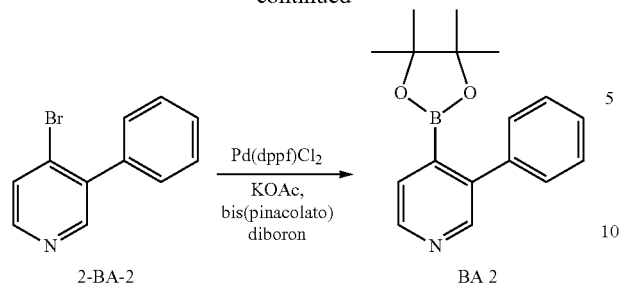

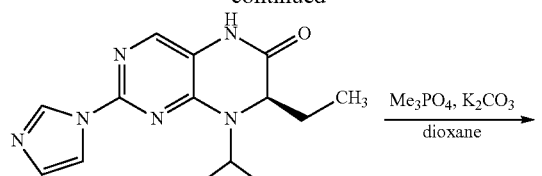

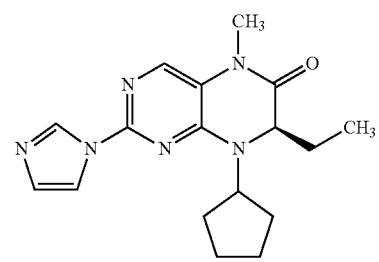

4-bromopyridine hydrochloride (1-BA-2, 1 g, 5.14 mmol) was dissolved in 5.1 mL of THF and the resulting solution was cooled to −78° C. LDA (10.28 mL of a 1 M solution in THF) was added over 10 minutes and the reaction mixture became brown. After stirring for 30 minutes, ZnCl$_2$ (10.3 mL of a 0.5 M solution in THF) was added over 10 minutes and the resulting mixture was stirred for 10 minutes and then allowed to warm to rt. Iodobenzene (0.229 mL, 2.06 mmol) and Pd(PPh$_3$)$_4$ (593 mg, 0.514 mmol) were added and the resulting mixture was stirred under reflux for 2 h. The reaction mixture was diluted with aqueous saturated ammonium chloride and extracted with ethyl acetate. The organic phase was dried over Na$_2$SO$_4$ and evaporated. The residue was purified by silica column (hexane:EtOAc) to give 4-bromo-3-phenylpyridine (2-BA-2, 741 mg, 62%); LCMS: 234.0 m/z (M+H)$^+$.

4-bromo-3-phenylpyridine (2-BA-2, 0.11 mg, 0.469 mmol), Pd(dppf)Cl$_2$ (34 mg, 0.0469 mmol), KOAc (138 mg, 1.41 mmol) and bis(pinacolato)diboron (238 mg, 0.939 mmol) were dissolved in 1.5 mL of DMF and a stream of nitrogen was bubbled through the solution for 5 minutes. The resulting solution was stirred at 90° C. for 18 hours and was subsequently diluted with ethyl acetate and washed with brine. The organic phase was dried over Na$_2$SO$_4$ and evaporated to give Boronic Acid 2 (741 mg, 62%); LCMS: 282.2 m/z (M+H)$^+$.

Example 3

Synthesis of (R)-8-cyclopentyl-7-ethyl-2-(1H-imidazol-1-yl)-5-methyl-7,8-dihydropteridin-6(5H)-one

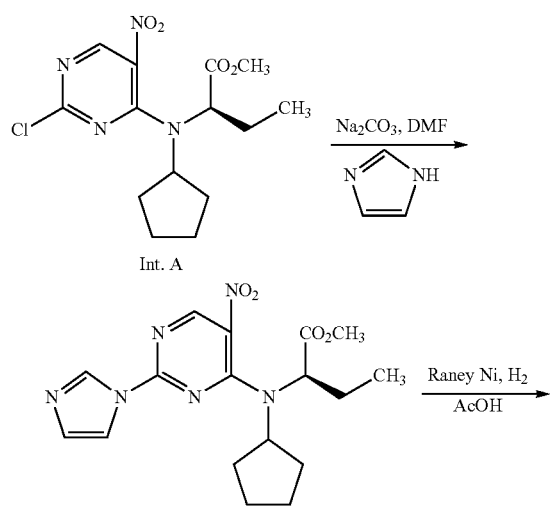

To a solution of intermediate A (340 mg, 1 mmol) in DMF (10 ml) was added Na$_2$CO$_3$ (106 mg, 1 eq) and 1H-imidazole (113 mg, 1.6 eq). The mixture was stirred at 100° C. for 3 hr under N$_2$, then was diluted with water and extracted with EtOAc. The solvent was removed by evaporation and the residue was purified by silica column to give (R)-methyl 2-((2-(1H-imidazol-1-yl)-5-nitropyrimidin-4-yl)(cyclopentyl)amino)-butanoate (300 mg, 80% yield).

To a solution of the above butanoate (192 mg) in AcOH (4 mL) was added Raney Ni (89 mg) and the mixture was stirred under H$_2$ at 75° C. for 5 hr until the starting material was consumed. The solvent was removed and the residue was purified by flash silica column to give (R)-8-cyclopentyl-7-ethyl-2-(1H-imidazol-1-yl)-7,8-dihydropteridin-6(5H)-one (120 mg, 72% yield).

To a solution of the above pteridinone (120 mg) in dioxane (5 mL) was added K$_2$CO$_3$ (106 mg, 2 eq) and trimethyl phosphate (538 mg, 10 eq). The mixture was stirred at 90° C. for 5 hr under N$_2$ then it was diluted with water and extracted with EtOAc. The solvent was removed by evaporation and the residue was purified by flash silica gel chromatography to give the title compound (108 mg, 89% yield). LCMS (0.01% ammonia): 327.2 m/z (M+H)$^+$; $^1$H-NMR (CDCl$_3$): δ: 8.50 (s, 1H), 7.78 (s, 1H), 7.76 (s, 1H), 7.14 (s, 1H), 4.31 (m, 2H), 2.01 (m, 1H), 1.87-2.00 (m, 6H), 1.70-1.78 (m, 3H), 0.88 (t, 3H, J=6.4 Hz).

Methods similar to those given in this example were used with suitable substitution of reactants, e.g. replacing Intermediate A with a suitable Intermediate, and/or replacing 1H-imidazole with a suitable optionally substituted ring, to prepare compounds as demonstrated in Examples 1, 2, 4, 18, 22, 24, 29, 30, 33, 42, 76, 80, 83, 101, 137, 144, 145, 160-163, 169, 170, 172, 180, 182, 184, 190-192, 203, 206, 211, 213, 218, 221, 225, 226, 230, 232-234, 236, 241, 244, 251-255, 268, 277, 282, 317, 326, 367, 376, 377, 380, 381, 386, 387, 418, and 431.

Example 5

Synthesis of (R)-8-cyclopentyl-7-ethyl-5-methyl-2-(pyridin-4-yl)-7,8-dihydropteridin-6(5H)-one

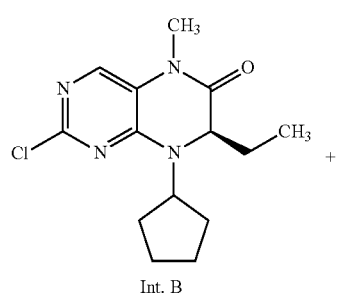
Int. B

+

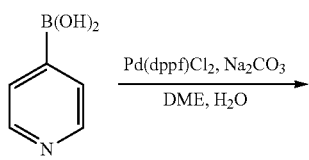

Pd(dppf)Cl$_2$, Na$_2$CO$_3$
DME, H$_2$O
→

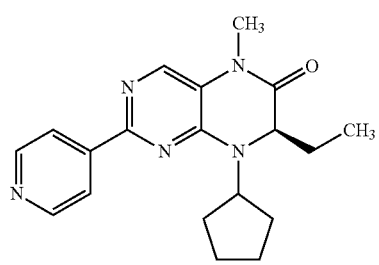

To a solution of 150 mg of intermediate B in DME (5 mL) and water (4:1) Pd(dppf)Cl$_2$ (75 mg), Na$_2$CO$_3$ (162 mg), and pyridin-4-ylboronic acid (90 mg) were added. The reaction mixture was heated in a microwave at 120° C. for 40 min. The mixture was concentrated and extracted with EtOAc and dried with Na$_2$SO$_4$. The solvent was removed and the residue was purified by silica column to give the title compound (107 mg, yield 64%). LCMS (0.05% TFA): 338.0 m/z (M+H)$^+$; $^1$H-NMR (CDCl$_3$, 400 MHz): δ: 8.72 (d, 2H, J=3.6 Hz), 8.17 (d, 2H, J=3.6 Hz), 7.80 (s, 1H), 4.46 (m, 1H), 4.32 (m, 1H), 3.40 (s, 3H), 2.17 (m, 1H), 2.06 (m, 1H), 1.99 (m, 1H), 1.92 (m, 4H), 1.70-1.76 (m, 3H), 0.88 (t, 3H, J=6 Hz).

Methods similar to those given in this example were used with suitable substitution of reactants, e.g. replacing Intermediate B with a suitable Intermediate, and/or replacing pyridin-4-ylboronic acid with a suitable boronic acid derivative, to prepare compounds as demonstrated in Examples 6-12, 23, 25, 31, 32, 34, 53, 57, 64, 66, 70-72, 85, 96, 98, 109, 110, 142, 146, 349, 353, 357, 363, 365, 370, 372, 382, 383, 393-396, 399, 400, 403, 404, 417, 419-427, 432, 434, and 435.

Example 7

Synthesis of (R)-8-cyclopentyl-7-ethyl-5-methyl-2-(1H-pyrazol-4-yl)-7,8-dihydropteridin-6(5H)-one

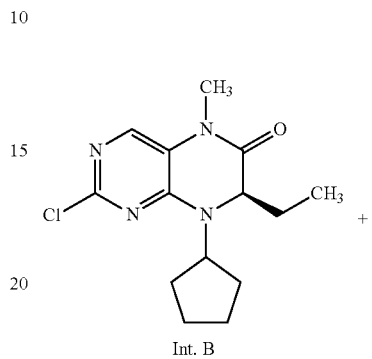
Int. B

+

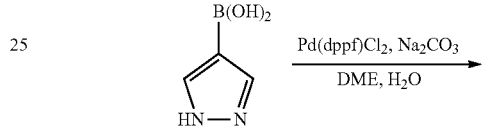

Pd(dppf)Cl$_2$, Na$_2$CO$_3$
DME, H$_2$O
→

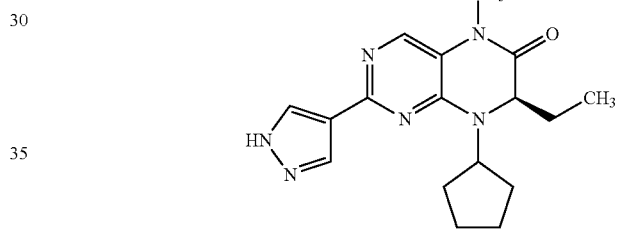

The title compound was prepared similarly to the methods described in Example 5, with pyrazol-4-ylboronic acid instead of pyridin-4-ylboronic acid. $^1$H NMR (CDCl$_3$) δ: 8.26 (broad, 2H) 7.86 (s, 1H), 4.37 (m, 1H), 4.27 (m, 1H), 3.35 (s, 3H), 2.1-1.6 (m, 10H) and 0.87 ppm (t, 3H); LCMS: 327.0 m/z (M+H)$^+$; ret. Time: 1.42 min (Analytical Method E).

Example 13

Synthesis of (R)-4-(8-cyclopentyl-7-ethyl-5-methyl-6-oxo-5,6,7,8-tetrahydropteridin-2-yl)pyridine 1-oxide

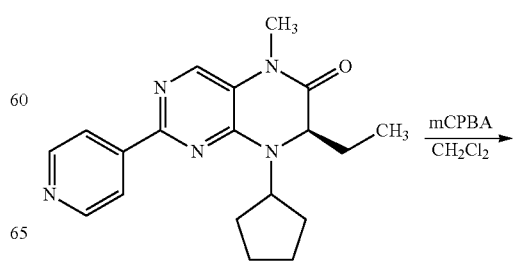

mCPBA
CH$_2$Cl$_2$
→

-continued

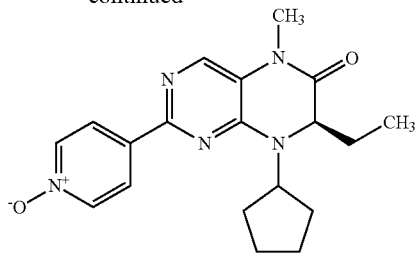

To a solution of (R)-8-cyclopentyl-7-ethyl-5-methyl-2-(pyridin-4-yl)-7,8-dihydropteridin-6(5H)-one (Example 5, 300 mg, 0.89 mmol) in 25 mL of DCM at 0° C., mCPBA (306 mg, 1.79 mmol) was added and the mixture was stirred at 0° C. for 3 hr, then at rt for another 3 hr. Saturated $Na_2S_2O_4$ was added and stirred at r.t. for 30 min. The mixture was extracted with DCM, washed with saturated $NaHCO_3$, concentrated and purified by preparative HPLC to give the title compound as a yellow oil (20 mg, 6.4%). $^1H$ NMR ($CDCl_3$) δ: 8.47 (d, 2H), 8.38 (d, 2H) 8.06 (s, 1H), 4.51 (m, 1H), 4.38 (m, 1H), 3.42 (s, 3H), 2.2-1.7 (m, 10H) and 0.89 ppm (t, 3H); LCMS: 354.2 m/z $(M+H)^+$; ret. Time: 1.79 min (Analytical Method E).

Example 14

Synthesis of (R)-8-cyclopentyl-7-ethyl-2-(2-hydroxypyridin-4-yl)-5-methyl-7,8-dihydropteridin-6(5H)-one

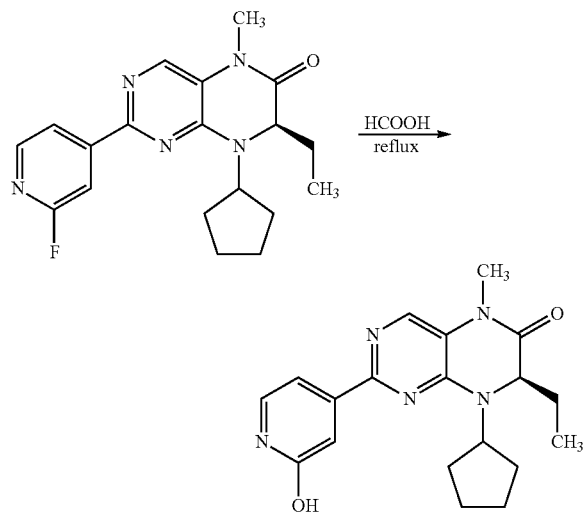

(R)-8-cyclopentyl-7-ethyl-2-(2-fluoropyridin-4-yl)-5-methyl-7,8-dihydropteridin-6(5H)-one (Example 16, 100 mg, 0.28 mmol) was dissolved in 3 mL of HCOOH. This mixture was heated to reflux for 18 h, then aqueous $NaHCO_3$ was added and the mixture was extracted with EtOAc. The combined organic phase was dried with $Na_2SO_4$, concentrated under reduced pressure and chromatographed on flash silica gel ($CH_2Cl_2$:$CH_3OH$=6:1) to give the title compound as a white solid (80 mg, 80% yield). $^1H$ NMR ($CD_3OD$) δ: 8.09 (s, 1H), 8.52 (d, 1H) 7.46 (s, 1H), 7.27 (m, 1H), 4.42-4.38 (m, 2H), 3.41 (s, 3H), 2.0-1.7 (m, 10H) and 0.86 ppm (t, 3H); LCMS: 354.2 m/z $(M+H)^+$; ret. Time: 1.36 min (Analytical Method E).

Example 16

Synthesis of (R)-8-cyclopentyl-7-ethyl-2-(2-fluoropyridin-4-yl)-5-methyl-7,8-dihydropteridin-6(5H)-one

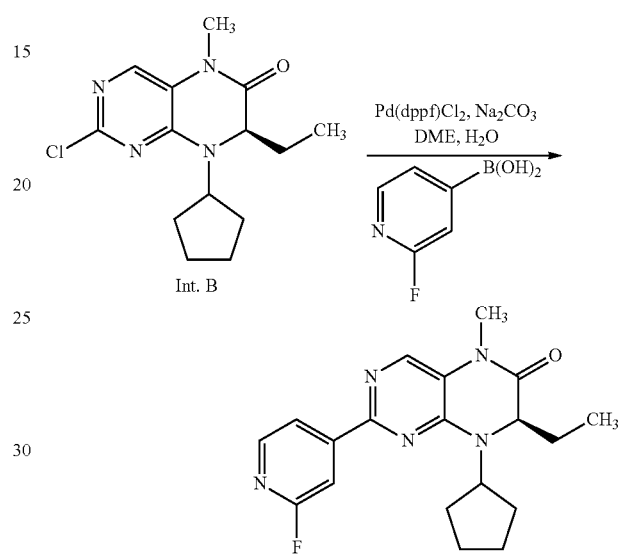

To a solution of intermediate B (300 mg, 1.2 mmol) in 6 mL of DME and 2 mL of water, 2-(fluoro)pyridin-4-ylboronic acid (719 mg, 5.1 mmol), Pd(dppf)$Cl_2$ (160 mg, 0.13 mmol), and 2M $Na_2CO_3$ (324 mg, 3.06 mL) were added. The mixture was microwave heated at 140° C. for about 40 min. The mixture was concentrated under reduced pressure and extracted with EtOAc. The combined organic phase was dried with $Na_2SO_4$ and concentrated under reduced pressure. The crude material was purified by silica gel flash column chromatography (PE:EA=75%) to give the title compound as a white solid (200 mg, 65% yield).

Example 19

Synthesis of (R)-8-cyclopentyl-7-ethyl-5-methyl-2-(1-methyl-2-oxo-1,2-dihydropyridin-4-yl)-7,8-dihydropteridin-6(5H)-one

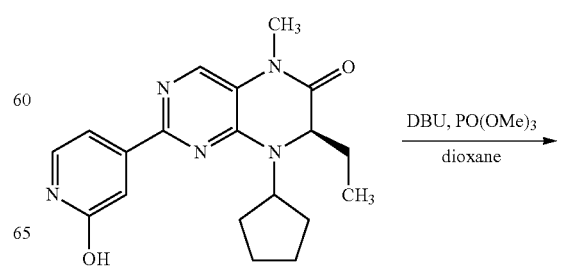

-continued

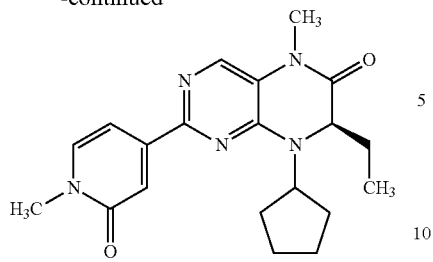

To a solution of (R)-8-cyclopentyl-7-ethyl-2-(2-hydroxy-pyridin-4-yl)-5-methyl-7,8-dihydropteridin-6(5H)-one (Example 14, 200 mg, 0.6 mmol) in 5 mL of 1,4-dioxane, DBU (26 mg, 3 mmol) and PO(OMe)$_3$ (42 mg, 3 mmol) were added, and the mixture was heated to reflux for 18 h, then concentrated under reduced pressure, and extracted with EtOAc. The combined organic phase was dried with Na$_2$SO$_4$, concentrated under reduced pressure and the residue was chromatographed (PE:EA=1:1) to give the title compound as a yellow solid (100 mg, 50% yield). $^1$H NMR (CDCl$_3$) δ: 7.95 (s, 1H), 7.53 (s, 1H) 7.35 (d, 1H), 7.11 (m, 1H), 4.54 (m, 1H), 4.29 (m, 1H), 3.6 (s, 3H), 3.38 (s, 3H), 2.2-1.6 (m, 10H) and 0.87 ppm (t, 3H); LCMS: 368.2 m/z (M+H)$^+$; ret. Time: 1.53 min (Analytical Method E).

Example 22

Synthesis of (R)-7-ethyl-2-(1H-imidazol-1-yl)-8-isopropyl-5-methyl-7,8-dihydropteridin-6(5H)-one

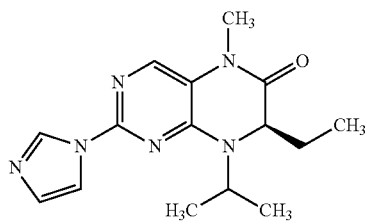 [SMILES: CC[C@@H]1C(=O)N(C)c2cnc(-n3ccnc3)nc2N1C(C)C]

The title compound was prepared similarly to the methods described in Example 3, with Intermediate C-1 instead of Intermediate A in the first step. $^1$H NMR (CDCl$_3$) δ: 8.5 (s, 1H), 7.79 (s, 1H), 7.75 (s, 1H), 7.13 (s, 1H), 4.51 (m, 1H), 4.36 (m, 1H), 3.37 (s, 3H), 1.99 (m, 1H), 1.78 (m, 1H), 1.45 (dd, 6H) and 0.87 ppm (t, 3H); LCMS: 301.2 m/z (M+H)$^+$; ret. Time: 1.31 min (Analytical Method E).

Example 26

Synthesis of (R)-8-cyclopentyl-7-ethyl-5-methyl-2-(2-phenyl-1H-imidazol-1-yl)-7,8-dihydropteridin-6(5H)-one

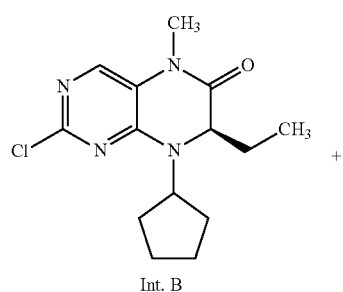

Int. B

-continued

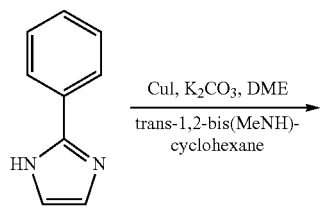

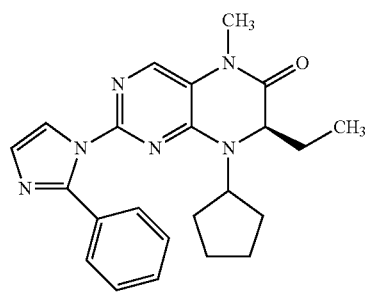

A mixture of intermediate B (50 mg, 0.17 mmol), 2-phenyl-1H-imidazole (3.4 mmol, 20 equivalents, 490 mg), CuI (0.05 equivalents, 0.009 mmol, 1.7 mg), trans-1,2-bis(methylamino)cyclohexane (14.2 mg, 0.003 mL) and K$_2$CO$_3$ (1.7 mmol, 233 mg) in 2 mL of DME were heated in a microwave at 200° C. for 2 h. The reaction was diluted with DME, filtered through Celite and evaporated. The residue was purified by reverse phase HPLC using a gradient of 30-50% CH$_3$CN (0.1% TFA) over 30 min with a flow rate of 20 mL/min eluting from a PCRP-5 column (2.5×30 cm). Following lyophylization, 22.8 mg of the title compound was obtained with a purity >99%. $^1$H NMR (CDCl$_3$) δ: 7.9-7.3 (m, 8H), 4.2 (m, 1H), 3.55 (m, 1H), 3.3 (s, 3H), 2.0-1.1 (m, 10H) and 0.85 ppm (t, 3H); LCMS: 403.2 m/z (M+H)$^+$; ret. Time: 3.77 min (Analytical Method A).

Methods similar to those given in this example were used with suitable substitution of reactants, e.g. replacing Intermediate B with a suitable Intermediate, and/or replacing 2-phenyl-1H-imidazole with a suitable optionally substituted ring, to prepare compounds as demonstrated in Examples 27, 47-52, 171, 183, 186, 205, 220, 227, and 228.

Example 35

Synthesis of (R)-2-(1-(8-cyclopentyl-7-ethyl-5-methyl-6-oxo-5,6,7,8-tetrahydropteridin-2-yl)-1H-imidazol-4-yl)acetonitrile

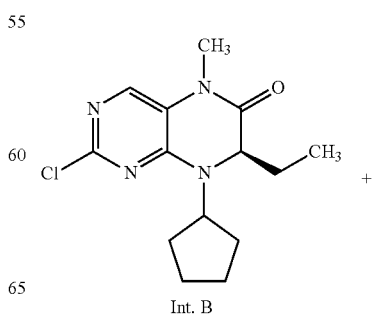

Int. B

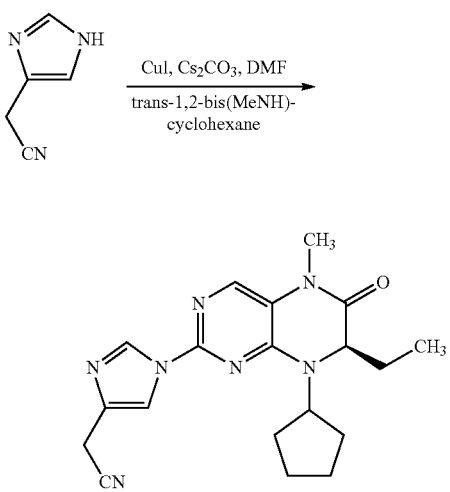

A mixture of intermediate B (150 mg, 0.509 mmol), 2-(1H-imidazol-4-yl)acetonitrile (1.01 mmol, 2 equivalents, 108 mg), CuI (0.1 equivalents, 0.0509 mmol, 10 mg), trans-1,2 bis(methylamino)cyclohexane (14 mg, 0.102 mmol) and $Cs_2CO_3$ (1.01 mmol, 331 mg) in DMF (1 mL) was purged with nitrogen and was subsequently heated in a sealed vial at 110° C. for 18 h. The reaction was diluted with ethyl acetate, filtered through Celite and evaporated. The residue was purified by reverse phase preparative HPLC and lyophilized to give the title compound (185 mg). $^1$H NMR (CDCl$_3$) δ: 8.66 (s, 1H), 7.91 (s, 1H), 7.76 (s, 1H), 4.31-4.37 (m, 2H), 3.91 (s, 2H), 3.38 (s, 3H), 1.70-2.13 (m, 10H), and 0.93 ppm (t, J=7.4 Hz, 3H); LCMS: 366.1 m/z (M+H)$^+$; ret. Time: 3.444 min (Analytical Method A).

Methods similar to those given in this example were used with suitable substitution of reactants, e.g. replacing Intermediate B with a suitable Intermediate, and/or replacing 2-(1H-imidazol-4-yl)acetonitrile with a suitable optionally substituted ring, to prepare compounds as demonstrated in Examples 36, 38, 43, 55, 56, 59, 67, and 111.

Example 37

Synthesis of (R)-1-(8-cyclopentyl-7-ethyl-5-methyl-6-oxo-5,6,7,8-tetrahydropteridin-2-yl)-1H-imidazole-4-carboxylic acid

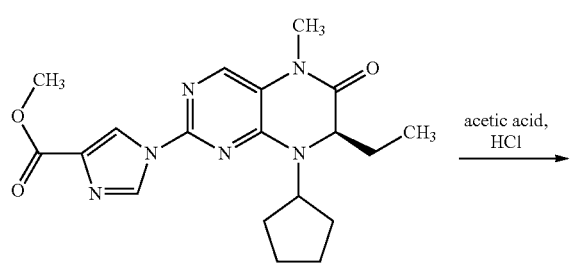

Ex. 38

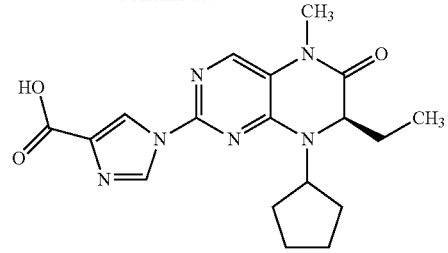

The title compound was prepared by dissolving (R)-methyl 1-(8-cyclopentyl-7-ethyl-5-methyl-6-oxo-5,6,7,8-tetrahydropteridin-2-yl)-1H-imidazole-4-carboxylate (Example 38, 0.51 g, 1.33 mmol) in 2 mL of acetic acid and 0.5 mL of concentrated aqueous HCl and heating the resulting solution to 100° C. for 4 hours. The solution was concentrated under vacuum and co-evaporated from toluene three times and the crude material was purified by preparative HPLC. $^1$H NMR (CDCl$_3$) δ: 8.73 (s, 1H), 8.50 (s, 1H), 7.78 (s, 1H), 4.44-4.45 (m, 1H), 4.32-4.36 (m, 1H), 3.39 (s, 3H), 1.71-2.17 (m, 10H), and 0.92 ppm (t, J=7.6 Hz, 3H); LCMS: 371.1 m/z (M+H)$^+$; ret. Time: 3.008 min (Analytical Method A).

Example 38

Synthesis of (R)-methyl 1-(8-cyclopentyl-7-ethyl-5-methyl-6-oxo-5,6,7,8-tetrahydropteridin-2-yl)-1H-imidazole-4-carboxylate

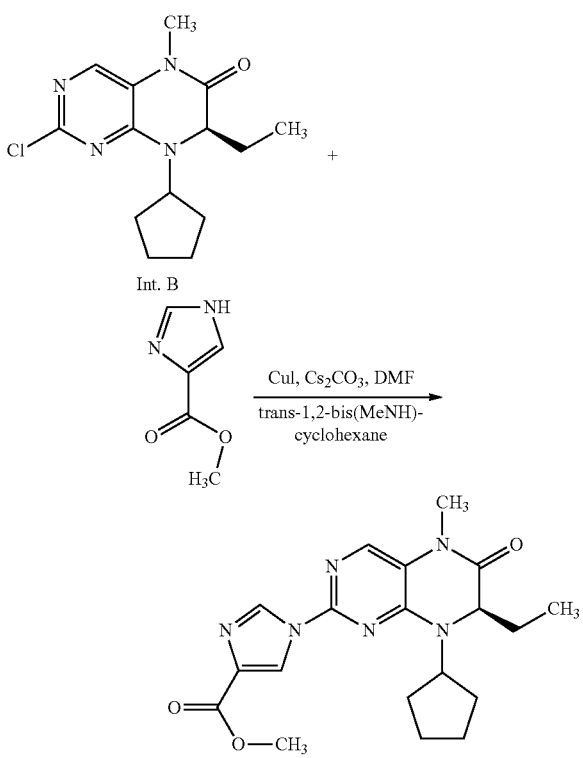

The title compound was prepared similarly to the methods described in Example 35, with methyl 1H-imidazole-4-carboxylate instead of 2-(1H-imidazol-4-yl)acetonitrile. $^1$H NMR (CDCl$_3$) δ: 8.67 (s, 1H), 8.45 (s, 1H), 7.76 (s, 1H), 4.31-4.47 (m, 2H), 3.94 (s, 3H), 3.38 (s, 3H), 1.73-2.14 (m, 10H), and 0.97 ppm (t, J=7.5 Hz, 3H); LCMS: 385.2 m/z (M+H)$^+$; ret. Time: 4.662 min (Analytical Method A).

Example 39

Synthesis of (R)-1-(8-cyclopentyl-7-ethyl-5-methyl-6-oxo-5,6,7,8-tetrahydropteridin-2-yl)-N,N-dimethyl-1H-pyrazole-4-carboxamide

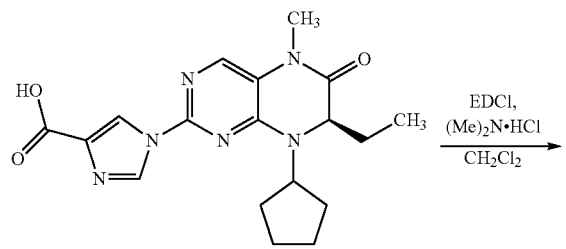

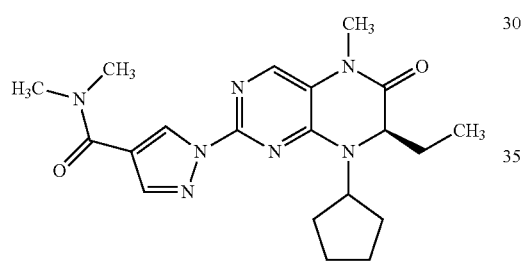

(R)-1-(8-Cyclopentyl-7-ethyl-5-methyl-6-oxo-5,6,7,8-tetrahydropteridin-2-yl)-1H-pyrazole-4-carboxylic acid (Example 44, 0.14 g, 0.378 mmol) was dissolved in 2 mL of DCM and EDCI (79 mg, 0.415 mmol), dimethylamine hydrochloride (46 mg, 0.567 mmol), HOAt (5 mg, 0.0379 mmol) and triethylamine (115 mg, 1.13 mmol) were added. The resulting solution was stirred at rt for 48 hours after which the reaction mixture was diluted with DCM and washed with 0.1 N aqueous HCl then 1 N aqueous NaOH, dried with Na$_2$SO$_4$, filtered, concentrated under vacuum and purified by preparative HPLC to give the title compound. $^1$H NMR (CDCl$_3$) δ: 7.55-7.57 (s, 1H), 7.40-7.51 (m, 2H), 4.26-4.51 (m, 2H), 3.11-3.39 (m, 9H), 1.64-2.18 (m, 10H), and 0.97 ppm (m, 3H); LCMS: 398.1 m/z (M+H)$^+$; ret. Time: 3.267 min (Analytical Method A).

Methods similar to those given in this example were used with suitable substitution of reactants, e.g. replacing the compound of Example 44 with a suitable carboxylic acid derivative compound, and/or replacing dimethylamine hydrochloride with a suitable amine compound, to prepare compounds as demonstrated in Examples 40, 41, 45, 46, 58, 61, 63, 69, and 384.

Example 40

Synthesis of (R)-1-(8-cyclopentyl-7-ethyl-5-methyl-6-oxo-5,6,7,8-tetrahydropteridin-2-yl)-N-methyl-1H-pyrazole-4-carboxamide

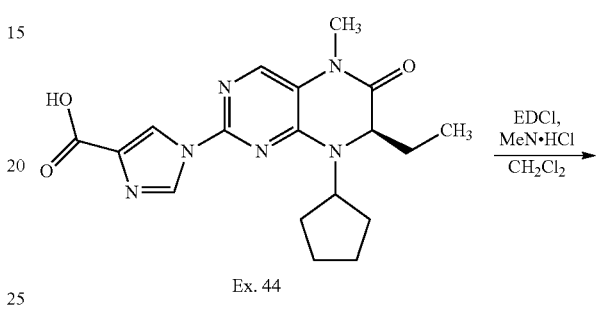

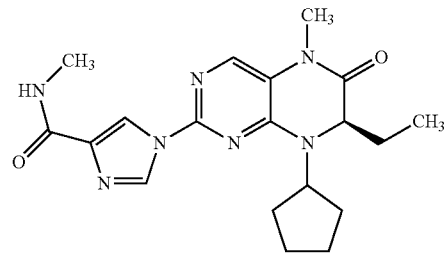

The title compound was prepared similarly to the methods described in Example 39, with methylamine hydrochloride instead of dimethylamine hydrochloride. $^1$H NMR (CDCl$_3$) δ: 8.90 (s, 1H), 7.91-8.10 (m, 2H), 4.53-4.60 (m, 1H), 4.29-4.32 (s, 1H), 3.39 (s, 3H), 2.99 (s, 3H), 1.70-2.20 (m, 10H), and 0.91 ppm (t, J=6.9 Hz, 3H); LCMS: 384.0 m/z (M+H)$^+$; ret. Time: 2.911 min (Analytical Method A).

Example 41

Synthesis of (R)-8-cyclopentyl-7-ethyl-5-methyl-2-(4-(morpholine-4-carbonyl)-1H-pyrazol-1-yl)-7,8-dihydropteridin-6(5H)-one

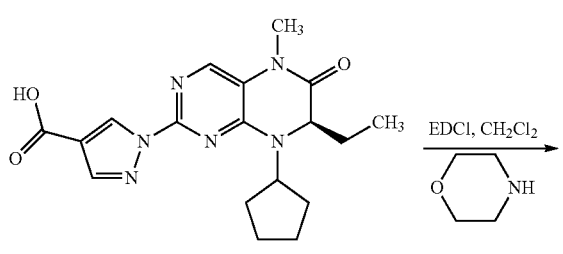

-continued

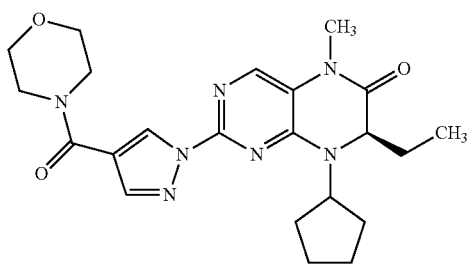

The title compound was prepared similarly to the methods described in Example 39, with morpholine instead of dimethylamine hydrochloride. $^1$H NMR (CDCl$_3$) δ: 8.80 (s, 1H), 7.98 (s, 1H), 7.94 (s, 1H), 4.51-4.59 (m, 1H), 4.39-4.42 (s, 1H), 3.77 (bs, 8H), 3.40 (s, 3H), 1.71-2.22 (m, 10H), and 0.89 ppm (t, J=7.7 Hz, 3H); LCMS: 440.1 m/z (M+H)$^+$; ret. Time: 3.303 min (Analytical Method A).

Example 44

Synthesis of (R)-1-(8-cyclopentyl-7-ethyl-5-methyl-6-oxo-5,6,7,8-tetrahydropteridin-2-yl)-1H-pyrazole-4-carboxylic acid

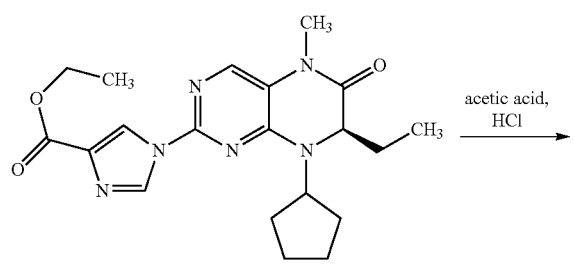

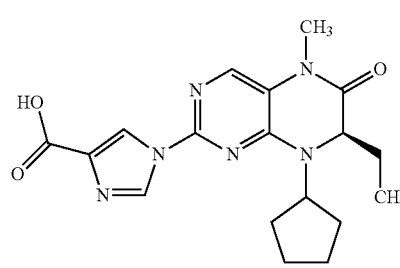

The title compound was prepared similarly to the methods described in Example 37, with (R)-ethyl 1-(8-cyclopentyl-7-ethyl-5-methyl-6-oxo-5,6,7,8-tetrahydropteridin-2-yl)-1H-pyrazole-4-carboxylate (Example 18) instead of (R)-methyl 1-(8-cyclopentyl-7-ethyl-5-methyl-6-oxo-5,6,7,8-tetrahydropteridin-2-yl)-1H-imidazole-4-carboxylate (Example 38). $^1$H NMR (CD$_3$OD) δ: 4.43-4.48 (m, 1H), 4.29-4.32 (m, 1H), 3.35 (s, 3H), 1.70-2.21 (m, 10H), and 0.86 ppm (bs, 3H); LCMS: 371.1 m/z (M+H)$^+$; ret. Time: 3.305 min (Analytical Method A).

Example 45

Synthesis of (R)-8-cyclopentyl-7-ethyl-5-methyl-2-(4-(morpholine-4-carbonyl)-1H-imidazol-1-yl)-7,8-dihydropteridin-6(5H)-one

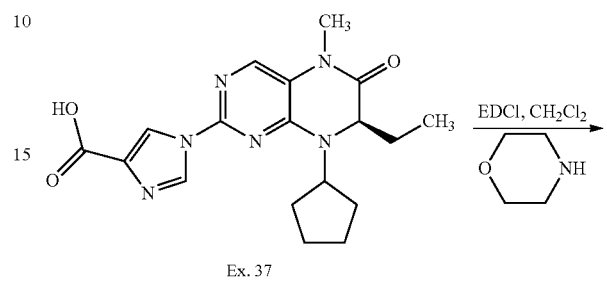

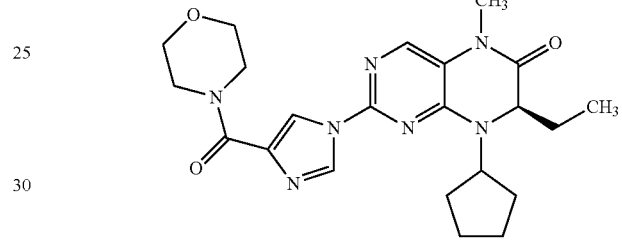

The title compound was prepared similarly to the methods described in Example 39, with (R)-1-(8-cyclopentyl-7-ethyl-5-methyl-6-oxo-5,6,7,8-tetrahydropteridin-2-yl)-1H-imidazole-4-carboxylic acid (Example 37) instead of (R)-1-(8-Cyclopentyl-7-ethyl-5-methyl-6-oxo-5,6,7,8-tetrahydropteridin-2-yl)-1H-pyrazole-4-carboxylic acid (Example 44), and with morpholine instead of dimethylamine hydrochloride. $^1$H NMR (CDCl$_3$) δ: 8.79 (s, 1H), 8.35 (s, 1H), 7.78 (s, 1H), 4.36-4.42 (m, 1H), 4.33-4.35 (m, 1H), 3.76-3.99 (bs, 8H), 3.39 (s, 3H), 1.71-1.93 (m, 10H), and 0.87 ppm (t, J=7.2 Hz, 3H); LCMS: 440.1 m/z (M+H)$^+$; ret. Time: 3.850 min (Analytical Method A).

Example 46

Synthesis of (R)-1-(8-cyclopentyl-7-ethyl-5-methyl-6-oxo-5,6,7,8-tetrahydropteridin-2-yl)-N-methyl-1H-imidazole-4-carboxamide

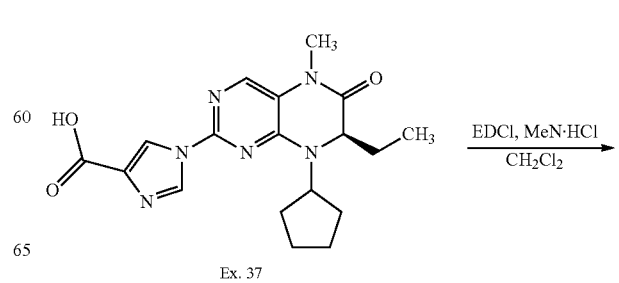

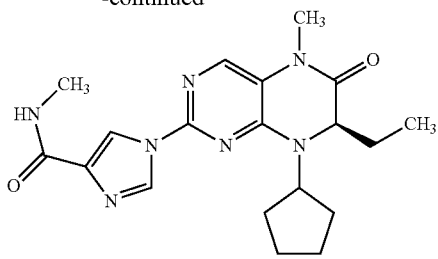

The title compound was prepared similarly to the methods described in Example 39, with (R)-1-(8-cyclopentyl-7-ethyl-5-methyl-6-oxo-5,6,7,8-tetrahydropteridin-2-yl)-1H-imidazole-4-carboxylic acid (Example 37) instead of (R)-1-(8-Cyclopentyl-7-ethyl-5-methyl-6-oxo-5,6,7,8-tetrahydropteridin-2-yl)-1H-pyrazole-4-carboxylic acid (Example 44), and with methylamine hydrochloride instead of dimethylamine hydrochloride. $^1$H NMR (CDCl$_3$) δ: 8.52 (s, 1H), 8.34 (s, 1H), 7.76 (s, 1H), 4.30-4.41 (m, 2H), 3.46 (s, 3H), 3.30 (s, 3H), 3.01 (s, 3H), 1.73-2.16 (m, 10H), and 0.87 ppm (t, J=7.7 Hz, 3H); LCMS: 398.1 m/z (M+H)$^+$; ret. Time: 3.367 min (Analytical Method A).

Example 54

Synthesis of (R)-8-cyclopentyl-7-ethyl-5-methyl-2-(4-(thiazol-4-yl)-1H-imidazol-1-yl)-7,8-dihydropteridin-6(5H)-one

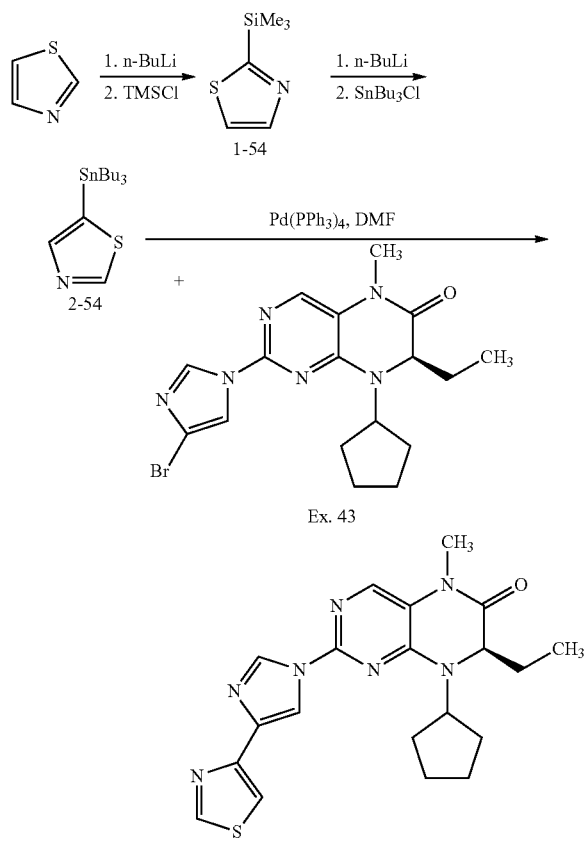

To a mixture of n-BuLi (2.5 M in hexane, 24 mL) and 18 mL of ether, a solution of 5.03 g thiazole dissolved in 59 mL of ether was added dropwise at −78° C. After 30 min, TMSCl (6.41 g) dissolved in 59 mL of ether was added at −78° C. The reaction mixture was stirred at −78° C. for 1 h and allowed to warm up to rt. The mixture was washed with saturated NaHCO$_3$ solution, dried over Na$_2$SO$_4$ and the solvent was evaporated. The residue was distilled (80° C./14 mmHg) to yield the desired compound 1-54 (yield: 90%); GC-MS: 157.10 m/z (M+H)$^+$.

n-BuLi (2.5 M in hexane, 7.88 mmol) was added to a solution of 1-54 (826 mg, 5.25 mmol) in 45 mL of anhydrous ether and stirred at −78° C. under Ar. After 20 min, tri-n-butylstannyl chloride (2.57 g, 7.88 mmol) was added, the solution was allowed to warm to room temperature, and stirred for another 1 h. The mixture was quenched and washed with 1N sodium hydroxide, dried with MgSO$_4$, and the solvent was evaporated to give compound 2-54. (2g, 100%); LCMS (0.05% TFA): 376.1 m/z (M+H)$^+$.

(R)-2-(4-bromo-1H-imidazol-1-yl)-8-cyclopentyl-7-ethyl-5-methyl-7,8-dihydropteridin-6(5H)-one (Example 43, 0.11 g, 0.271 mmol), 4-(tributylstannyl)thiazole (2-54, 0.10 g, 0.271 mmol) and Pd(PPh$_3$)$_4$ (31 mg, 0.0271) were dissolved in DMF in a screw cap vial and a stream of nitrogen was bubbled through the mixture for 2 minutes. The vial was sealed and the resulting solution was stirred at 100° C. for 19 h. The reaction mixture was diluted with brine, extracted with EtOAc, dried with Na$_2$SO$_4$ then purified by flash chromatography with a silica gel column by eluting with a mixture of Hexane:EtOAc and then further purified by preparative HPLC to give the title compound (20.7 mg). LCMS: 410.1 m/z (M+H)$^+$; ret. Time: 3.94 (Analytical Method A).

Methods similar to those given in this example were used with suitable substitution of reactants, e.g. replacing the compound of Example 43 with a suitable bromo derivative compound, and/or replacing 4-(tributylstannyl)thiazole with a suitable tributylstannyl derivative compound (prepared similarly to methods of this example), to prepare compounds as demonstrated in Examples 60, 68, 74, 95.

Example 55

Synthesis of (R)-8-cyclopentyl-7-ethyl-5-methyl-2-(4-methyl-1H-imidazol-1-yl)-7,8-dihydropteridin-6(5H)-one

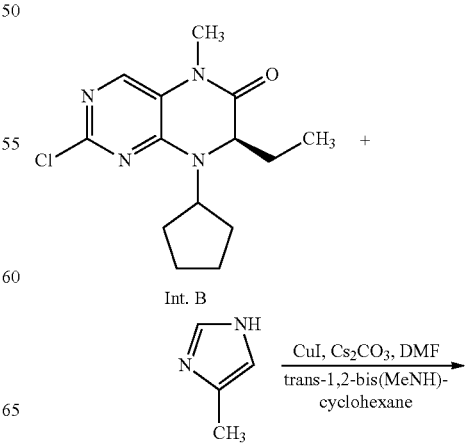

-continued

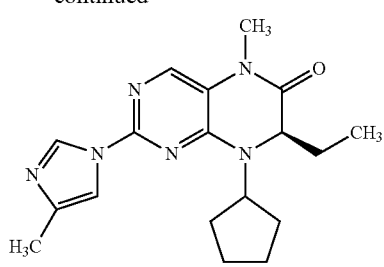

The title compound was prepared similarly to the methods described in Example 35, with 4-methyl-1H-imidazole instead of 2-(1H-imidazol-4-yl)acetonitrile. LCMS: 341.1 m/z (M+H)$^+$; ret. Time: 6.46 min (Analytical Method C).

Example 56

Synthesis of (R)-1-(8-cyclopentyl-7-ethyl-5-methyl-6-oxo-5,6,7,8-tetrahydropteridin-2-yl)-1H-pyrazole-3-carboxylic acid

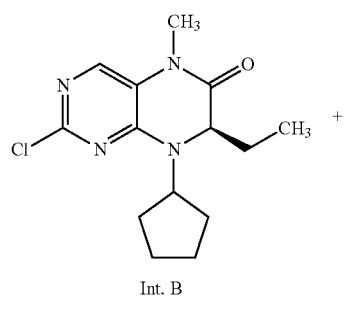

Int. B

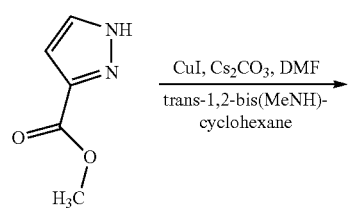

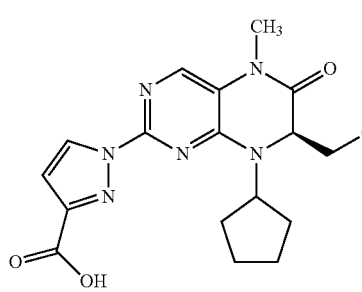

The title compound was prepared similarly to the methods described in Example 35, with methyl 1H-pyrazole-3-carboxylate instead of 2-(1H-imidazol-4-yl)acetonitrile. The methyl ester saponified under the reaction conditions to give the title compound. LCMS: 371.1 m/z (M+H)$^+$; ret. Time: 3.94 min (Analytical Method A).

Example 58

Synthesis of (R)-1-(8-cyclopentyl-7-ethyl-5-methyl-6-oxo-5,6,7,8-tetrahydropteridin-2-yl)-N-methyl-1H-pyrazole-3-carboxamide

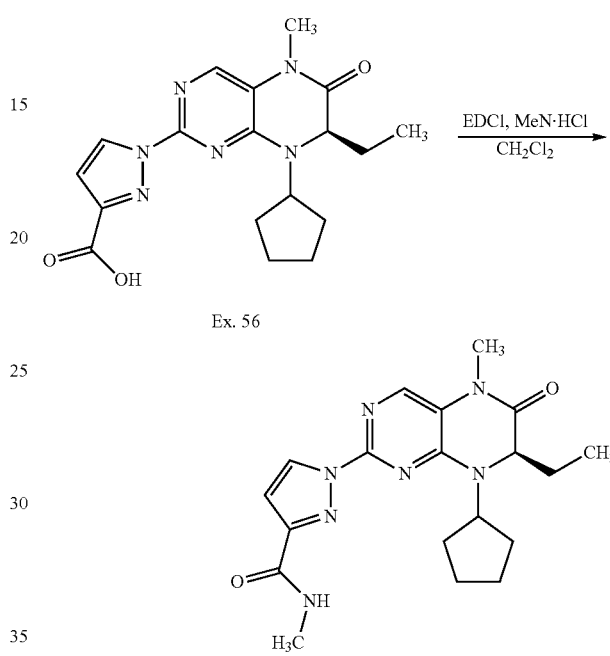

Ex. 56

The title compound was prepared similarly to the methods described in Example 39, with (R)-1-(8-cyclopentyl-7-ethyl-5-methyl-6-oxo-5,6,7,8-tetrahydropteridin-2-yl)-1H-pyrazole-3-carboxylic acid (Example 56) used instead of (R)-1-(8-Cyclopentyl-7-ethyl-5-methyl-6-oxo-5,6,7,8-tetrahydropteridin-2-yl)-1H-pyrazole-4-carboxylic acid (Example 44) and methylamine hydrochloride instead of dimethylamine hydrochloride. LCMS: 384.2 m/z (M+H)$^+$; ret. Time: 3.65 min (Analytical Method A).

Example 59

Synthesis of (R)-8-cyclopentyl-7-ethyl-5-methyl-2-(4-(pyridin-3-yl)-1H-imidazol-1-yl)-7,8-dihydropteridin-6(5H)-one

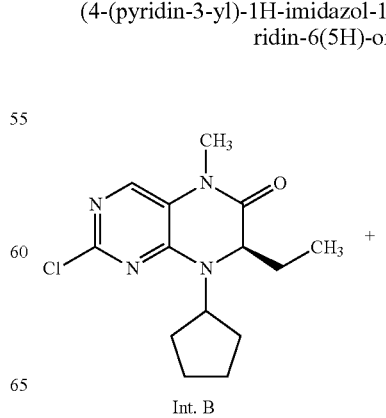

Int. B

-continued

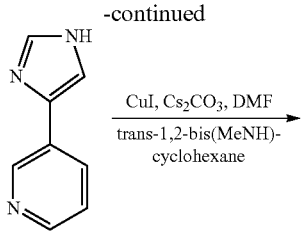

The title compound was prepared similarly to the methods described in Example 35, with 3-(1H-imidazol-4-yl)pyridine instead of 2-(1H-imidazol-4-yl)acetonitrile. LCMS: 404.1 m/z (M+H)⁺; ret. Time: 2.89 min (Analytical Method A).

Example 61

Synthesis of (R)-1-(8-cyclopentyl-7-ethyl-5-methyl-6-oxo-5,6,7,8-tetrahydropteridin-2-yl)-N,N-dimethyl-1H-pyrazole-3-carboxamide

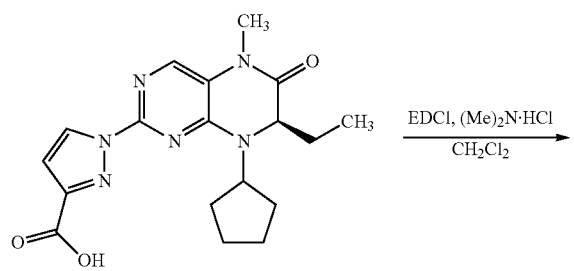

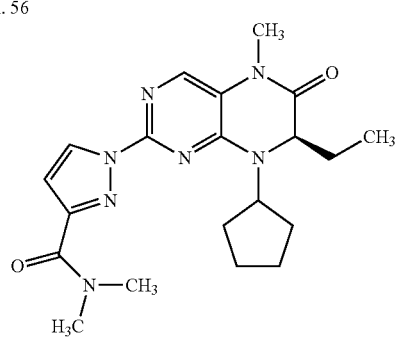

The title compound was prepared similarly to the methods described in Example 39, with (R)-1-(8-cyclopentyl-7-ethyl-5-methyl-6-oxo-5,6,7,8-tetrahydropteridin-2-yl)-1H-pyrazole-3-carboxylic acid (Example 56) used instead of (R)-1- (8-Cyclopentyl-7-ethyl-5-methyl-6-oxo-5,6,7,8-tetrahydropteridin-2-yl)-1H-pyrazole-4-carboxylic acid (Example 44). LCMS: 398.1 m/z (M+H)⁺; ret. Time: 3.34 min (Analytical Method A).

Example 62

Synthesis of (R)-2-(4-(2-aminoethyl)-1H-imidazol-1-yl)-8-cyclopentyl-7-ethyl-5-methyl-7,8-dihydropteridin-6(5H)-one

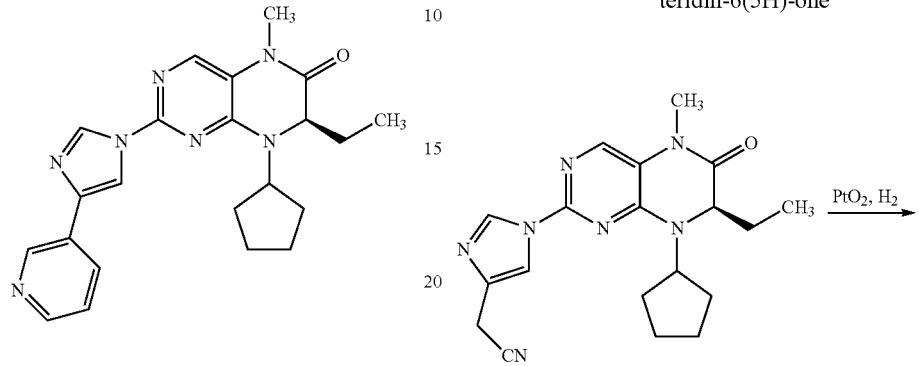

(R)-2-(1-(8-cyclopentyl-7-ethyl-5-methyl-6-oxo-5,6,7,8-tetrahydropteridin-2-yl)-1H-imidazol-4-yl)acetonitrile (Example 35, 0.08 g, 0.218 mmol) and PtO₂ (40 mg) were suspended in 2 mL of EtOAc and the resulting mixture was stirred under an atmosphere of hydrogen (1 atm, balloon) for 18 h. The resulting solution was filtered through Celite, concentrated, then purified by preparative HPLC to give the title compound (34 mg). LCMS: 370.1 m/z (M+H)⁺; ret. Time: 4.09 (Analytical Method C).

Example 63

Synthesis of (R)-1-(8-cyclopentyl-7-ethyl-5-methyl-6-oxo-5,6,7,8-tetrahydropteridin-2-yl)-1H-pyrazole-3-carboxamide

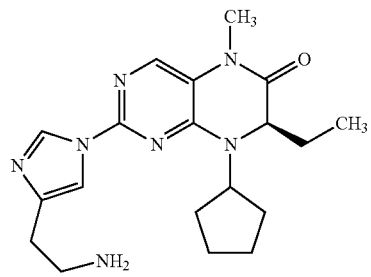

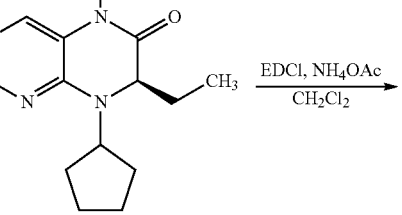

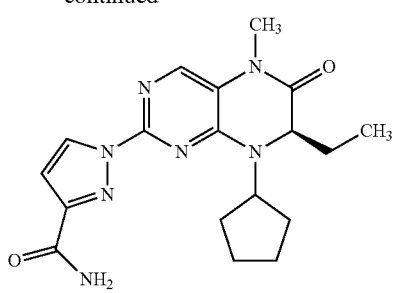

The title compound was prepared similarly to the methods described in Example 39, with (R)-1-(8-cyclopentyl-7-ethyl-5-methyl-6-oxo-5,6,7,8-tetrahydropteridin-2-yl)-1H-pyrazole-3-carboxylic acid (Example 56) used instead of (R)-1-(8-Cyclopentyl-7-ethyl-5-methyl-6-oxo-5,6,7,8-tetrahydropteridin-2-yl)-1H-pyrazole-4-carboxylic acid (Example 44) and ammonium acetate instead of dimethylamine hydrochloride. LCMS: 370.1 m/z (M+H)+; ret. Time: 3.39 min (Analytical Method A).

Example 65

Synthesis of (R)-2-(2-bromo-1H-imidazol-1-yl)-8-cyclopentyl-7-ethyl-5-methyl-7,8-dihydropteridin-6 (5H)-one

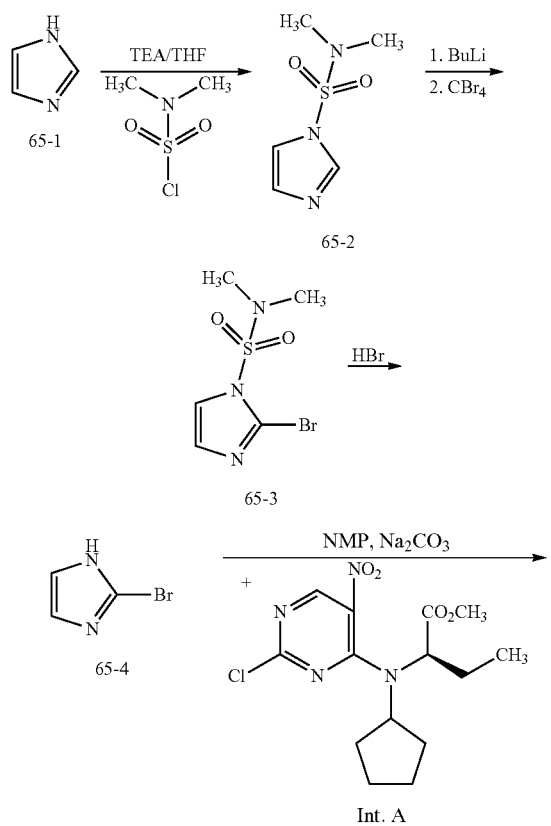

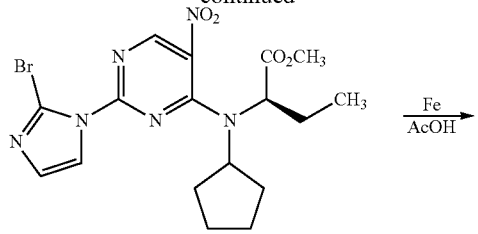

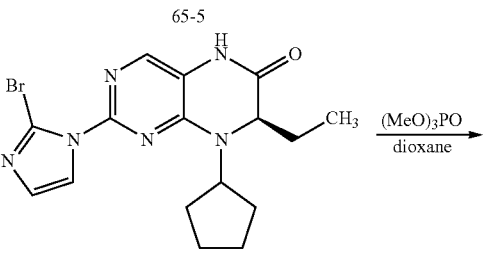

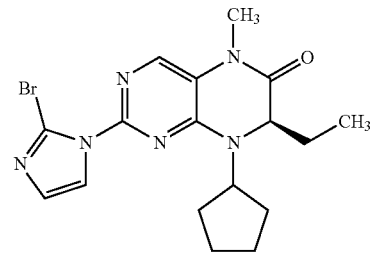

1H-imidazole (65-1, 10 g) was dissolved in 150 mL of THF with dimethylsulfamoyl chloride (19 g), followed by the drop-wise addition of TEA (20 g). The mixture was stirred at rt for 16 h, then poured into 200 mL of water and extracted with EtOAc. The organic layer was dried with Na$_2$SO$_4$. Solvent was removed to give compound 65-2 as a light yellow oil.

Compound 65-2 (1.5 g) was dissolved in 20 mL of THF and cooled to −78° C. and n-BuLi (4.1 ml, 2.5 M in hexanes) was added drop-wise at −78° C., then CBr$_4$ (1.1 eq) was added and the mixture was stirred at rt for 16 h. Forty mL of water was added and the suspension was extracted with EtOAc and dried with Na$_2$SO$_4$. The solvent was removed and the residue was purified with silica column (PE:DCM) to give compound 65-3.

Compound 65-3 (1.1 g) was placed in a 50 ml round flask and HBr (40%, 10 ml in water) was added to give a suspension. The mixture was stirred at rt for 16 h to give a deep yellow solution, then the pH was adjusted to 8 and the mixture was extracted with EtOAc. The solvent was removed to give compound 65-4 as a yellow solid.

Intermediate A (13.6 g) was dissolved in 80 mL of NMP and compound 65-4 (6.5 g) and Na$_2$CO$_3$ (4.6 g) were added. The solution was stirred at 90° C. for 6 h, then NMP was removed under reduced pressure. The residue was dissolved in EtOAc, washed with water and purified by silica gel flash chromatography (PE:EA=2:1) to give compound 65-5 as a yellow oil.

Compound 65-5 (13.7 g) was dissolved in 150 mL of AcOH, iron powder (20 g) was added and the mixture was stirred at 42° C. for 40 min. The cooled solution was added carefully to aq. Na$_2$CO$_3$ and extracted with EtOAc, then purified by flash chromatography (DCM:EA=85:15 then 1:1) to give compound 65-6.

Compound 65-6 (9.5 g) was dissolved in 200 mL of dioxane, then trimethylphosphate (18 g) and $K_2CO_3$ (7 g) were added. The mixture was stirred at 100° C. for 16 h. The solvent was removed, the residue taken up into EtOAc and this solution was washed with water. The organic layer was dried over $Na_2SO_4$, then concentrated and the residue was purified by silica column (PE:EA=1:10 to 1:1) to give the title compound. LCMS (0.05% TFA): 405.1,407.1 m/z $(M+H)^+$; $^1$H-NMR ($CDCl_3$, 500 MHz): δ: 7.83 (s, 1H), 7.70 (d, 1H, J=1.5 Hz), 7.07 (d, 1H, J=1.5 Hz), 4.52 (m, 1H), 4.32 (m, 1H), 3.38 (s, 3H), 1.99~1.66 (m, 10H), 0.89 (t, 3H, J=7.5 Hz).

Example 69

Synthesis of (R)-1-(8-cyclopentyl-7-ethyl-5-methyl-6-oxo-5,6,7,8-tetrahydropteridin-2-yl)-1H-imidazole-4-carboxamide

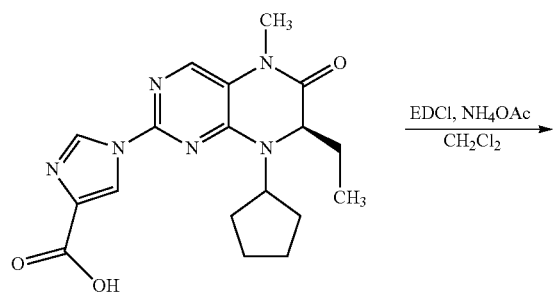

The title compound was prepared similarly to the methods described in Example 39, with (R)-1-(8-cyclopentyl-7-ethyl-5-methyl-6-oxo-5,6,7,8-tetrahydropteridin-2-yl)-1H-imidazole-4-carboxylic acid (Example 37) used instead of (R)-1-(8-Cyclopentyl-7-ethyl-5-methyl-6-oxo-5,6,7,8-tetrahydropteridin-2-yl)-1H-pyrazole-4-carboxylic acid (Example 44) and ammonium acetate instead of dimethylamine hydrochloride. LCMS: 370.2 m/z $(M+H)^+$; ret. Time: 3.97 (Analytical Method D).

Example 73

Synthesis of (R)-8-cyclopentyl-7-ethyl-2-(4-iminopyridin-1(4H)-yl)-5-methyl-7,8-dihydropteridin-6 (5H)-one

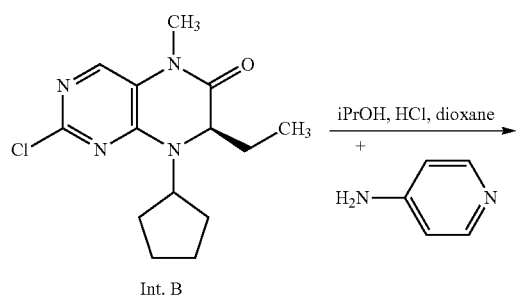

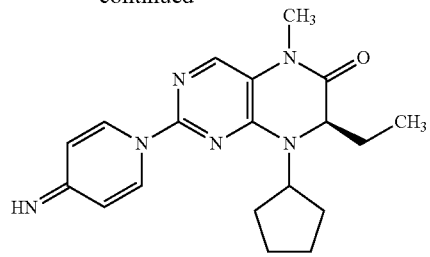

To a solution of the Intermediate B (400 mg, 1.36 mmol) in 5 mL of isopropanol in a microwave vial, 4N HCl in dioxane (0.43 mL) and 4-aminopyridine (320 mg, 2 eq) were added and the vial was heated in a microwave oven at 160° C. for 1 hour. Solvent was removed under reduced pressure and the resulting yellow solid was purified by reversed phase HPLC to give the title compound. $^1$H NMR ($CDCl_3$) δ: 9.62 (bs, 1H), 8.91 (d, J=7.7 Hz, 2H), 7.81 (s, 1H), 7.37 (d, J=7.8 Hz, 2H), 4.44-4.36 (m, 2H), 3.41 (s, 3H), 2.08-1.71 (m, 10H), 0.89 (t, J=7.5 Hz, 3H).

Example 76

Synthesis of (S)-6a-ethyl-5-methyl-2-(2-phenyl-1H-imidazol-1-yl)-6a,7,8,9-tetrahydropyrrolo[2,1-h]pteridin-6(5H)-one

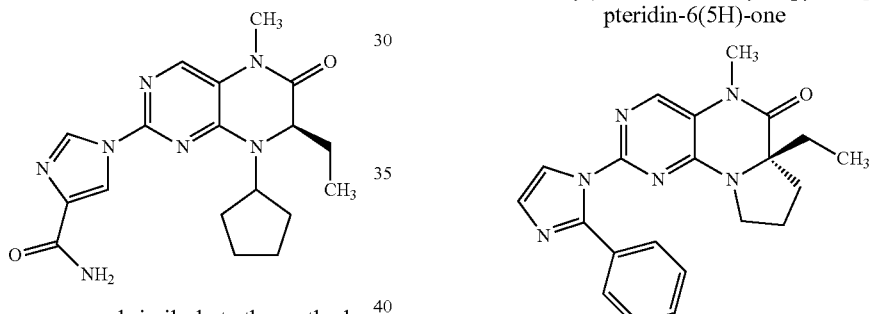

The title compound was prepared similarly to the methods described in Example 3, with Intermediate K-1 instead of Intermediate A, and 2-phenyl-1H-imidazole instead of 1H-imidazole in the first step. LCMS: 375.2 m/z $(M+H)^+$; ret. Time: 5.24 min (Analytical Method C).

Example 77

Synthesis of (R)-7-ethyl-8-isopropyl-5-methyl-2-(2-phenyl-1H-imidazol-1-yl)-7,8-dihydropteridin-6 (5H)-one

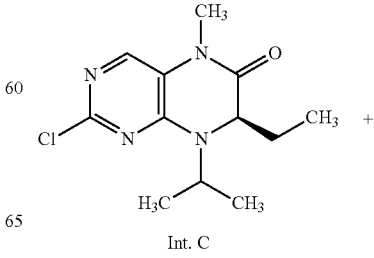

-continued

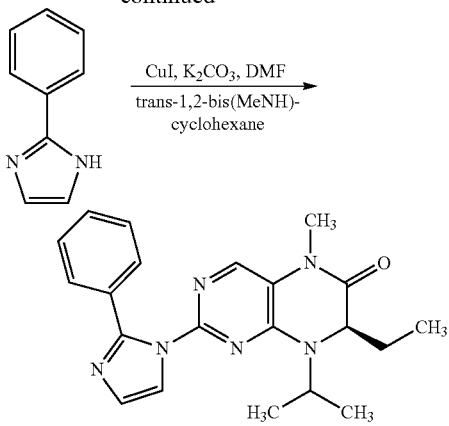

A mixture of Intermediate C (100 mg, 0.37 mmol), 2-phenyl-1H-imidazole (533 mg, 3.7 mmol), CuI (35 mg, 0.18 mmol), trans-1,2-bis(methylamino)cyclo-hexane (52.5 mg, 0.07 mL, 0.37 mmol) and solid $K_2CO_3$ (511 mg, 3.7 mmol) in 2 mL of DMF was heated in a microwave reaction apparatus for 2 h at 200° C. After this time the reaction was transferred to a round bottom flask with the aid of EtOAc, then evaporated. The residue was purified by reverse-phase HPLC (PL-RPS C-18 column, eluting with a gradient of 20-25% acetonitrile in water over 30 min) to give the title compound. LCMS: 377.2 m/z $(M+H)^+$; ret. Time: 2.56 min (Analytical Method A); $^1$H NMR (400 MHz, CDCl$_3$) δ: 7.9-7.8 (dd, 2H), 7.6-7.3 (m, 6H), 4.3 (dd, 1H), 3.8 (m, 1H), 3.4 (s, 3H), 1.9 (dd, 1H), 1.7 (dd, 1H), 1.05 (d, 3H), 0.9 (d, 3H) and 0.8 (d, 3H) ppm.

Methods similar to those given in this example were used with suitable substitution of reactants, e.g. replacing Intermediate C with a suitable Intermediate, and/or replacing 2-phenyl-1H-imidazole with a suitable optionally substituted ring, to prepare compounds as demonstrated in Examples 81, 100, 140, 141, 143, 147-159, 166, 174, 176, 194, 196, 204, 212, 224, 229, 271, 279, and 385.

Example 78

Synthesis of (R)-3-(1-(8-cyclopentyl-7-ethyl-5-methyl-6-oxo-5,6,7,8-tetrahydropteridin-2-yl)-1H-imidazol-2-yl)oxazolidin-2-one

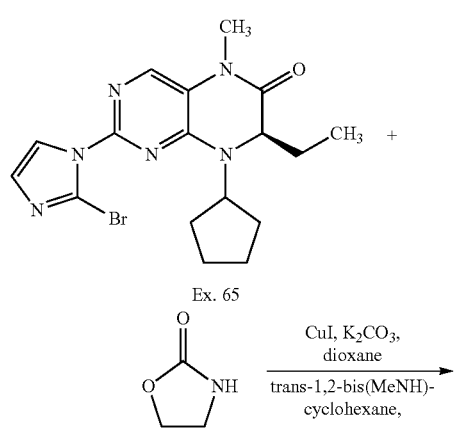

-continued

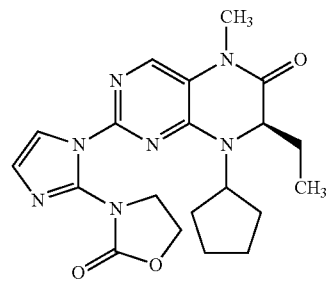

(R)-2-(2-bromo-1H-imidazol-1-yl)-8-cyclopentyl-7-ethyl-5-methyl-7,8-dihydropteridin-6(5H)-one (Example 65, 0.11 g, 0.271 mmol), oxazolidin-2-one (35 mg, 0.406 mmol), CuI (10 mg, 0.054 mmol), trans-1,2-bis(methylamino)cyclohexane (15 mg, 0.108 mmol) and $K_2CO_3$ (74 mg, 0.542 mmol) were dissolved in 1 mL of dioxane in a screw cap vial and a stream of nitrogen was bubbled through the mixture for 2 minutes. The resulting solution was stirred at 110° C. for 18 h. The reaction mixture filtered and concentrated, then purified by preparative HPLC to give the title compound (7.1 mg). LCMS: 412.2 m/z $(M+H)^+$; ret. Time: 3.24 min (Analytical Method A).

Methods similar to those given in this example were used with suitable substitution of reactants, e.g. replacing the compound of Example 65 with a suitable bromo derivative compound, and/or replacing oxazolidin-2-one with a suitable optionally substituted ring, to prepare compounds as demonstrated in Examples 82, 89, and 113.

Example 79

Synthesis of (R)-8-cyclopentyl-7-ethyl-5-methyl-2-(2-(4-(methylsulfonyl)phenyl)-1H-imidazol-1-yl)-7,8-dihydropteridin-6(5H)-one

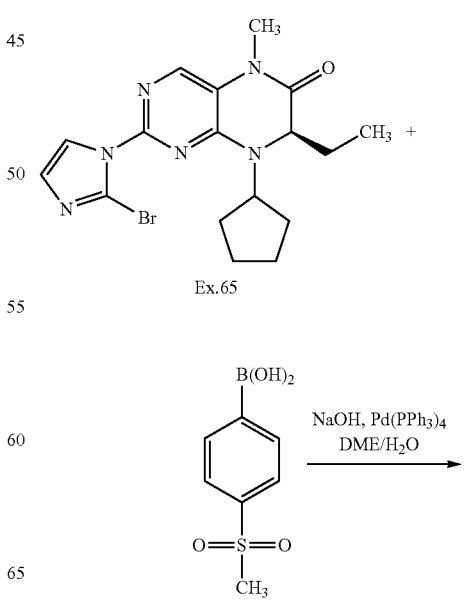

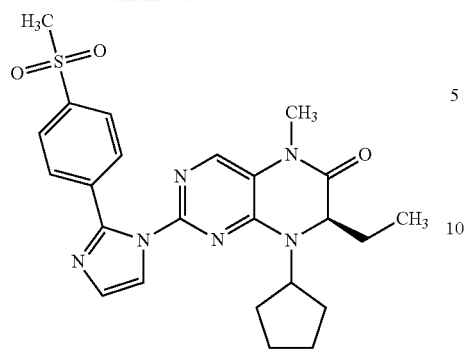

(R)-2-(2-bromo-1H-imidazol-1-yl)-8-cyclopentyl-7-ethyl-5-methyl-7,8-dihydropteridin-6(5H)-one (Example 65, 0.15 g, 0.37 mmol), 4-(methylsulfonyl)phenylboronic acid (0.148 g, 0.74 mmol), aqueous sodium hydroxide (240 μL of 3N) and Pd(PPh$_3$)$_4$ (42 mg, 0.037 mmol) were dissolved in 1.2 mL of DME/H$_2$O (5/1, v/v) and a stream of nitrogen was bubbled through the mixture for 2 minutes. The resulting solution was stirred at 90° C. for 18 h. The reaction mixture was diluted with brine, extracted with EtOAc, dried with Na$_2$SO$_4$ then purified by silica gel column chromatography and preparative HPLC to give to give the title compound (3.8 mg). LCMS: 481.2 m/z (M+H)$^+$; ret. Time: 6.19 min (Analytical Method C).

Methods similar to those given in this example were used with suitable substitution of reactants, e.g. replacing the compound of Example 65 with a suitable bromo derivative compound, and/or replacing 4-(methylsulfonyl)phenylboronic acid with a suitable boronic acid, to prepare compounds as demonstrated in Examples 97, 99, and 231.

Example 80

Synthesis of (S)-5,6a-dimethyl-2-(2-phenyl-1H-imidazol-1-yl)-6a,7,8,9-tetrahydropyrrolo[2,1-h]pteridin-6(5H)-one

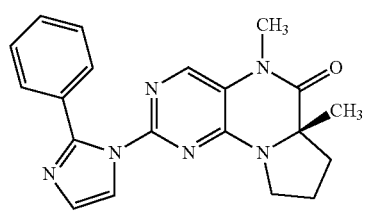 [SMILES: CN1C(=O)[C@]2(C)CCCN2c2nc(-n3ccnc3-c3ccccc3)ncc21]

The title compound was prepared similarly to the methods described in Example 3, with Intermediate L-1 instead of Intermediate A, and 2-phenyl-1H-imidazole instead of 1H-imidazole in the first step. LCMS: 361.1 m/z (M+H)$^+$; ret. Time: 4.55 min (Analytical Method C).

Example 81

Synthesis of (R)-8-cyclobutyl-7-ethyl-5-methyl-2-(2-(pyridin-4-yl)-1H-imidazol-1-yl)-7,8-dihydropteridin-6(5H)-one

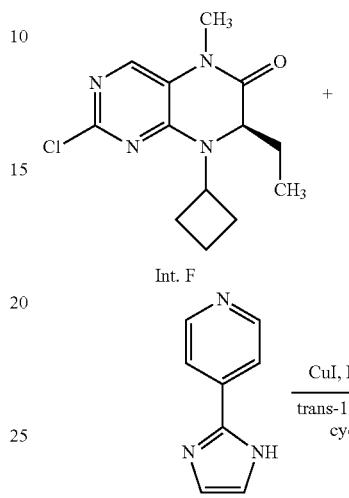

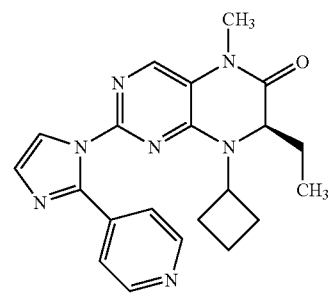

The title compound was prepared similarly to the methods described in Example 77, with Intermediate F instead of Intermediate C, and 2-(pyridin-4-yl)-1H-imidazole instead of 2-phenyl-1H-imidazole. LCMS: 390.2 m/z (M+H)$^+$; ret. Time: 1.92 min (Analytical Method A).

Example 83

Synthesis of (R)-8-cyclopentyl-7-ethyl-5-methyl-2-(2-(pyridin-4-yl)-1H-imidazol-1-yl)-7,8-dihydropteridin-6(5H)-one

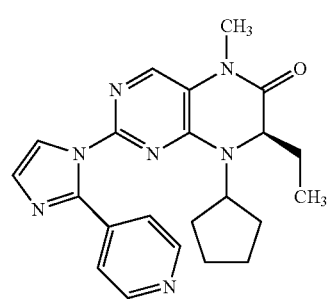 [SMILES: CC[C@@H]1C(=O)N(C)c2cnc(-n3ccnc3-c3ccncc3)nc2N1C1CCCC1]

The title compound was prepared similarly to the methods described in Example 3, with 2-(pyridin-4-yl)-1H-imidazole instead of 1H-imidazole in the first step. LCMS: 404.2 m/z (M+H)+; ret. Time: 6.54 min (Analytical Method C).

Example 95

Synthesis of (R)-8-cyclopentyl-7-ethyl-5-methyl-2-(2-(oxazol-2-yl)-1H-imidazol-1-yl)-7,8-dihydropteridin-6(5H)-one

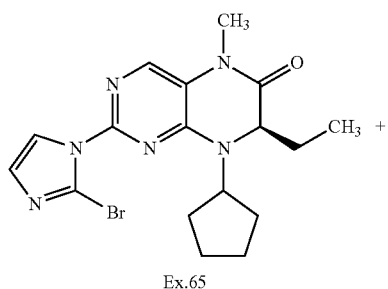

Ex. 65

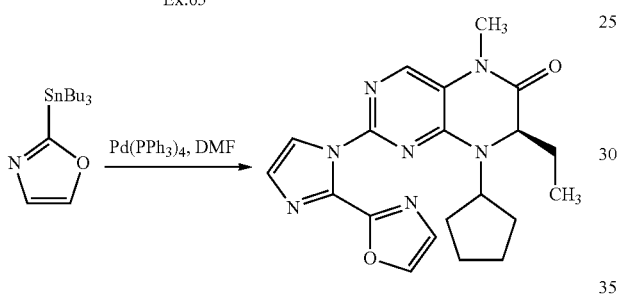

The title compound was prepared similarly to the methods described in Example 54, with (Example 65) instead of (Example 43) and 2-(tributylstannyl)oxazole instead of 4-(tributylstannyl)thiazole. LCMS: 394.1 m/z (M+H)+; ret. Time: 3.32 min (Analytical Method A).

Example 97

Synthesis of (R)-2-(2-(1H-pyrazol-4-yl)-1H-imidazol-1-yl)-8-cyclopentyl-7-ethyl-5-methyl-7,8-dihydropteridin-6(5H)-one

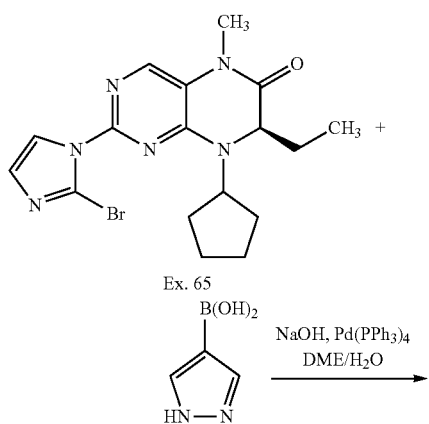

Ex. 65

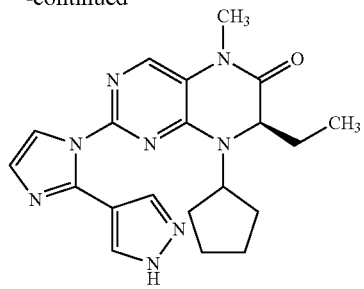

The title compound was prepared similarly to the methods described in Example 79, with pyrazole-4-yl boronic acid instead of 4-(methanesulfonyl)phenyl boronic acid. LCMS: 393.2 m/z (M+H)+; ret. Time: 5.16 (Analytical Method C).

Example 100

Synthesis of (R)-7-ethyl-5-methyl-2-(2-(pyridin-4-yl)-1H-imidazol-1-yl)-8-(tetrahydro-2H-pyran-4-yl)-7,8-dihydropteridin-6(5H)-one

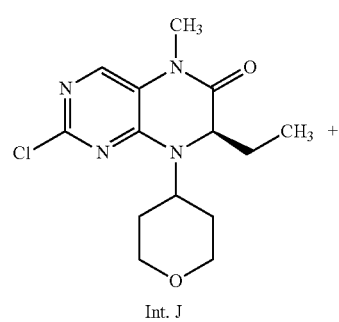

Int. J

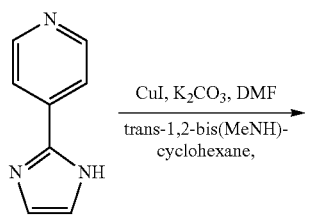

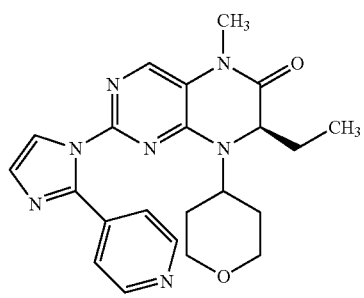

The title compound was prepared similarly to the methods described in Example 77, with Intermediate J instead of Intermediate C and with 4-(1H-imidazol-2-yl)pyridine instead of 2-phenyl-1H-imidazole. LCMS: 420.2 m/z (M+H)+; ret. Time: 3.51 (Analytical Method C).

Example 101

Synthesis of (S)-6a-ethyl-5-methyl-2-(2-(pyridin-4-yl)-1H-imidazol-1-yl)-6a,7,8,9-tetrahydropyrrolo[2,1-h]pteridin-6(5H)-one

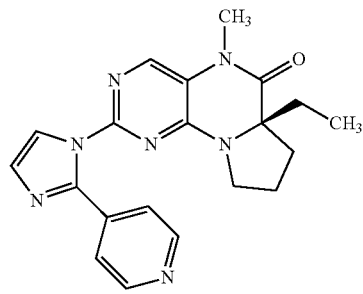 [SMILES: CC[C@@]12CCCN1c1nc(-n3ccnc3-c3ccncc3)ncc1N(C)C2=O]

The title compound was prepared similarly to the methods described in Example 3, with Intermediate K-1 instead of Intermediate A, and 4-(1H-imidazol-2-yl)pyridine instead of 1H-imidazole in the first step. LCMS: 376.2 m/z (M+H)+; ret. Time: 4.97 min (Analytical Method D).

Example 109

Synthesis of (R)-8-cyclobutyl-7-ethyl-5-methyl-2-(pyridin-4-yl)-7,8-dihydropteridin-6(5H)-one

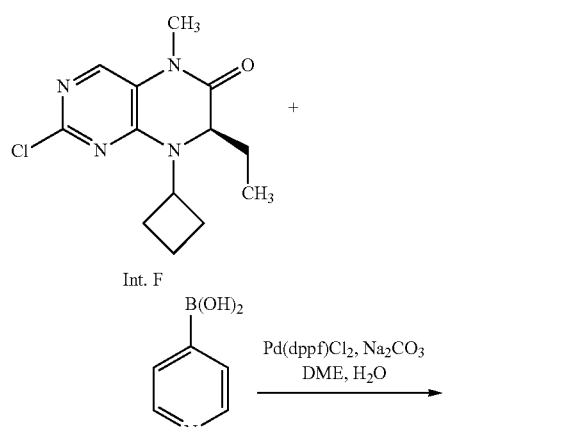

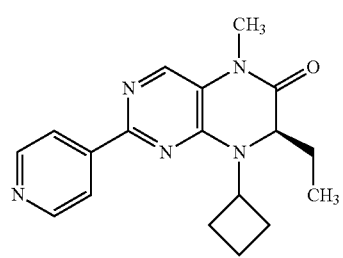

The title compound was prepared similarly to the methods described in Example 5, with Intermediate F instead of Intermediate B. LCMS: 324.2 m/z (M+H)+; ret. Time: 1.41 min (Analytical Method C).

Example 110

Synthesis of (R)-7-ethyl-8-isopropyl-5-methyl-2-(3-phenylpyridin-4-yl)-7,8-dihydropteridin-6(5H)-one

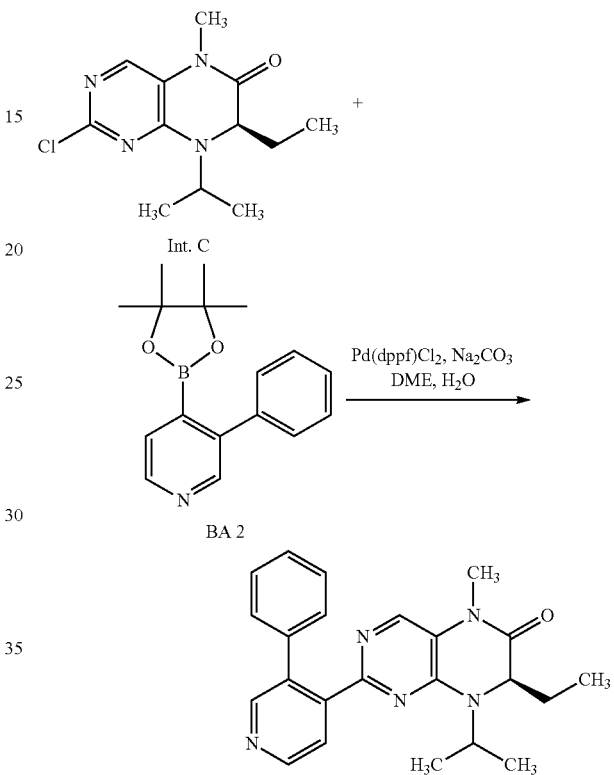

The title compound was prepared similarly to the methods described in Example 5, with Intermediate C instead of Intermediate B and with 3-phenyl-4-(4,4,5,5-tetramethyl-1,3,2-dioxaborolan-2-yl)pyridine (Boronic Acid 2) instead of pyridin-4-ylboronic acid. LCMS: 388.2 m/z (M+H)+; ret. Time: 6.56 min (Analytical Method C).

Example 111

Synthesis of (R)-8-cyclobutyl-7-ethyl-2-(1H-imidazol-1-yl)-5-methyl-7,8-dihydropteridin-6(5H)-one

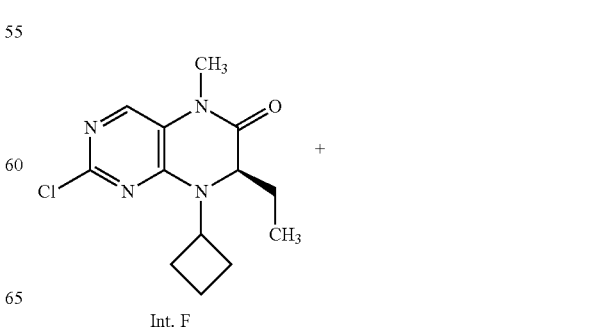

-continued

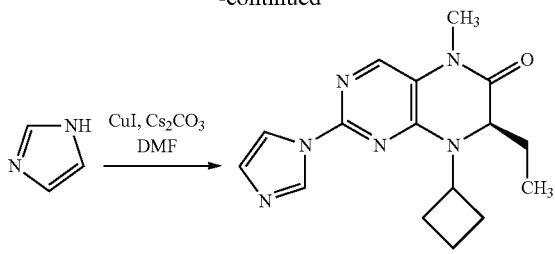

The title compound was prepared similarly to the methods described in Example 35, with Intermediate F instead of Intermediate B and with 1H-imidazole instead of 2-(1H-imidazol-4-yl)acetonitrile. LCMS: 313.2 m/z (M+H)$^+$; ret. Time: 4.49 min (Analytical Method C).

Example 132

Synthesis of (R)-8-cyclopentyl-7-ethyl-5-methyl-2-(4-phenylpyrimidin-5-yl)-7,8-dihydropteridin-6(5H)-one

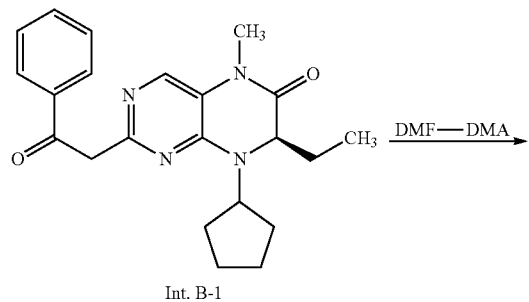

Int. B-1

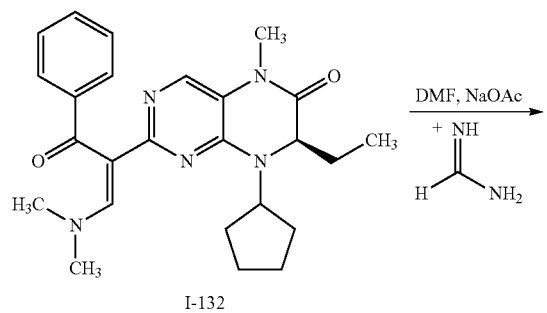

I-132

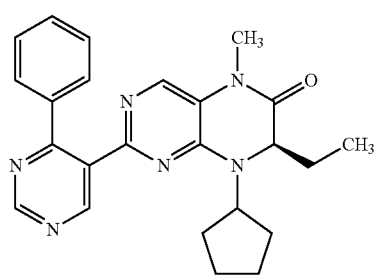

A suspension of (R)-8-cyclopentyl-7-ethyl-5-methyl-2-(2-oxo-2-phenylethyl)-7,8-dihydropteridin-6(5H)-one (Intermediate B-1, 700 mg) in 10 mL of DMF-DMA was heated at 110° C. for 3 hours. The resulting mixture was concentrated to give the desired (R,Z)-8-cyclopentyl-2-(1-(dimethylamino)-3-oxo-3-phenylprop-1-en-2-yl)-7-ethyl-5-methyl-7,8-dihydropteridin-6(5H)-one (compound I-132).

Compound I-132 (300 mg) was dissolved in 5 mL of DMF, then acetate formimidamide (2.0 eq) and NaOAc (3.0 eq) were added, and the mixture was refluxed for 2 hours. The mixture was poured into ice-water, adjusted with aqueous Na$_2$CO$_3$ until PH>8, then extracted with EtOAc (3×50 mL) and purified by preparative HPLC to give the title compound (100 mg, yield=42%). LCMS: 415.2 m/z (M+H)$^+$; ret. time 1.68 min (Analytical Method A).

Methods similar to those given in this example were used with suitable substitution of reactants, e.g. replacing Intermediate B-1 with a suitable Intermediate, to prepare compounds as demonstrated in Examples 168, 197, and 222.

Example 133

Synthesis of (R)-8-cyclopentyl-7-ethyl-5-methyl-2-(5-phenylisoxazol-4-yl)-7,8-dihydropteridin-6(5H)-one

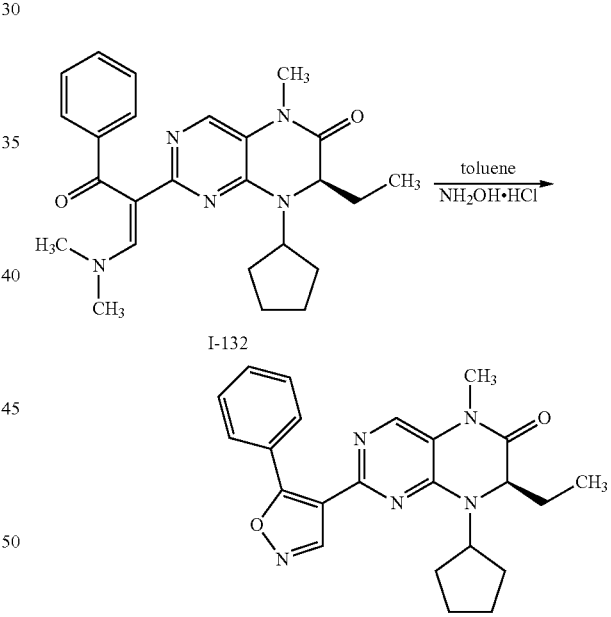

Compound I-132 (from Example 132, 150 mg) was dissolved in 3 mL of toluene, then NH$_2$OH HCl (5.0 eq) was added and the mixture was refluxed for 2 hours. The mixture was poured into ice-water, adjusted with aqueous Na$_2$CO$_3$ until PH>8, then extracted with EtOAc (3×50 mL) and purified by silica gel column (PE:EA=3:2) to give the title compound (134 mg, yield=96%). LCMS: 404.2 m/z (M+H)$^+$; ret. time 1.83 min (Analytical Method A).

Methods similar to those given in this example were used with suitable substitution of reactants, e.g. replacing compound I-132 with a suitable compound (prepared per the first step of Example 132 by replacing Intermediate B-1 with a suitable intermediate), to prepare compounds as demonstrated in Examples 173, 187, 413, and 414.

Example 134

Synthesis of (R)-8-cyclopentyl-7-ethyl-5-methyl-2-(5-phenyl-1H-pyrazol-4-yl)-7,8-dihydropteridin-6(5H)-one

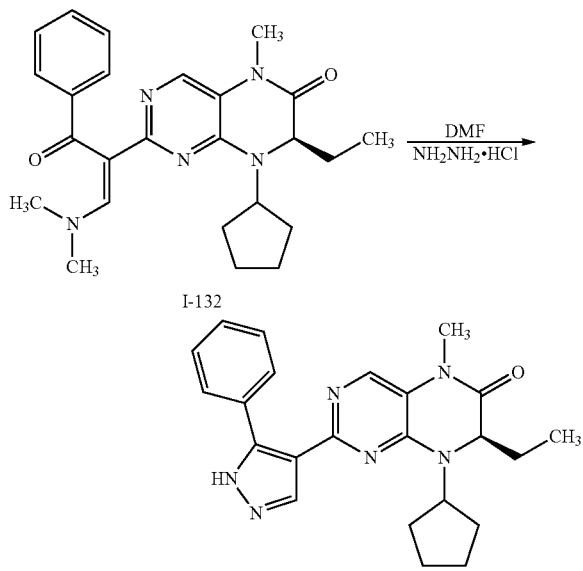

I-132

Compound I-132 (from Example 132, 250 mg) was dissolved in 5 mL of DMF, then NH$_2$NH$_2$.HCl (3.0 eq) was added and the mixture was refluxed for 2 hours. The mixture was poured into ice-water, adjusted with aqueous Na$_2$CO$_3$ until PH>8, then extracted with EtOAc (3×50 mL) and purified by preparative HPLC to give the title compound (130 mg, yield=40%). LCMS: 403.2 m/z (M+H)$^+$; ret. time 1.45 min (Analytical Method A).

Methods similar to those given in this example were used with suitable substitution of reactants, e.g. replacing compound I-132 with a suitable compound (prepared per the first step of Example 132 by replacing Intermediate B-1 with a suitable intermediate), to prepare compounds as demonstrated in Examples 164, 167, 181, 305, 338, 344, 345, and 405.

Example 135

Synthesis of (R)-8-cyclopentyl-7-ethyl-5-methyl-2-(5-phenyl-1H-1,2,4-triazol-1-yl)-7,8-dihydropteridin-6(5H)-one

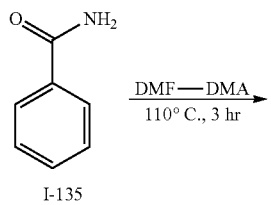

I-135

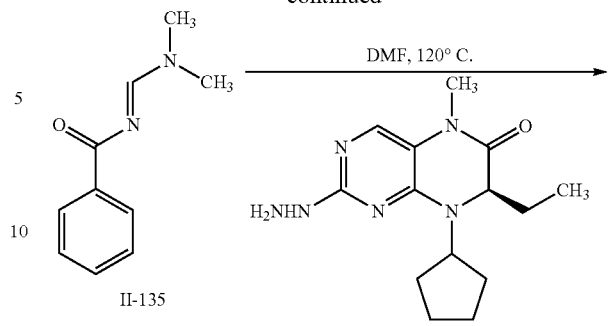

II-135

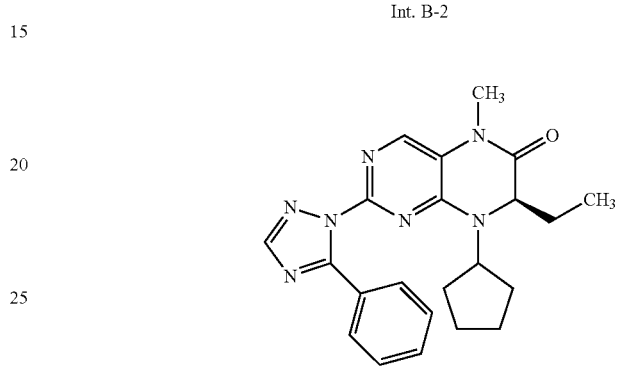

Int. B-2

A solution of benzamide (1-135) in DMF-DMA was stirred for 3 h at 110° C., then cooled to rt. The solid was collected by filtration, the filter cake washed with PE and air dried to give the desired (E)-N-((dimethylamino)methylene)benzamide (compound II-135).

Compound II-135 (1.5 eq) and Intermediate B-2 (1 eq) in DMF was stirred for 3 h at 110° C. The mixture was cooled to rt, diluted with water and extracted with EtOAc. The organic layer was dried with Na$_2$SO$_4$, concentrated and the residue was purified by silica gel column chromatography to give the title compound. LCMS (0.05% TFA): 404.2 m/z (M+H)$^+$; $^1$H-NMR (MeOD, 500 MHz): δ: 8.10 (s, 1H), 7.93 (s, 1H), 7.37 (m, 5H), 4.21 (m, 1H), 3.58 (m, 1H), 3.29 (s, 3H), 1.65-1.23 (m, 10H), 0.69 (t, 3H, J=7.5 Hz).

Example 137

Synthesis of (S)-6a-ethyl-5-methyl-2-(2-(pyridin-3-yl)-1H-imidazol-1-yl)-6a,7,8,9-tetrahydropyrrolo[2,1-h]pteridin-6(5H)-one

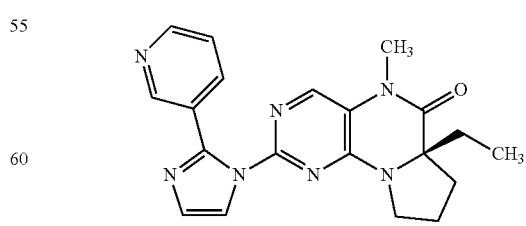

The title compound was prepared similarly to the methods described in Example 3, with Intermediate K-1 instead of Intermediate A, and 3-(1H-imidazol-2-yl)pyridine instead of 1H-imidazole in the first step. LCMS: 376.2 m/z (M+H)$^+$; ret. Time: 4.25 min (Analytical Method C).

Example 138

Synthesis of (R)-8-cyclopentyl-7-ethyl-5-methyl-2-(3-phenylpyrazin-2-yl)-7,8-dihydropteridin-6(5H)-one

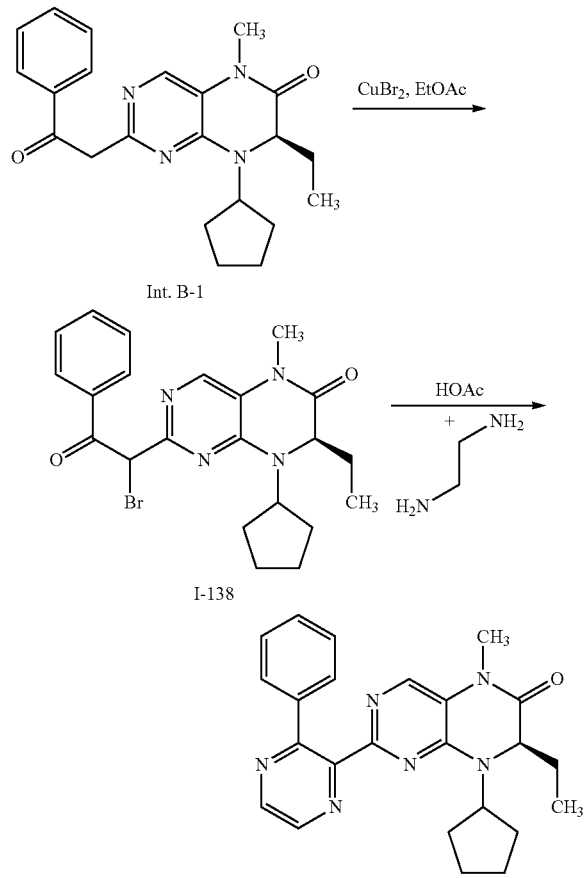

To a solution of (R)-8-cyclopentyl-7-ethyl-5-methyl-2-(2-oxo-2-phenylethyl)-7,8-dihydropteridin-6(5H)-one (Intermediate B-1, 300 mg) in 10 mL of EtOAc, CuBr$_2$ (10.0 eq) was added and the reaction was stirred at reflux state for 1.5 hours. The mixture was filtered and 50 mL of water was added to the filtrate, adjusted PH>8 with Na$_2$CO$_3$ aqueous, extracted with EtOAc (3×50 mL), and concentrated to give the desired (7R)-2-(1-bromo-2-oxo-2-phenylethyl)-8-cyclopentyl-7-ethyl-5-methyl-7,8-dihydropteridin-6(5H)-one (compound I-138, 350 mg).

Compound I-138 (200 mg) was dissolved in 4 mL of HOAc, then 0.5 mL of ethane-1,2-diamine was added and the mixture was refluxed for 5 hours in open air. The mixture was poured into ice-water, adjusted with aqueous Na$_2$CO$_3$ until PH>9, then extracted with EtOAc (3×50 mL) and purified by preparative HPLC to give the title compound (16 mg, yield=9%). LCMS: 415.2 m/z (M+H)$^+$; ret. time: 2.15 min (Analytical Method C: Solvent A-Water (0.01% NH3)/Solvent B-Acetonitrile, gradient: 5%-95% Solvent B in 1.6 min, column XBridge C18, 4.6×50 mm, 3.5 um, oven temp. 40° C.).

Methods similar to those given in this example were used with suitable substitution of reactants, e.g. replacing Intermediate B-1 with a suitable Intermediate, to prepare compounds as demonstrated in Examples 175, 177, and 316.

Example 139

Synthesis of (R)-8-cyclopentyl-7-ethyl-5-methyl-2-(5-phenylpyridazin-4-yl)-7,8-dihydropteridin-6(5H)-one

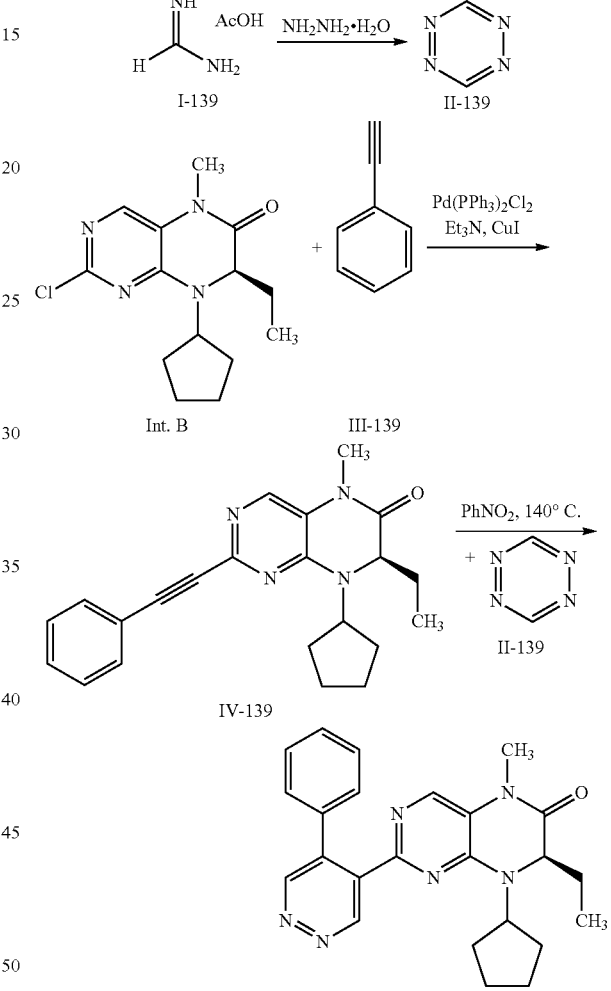

To the acetate of formimidamide (compound I-139, 3.12 g, 0.03 mol) cooled in ice, 4 ml of hydrazine hydrate (0.08 mol) was added slowly. The resulting mixture was stirred for 1 hour at rt. After addition of 2 ml of water and stirring at 0° C. for 1 hour, the precipitate was filtered off. The precipitate was dissolved in 10 mL of acetic acid and 1 g of sodium nitrite was added in small portions at about 5° C. After stirring for 1 hour, 15 mL of water was added and the mixture was extracted with DCM (4×15 mL). The combined DCM layers were washed with aqueous NaHCO$_3$ until neutralized, dried with MgSO$_4$ and concentrated to give 1,2,4,5-tetrazine (compound II-139) as a red solid.

To a solution of Intermediate B (1.0 eq) in DMF, ethynylbenzene (compound III-139, 3.0 eq), Pd(PPh$_3$)$_2$Cl$_2$ (0.2 eq), CuI (0.25 eq) and Et$_3$N (5.0 eq) were added. The mixture was refluxed for 18 h under argon, extracted with EtOAc and purified by silica gel column to give (R)-8-cyclopentyl-7-ethyl-5-methyl-2-(phenylethynyl)-7,8-dihydropteridin-6(5H)-one (compound IV-139).

Compound II-139 (2.0 eq) and compound IV-139 (1.0 eq) were combined with nitrobenzene in a sealed tube and heated to 140° C. for 3 hours. Solvent was removed under reduced pressure and the residue was purified by reverse phase HPLC to give the title compound as a tan solid. LCMS (0.05% TFA): 415.2 m/z (M+H)+; $^1$H-NMR (DMSO-d6, 500 MHz): δ: 9.50 (s, 1H), 9.34 (s, 1H), 8.18 (s, 1H), 7.41 (m, 3H), 7.29 (m, 2H), 4.24 (m, 1H), 3.53 (m, 1H), 3.30 (s, 3H), 1.67-1.28 (m, 10H), 0.67 (t, 3H, J=7.5 Hz).

Example 140

Synthesis of (R)-7-ethyl-5-methyl-2-(2-(pyrazin-2-yl)-1H-imidazol-1-yl)-8-(tetrahydro-2H-pyran-4-yl)-7,8-dihydropteridin-6(5H)-one

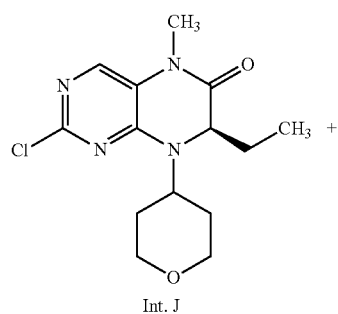

Int. J

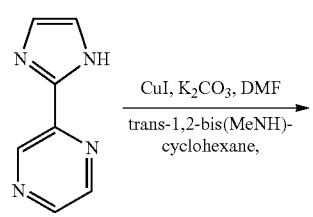

CuI, K$_2$CO$_3$, DMF
trans-1,2-bis(MeNH)-cyclohexane,

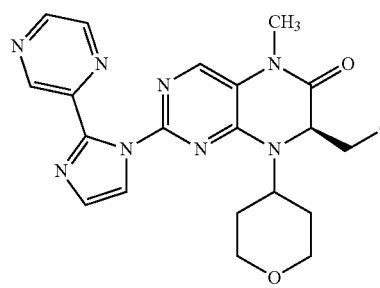

The title compound was prepared similarly to the methods described in Example 77, with Intermediate J instead of Intermediate C and with 2-(1H-imidazol-2-yl)pyrazine instead of 2-phenyl-1H-imidazole. LCMS: 421.2 m/z (M+H)+; ret. Time: 3.33 min (Analytical Method C).

Example 144

Synthesis of (S)-6a-ethyl-5-methyl-2-(2-(pyrazin-2-yl)-1H-imidazol-1-yl)-6a,7,8,9-tetrahydropyrrolo[2,1-h]pteridin-6(5H)-one

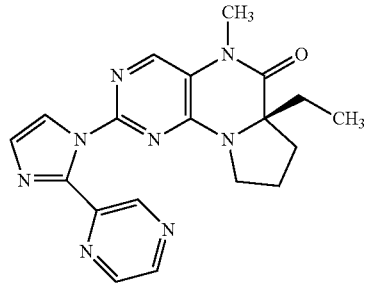 [SMILES: CC[C@@]12CCCN1c1nc(-n3ccnc3-c3cnccn3)ncc1N(C)C2=O]

The title compound was prepared similarly to the methods described in Example 3, with Intermediate K-1 instead of Intermediate A, and 2-(1H-imidazol-2-yl)pyrazine instead of 1H-imidazole in the first step. LCMS: 377.2 m/z (M+H)+; ret. Time: 3.99 min (Analytical Method C).

Example 145

Synthesis of (S)-6a-ethyl-5-methyl-2-(2-(pyridin-2-yl)-1H-imidazol-1-yl)-6a,7,8,9-tetrahydropyrrolo[2,1-h]pteridin-6(5H)-one

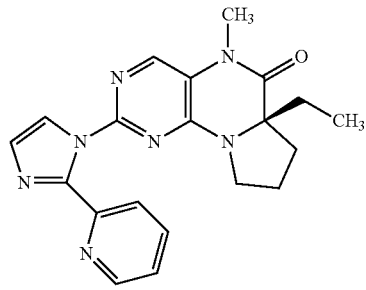 [SMILES: CC[C@@]12CCCN1c1nc(-n3ccnc3-c3ccccn3)ncc1N(C)C2=O]

The title compound was prepared similarly to the methods described in Example 3, with Intermediate K-1 instead of Intermediate A, and 2-(1H-imidazol-2-yl)pyridine instead of 1H-imidazole in the first step. LCMS: 376.2 m/z (M+H)+; ret. Time: 4.25 min (Analytical Method C).

Example 147

Synthesis of (R)-8-cyclopropyl-7-ethyl-5-methyl-2-(2-(pyridin-4-yl)-1H-imidazol-1-yl)-7,8-dihydropteridin-6(5H)-one

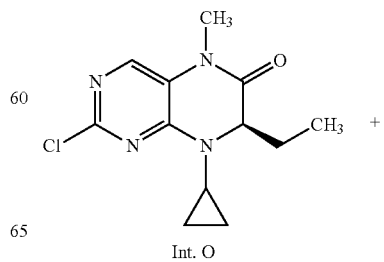

Int. O

-continued

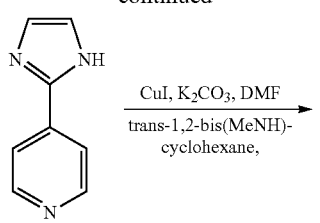

The title compound was prepared similarly to the methods described in Example 77, with Intermediate O instead of Intermediate C and with 4-(1H-imidazol-2-yl)pyridine instead of 2-phenyl-1H-imidazole. LCMS: 376.1 m/z (M+H)+; ret. Time: 3.90 min (Analytical Method C).

Example 148

Synthesis of (R)-7-ethyl-8-isopropyl-5-methyl-2-(2-(pyrimidin-2-yl)-1H-imidazol-1-yl)-7,8-dihydropteridin-6(5H)-one

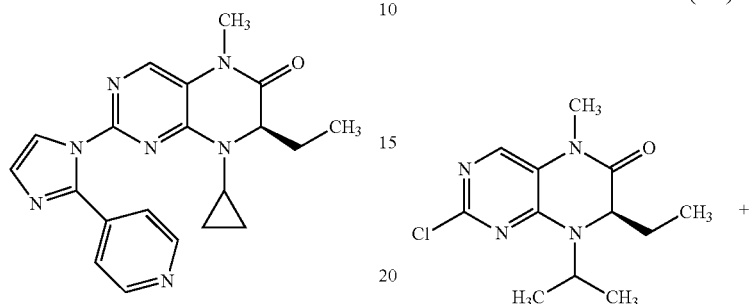

The title compound was prepared similarly to the methods described in Example 77, with 2-(1H-imidazol-2-yl)pyrimidine instead of 2-phenyl-1H-imidazole. LCMS: 379.2 m/z (M+H)+; ret. Time: 4.15 min (Analytical Method C).

Example 149

Synthesis of (R)-7-ethyl-8-isopropyl-5-methyl-2-(2-(pyrimidin-5-yl)-1H-imidazol-1-yl)-7,8-dihydropteridin-6(5H)-one

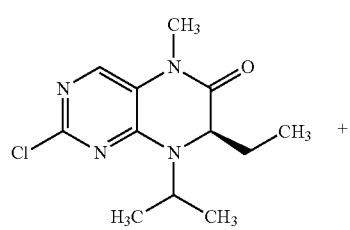

The title compound was prepared similarly to the methods described in Example 77, with 5-(1H-imidazol-2-yl)pyrimidine instead of 2-phenyl-1H-imidazole. LCMS: 379.1 m/z (M+H)+; ret. Time: 4.16 min (Analytical Method C).

Example 152

Synthesis of (R)-7-ethyl-8-isopropyl-5-methyl-2-(2-(pyridazin-3-yl)-1H-imidazol-1-yl)-7,8-dihydropteridin-6(5H)-one

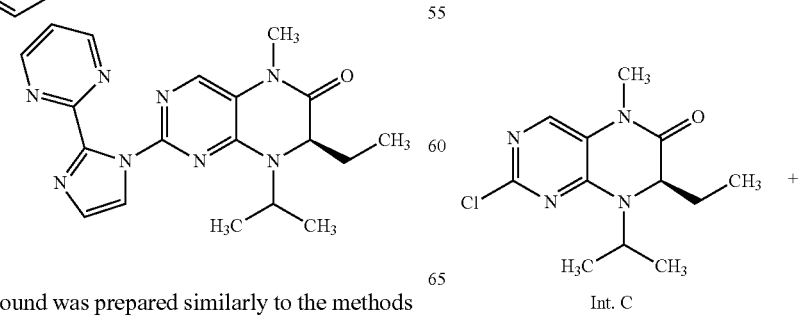

-continued

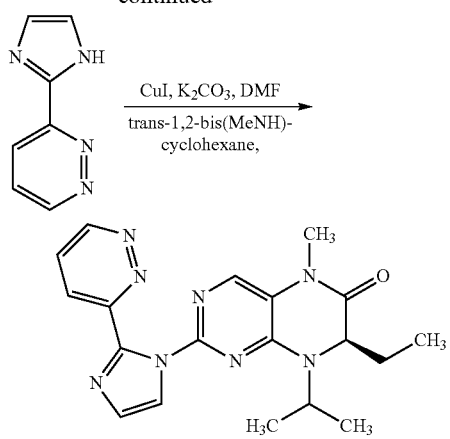

The title compound was prepared similarly to the methods described in Example 77, with 3-(1H-imidazol-2-yl)pyridazine instead of 2-phenyl-1H-imidazole. LCMS: 379.1 m/z (M+H)⁺; ret. Time: 4.67 min (Analytical Method C).

Example 153

Synthesis of (R)-7-ethyl-8-isopropyl-5-methyl-2-(2-(pyridin-2-yl)-1H-imidazol-1-yl)-7,8-dihydropteridin-6(5H)-one

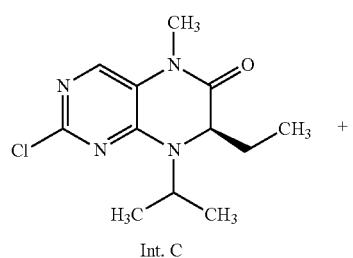

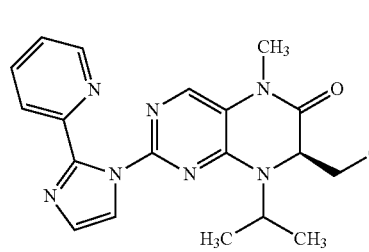

The title compound was prepared similarly to the methods described in Example 77, with 2-(1H-imidazol-2-yl)pyridine instead of 2-phenyl-1H-imidazole. LCMS: 378.2 m/z (M+H)⁺; ret. Time: 4.67 min (Analytical Method C).

Example 154

Synthesis of (R)-7-ethyl-8-isopropyl-5-methyl-2-(2-(pyridin-3-yl)-1H-imidazol-1-yl)-7,8-dihydropteridin-6(5H)-one

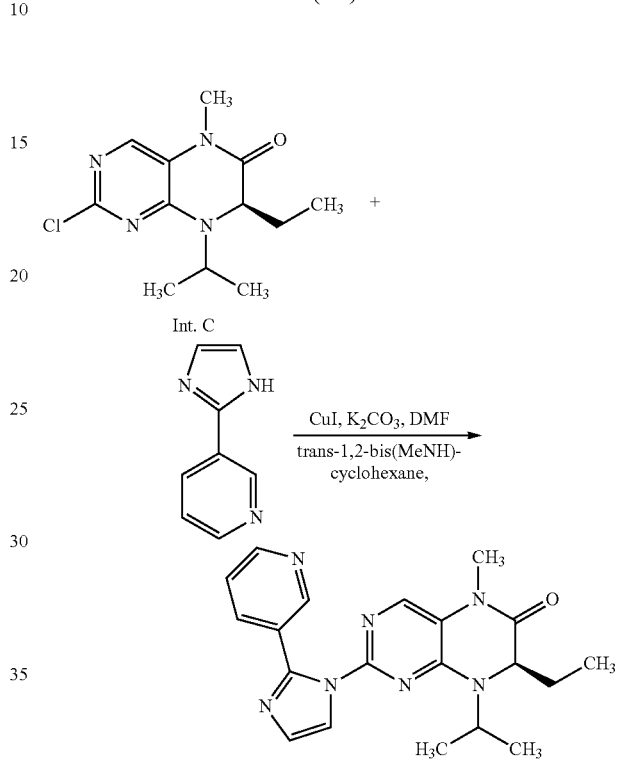

The title compound was prepared similarly to the methods described in Example 77, with 3-(1H-imidazol-2-yl)pyridine instead of 2-phenyl-1H-imidazole. LCMS: 378.1 m/z (M+H)⁺; ret. Time: 4.09 min (Analytical Method C).

Example 157

Synthesis of (R)-7-ethyl-5-methyl-8-(tetrahydro-2H-pyran-4-yl)-2-(2-(thiazol-2-yl)-1H-imidazol-1-yl)-7,8-dihydropteridin-6(5H)-one

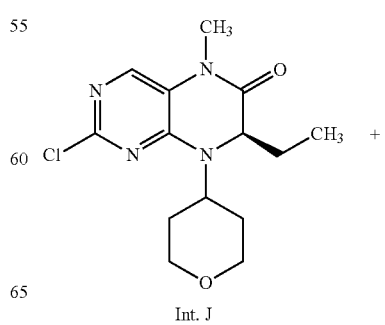

-continued

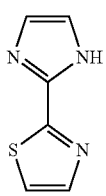
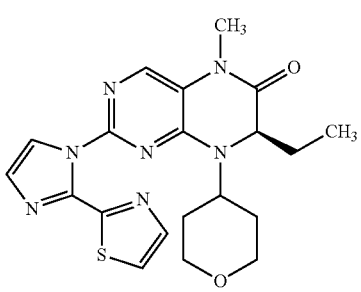

→ CuI, K₂CO₃, DMF
trans-1,2-bis(MeNH)-cyclohexane,

The title compound was prepared similarly to the methods described in Example 77, with Intermediate J instead of Intermediate C and with 2-(1H-imidazol-2-yl)thiazole instead of 2-phenyl-1H-imidazole. LCMS: 426.1 m/z (M+H)⁺; ret. Time: 4.57 min (Analytical Method C).

Example 159

Synthesis of (R)-8-cyclopentyl-7-ethyl-5-methyl-2-(2-(pyrimidin-5-yl)-1H-imidazol-1-yl)-7,8-dihydropteridin-6(5H)-one

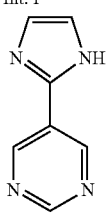

Int. B

→ CuI, K₂CO₃, DMF
trans-1,2-bis(MeNH)-cyclohexane,

The title compound was prepared similarly to the methods described in Example 77, with Intermediate B instead of Intermediate C and with 5-(1H-imidazol-2-yl)pyrimidine instead of 2-phenyl-1H-imidazole. LCMS: 405.2 m/z (M+H)⁺; ret. Time: 5.44 min (Analytical Method C).

Example 176

Synthesis of (R)-8-cyclobutyl-7-ethyl-5-methyl-2-(2-(pyrimidin-5-yl)-1H-imidazol-1-yl)-7,8-dihydropteridin-6(5H)-one

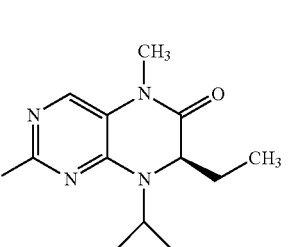

Int. F

→ CuI, K₂CO₃, DMF
trans-1,2-bis(MeNH)-cyclohexane,

The title compound was prepared similarly to the methods described in Example 77, with Intermediate F instead of Intermediate C and with 5-(1H-imidazol-2-yl)pyrimidine instead of 2-phenyl-1H-imidazole. LCMS: 391.2 m/z (M+H)⁺; ret. Time: 4.74 min (Analytical Method C).

Example 183

Synthesis of (R)-8-cyclobutyl-7-ethyl-5-methyl-2-(2-(pyrimidin-2-yl)-1H-imidazol-1-yl)-7,8-dihydropteridin-6(5H)-one Int. F

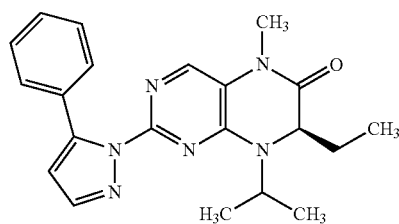

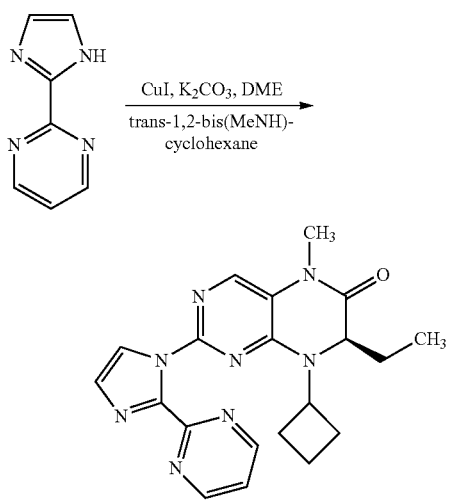

The title compound was prepared similarly to the methods described in Example 26, with Intermediate F instead of Intermediate B and with 2-(1H-imidazol-2-yl)pyrimidine instead of 2-phenyl-1H-imidazole. LCMS: 391.2 m/z (M+H)+; ret. Time: 4.73 min (Analytical Method C).

Example 188

Synthesis of (R)-7-ethyl-8-isopropyl-5-methyl-2-(5-phenyl-1H-pyrazol-1-yl)-7,8-dihydropteridin-6(5H)-one

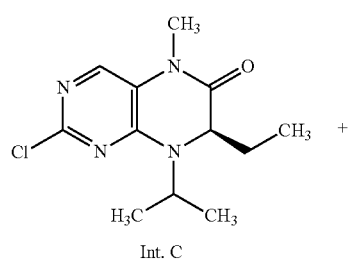

Int. C

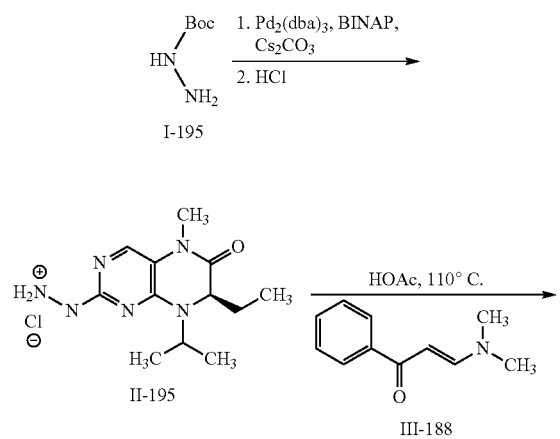

Compound II-195 was prepared as described in Example 195.

Compound II-195 was then taken up in 2 mL of AcOH and charged to a 30 mL reaction vial. (3-(dimethylamino)-1-phenylprop-2-en-1-one (III-188, 2 eq) was added, and the reaction vial was sealed under a Teflon septum. The mixture was heated to 110° C. for 2 h. After cooling to 23° C., the reaction mixture was brought to pH 8 by slow addition of an aqueous solution of 4N K$_2$CO$_3$. The resulting mixture was extracted with EtOAc and rinsed sequentially with saturated, aqueous solutions of ammonium chloride, sodium bicarbonate, and brine. The resulting organic liquid was dried over sodium sulfate and decanted into a 250 mL round bottom flask. After concentration of the product under reduced pressure, the resulting residue was purified by HPLC (35-55% MeCN, 20 mL/min, 210 nM, 0.1% TFA. Stationary Phase: Phenomenex Luna C18, 2×25 cm) to give 26 mg of the title compound. LCMS [M+H]: 377.2; ret. Time: 4.53 min (Analytical Method C).

Methods similar to those given in this example were used with suitable substitution of reactants, e.g. replacing Intermediate C with a suitable Intermediate, to prepare compounds as demonstrated in Examples 193, 207, and 209.

Example 189

Synthesis of (S)-6a-ethyl-5-methyl-2-(5-phenyl-1H-1,2,4-triazol-1-yl)-6a,7,8,9-tetrahydropyrrolo[2,1-h]pteridin-6(5H)-one

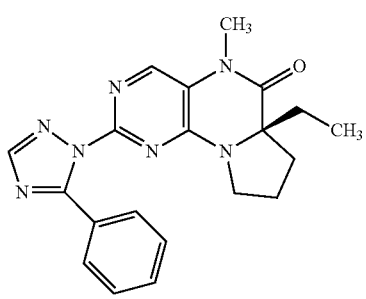 [SMILES: CC[C@@]12CCCN1c1nc(-n3ncnc3-c3ccccc3)ncc1N(C)C2=O]

The title compound was prepared similarly to the methods described in Example 195, with Intermediate K instead of Intermediate C in the first step. LCMS: 376.2 m/z (M+H)+; ret. Time: 3.37 min (Analytical Method C).

Example 195

Synthesis of (R)-7-ethyl-8-isopropyl-5-methyl-2-(5-phenyl-1H-1,2,4-triazol-1-yl)-7,8-dihydropteridin-6(5H)-one

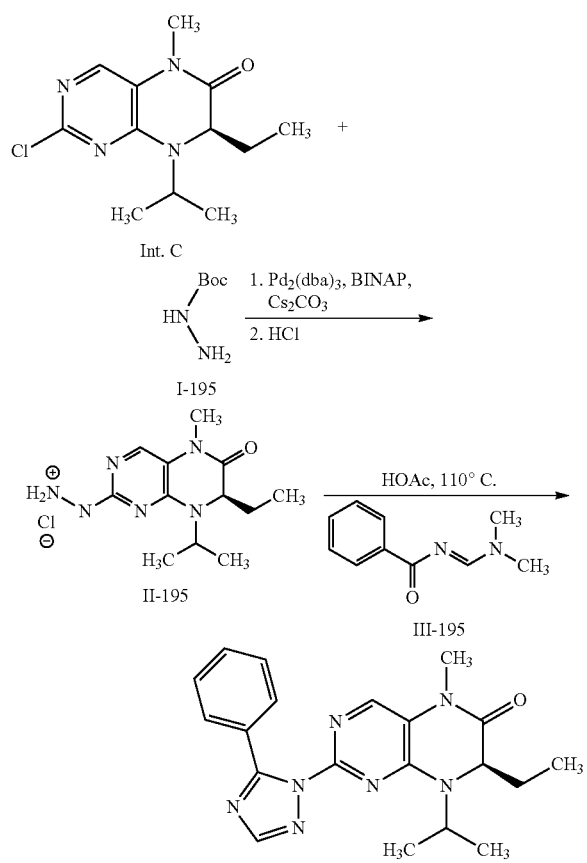

A 5 mL microwave vial was charged with Intermediate C (150 mg, 0.56 mmol), tert-butyl hydrazinecarboxylate (1-195, 222 mg, 1.68 mmol), Pd$_2$(dba)$_3$ (110 mg, 0.12 mmol), BINAP (150 mg, 0.24 mmol), Cs$_2$CO$_3$ (546 mg, 1.68 mmol), and 4 mL of dioxane. The vial was sealed and heated in a microwave to 150° C. for 0.5 h. Upon cooling to 23° C., the reaction mix was diluted with EtOAc, and rinsed sequentially with saturated, aqueous solutions of ammonium chloride, sodium bicarbonate, and brine. The resulting organic liquid was dried over sodium sulfate and decanted into a 250 mL round bottom flask. After concentration of the product under reduced pressure, the resulting residue was purified by MPLC (0 to 100% EtOAc/hexanes) to give 140 mg of the desired intermediate, half of which was taken directly (2 mL of DCM solution) into 4 N HCl in dioxane. After 1 h, the solution was concentrated under reduced pressure to give the HCl salt (compound II-195).

Compound II-195 was then taken up in 2 mL of AcOH and charged to a 30 mL reaction vial. (E)-N-((dimethylamino)methylene)benzamide (III-195, 2 eq) was added, and the reaction vial was sealed under a Teflon septum. The mixture was heated to 110° C. for 2 h. After cooling to 23° C., the reaction mixture was brought to pH 8 by slow addition of an aqueous solution of 4N K$_2$CO$_3$. The resulting mixture was extracted with EtOAc and rinsed sequentially with saturated, aqueous solutions of ammonium chloride, sodium bicarbonate, and brine. The resulting organic liquid was dried over sodium sulfate and decanted into a 250 mL round bottom flask. After concentration of the product under reduced pressure, the resulting residue was purified by HPLC (30-60% MeCN, 18 mL/min, 210 nM, 0.1% TFA. Stationary Phase: Phenomenex Luna C18, 2×25 cm) to give 26 mg of the title compound. LCMS [M+H]: 378.2; ret. Time: 4.12 min (Analytical Method C).

Methods similar to those given in this example were used with suitable substitution of reactants, e.g. replacing Intermediate C with a suitable Intermediate, and/or replacing (E)-N-((dimethylamino)methylene)benzamide with a suitable compound, to prepare compounds as demonstrated in Examples 189, 208, 215-217, 219, and 235.

Example 221

Synthesis of (7R)-7-ethyl-5-methyl-8-(tetrahydrofuran-3-yl)-2-(2-(thiazol-2-yl)-1H-imidazol-1-yl)-7,8-dihydropteridin-6(5H)-one

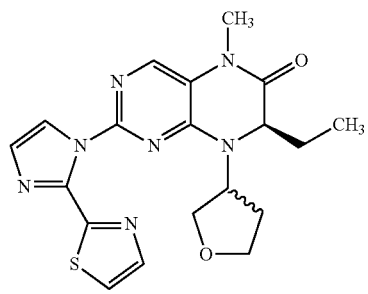 [SMILES: CC[C@@H]1C(=O)N(C)c2cnc(-n3ccnc3-c3nccs3)nc2N1C1CCOC1]

The title compound was prepared similarly to the methods described in Example 3, with Intermediate N-1 instead of Intermediate A, and 2-(1H-imidazol-2-yl)thiazole instead of 1H-imidazole in the first step. LCMS: 412.1 m/z (M+H)$^+$; ret. Time: 4.39 (Analytical Method C).

Example 230

Synthesis of (7R)-7-ethyl-2-(2-(4-fluorophenyl)-1H-imidazol-1-yl)-5-methyl-8-(tetrahydrofuran-3-yl)-7,8-dihydropteridin-6(5H)-one

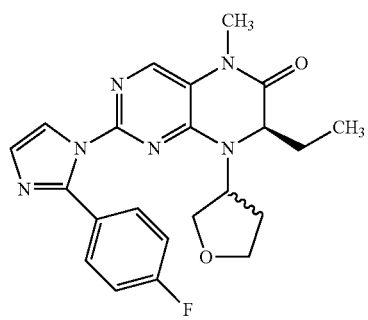 [SMILES: CC[C@@H]1C(=O)N(C)c2cnc(-n3ccnc3-c3ccc(F)cc3)nc2N1C1CCOC1]

The title compound was prepared similarly to the methods described in Example 3, with Intermediate N-1 instead of Intermediate A, and 2-(4-fluorophenyl)-1H-imidazole instead of 1H-imidazole in the first step. LCMS: 423.2 m/z (M+H)$^+$; ret. Time: 4.84 (Analytical Method C).

Example 245

Synthesis of (R)-8-cyclopentyl-7-ethyl-5-methyl-2-(4-phenyl-1H-pyrazol-3-yl)-7,8-dihydropteridin-6(5H)-one

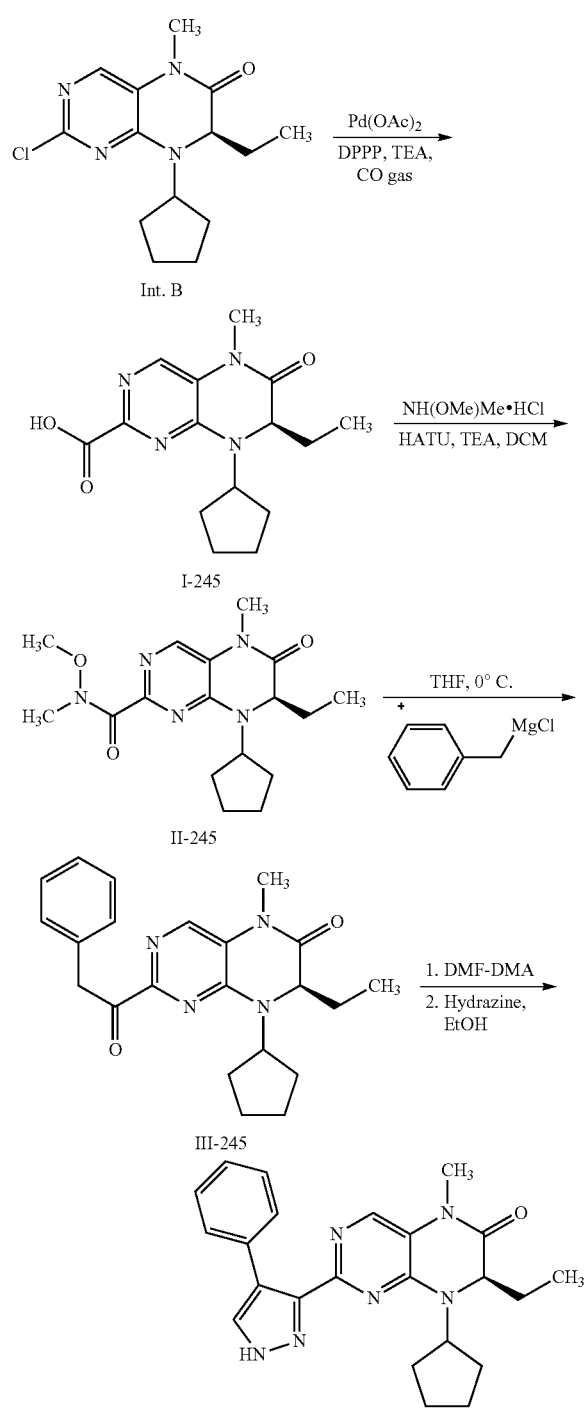

Intermediate B (10.0 g, 34.01 mmol) was dissolved in 15 mL of DMSO and 185 mL of tBuOH and Pd(OAc)₂ (1.14 g, 5.1 mmol), DPPP (2.2 g, 5.1 mmol) and TEA (7.7 g, 76.5 mmol) were added. The solution was stirred at 80° C. for 10 h under CO (10 atm). The solvent was removed under reduced pressure and the residue was dissolved in EtOAc. The organic layer was washed with water and brine, dried with Na₂SO₄, purified by silica gel column (DCM:MeOH=20:1) to give (R)-8-cyclopentyl-7-ethyl-5-methyl-6-oxo-5,6,7,8-tetrahydropteridine-2-carboxylic acid (compound I-245, 2.2 g) as a yellow solid.

Compound I-245 (2.0 g, 6.58 mmol) was dissolved in 30 mL of DCM, NH(OMe)Me·HCl (770 mg, 7.90 mmol) was added, followed by the addition of TEA (1.99 g, 19.74 mmol) and HATU (3.0 g, 7.90 mmol) to the solution at 0° C. The mixture was warmed to rt and stirred for 2 h, then washed with water, brine, dried and the solvent removed. The resulting material was purified by silica gel column (PE:EtOAc:MeOH=1:1:0.1) to give (R)-8-cyclopentyl-7-ethyl-N-methoxy-N,5-dimethyl-6-oxo-5,6,7,8-tetrahydropteridine-2-carboxamide (compound II-245) as a white solid.

Compound II-245 (1.5 g, 4.32 mmol) was dissolved in 20 mL of dry THF and cooled to 0° C. Benzyl magnesium chloride (2M in THF, 2.6 ml, 5.19 mmol) was added dropwise. The mixture was stirred for 2 h at 0° C., then the reaction quenched with water at 0° C. The THF was removed under reduced pressure and the water layer was extracted with EtOAc. The organic layer was washed with brine, dried and purified by silica gel column (PE:EtOAc=2:1) to give (R)-8-cyclopentyl-7-ethyl-5-methyl-2-(2-phenylacetyl)-7,8-dihydropteridin-6(5H)-one (compound III-245) as a yellow oil.

Compound III-245 (200 mg, 0.53 mmol) was dissolved in 2.0 mL of DMF-DMA. The mixture was refluxed for 2 h and the solvent was removed. The resulting oil was dissolved in 2.0 mL of DMF and excess hydrazine hydrogen chloride was added and this mixture was stirred at 110° C. for 18 h. The mixture was washed with water, extracted with 20 mL of EtOAc, the organic layer was dried, evaporated and purified by silica gel column (PE:EtOAc:MeOH=1:1:0.2) to give the title compound as a brown solid. LCMS (0.01% TFA): 403.2 m/z (M+H)⁺; ¹H-NMR (CDCl₃, 500 MHz): δ: 8.03 (s, 1H), 7.68 (s, 1H), 7.53 (d, 2H, J=7.5 Hz), 7.36 (t, 2H, J=7.5 Hz), 7.29 (t, 1H, J=7.5 Hz), 4.19 (m, 2H), 3.36 (s, 3H), 1.78~1.26 (m, 10H), 0.83 (t, 3H, J=7.5 Hz).

Example 246

Synthesis of (R)-7-ethyl-8-isopropyl-5-methyl-2-(2-phenyl-4,5-dihydro-1H-imidazol-1-yl)-7,8-dihydropteridin-6(5H)-one

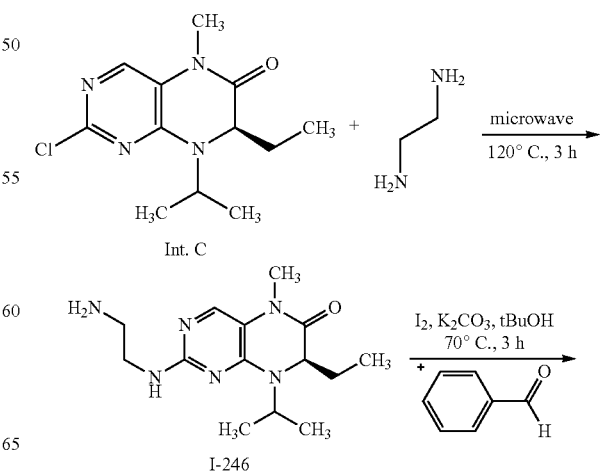

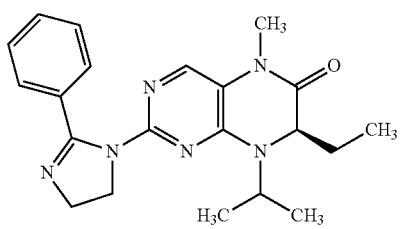

Intermediate C (1 mmol, 269 mg) in ethylenediamine (10 mmol, 600 mg, 0.7 mL) was heated at 120° C. in a microwave for 3 h. The reaction was evaporated, taken up in EtOAc and washed 3× with water, then dried with MgSO$_4$ and evaporated to give (R)-2-(2-aminoethylamino)-7-ethyl-8-isopropyl-5-methyl-7,8-dihydropteridin-6(5H)-one (compound I-246).

Compound I-246 (1.1 mmol) and benzaldehyde (1.1 mmol, 116 mg, 0.1 mL) were stirred in tBuOH at rt for 18 h, then K$_2$CO$_3$ (solid, 415 mg, 3 mmol) and I$_2$ (317 mg, 1.25 mmol) were added. The mixture was stirred at 70° C. for 3 h, then filtered, evaporated and partitioned between CHCl$_3$ and water. The organic layer was washed with aqueous saturated NaHCO$_3$ solution and brine, then dried with MgSO$_4$ and evaporated. The residue was purified with HPLC (first: reverse phase eluting with 30-60% acetonitrile in water with NH$_4$OH (0.1%) over 25 min at 18 mL/min on a Phenomenex Luna C-18 column, 2×25 cm, 5 micron packing; then the resulting sample was further purified with normal phase isocratic elution [15% EtOH/85% Hexane] using a ChiralPak AD column 2×25 cm, 5 micron packing) to give the title compound. LCMS: 379.3 m/z (M+H)$^+$; ret. Time: 7.01 min (Analytical Method A); $^1$H NMR (400 MHz, CDCl$_3$) δ: 7.6 (s, 1H), 7.5 (dd, 2H), 7.4 (m, 3H), 4.3 (m, 2H), 4.0 (m, 2H), 3.4 (ddd, 1H), 3.2 (s, 3H), 1.8 (m, 1H) (d, 3H), 0.9 (dd, 2H) and 0.8-0.7 ppm (m, 6H).

Example 247-275

Synthesis of tert-butyl 7-ethyl-6-oxo-2-(2-phenyl-1H-imidazol-1-yl)-6,7-dihydropteridin-8(5H)-ylcarbamate and tert-butyl 7-ethyl-5-methyl-6-oxo-2-(2-phenyl-1H-imidazol-1-yl)-6,7-dihydropteridin-8(5H)-ylcarbamate

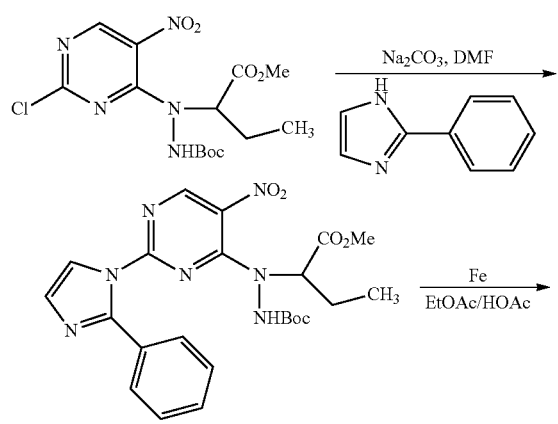

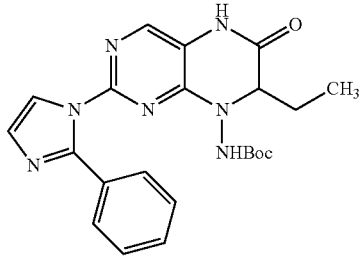

Ex. 274

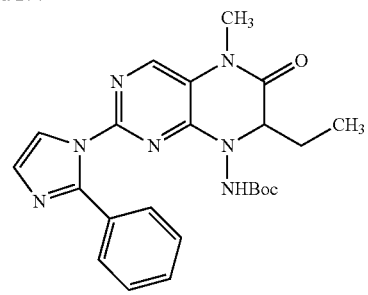

Ex. 275 tert-Butyl 7-ethyl-6-oxo-2-(2-phenyl-1H-imidazol-1-yl)-6,7-dihydropteridin-8(5H)-ylcarbamate (Example 274) and tert-butyl 7-ethyl-6-oxo-2-(2-phenyl-1H-imidazol-1-yl)-6,7-dihydropteridin-8(5H)-ylcarbamate (Example 275) were prepared similarly to the methods described in Example 3, with tert-butyl 2-(2-chloro-5-nitropyrimidin-4-yl)-2-(1-methoxy-1-oxobutan-2-yl)hydrazinecarboxylate (prepared as described in PCT publication WO 2009130016, the contents of which are hereby incorporated by reference with respect to this compound) instead of Intermediate A, and 2-phenyl-1H-imidazole instead of 1H-imidazole in the first step.

Example 274: $^1$H NMR (CDCl$_3$) δ: 7.68 (s, 1H), 7.64 (s, 1H), 7.58 (s, 1H), 7.50-7.40 (m, 2H), 7.40-7.30 (m, 4H), 7.18 (s, 1H), 5.78 (s, 1H), 4.55 (br s, 1H), 2.18-2.05 (m, 1H), 2.05-1.90 (m, 1H), 1.43 (s, 9H), 0.89 (t, J=7.4 Hz, 3H); LCMS: 364.1 m/z (M+H)$^+$; ret. Time: 5.87 min (Analytical Method C). Example 275: $^1$H NMR (CDCl$_3$) δ: 7.81 (s, 1H), 7.65 (s, 1H), 7.55-7.30 (m, 5H), 7.18 (s, 1H), 5.78 (s, 1H), 4.56 (br s, 1H), 3.35 (s, 3H), 2.20-2.03 (m, 1H), 2.03-1.88 (m, 1H), 1.42 (s, 9H), 0.82 (t, J=7.4 Hz, 3H); LCMS: 450.2 m/z (M+H)$^+$; ret. Time: 6.89 min (Analytical Method C).

Example 278

Synthesis of 8-amino-7-ethyl-5-methyl-2-(2-phenyl-1H-imidazol-1-yl)-7,8-dihydropteridin-6(5H)-one Ex. 275

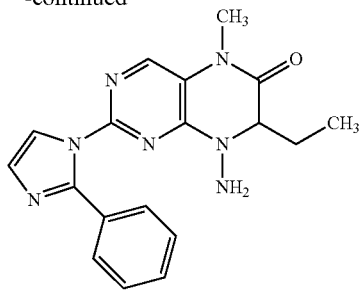

tert-Butyl 7-ethyl-6-oxo-2-(2-phenyl-1H-imidazol-1-yl)-6,7-dihydropteridin-8(5H)-ylcarbamate (Example 275, 281 mg, 0.63 mmol) was dissolved in 4N HCl (1 mL dioxane) at 0° C., then allowed to warm to rt for 1 h. The reaction mixture was concentrated, and a portion of the material was purified by preparative HPLC to give the title compound: $^1$H NMR (CD$_3$OD) δ: 8.27 (s, 1H), 7.83 (s, 1H), 7.70 (s, 1H), 7.68-7.50 (m, 5H), 4.38 (br s, 1H), 3.33 (s, 3H), 2.15-1.90 (m, 2H), 0.76 (t, J=7.4 Hz, 3H); LCMS: 350.1 m/z (M+H)$^+$; ret. Time: 3.46 min (Analytical Method C).

Example 280

Synthesis of 7-ethyl-5-methyl-2-(2-phenyl-1H-imidazol-1-yl)-8-(pyrrolidin-1-yl)-7,8-dihydropteridin-6(5H)-one

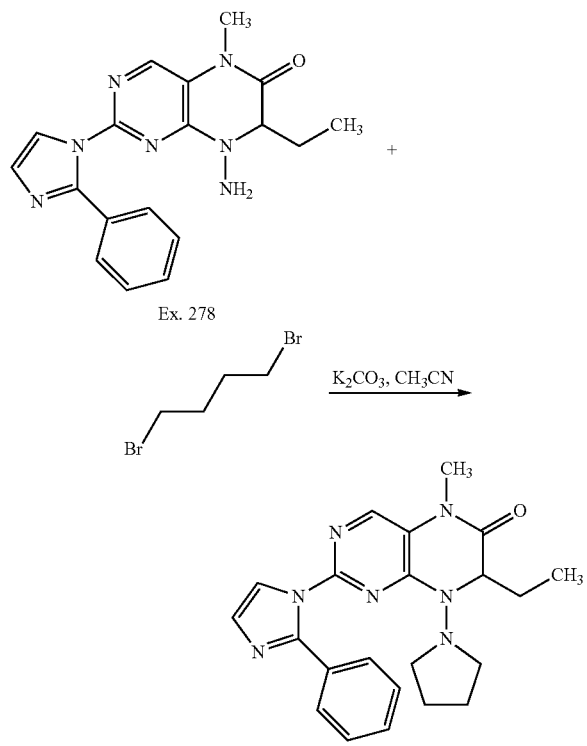

8-amino-7-ethyl-5-methyl-2-(2-phenyl-1H-imidazol-1-yl)-7,8-dihydropteridin-6(5H)-one hydrochloride salt (Example 278, 28 mg, 0.073 mmol) was combined with 1,4-dibromobutane (0.05 mL, 0.42 mmol) and potassium carbonate (38 mg, 0.27 mmol) in 0.2 mL of CH$_3$CN. This mixture was heated to 80° C. for 19 h, then filtered, washed with EtOAc, and the filtrate concentrated under reduced pressure. The residue was purified by HPLC to give the title compound. $^1$H NMR (CD$_3$OD) δ: 8.01 (s, 2H), 7.73 (d, J=1.8 Hz, 1H), 7.70-7.50 (m, 5H), 4.43 (t, J=4.1 Hz, 1H), 3.36 (s, 3H), 2.98-2.83 (m, 2H), 2.83-2.70 (m, 2H), 2.12-1.95 (m, 2H), 1.60-1.40 (m, 4H), 0.79 (t, J=7.5 Hz, 3H); LCMS [M+H]: 404.1 m/z (M+H)$^+$; ret. Time: 6.82 min (Analytical Method C).

Example 291

Synthesis of 7-ethyl-2-(2-(4-fluorophenyl)-1H-imidazol-1-yl)-5-methyl-8-phenyl-7,8-dihydropteridin-6(5H)-one

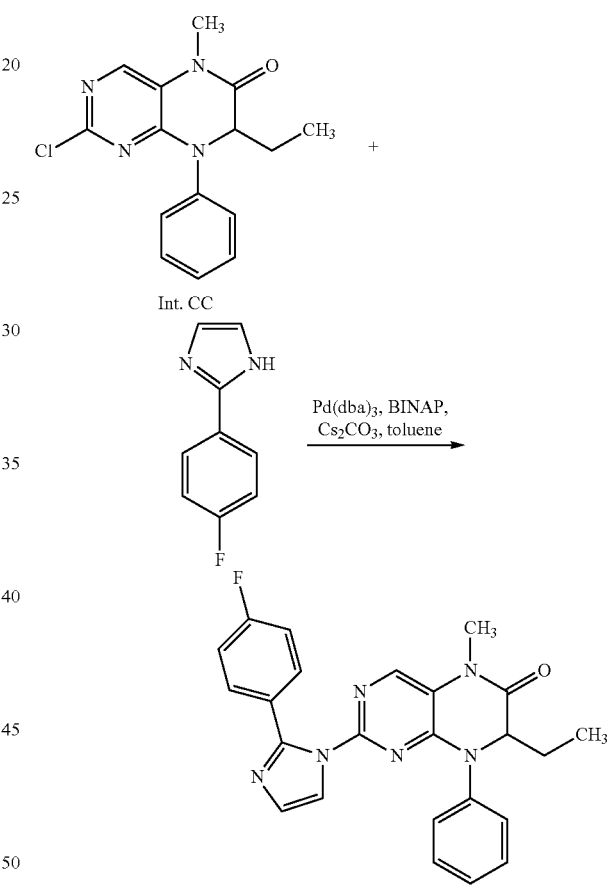

Intermediate CC (110 mg, 0.363 mmol), 2-(4-fluorophenyl)-1H-imidazole (70 mg, 0.435 mmol), Pd$_2$(dba)$_3$CHCl$_3$ (166 mg, 0.182 mmol), BINAP (226 mg, 0.3638 mmol), and Cs$_2$CO$_3$ (354 mg, 1.08 mmol) were dissolved in 1 mL of toluene in a microwave vial and a stream of nitrogen was bubbled through the mixture for 2 minutes. The resulting solution was heated at 140° C. for 1 h in a microwave. The reaction mixture was diluted with ethyl acetate and washed with saturated sodium bicarbonate solution. The organic extracts were dried with Na$_2$SO$_4$, filtered and evaporated, and the residue was purified by preparative HPLC to give the title compound (48 mg). LCMS: 429.1 m/z (M+H)$^+$; ret. Time 3.23 min (Analytical Method A).

Methods similar to those given in this example were used with suitable substitution of reactants, e.g. replacing Intermediate CC with a suitable Intermediate, and/or replacing 2-(4-fluorophenyl)-1H-imidazole with a suitable optionally substituted ring, to prepare compounds as demonstrated in Examples 237, 242, 247, 260, 276, 289, 290, 293, 294, 298, 322, 324, 332, 342, 346, 350, 351, 358, 359, 366, and 388.

Example 296

Synthesis of (R)-7-ethyl-2-(5-(4-fluorophenyl)isothiazol-4-yl)-8-isopropyl-5-methyl-7,8-dihydropteridin-6(5H)-one

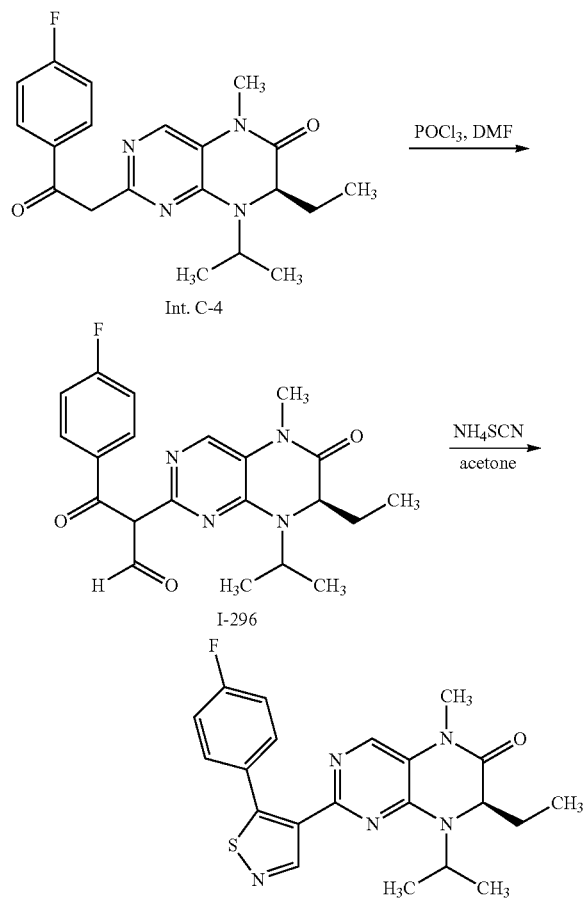

A mixture of Intermediate C-4 (0.26 g, 0.691 mmol) in 2 mL of anhydrous DMF was cooled to 0° C. under N₂ (g) inlet prior to dropwise addition of phosphorus oxychloride (0.15 mL, 1.61 mmol). The reaction mixture was warmed to rt, placed in an oil bath set at 80° C. for 4 h and then quenched with water. The mixture was partitioned between water and ethyl acetate and the organic layer was dried (sodium sulfate), filtered and concentrated to give 2-((R)-7-ethyl-8-isopropyl-5-methyl-6-oxo-5,6,7,8-tetrahydropteridin-2-yl)-3-(4-fluorophenyl)-3-oxopropanal (compound I-296). MS; m/z 417.1 (M+H)⁺; retention time=1.937.

To compound I-296 (0.085 g, 0.204 mmol) in 1.4 mL of anhydrous acetone, ammonium thiocyanate (0.068 g, 0.893 mmol) was added. The reaction mixture was placed in an oil bath set at 50° C. with N₂ (g) inlet for 4 h and then cooled and concentrated, the purified by preparative HPLC to give the title compound. LCMS: 412.1 m/z (M+H)⁺; ret. Time: 4.61 min (Analytical Method A).

Example 299

Synthesis of (7R)-7-ethyl-2-(1H-imidazol-1-yl)-5-methyl-8-(tetrahydrofuran-3-yl)-7,8-dihydropteridin-6(5H)-one

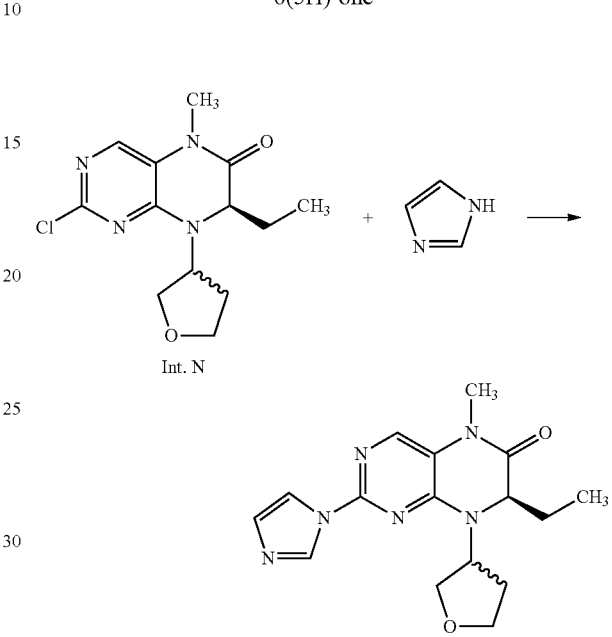

Intermediate N (120 mg, 0.404 mmol as a single diastereomer with unknown stereochemistry for the tetrahydrofuran ring) and 1H-imidazole (500 mg) were heated at 120° C. for 20 h. The resulting mixture was diluted with DCM and washed with saturated sodium bicarbonate solution. The organic extracts were dried with Na₂SO₄, filtered and evaporated, and the residue was purified by preparative HPLC to give the title compound (43 mg). LCMS: 329.1 m/z (M+H)⁺; ret. Time 6.52 min (Analytical Method D).

Methods similar to those given in this example were used with suitable substitution of reactants, e.g. replacing Intermediate N with a suitable Intermediate, to prepare compounds as demonstrated in Examples 300-302, 333, 336, and 343.

Example 306

Synthesis of (R)-8-cyclopentyl-7-ethyl-5-methyl-2-(5-(pyridin-2-yl)-1H-pyrazol-4-yl)-7,8-dihydropteridin-6(5H)-one

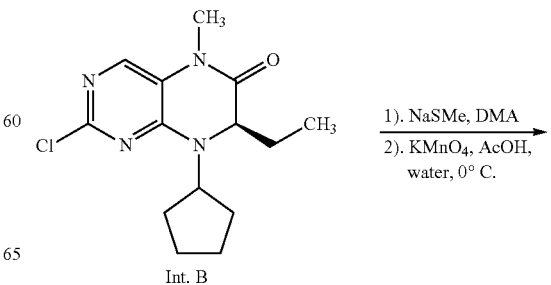

1). NaSMe, DMA
2). KMnO₄, AcOH, water, 0° C.

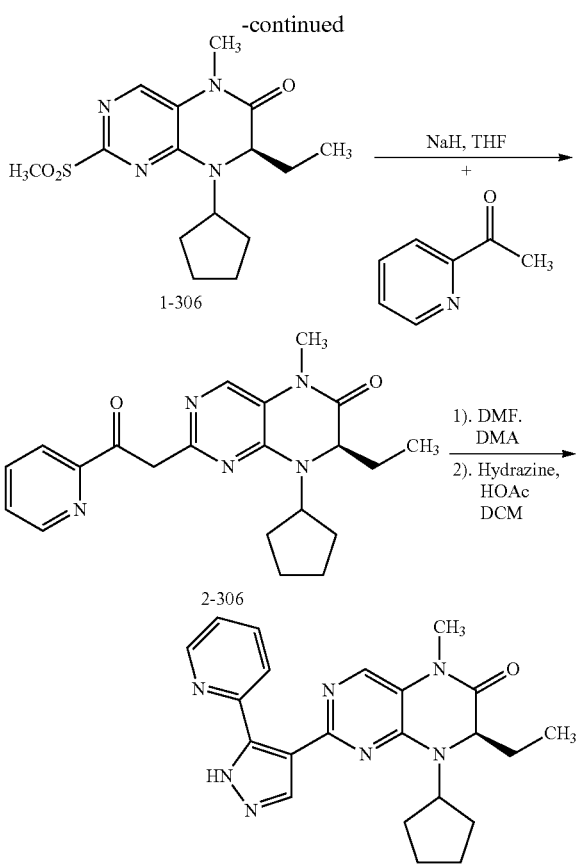

To a stirring mixture of Intermediate B (600 mg, 1 eq) in 2.1 mL of DMA, sodium methanethiolate (286 mg, 2.0 eq) was added. The reaction mixture was placed in a 150° C. preheated oil bath and stirred for 2 hr. The reaction mixture was cooled to rt and slowly diluted with ethyl ether and brine. The layers were separated. The aqueous layer was extracted with ethyl ether (2×30 mL). The combined organic layers were dried over MgSO$_4$, filtered, and concentrated under reduced pressure. To a stirring mixture of the crude methyl sulfide pteridine in 5 mL of HOAc at 0° C., a solution of KMnO$_4$ (643 mg, 2 eq) in 5 mL of water was added slowly over 10 min. The reaction mixture was reacted for 1 h before additional KMnO$_4$ (320 mg, 0.5 eq) in water was added. Cold water and a 10% Na$_2$S$_2$O$_3$ solution were added. The reaction mixture was diluted with EtOAc. The layers were separated and the aqueous layer was extracted with EtOAc (2×25 mL). The combined organic layers were dried over MgSO$_4$, filtered, and concentrated under reduced pressure. The resulting material was purified by MPLC to give compound I-306. LCMS: 339.1 m/z (M+H)$^+$.

To a stirring mixture of the compound I-306 (50 mg, 1 eq) and 1-(pyridin-2-yl)ethanone (54 mg, 3 eq) in 1 mL of THF at rt, NaH (18 mg, 3 eq) was added in small portions. The reaction mixture was warmed to reflux for 20 min. The reaction mixture was cooled to rt and the reaction was quenched with brine and EtOAc. The layers were separated and the aqueous layer was extracted with EtOAc (2×25 mL). The organic layers were dried over MgSO$_4$, filtered, and concentrated under reduced pressure to give compound 2-306. LC/MS: 380.2 m/z (M+H)$^+$.

Compound 2-306 was dissolved in 2 mL of DMF DMA. The reaction mixture was warmed to 72° C. for 45 min. The reaction mixture was concentrated under reduced pressure. This product was dissolved in 1.5 mL of DCM and hydrazine (3 drops) and HOAc (3 drops) were added to the stirring mixture. The reaction mixture was warmed to reflux for 10 min, then cooled to rt and slowly quenched with a saturated NaHCO$_3$ solution. The aqueous layer was extracted with DCM (2×10 mL). The organic layers were dried over MgSO$_4$, filtered, and concentrated under reduced pressure. The product was purified by preparative HPLC to give the title compound. LCMS: 404.1 m/z (M+H)$^+$; ret. Time: 3.19 min (Analytical Method A); $^1$H-NMR (CDCl$_3$, 300 MHz): δ: 8.94-8.93 (m, 1H), 8.60 (s, 1H), 8.15-8.10 (m, 1H), 8.0 (s, 1H), 7.84-7.80 (m, 1H), 7.45-7.39 (m, 1H), 4.40-4.37 (m, 1H), 4.15-4.09 (m, 1H), 3.50 (s, 3H), 2.06-1.56 (m, 10H), 0.88 (t, J=7.4 Hz, 3H).

Methods similar to those given in this example were used with suitable substitution of reactants, e.g. replacing Intermediate B with a suitable Intermediate, and/or replacing 1-(pyridin-2-yl)ethanone with a suitable ketone, to prepare compounds as demonstrated in Examples 307, 310, 312, 313, 320, and 323.

Example 308 and 309

Synthesis of 5-methyl-2-(2-phenyl-1H-imidazol-1-yl)-8,9-dihydro-7H-6a,9-ethanopyrrolo[2,1-h]pteridin-6(5H)-one (308) and (6aS,9R)-6a,9-diethyl-5-methyl-2-(2-phenyl-1H-imidazol-1-yl)-6a,7,8,9-tetrahydropyrrolo[2,1-h]pteridin-6(5H)-one (309)

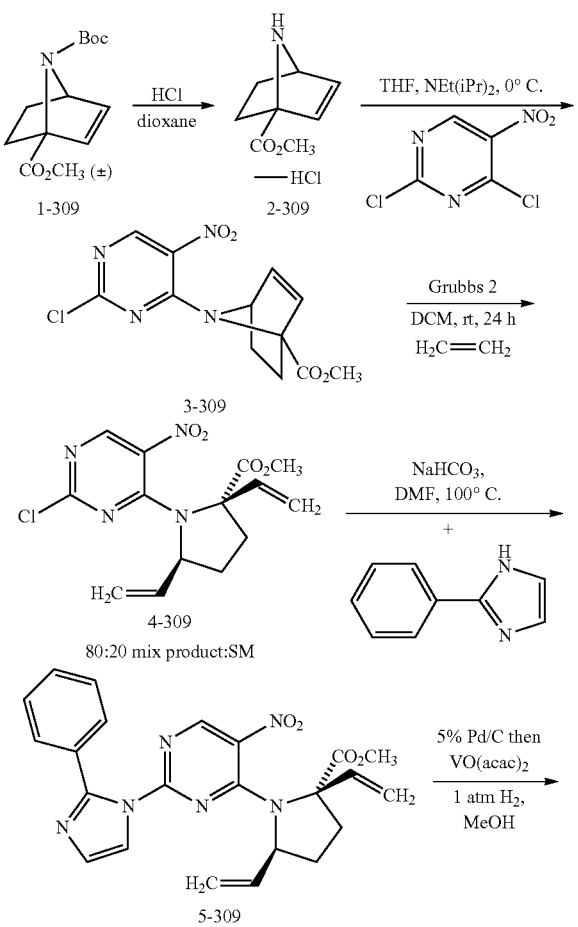

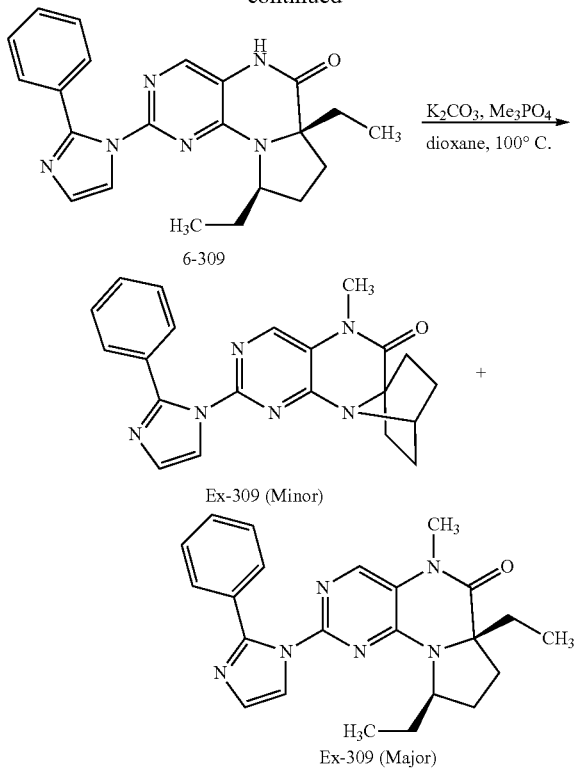

6-309

Ex-309 (Minor)

Ex-309 (Major)

Example 309 was prepared from 2,4-dichloro-5-nitropyrimidine and (+)-7-tert-butyl 1-methyl 7-azabicyclo[2.2.1]hept-5-ene-1,7-dicarboxylate (Compound 1-309), which was prepared according to the literature method: Carreras, J. et al. *Org. Lett.* 2007, 9, 1235-1238. Example 308 was isolated by HPLC as a minor by-product prepared along with Example 309.

Compound 1-309 (1.1 g, 4.5 mmol) was dissolved in 4 N HCl in 5 mL of dioxane at 0° C., then allowed to warm to rt for 1 h. The mixture was diluted with diethyl ether, and the resulting solid filtered through a sintered glass funnel, and washed with a few mL of cold diethyl ether to give compound 2-309 as a crude off-white solid (700 mg, 82%).

Compound 2-309 (700 mg, 3.7 mmol) was suspended in 7 mL of dry THF at 0° C., and 2,4-dichloro-5-nitropyrimidine (AK Scientific, 725 mg, 3.74 mmol) was added. Diisopropylethylamine (1.36 mL, 7.77 mmol) was added dropwise by syringe to this mixture with stirring. After 1 h, the reaction mixture was concentrated under reduced pressure, and the residue purified by flash chromatography (EtOAc/hexanes elution) to give compound 3-309 (1.14 g, 99%): LCMS: 311.0 m/z (M+H)+.

Compound 4-309 was synthesized similarly to the literature procedure: *Heterocycles* 2006, 68, 2079. Compound 3-309 (86 mg, 0.28 mmol) was dissolved in 14 mL of dry DCM, which was saturated in ethylene (g). Second generation Grubbs' catalyst [1,3-bis(2,4,6-trimethylphenyl)-2-imidazolidinylidene]dichloro(phenylmethylene)-(tricyclohexylphosphine)ruthenium] (30.1 mg, 0.035 mmol) was added, and the reaction was performed under an atmosphere of ethylene, with vigorous stirring at rt. After 27 h, the reaction was concentrated, and the mixture purified by flash chromatography (0-30% EtOAc/hexanes elution) to give a mixture of 3-309 and 4-309 (LCMS: 339.1 m/z (M+H)+).

Compound 4-309 (94 mg, 0.278 mmol, some 3-309) was dissolved in 1 mL of dry DMF, and NaHCO$_3$ (73 mg, 0.869 mmol) and 2-phenyl-1H-imidazole (118 mg, 0.821 mmol) were added. This mixture was heated to 100° C. for 15 h, then the solvents were removed, and the residue purified by flash chromatography (50-100% EtOAc/hexanes elution) to give compound 5-309 (67 mg, 54%): LCMS: 447.2 m/z (M+H)+.

According to the method outlined in WO 2009/019205, p. 13, compound 5-309 (67 mg, 0.15 mmol) was dissolved in 1 mL of MeOH, and 5% palladium on carbon (41 mg) was added. This was placed under a H$_2$ atm with stirring at rt. After 3 h, vanadyl acetylacetonate (27 mg, 0.10 mmol) was added, and the H$_2$ atm replaced. This was stirred at rt for 16 h, then the reaction mixture was filtered through diatomaceous earth, washed with MeOH, and the filtrate concentrated under reduced pressure to give compound 6-309. LCMS: 389.2 m/z (M+H)+.

Compound 6-309 (58 mg, 0.15 mmol) was dissolved in 1 mL of dioxane, and potassium carbonate (62 mg, 0.45 mmol) and trimethylphosphate (0.05 mL, 0.43 mmol) were added. This mixture was heated to 100° C. for 22 h, then the solvents were removed, and the crude material purified by HPLC to yield Example 308 as the minor product and Example 309 as the major product.

Example 308 (minor product): $^1$H NMR (CD$_3$OD) δ: 8.17 (br s, 1H), 8.06 (s, 1H), 7.70-7.50 (m, 6H), 4.11 (t, J=4.3 Hz, 1H), 3.63 (s, 2H), 3.38 (s, 3H), 2.02-1.92 (m, 2H), 1.90-1.78 (m, 2H), 1.65-1.45 (m, 4H); LCMS: 373.2 m/z (M+H)+; ret. Time: 5.42 min (Analytical Method C).

Example 309 (major product): $^1$H NMR (CD$_3$OD) δ: 8.06 (br s, 1H), 7.94 (s, 1H), 7.69 (br s, 1H), 7.61 (t, J=4.2 Hz, 1H), 7.55 (s, 2H), 7.54 (s, 2H), 3.70-3.50 (m, 1H), 3.36 (s, 3H), 2.22-2.13 (m, 1H), 2.10-2.00 (m, 1H), 1.94-1.83 (m, 1H), 1.76-1.62 (m, 2H), 1.60-1.47 (m, 1H), 0.98-0.85 (m, 1H), 0.75 (t, J=7.4 Hz, 3H), 0.63 (t, J=7.4 Hz, 3H); LCMS: 403.1 m/z (M+H)+; ret. Time: 3.44 min (Analytical Method C).

Example 314 and Example 315

Synthesis of (S)-6a-ethyl-5-methyl-2-(2-phenyl-1H-imidazol-1-yl)-6a,7,9,10-tetrahydro-[1,4]oxazino[3,4-h]pteridin-6(5H)-one (314) and (R)-6a-ethyl-5-methyl-2-(2-phenyl-1H-imidazol-1-yl)-6a,7,9,10-tetrahydro-[1,4]oxazino[3,4-h]pteridin-6(5H)-one (315)

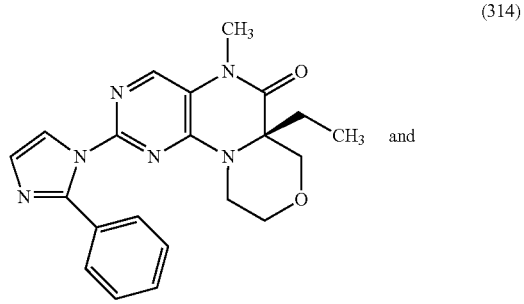

(314)

and (315)

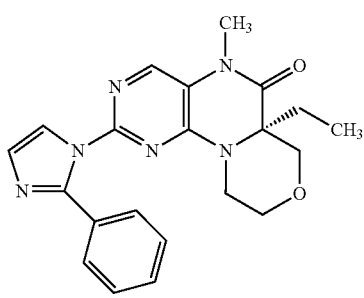

(+/−)-6a-Ethyl-5-methyl-2-(2-phenyl-1H-imidazol-1-yl)-6a,7,9,10-tetrahydro-[1,4]oxazino[3,4-h]pteridin-6(5H)-one (Example 317) was separated into pure enantiomers by chiral chromatography with a ChiralPak OD-H (2×25 cm) column with an isocratic mixture of 1:4 ethanol:hexane at a flow rate of 9 mL/min; compound was detected at a wavelength of 220 nm.

Example 314 was isolated as the first eluting enantiomer. $^1$H NMR (400 MHz, CDCl$_3$) δ: 7.76 (s, 1H), 7.73 (s, 1H), 7.44 (m, 1H), 7.33 (m, 4H), 7.18 (s, 1H), 4.13 (d, J=11.6 Hz, 1H), 3.72 (d, J=11.2 Hz, 1H), 3.61 (d, J=11.8 Hz, 1H), 3.35 (s, 3H), 3.23 (m, 2H), 2.63 (m, 1H), 2.23 (m, 1H), 1.91 (m, 1H), 0.74 (t, J=7.4 Hz, 3H); LCMS: 390.1 m/z (M+H)$^+$; ret. Time: 5.24 min (Analytical Method C).

Example 315 was isolated as the second eluting enantiomer. LCMS: 390.1 m/z (M+H)$^+$; ret. Time: 5.21 min (Analytical Method C).

The absolute configuration of these compounds has been assigned based on their relative PLK2 activities, Example 314 being the more active compound.

Example 317

Synthesis of 6a-ethyl-5-methyl-2-(2-phenyl-1H-imidazol-1-yl)-6a,7,9,10-tetrahydro-[1,4]oxazino[3,4-h]pteridin-6(5H)-one

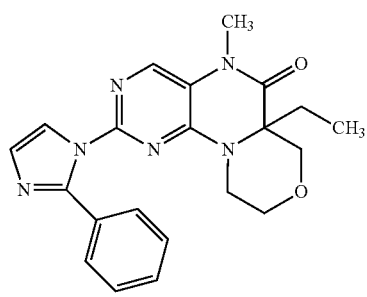 [SMILES: CCC12COCCN1c1nc(-n3ccnc3-c3ccccc3)ncc1N(C)C2=O]

The title compound (racemic mixture) was prepared similarly to the methods described in Example 3, with Intermediate Z-1 instead of Intermediate A, and 2-phenyl-1H-imidazole instead of 1H-imidazole in the first step. LCMS: 390.2 m/z (M+H)$^+$; ret. Time: 5.18 (Analytical Method C).

Example 318

Synthesis of (R)-2-(2-amino-4-(4-fluorophenyl)thiazol-5-yl)-7-ethyl-8-isopropyl-5-methyl-7,8-dihydropteridin-6(5H)-one

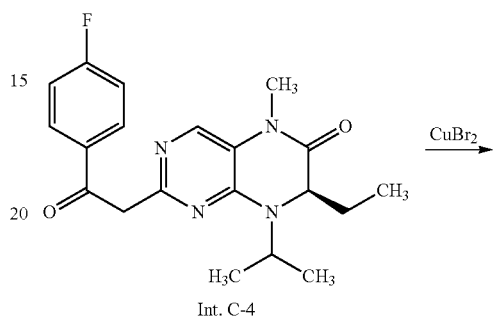

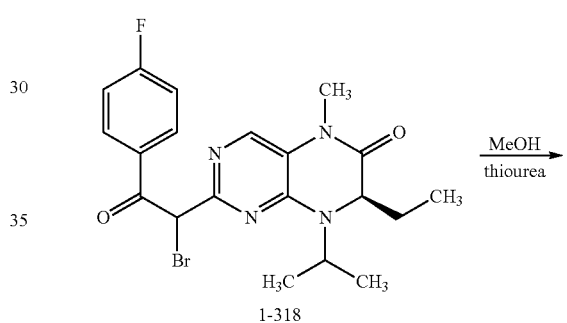

To a solution of Intermediate C-4 (0.33 g, 0.891 mmol) in 9.5 mL of ethyl acetate, copper (II) bromide was added. The reaction mixture was placed in an oil bath set at 50° C. for 1.5 h. The mixture was partitioned between saturated NaHCO$_3$ and ethyl acetate and the organic layer was dried with sodium sulfate, filtered and concentrated to give (7R)-2-(bromo-2-(4-fluorophenyl)-2-oxoethyl)-7-ethyl-8-isopropyl-5-methyl-7,8-dihydropteridin-6(5H)-one (compound I-318). LCMS: 451.1 m/z (M+H)$^+$.

To a solution of compound I-318 (0.16 g, 0.347 mmol) in 1 mL of methanol, thiourea (0.026 g, 0.342 mmol) was added. The reaction mixture was place in an oil bath set at 90° C. for 2 h and then concentrated and purified by preparative HPLC. LCMS: 426.9 m/z (M+H)+; ret. Time: 3.65 min (Analytical Method A).

Example 319

Synthesis of (R)-7-ethyl-2-(4-(4-fluorophenyl)thiazol-5-yl)-8-isopropyl-5-methyl-7,8-dihydropteridin-6(5H)-one

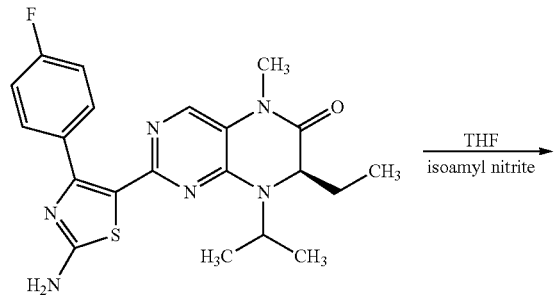

Ex. 318

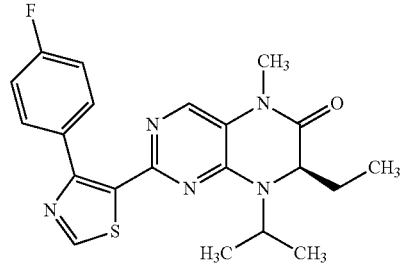

To a solution of (R)-2-(2-amino-4-(4-fluorophenyl)thiazol-5-yl)-7-ethyl-8-isopropyl-5-methyl-7,8-dihydropteridin-6(5H)-one (Example 318, 0.14 g, 0.324 mmol) in 1.5 mL anhydrous THF, isoamyl nitrite (0.1 mL, 0.751 mmol) was added. The reaction mixture was place in an oil bath set at 85° C. for 2 h and then concentrated and purified by preparative HPLC. LCMS: 412.2 m/z (M+H)+; ret. Time: 4.84 min (Analytical Method A).

Example 323

Synthesis of (R)-7-ethyl-5-methyl-8-(tetrahydro-2H-pyran-4-yl)-2-(5-(thiazol-2-yl)-1H-pyrazol-4-yl)-7,8-dihydropteridin-6(5H)-one

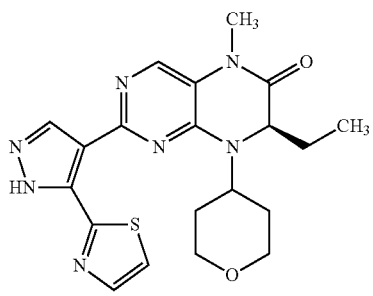 [SMILES: CC[C@@H]1C(=O)N(C)c2cnc(-c3cn[nH]c3-c3nccs3)nc2N1C1CCOCC1]

The title compound was prepared similarly to the methods described in Example 306, with Intermediate J instead of Intermediate B, and 1-(thiazol-2-yl)ethanone instead of 1-(pyridin-2-yl)ethanone. LCMS: 426.1 m/z (M+H)+; ret. Time: 5.60 min (Analytical Method C).

Example 326

Synthesis of 5-methyl-2-(2-phenyl-1H-imidazol-1-yl)-9H-6a,9-ethanopyrrolo[2,1-h]pteridin-6(5H)-one

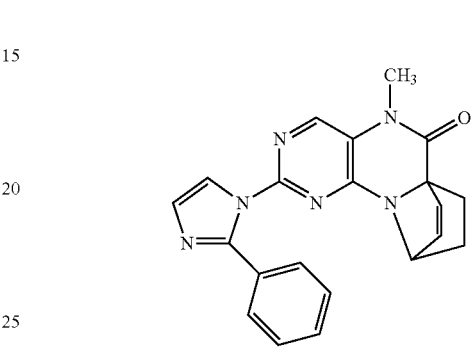

The title compound was prepared similarly to the methods described in Example 3, with Compound 3-309 from Example 309 instead of Intermediate A and with 2-phenyl-1H-imidazole instead of 1H-imidazole in the first step. $^1$H NMR (400 MHz, CD$_3$OD) δ: 8.27 (d, J=2.2 Hz, 1H), 8.11 (s, 1H), 7.75 (d, J=2.2 Hz, 1H), 7.70 (q, J=4.5 Hz, 1H), 7.65-7.60 (m, 4H), 6.36 (d, J=4.8 Hz, 1H), 6.30 (dd, J=4.8, 2.1 Hz, 1H), 4.54 (q, J=2.1 Hz, 1H), 3.40 (s, 3H), 1.96 (ddd, J=12.3, 9.4, 3.4 Hz, 1H), 1.73 (ddd, J=12.1, 8.8, 4.1 Hz, 1H), 1.63 (ddd, J=11.7, 8.5, 3.6 Hz, 1H), 1.22 (ddd, J=11.7, 8.5, 3.5 Hz, 1H); LCMS: 371.1 m/z (M+H)+; ret. Time 4.49 (Analytical Method C).

Example 327

Synthesis of (R)-2-(5-(1H-pyrazol-5-yl)-1H-1,2,4-triazol-1-yl)-7-ethyl-8-isopropyl-5-methyl-7,8-dihydropteridin-6(5H)-one

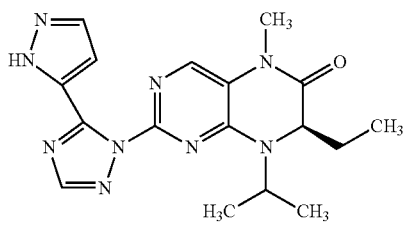 [SMILES: CC[C@@H]1C(=O)N(C)c2cnc(-n3ncnc3-c3ccn[nH]3)nc2N1C(C)C]

The title compound was prepared similarly to the methods described in Example 135, with 1H-pyrazole-5-carboxamide instead of benzamide in the first step and with Intermediate C-6 instead of Intermediate B-2 in the last step. LCMS: 368.0 m/z (M+H)+; ret. Time 4.90 min (Analytical Method C).

Example 328

Synthesis of (R)-7-ethyl-2-(2-(4-fluorophenyl)-1H-imidazol-1-yl)-5-methyl-8-(oxetan-3-yl)-7,8-dihydropteridin-6(5H)-one

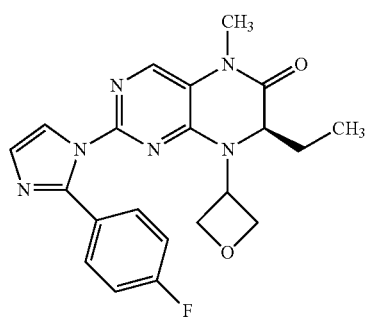 [SMILES: CC[C@@H]1C(=O)N(C)c2cnc(-n3ccnc3-c3ccc(F)cc3)nc2N1C1COC1]

To a stirring mixture of Intermediate RR-1 (112 mg, 0.338 mmol) in 0.7 mL of DMSO, 2-(4-fluorophenyl)-1H-imidazole (109 mg, 0.67 mmol) was added. The reaction mixture was placed in a 120° C. oil bath for 2 h. The crude mixture was directly loaded and purified by silica gel chromatography to give the coupled nitro ester. LCMS: 457.1 m/z (M+H)$^+$. To a stirring mixture of the coupled nitro ester in 1.2 mL of MeOH, Pt/C (42 mg) was added and the reaction mixture was placed under 1 atm of hydrogen for 2 h. The hydrogen balloon was removed and VO(acac)$_2$ (5 mg) was added. This reaction mixture was placed under 1 atm of hydrogen overnight. The crude mixture was filtered through a plug of Celite and the plug was washed several times with EtOAc. The filtrate was concentrated under reduced pressure. To this cyclized product, 0.5 mL of dioxane, potassium bicarbonate (100 mg) and trimethylphosphate (200 mg) were added. The reaction mixture was warmed to 100° C. for several hours. The crude product mixture was cooled to rt and diluted with EtOAc and water. The layers were separated and the aqueous layer was extracted with EtOAc. The organic layers were dried over MgSO$_4$, filtered, and concentrated under reduced pressure. The resulting material was purified by preparative HPLC to give the title compound. LCMS: 409.1 m/z (M+H)$^+$; ret. Time 4.07 min (Analytical Method D).

Example 331

Synthesis of 7-ethyl-2-(2-(4-fluorophenyl)-1H-imidazol-1-yl)-5-methyl-8-(1H-pyrazol-4-yl)-7,8-dihydropteridin-6(5H)-one

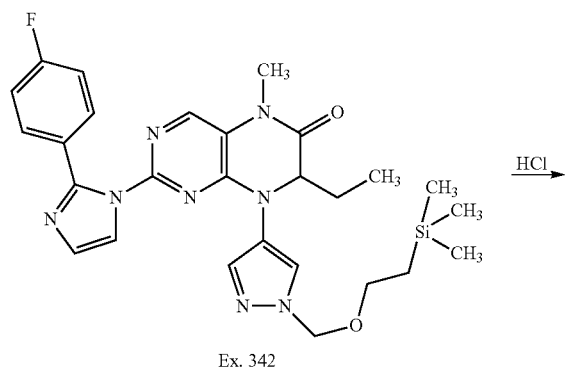

Ex. 342

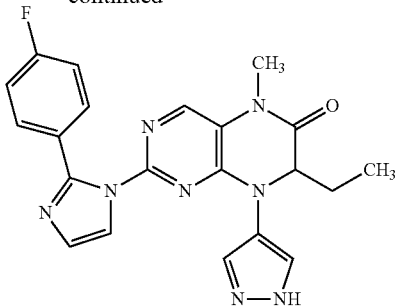

HCl (2 mL of a 4 N solution in dioxane) was added to a solution of 7-ethyl-2-(2-(4-fluorophenyl)-1H-imidazol-1-yl)-5-methyl-8-(1-((2-(trimethylsilyl)ethoxy)methyl)-1H-pyrazol-4-yl)-7,8-dihydropteridin-6(5H)-one (Example 342, 49 mg, 0.0893 mmol) in 2 mL of methanol and the resulting solution was stirred at 60° C. for 2 hours. The mixture was concentrated under vacuum and purified by HPLC to give the title compound. $^1$H-NMR (CDCl$_3$, 400 MHz): δ: 7.90 (s, 1H), 7.75 (s, 1H), 7.50-7.54 (m, 3H), 7.35 (s, 2H), 7.03-7.07 (m, 2H), 4.59-4.61 (m, 1H), 3.46 (s, 3H), 1.98-2.03 (m, 1H), 1.77-1.84 (m, 1H), 0.84 (t, 3H, J=7.4 Hz); LCMS: 418.9 m/z (M+H)$^+$; ret. Time: 3.98 min (Analytical Method C).

Example 343

Synthesis of 7-ethyl-2-(1H-imidazol-1-yl)-5-methyl-8-(1H-pyrazol-4-yl)-7,8-dihydropteridin-6(5H)-one

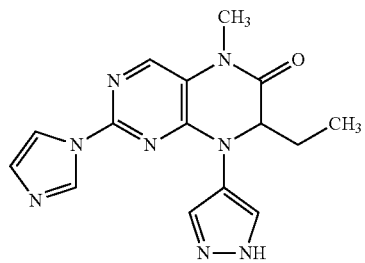 [SMILES: CCC1C(=O)N(C)c2cnc(-n3ccnc3)nc2N1c1cn[nH]c1]

The title compound was prepared similarly to the methods described in Example 299, with Intermediate KK instead of Intermediate N. The SEM group was removed similarly to the method described in Example 331 to provide the title compound. LCMS: 325.1 m/z (M+H)$^+$.

Example 344 and Example 345

Synthesis of (S)-6a-ethyl-5-methyl-2-(5-(thiazol-2-yl)-1H-pyrazol-4-yl)-6a,7,9,10-tetrahydro-[1,4]oxazino[3,4-h]pteridin-6(5H)-one (344) and (R)-6a-ethyl-5-methyl-2-(5-(thiazol-2-yl)-1H-pyrazol-4-yl)-6a,7,9,10-tetrahydro-[1,4]oxazino[3,4-h]pteridin-6(5H)-one (345)

(344)

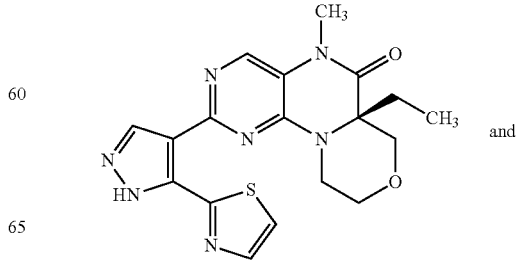

and

-continued (345)

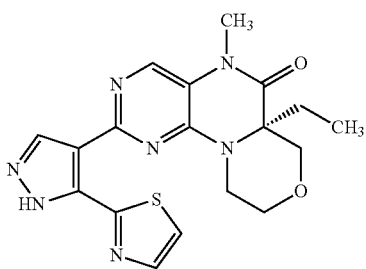

The title compounds were prepared similarly to the methods described in Example 134, starting from Intermediate Z-3 instead of Intermediate B-1 (per method of Example 132 to give the analog of Compound I-132). The resulting racemic mixture was separated by chiral chromatography using ChiralPak OD-H (2×25 cm) column, eluting with isocratic 30% EtOH:70% hexane, flow rate of 9 mL/min, detection at 220 nm.
Example 344 LCMS: 398.1 m/z (M+H)$^+$; ret. Time 5.39 min (Analytical Method A).
Example 345 LCMS: 398.1 m/z (M+H)$^+$; ret. Time 5.42 min (Analytical Method A).
The absolute configuration of these compounds has been assigned based on their relative PLK2 activities, Example 344 being the more active compound.

Example 360 and Example 361

Synthesis of (S)-7-ethyl-2-(2-(4-fluorophenyl)-1H-imidazol-1-yl)-5-methyl-8-(1H-pyrazol-4-yl)-7,8-dihydropteridin-6(5H)-one (360) and (R)-7-ethyl-2-(2-(4-fluorophenyl)-1H-imidazol-1-yl)-5-methyl-8-(1H-pyrazol-4-yl)-7,8-dihydropteridin-6(5H)-one (361)

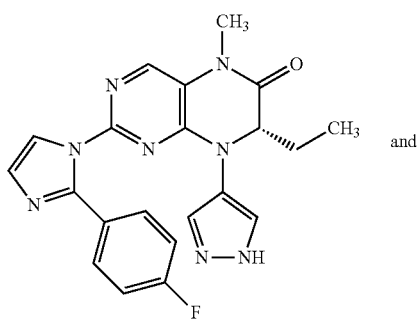
(360)

and

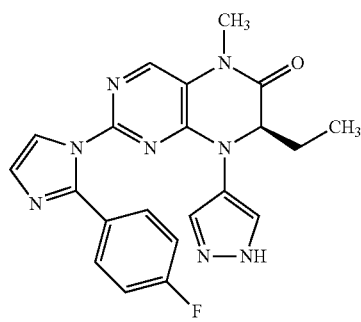
(361)

The title compounds were isolated from the racemic mixture of Example 331 by chiral HPLC, using ChiralPak AD (2×25 cm) column eluted with Ethanol:Hexane (2:3, 1 mL/min) solvent mixture.
Example 360: $^1$H-NMR (CDCl$_3$, 400 MHz): δ: 7.90 (s, 1H), 7.75 (s, 1H), 7.50-7.54 (m, 3H), 7.35 (s, 2H), 7.03-7.07 (m, 2H), 4.59-4.61 (m, 1H), 3.46 (s, 3H), 1.98-2.03 (m, 1H), 1.77-1.84 (m, 1H), 0.84 (t, 3H, J=7.4 Hz); LCMS: 419.2 m/z (M+H)$^+$; ret. Time: 5.43 min (Analytical Method C). The absolute configuration of this Example has been assigned based on its PLK2 activity relative to the opposite enantiomer.
Example 361: $^1$H-NMR (CDCl$_3$, 400 MHz): δ: 7.90 (s, 1H), 7.75 (s, 1H), 7.50-7.54 (m, 3H), 7.35 (s, 2H), 7.03-7.07 (m, 2H), 4.59-4.61 (m, 1H), 3.46 (s, 3H), 1.98-2.03 (m, 1H), 1.77-1.84 (m, 1H), 0.84 (t, 3H, J=7.4 Hz); LCMS: 419.2 m/z (M+H)$^+$; ret. Time: 5.49 min (Analytical Method C).
The absolute configuration of these compounds has been assigned based on their PLK2 activities, with Example 361 being the more active compound.

Example 362

Synthesis of 7-ethyl-2-(2-(4-fluorophenyl)-1H-imidazol-1-yl)-5-methyl-8-(1-methyl-1H-pyrazol-4-yl)-7,8-dihydropteridin-6(5H)-one

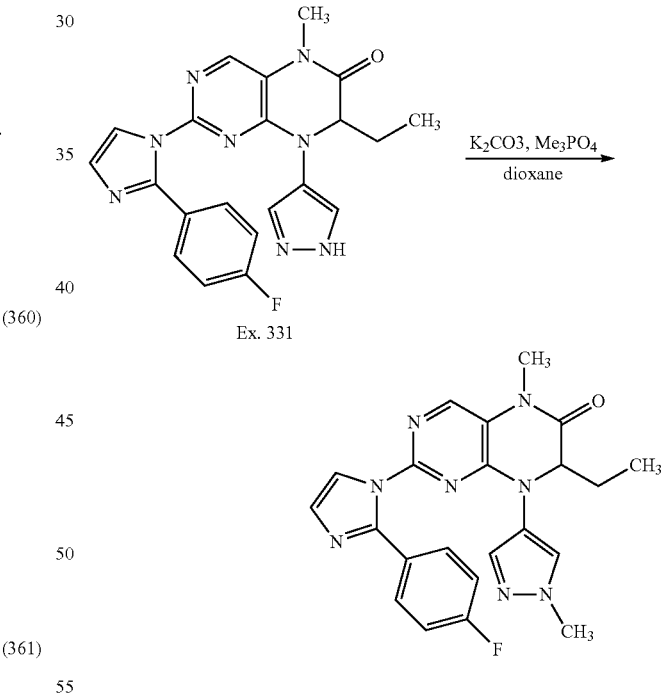

7-ethyl-2-(2-(4-fluorophenyl)-1H-imidazol-1-yl)-5-methyl-8-(1H-pyrazol-4-yl)-7,8-dihydropteridin-6(5H)-one (Example 331, 55 mg, 0.131 mmol) was dissolved in 3 mL of dioxane and Me$_3$PO$_4$ (37 mg, 0.262 mmol) and K$_2$CO$_3$ (90 mg, 0.655 mmol) were added and the reaction mixture was stirred for 18 h at 90° C. The reaction mixture was diluted with brine and extracted with EtOAc. The organic phase was dried with Na$_2$SO$_4$, filtered, concentrated under vacuum and purified by HPLC to give the title compound (7.6 mg).
$^1$H-NMR (CDCl$_3$, 400 MHz): δ: 7.91 (s, 1H), 7.71 (s, 1H), 7.50-7.60 (m, 3H), 7.12 (s, 1H), 7.08-7.10 (m, 2H), 7.01 (s, 1H), 4.57-4.61 (m, 1H), 3.79 (s, 3H), 3.46 (s, 3H), 1.82-1.98

(m, 1H), 1.78-1.82 (m, 1H), 0.82 (t, 3H, J=7.4 Hz); LCMS: 433.2 m/z (M+H)⁺; ret. Time: 4.36 min (Analytical Method C).

Example 363

Synthesis of 7-ethyl-5-methyl-8-(1H-pyrazol-4-yl)-2-(5-(thiazol-2-yl)-1H-pyrazol-4-yl)-7,8-dihydropteridin-6(5H)-one

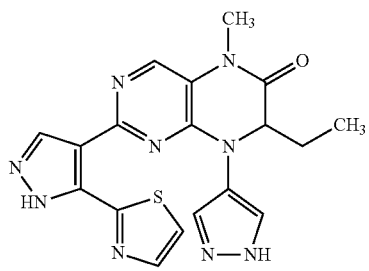 [SMILES: CCC1C(=O)N(C)c2cnc(-c3cn[nH]c3-c3nccs3)nc2N1c1cn[nH]c1]

The title compound was prepared similarly to the methods described in Example 5, with Intermediate KK instead of Intermediate B and with 5-(thiazol-2-yl)-1-((2-(trimethylsilyl)ethoxy)methyl)-1H-pyrazol-4-ylboronic acid (Boronic Acid 1) instead of pyridin-4-ylboronic acid. The resulting coupling product is then deprotected by the method described in Example 331 to give the title compound. LCMS: 408.0 m/z (M+H)⁺; ret. Time: 4.62 min. (Analytical Method C).

Example 365

Synthesis of (7R)-7-ethyl-5-methyl-8-(tetrahydrofuran-3-yl)-2-(5-(thiazol-2-yl)-1H-pyrazol-4-yl)-7,8-dihydropteridin-6(5H)-one

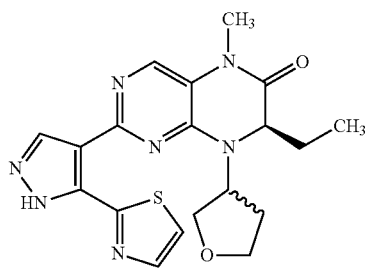 [SMILES: CC[C@@H]1C(=O)N(C)c2cnc(-c3cn[nH]c3-c3nccs3)nc2N1C1CCOC1]

The title compound was prepared similarly to the methods described in Example 5, with Intermediate N instead of Intermediate B and with 5-(thiazol-2-yl)-1-((2-(trimethylsilyl)ethoxy)methyl)-1H-pyrazol-4-ylboronic acid (Boronic Acid 1) instead of pyridin-4-ylboronic acid. The resulting coupling product is then deprotected by the method described in Example 331 to give the title compound. LCMS: 412.1 m/z (M+H)⁺; ret. Time: 2.24 min. (Analytical Method A).

Example 366

Synthesis of 4-(7-ethyl-2-(2-(4-fluorophenyl)-1H-imidazol-1-yl)-5-methyl-6-oxo-6,7-dihydropteridin-8(5H)-yl)benzonitrile

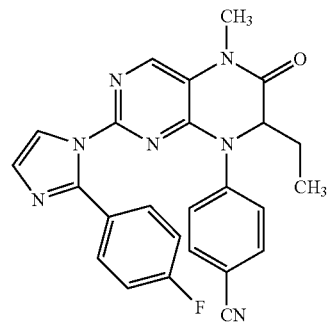 [SMILES: CCC1C(=O)N(C)c2cnc(-n3ccnc3-c3ccc(F)cc3)nc2N1c1ccc(C#N)cc1]

The title compound was prepared similarly to the methods described in Example 291, with Intermediate PP instead of Intermediate CC. LCMS: 412.1 m/z (M+H)⁺; ret. Time: 2.24 min. (Analytical Method C).

Example 367

Synthesis of 7-ethyl-2-(2-(4-fluorophenyl)-1H-imidazol-1-yl)-5-methyl-8-(1H-pyrazol-3-yl)-7,8-dihydropteridin-6(5H)-one

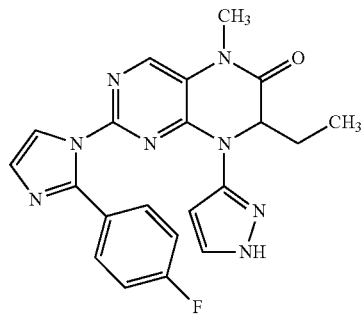 [SMILES: CCC1C(=O)N(C)c2cnc(-n3ccnc3-c3ccc(F)cc3)nc2N1c1cc[nH]n1]

The title compound was prepared similarly to the methods described in Example 3, with Intermediate QQ-1 instead of Intermediate A, and 2-(4-fluorophenyl)-1H-imidazole instead of 1H-imidazole in the first step. The deprotection of SEM in the final step similarly to the method described for Example 331 to give the title compound. LCMS: 419.1 m/z (M+H)⁺; ret. Time: 4.48 min. (Analytical Method C).

Example 368 and Example 369

Synthesis of (S)-6a-ethyl-5-methyl-2-(4-phenyl-1,2,3-thiadiazol-5-yl)-6a,7,9,10-tetrahydro-[1,4]oxazino[3,4-h]pteridin-6(5H)-one (368) and (R)-6a-ethyl-5-methyl-2-(4-phenyl-1,2,3-thiadiazol-5-yl)-6a,7,9,10-tetrahydro-[1,4]oxazino[3,4-h]pteridin-6(5H)-one (369)

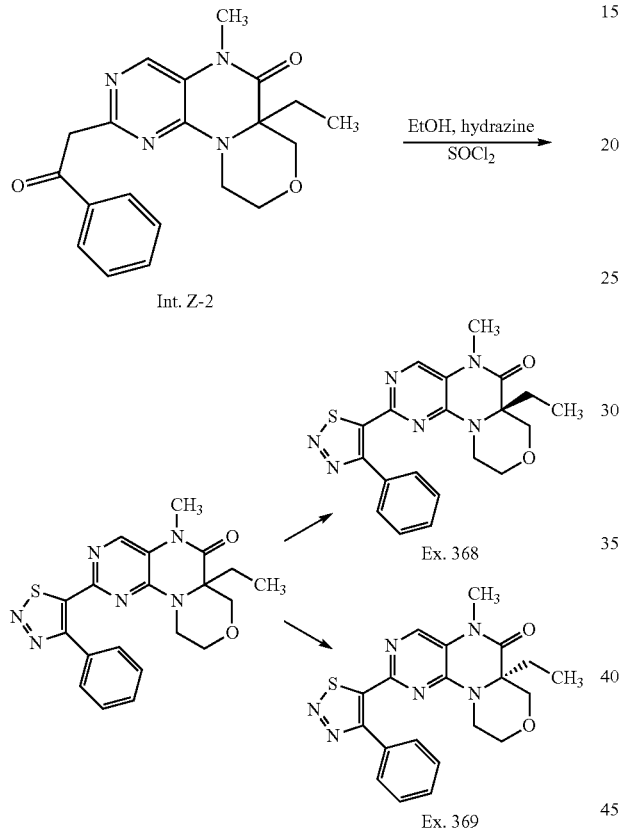

To a solution of Intermediate Z-2 (0.2109 mmol, 0.074 g) in 2 mL of EtOH, hydrazine (0.707 mmol, 0.023 mL) was added. The reaction mixture was plunged into a preheated 80° C. oil bath and was stirred for 18 h. The reaction mixture was cooled to rt and concentrated. Thionyl chloride (2 mL) was slowly added to the resulting residue. The reaction mixture was stirred for 15 minutes, then concentrated. The resulting residue was dissolved in 10 mL of DCM and washed with saturated NaHCO₃, dried with Na₂SO₄, filtered and concentrated to give a racemic mixture of the two title compounds.

The resulting racemic mixture was resolved by chiral HPLC using an isocratic mixture of EtOH:hexane (20:80; 1 mL/min) as eluent with a Chiracel IA 4.6×250 mm column to give isolated Example 368 and Example 369.
Example 368: ¹H NMR (400 MHz, CDCl₃) δ: 7.83 (s, 1H), 7.74 (m, 2H), 7.44 (m, 3H), 4.14 (d, J=11.2 Hz, 1H), 3.84 (m, 1H), 3.62 (m, 2H), 3.40 (m, 1H), 3.35 (s, 3H), 2.84 (m, 1H), 2.23 (m, 3H), 1.97 (m, 1H), 0.76 (t, J=7.4 Hz, 3H) LCMS: 409.0 m/z (M+H)⁺; ret. Time: 6.91 min (Analytical Method A).

Example 369: ¹H NMR (300 MHz, CDCl₃) δ: 7.83 (s, 1H), 7.73 (m, 2H), 7.43 (m, 3H), 4.17 (d, J=11.2 Hz, 1H), 3.84 (dd, J=11.5, 3.78 Hz, 1H), 3.62 (m, 2H), 3.40 (dt, J=12.2, 3.12 Hz, 1H), 3.35 (s, 3H), 2.83 (m, 1H), 2.23 (m, 1H), 1.97 (m, 1H), 0.75 (t, J=7.4 Hz, 3H) LCMS: 409.0 m/z (M+H)⁺; ret. Time: 6.91 min (Analytical Method A).
The absolute configuration of these compounds has been assigned based on their PLK2 activities, with Example 368 being the more active compound.

Example 371

Synthesis of 6a-ethyl-5,8-dimethyl-2-(2-phenyl-1H-imidazol-1-yl)-7,8,9,10-tetrahydro-5H-pyrazino[2,1-h]pteridin-6(6aH)-one

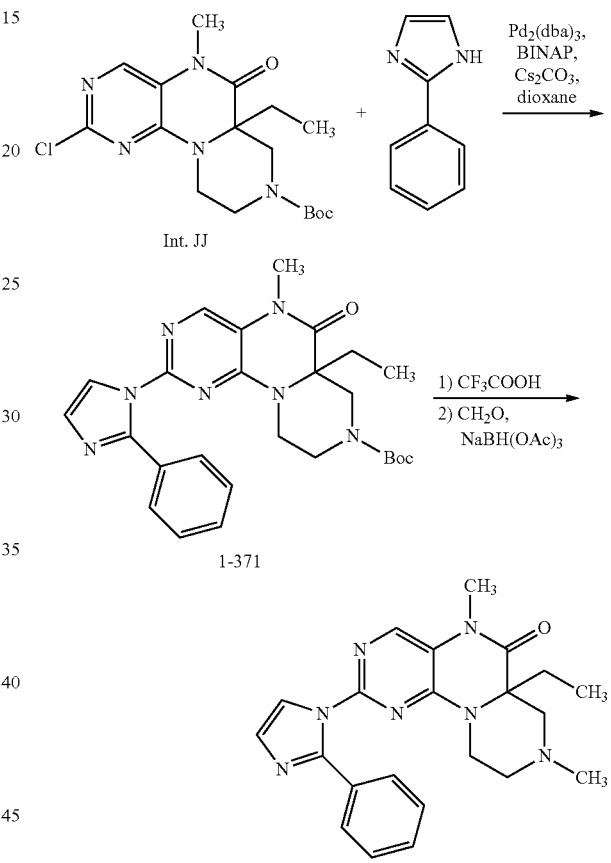

Compound 1-371 was prepared similarly to the methods described in Example 185 with Intermediate JJ instead of Intermediate C and with 2-phenyl-1H-imidazole instead of 2-(3,5-dichlorophenyl)-1H-imidazole.

Compound 1-371 (107 mg, 0.22 mmol) was dissolved in 3 mL of dry DCM at 0° C., and 3 mL of trifluoroacetic acid was added. This was then allowed to warm to rt for 2 h, then concentrated and dissolved in 5 mL of 1,2-dichloroethane and formalin (37% in water, 0.2 mL) and sodium triacetoxyborohydride (0.47 g) were added with vigorous stirring at rt. After 3 h, the reaction mixture was filtered (filter cake washed with DCM), and filtrates concentrated under reduced pressure. The residue was purified by HPLC using a Phenomenex C18, 2×25 cm column with 5 μm packing, 30-70% CH₃CN/H₂O elution with 0.1% NH₄OH modifier to give the title compound. ¹H NMR (400 MHz, CD₃OD) δ: 7.89 (s, 1H), 7.78 (s, 1H), 7.45-7.30 (m, 5H), 7.13 (s, 1H), 3.50-3.30 (m, 1H), 3.35 (s, 3H), 3.15 (d, J=11.4 Hz, 1H), 2.62-2.50 (m, 2H), 2.35-2.25 (m, 1H), 2.25 (s, 3H), 2.13 (d, J=11.6 Hz, 1H), 1.90-1.78 (m, 1H), 1.72 (t, J=11.9 Hz, 1H), 0.67 (t, J=7.4 Hz, 3H); LCMS: 404.2 m/z (M+H)⁺; ret. Time 5.39 (Analytical Method D).

Example 373

Synthesis of (S)-6a-ethyl-5-methyl-2-(4-phenyl-1H-1,2,3-triazol-5-yl)-6a,7,9,10-tetrahydro-[1,4]oxazino[3,4-h]pteridin-6(5H)-one

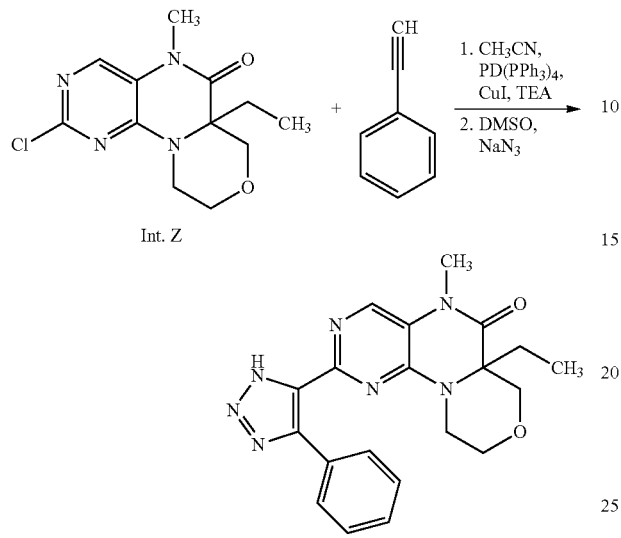

To a solution of Intermediate Z (0.247 mmol, 0.07 g) in 2 mL of acetonitrile, Pd(PPh$_3$)$_4$ (0.007 mmol, 0.008 g), phenylacetylene (0.296 mmol, 0.032 mL), CuI (0.007 mmol, 0.001 g), and triethylamine (0.741 mmol, 0.09 mL) were added. The reaction mixture was microwaved for 25 minutes at 140° C. The reaction mixture was filtered and concentrated. The resulting residue was purified by flash chromatography (30% EtOAc in hexanes). The resulting residue was dissolved in 1 mL of DMSO and sodium azide (0.071 mmol, 0.005 g) was added. The reaction mixture was microwaved for 30 minutes at 175° C. The reaction mixture was diluted with 10 mL of EtOAc, washed with 10 mL of water, dried with Na$_2$SO$_4$, filtered and concentrated. The resulting residue was purified by reverse phase HPLC to provide the title compound as a white solid (1.9 mg, 11%); $^1$H NMR (400 MHz, CDCl$_3$) δ: 7.96 (m, 1H), 7.83 (m, 2H), 7.40 (3H), 4.20 (d, J=11.6 HZ, 1H), 3.85 (m, 2H), 3.67 (m, 1H), 3.46 (m, 1H), 3.37 (s, 3H), 3.00 (m, 1H), 2.25 (m, 1H), 1.96 (m, 1H), 0.77 (t, J=7.5 Hz, 3H), LCMS: 392.1 m/z (M+H)$^+$; ret. Time: 2.33 min (Analytical Method A).

Example 374 and Example 375

Synthesis of (S)-6a-ethyl-5,8-dimethyl-2-(2-phenyl-1H-imidazol-1-yl)-7,8,9,10-tetrahydro-5H-pyrazino[2,1-h]pteridin-6(6aH)-one (374) and (R)-6a-ethyl-5,8-dimethyl-2-(2-phenyl-1H-imidazol-1-yl)-7,8,9,10-tetrahydro-5H-pyrazino[2,1-h]pteridin-6(6aH)-one (375)

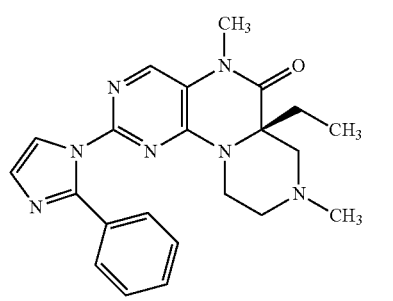

(374)

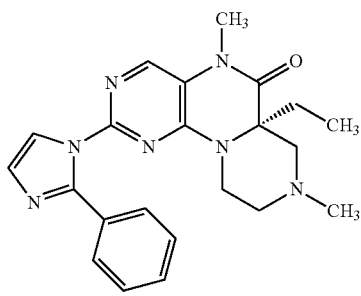

(375)

The title compounds were isolated from the racemic mixture of Example 371 by chiral HPLC, using ChiralPak IA 2×25 cm column, 10% EtOH/hexane elution at 10 mL/min.

Example 374: $^1$H NMR (400 MHz, CD$_3$OD) δ: 7.89 (s, 1H), 7.78 (s, 1H), 7.45-7.30 (m, 5H), 7.13 (s, 1H), 3.50-3.30 (m, 1H), 3.35 (s, 3H), 3.15 (d, J=11.4 Hz, 1H), 2.62-2.50 (m, 2H), 2.35-2.25 (m, 1H), 2.25 (s, 3H), 2.13 (d, J=11.6 Hz, 1H), 1.90-1.78 (m, 1H), 1.72 (t, J=11.9 Hz, 1H), 0.67 (t, J=7.4 Hz, 3H); LCMS: 404.2 m/z (M+H)$^+$; ret. Time 13.58 (Analytical Method D with a ChiralPak IA 10 column); (−) rotating enantiomer.

Example 375: $^1$H NMR (400 MHz, CD$_3$OD) δ: 7.89 (s, 1H), 7.78 (s, 1H), 7.45-7.30 (m, 5H), 7.13 (s, 1H), 3.50-3.30 (m, 1H), 3.35 (s, 3H), 3.15 (d, J=11.4 Hz, 1H), 2.62-2.50 (m, 2H), 2.35-2.25 (m, 1H), 2.25 (s, 3H), 2.13 (d, J=11.6 Hz, 1H), 1.90-1.78 (m, 1H), 1.72 (t, J=11.9 Hz, 1H), 0.67 (t, J=7.4 Hz, 3H); LCMS: 404.2 m/z (M+H)$^+$; ret. Time 16.16 (Analytical Method D with a ChiralPak IA 10 column); (+) rotating enantiomer.

The absolute configuration of these compounds has been assigned based on their PLK2 activities, with Example 374 being the more active compound.

Example 376 and Example 377

Synthesis of (S)-2-(2-(2,4-difluorophenyl)-1H-imidazol-1-yl)-6a-ethyl-5-methyl-6a,7,9,10-tetrahydro-[1,4]oxazino[3,4-h]pteridin-6(5H)-one (376) and (R)-2-(2-(2,4-difluorophenyl)-1H-imidazol-1-yl)-6a-ethyl-5-methyl-6a,7,9,10-tetrahydro-[1,4]oxazino[3,4-h]pteridin-6(5H)-one (377)

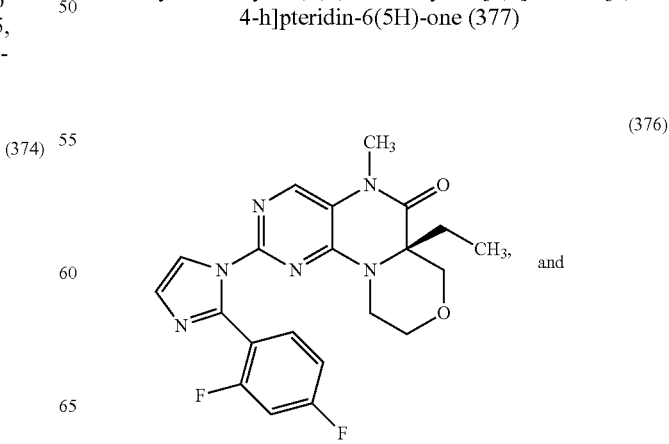

(376)

(377)

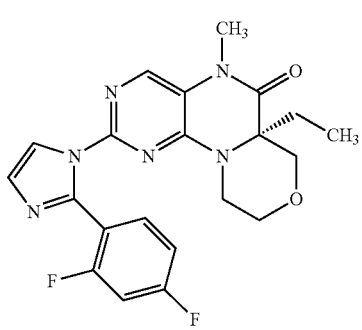

A racemic mixture of the title compounds was prepared similarly to the methods described in Example 3, with Intermediate Z-1 instead of Intermediate A, and 2-(2,4-difluorophenyl)-1H-imidazole instead of 1H-imidazole in the first step. The enantiomers were resolved by chiral HPLC with an isocratic mixture of EtOH:hexane (25:75; 1 mL/min flow rate) as eluent and a Chiracel OJ-H 0.46×250 mm column.
Example 376 LCMS: 427.1 m/z (M+H)+; ret. Time: 5.99 min (Analytical Method C).
Example 377 LCMS: 427.1 m/z (M+H)+; ret. Time: 5.98 min (Analytical Method C).
The absolute configuration of these compounds has been assigned based on their PLK2 activities, with Example 376 being the more active compound.

Example 378 and Example 379

Synthesis of (R)-7-ethyl-5-methyl-8-(1H-pyrazol-4-yl)-2-(5-(thiazol-2-yl)-1H-pyrazol-4-yl)-7,8-dihydropteridin-6(5H)-one (378) and (S)-7-ethyl-5-methyl-8-(1-pyrazol-4-yl)-2-(5-(thiazol-2-yl)-1H-pyrazol-4-yl)-7,8-dihydropteridin-6(5H)-one (379)

(378)

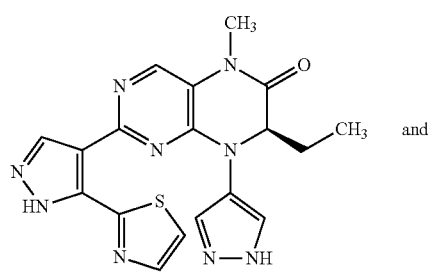 and (379)

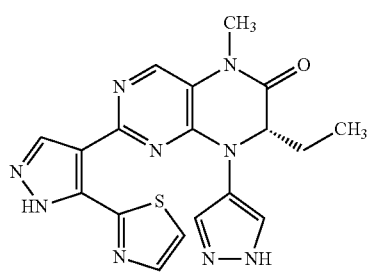

The title compounds were isolated from the racemic mixture of Example 363 by chiral HPLC, with a ChiralPak IA (2×25 cm) column eluted with Ethanol:Hexane (2:3, 1 mL/min) solvent mixture.

Example 378: $^1$H-NMR (CDCl$_3$, 400 MHz): δ 8.19 (s, 1H), 8.14 (s, 1H), 7.98 (s, 2H), 7.90 (s, 1H), 7.43 (s, 1H), 4.62-4.681 (m, 1H), 3.48 (s, 3H), 1.98-2.02 (m, 1H), 1.89-1.94 (m, 1H), 0.89 (t, 3H, J=7.5 Hz); LCMS: 408.0 m/z (M+H)+; ret. Time: 4.62 min (Analytical Method C).
Example 379: $^1$H-NMR (CDCl$_3$, 400 MHz): δ 8.19 (s, 1H), 8.14 (s, 1H), 7.98 (s, 2H), 7.90 (s, 1H), 7.43 (s, 1H), 4.62-4.681 (m, 1H), 3.48 (s, 3H), 1.98-2.02 (m, 1H), 1.89-1.94 (m, 1H), 0.89 (t, 3H, J=7.5 Hz); LCMS: 408.0 m/z (M+H)+; ret. Time: 4.62 min (Analytical Method C).
The absolute configuration of these compounds has been assigned based on their PLK2 activities, with Example 378 being the more active compound.

Example 380 and Example 381

Synthesis of (S)-6a-ethyl-2-(2-(5-fluoropyridin-2-yl)-1H-imidazol-1-yl)-5-methyl-6a,7,9,10-tetrahydro-[1,4]oxazino[3,4-h]pteridin-6(5H)-one (380) and (R)-6a-ethyl-2-(2-(5-fluoropyridin-2-yl)-1H-imidazol-1-yl)-5-methyl-6a,7,9,10-tetrahydro-[1,4]oxazino[3,4-h]pteridin-6(5H)-one (381)

(380)

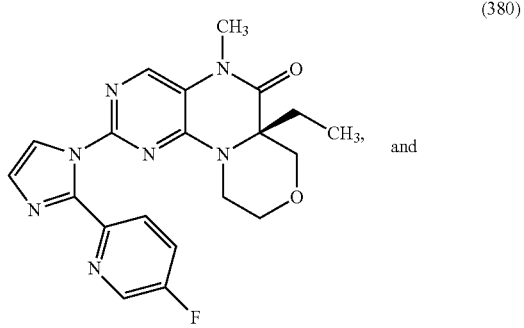 and (381)

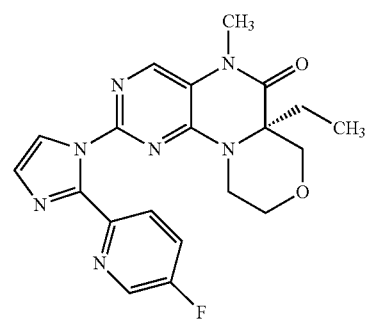

A racemic mixture of the title compounds was prepared similarly to the methods described in Example 3, with Intermediate Z-1 instead of Intermediate A, and 5-fluoro-2-(1H-imidazol-2-yl)pyridine instead of 1H-imidazole in the first step. The enantiomers were resolved by chiral HPLC with an isocratic mixture of EtOH:hexane (25:75; 1 mL/min flow rate) as eluent and a Chiracel OJ-H (0.46×250 mm) column.
Example 380 LCMS: 410.1 m/z (M+H)+; ret. Time: 4.78 min (Analytical Method C).
Example 381 LCMS: 410.1 m/z (M+H)+; ret. Time: 4.77 min (Analytical Method C).
The absolute configuration of these compounds has been assigned based on their PLK2 activities, with Example 380 being the more active compound.

Example 386 and Example 387

Synthesis of (R)-6a-ethyl-5-methyl-2-(2-(thiazol-2-yl)-1H-imidazol-1-yl)-6a,7,9,10-tetrahydro-[1,4]oxazino[3,4-h]pteridin-6(5H)-one (386) and (S)-6a-ethyl-5-methyl-2-(2-(thiazol-2-yl)-1H-imidazol-1-yl)-6a,7,9,10-tetrahydro-[1,4]oxazino[3,4-h]pteridin-6(5H)-one (387)

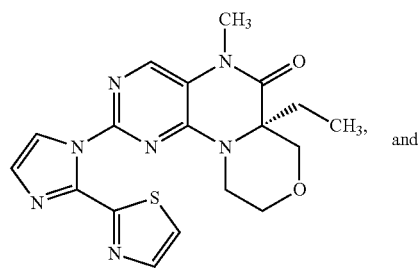
(386)

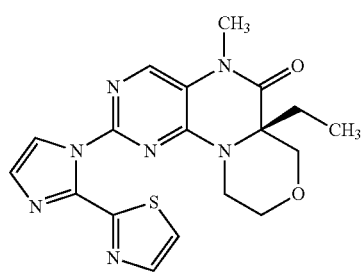
(387)

A racemic mixture of the title compounds was prepared similarly to the methods described in Example 3, with Intermediate Z-1 instead of Intermediate A, and 2-(1H-imidazol-2-yl)thiazole instead of 1H-imidazole in the first step. The enantiomers were resolved by chiral HPLC with EtOH:Hexane (1:3, 1 mL/min) as eluent from a Chiracel OJ-H (0.46× 250 mm) column.

Example 386 LCMS [M+H]: 398.1 m/z (M+H)$^+$; ret. Time: 4.77 min (Analytical Method C).
Example 387 LCMS [M+H]: 398.1 m/z (M+H)$^+$; ret. Time: 4.81 min (Analytical Method C).

The absolute configuration of these compounds has been assigned based on their PLK2 activities, with Example 387 being the more active compound.

Example 389 and Example 390

Synthesis of (R)-7-ethyl-2-(2-(4-fluorophenyl)-1H-imidazol-1-yl)-5-methyl-8-(1-methyl-1H-pyrazol-4-yl)-7,8-dihydropteridin-6(5H)-one (389) and (S)-7-ethyl-2-(2-(4-fluorophenyl)-1H-imidazol-1-yl)-5-methyl-8-(1-methyl-1H-pyrazol-4-yl)-7,8-dihydropteridin-6(5H)-one (390)

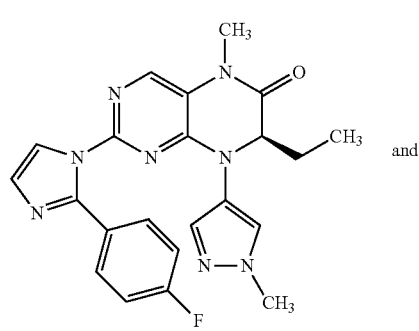
(389)

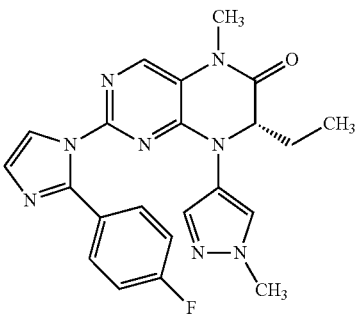
(390)

The title compounds were isolated from the racemic mixture of Example 362 by chiral HPLC, using an isocratic mixture of Ethanol:Hexane (33:67, 1 mL/min) eluting from a ChiralPak IA (5×50 cm) column.

Example 389: $^1$H-NMR (CDCl$_3$, 400 MHz): δ: 7.91 (s, 1H), 7.58 (d, 1H, J=1.4 Hz), 7.48 (dd, 2H, J=8.8, 5.3 Hz), 7.24 (s, 1H), 7.18 (d, 1H, J=1.4 Hz), 6.97-7.03 (m, 2H), 4.60 (dd, 2H, J=6.5, 3.7 Hz), 3.75 (s, 3H), 3.43 (s, 3H), 1.91-1.98 (m, 1H), 1.78-1.82 (m, 1H), 0.82 (t, 3H, J=7.4 Hz); LCMS: 433.2 m/z (M+H)$^+$; ret. Time: 4.40 min (Analytical Method C).

Example 390: $^1$H-NMR (CDCl$_3$, 400 MHz): δ: 7.92 (s, 1H), 7.58 (d, 1H, J=1.4 Hz), 7.48 (dd, 2H, J=8.8, 5.3 Hz), 7.24 (s, 1H), 7.19 (d, 1H, J=1.4 Hz), 6.97-7.03 (m, 2H), 4.60 (dd, 2H, J=6.5, 3.7 Hz), 3.75 (s, 3H), 3.44 (s, 3H), 1.91-1.98 (m, 1H), 1.78-1.82 (m, 1H), 0.82 (t, 3H, J=7.4 Hz); LCMS: 433.2 m/z (M+H)$^+$; ret. Time: 4.45 min (Analytical Method C).

The absolute configuration of these compounds has been assigned based on their PLK2 activities, with Example 389 being the more active compound.

Example 394 and Example 396

Synthesis of (S)-6a-ethyl-5-methyl-2-(3-phenylpyridin-4-yl)-6a,7,9,10-tetrahydro-[1,4]oxazino[3,4-h]pteridin-6(5H)-one (394) and (R)-6a-ethyl-5-methyl-2-(3-phenylpyridin-4-yl)-6a,7,9,10-tetrahydro-[1,4]oxazino[3,4-h]pteridin-6(5H)-one (396)

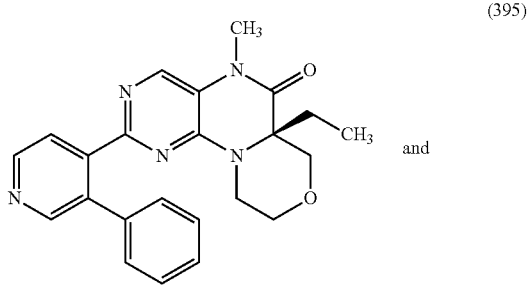
(395)

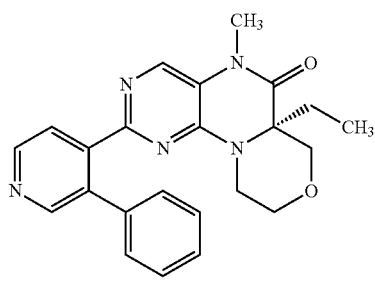

(396)

A racemic mixture of the title compounds was prepared similarly to the methods described in Example 5, with Intermediate Z instead of Intermediate B, and 3-phenyl-4-(4,4,5,5-tetramethyl-1,3,2-dioxaborolan-2-yl)pyridine (Boronic Acid 2) instead of pyridin-4-ylboronic acid. The pure enantiomers were isolated using chiral HPLC by eluting with an isocratic EtOH:Hexane (1:1, 1 mL/min) as eluent from a Chiracel OD-H (0.46×250 mm) column.

Example 394 LCMS: 402.2 m/z (M+H)$^+$; ret. Time: 5.84 min (Analytical Method D). The absolute configuration of this Example has been assigned based on its PLK2 activity.

Example 396 LCMS: 402.2 m/z (M+H)$^+$; ret. Time: 5.89 min (Analytical Method D).

The absolute configuration of these compounds has been assigned based on their PLK2 activities, with Example 394 being the more active compound.

Example 397 and Example 398

Synthesis of (S)-2-(4-(2,4-difluorophenyl)-1,2,3-thiadiazol-5-yl)-6a-ethyl-5-methyl-6a,7,9,10-tetrahydro-[1,4]oxazino[3,4-h]pteridin-6(5H)-one (397) and (R)-2-(4-(2,4-difluorophenyl)-1,2,3-thiadiazol-5-yl)-6a-ethyl-5-methyl-6a,7,9,10-tetrahydro-[1,4]oxazino[3,4-h]pteridin-6(5H)-one (398)

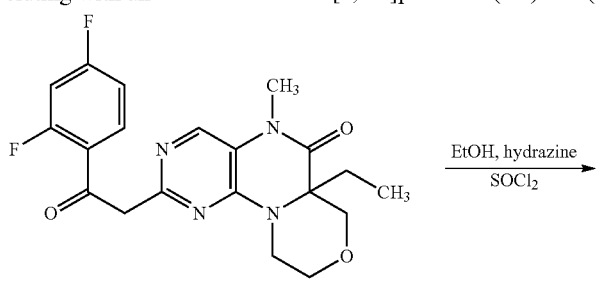

Int. Z-4

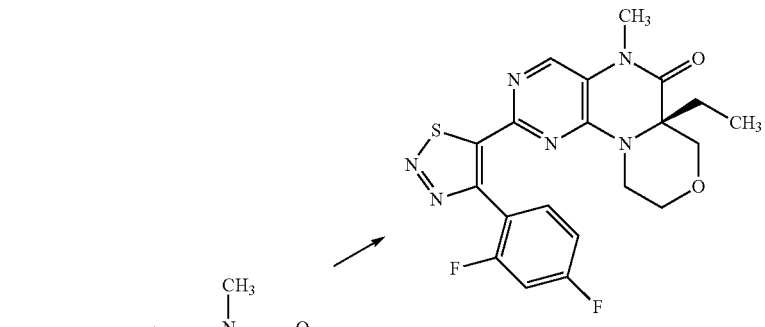

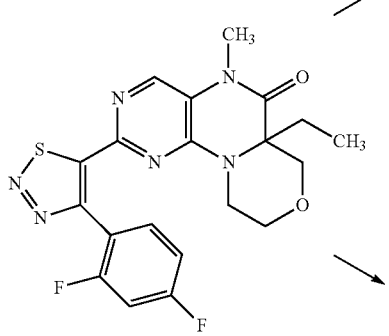

Ex. 397

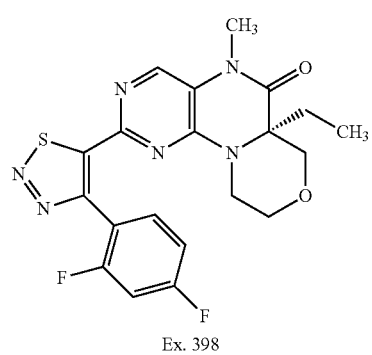

Ex. 398

The title compounds were prepared and isolated similarly to the methods described in the synthesis of Examples 368 and 369, with Intermediate Z-4 instead of Intermediate Z-2. The racemic mixture was resolved by chiral HPLC using an isocratic mixture of EtOH:Hexane (3:7, 1 mL/min) as eluent from a ChiralPak IC column. Under these conditions Example 397 has a retention time of 12.93 min; Example 398 has a retention time of 16.98 min.

Example 397: $^1$H NMR (CD$_3$OD) δ: 7.97 (s, 1H), 7.69 (dt, J=8.4, 6.6 Hz, 1H), 7.20-7.10 (m, 2H), 4.05 (d, J=11.8 Hz, 1H), 3.81 (dd, J=11.6, 3.8 Hz, 1H), 3.65 (d, J=11.6 Hz, 1H), 3.57 (dd, J=13.7, 2.4 Hz, 1H), 3.49-3.37 (m, 1H), 3.32 (s, 3H), 2.95-2.85 (m, 1H), 2.37-2.25 (m, 1H), 1.97-1.83 (m, 1H), 0.73 (t, J=7.6 Hz, 3H); LCMS: 445.1 m/z (M+H)$^+$; ret. Time 7.15 min (Analytical Method A).

Example 398: $^1$H NMR (CD$_3$OD) δ: 7.97 (s, 1H), 7.69 (dt, J=8.4, 6.6 Hz, 1H), 7.20-7.10 (m, 2H), 4.05 (d, J=11.8 Hz, 1H), 3.81 (dd, J=11.6, 3.8 Hz, 1H), 3.65 (d, J=11.6 Hz, 1H), 3.57 (dd, J=13.7, 2.4 Hz, 1H), 3.49-3.37 (m, 1H), 3.32 (s, 3H), 2.95-2.85 (m, 1H), 2.37-2.25 (m, 1H), 1.97-1.83 (m, 1H), 0.73 (t, J=7.6 Hz, 3H); LCMS: 445.1 m/z (M+H)$^+$; ret. Time 7.15 min (Analytical Method A).

The absolute configuration of these compounds has been assigned based on their PLK2 activities, with Example 397 being the more active compound.

Example 399

Synthesis of 7-ethyl-5-methyl-8-(1-methyl-1H-pyrazol-4-yl)-2-(5-(pyridin-2-yl)-1H-pyrazol-4-yl)-7,8-dihydropteridin-6(5H)-one

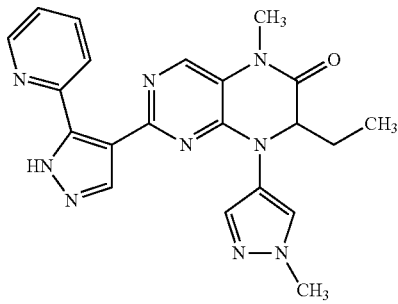 [SMILES: CCC1C(=O)N(C)c2cnc(-c3cn[nH]c3-c3ccccn3)nc2N1c1cnn(C)c1]

The title compound was prepared similarly to the methods described in Example 5, with Intermediate KK-3 instead of Intermediate B and with 5-(pyridin-2-yl)-1-((2-(trimethylsilyl)ethoxy)methyl)-1H-pyrazol-4-ylboronic acid (Boronic Acid 3) instead of pyridin-4-ylboronic acid. The resulting coupling product is then deprotected by the method described in Example 331 to give the title compound. LCMS: 463.1 m/z (M+H)$^+$; ret. Time: 4.16 min. (Analytical Method A).

Example 400

Synthesis of 8-(1-(cyclopropylmethyl)-1H-pyrazol-4-yl)-7-ethyl-5-methyl-2-(5-(thiazol-2-yl)-1H-pyrazol-4-yl)-7,8-dihydropteridin-6(5H)-one

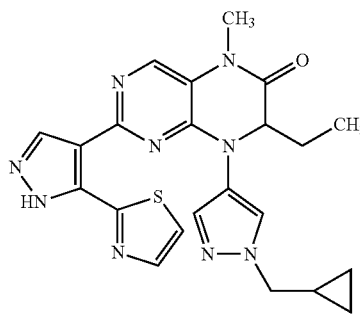

The title compound was prepared similarly to the methods described in Example 5, with Intermediate KK-4 instead of Intermediate B and with 5-(thiazol-2-yl)-1-((2-(trimethylsilyl)ethoxy)methyl)-1H-pyrazol-4-ylboronic acid (Boronic Acid 1) instead of pyridin-4-ylboronic acid. The resulting coupling product is then deprotected by the method described in Example 331 to give the title compound. LCMS: 462.2 m/z (M+H)$^+$; ret. Time: 2.96 min. (Analytical Method A).

Example 401

Synthesis of 3-(7-ethyl-2-(5-(4-fluorophenyl)isothiazol-4-yl)-5-methyl-6-oxo-6,7-dihydropteridin-8(5H)-yl)benzonitrile

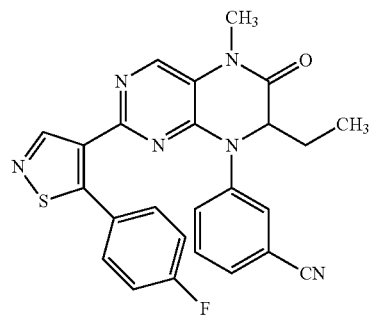 [SMILES: CCC1C(=O)N(C)c2cnc(-c3cnsc3-c3ccc(F)cc3)nc2N1c1cccc(C#N)c1]

The title compounds was prepared similarly to the methods described in Example 296, with Intermediate OO-1 instead of Intermediate C-4. The enantiomers were resolved by chiral HPLC as described in Example 391 and Example 392.

Example 402

Synthesis of 3-(7-ethyl-2-(5-(4-fluorophenyl)isothiazol-4-yl)-5-methyl-6-oxo-6,7-dihydropteridin-8(5H)-yl)benzonitrile

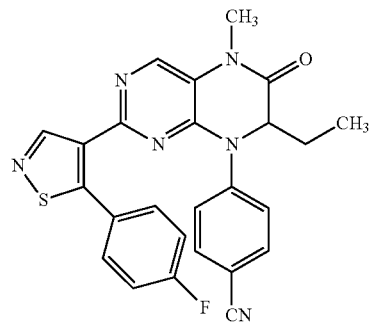 [SMILES: CCC1C(=O)N(C)c2cnc(-c3cnsc3-c3ccc(F)cc3)nc2N1c1ccc(C#N)cc1]

The title compound was prepared similarly to the methods described in Example 296, with intermediate PP-1 instead of Intermediate C-4. LCMS: 471.1 m/z (M+H)$^+$; ret. Time: 5.98 min (Analytical Method A).

Example 403 and Example 404

Synthesis of (S)-6a-ethyl-5-methyl-2-(2-phenylpyridin-3-yl-6a,7,9,10-tetrahydro-[1,4]oxazino[3,4-h]pteridin-6(5H)-one (403) and (R)-6a-ethyl-5-methyl-2-(2-phenylpyridin-3-yl-6a,7,9,10-tetrahydro-[1,4]oxazino[3,4-h]pteridin-6(5H)-one (404)

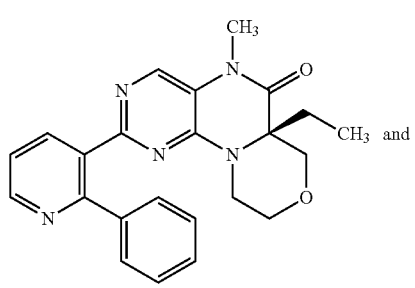

Ex 403 and

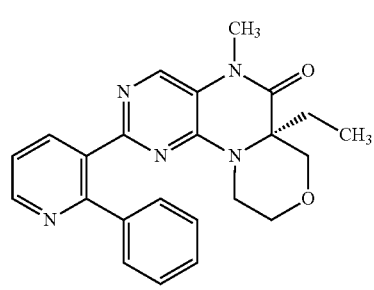

Ex 404

The title compounds were prepared similarly to the methods described in Example 5, with Intermediate Z instead of Intermediate B and with 2-phenyl-3-(4,4,5,5-tetramethyl-1,3,2-dioxaborolan-2-yl)pyridine (prepared similarly to the methods used for Boronic Acid 2) instead of pyridin-4-ylboronic acid. The resulting racemic mixture was resolved by chiral HPLC using an isocratic mixture of EtOH:Hexane (3:7, 1 mL/min) as eluent from a Chiracel OD-H column (0.46× 250 mm) to give the title compounds.
Example 403 LCMS: 401.1 m/z (M+H)$^+$; ret. Time: 5.12 min (Analytical Method A).
Example 404 LCMS: 401.2 m/z (M+H)$^+$; ret. Time: 5.12 min (Analytical Method A).
The absolute configuration of these compounds has been assigned based on their PLK2 activities, with Example 403 being the more active compound.

Example 405

Synthesis of 2-(5-(2,4-difluorophenyl)-1H-pyrazol-4-yl)-6a-ethyl-5-methyl-6a,7,9,10-tetrahydro-[1,4]oxazino[3,4-h]pteridin-6(5H)-one

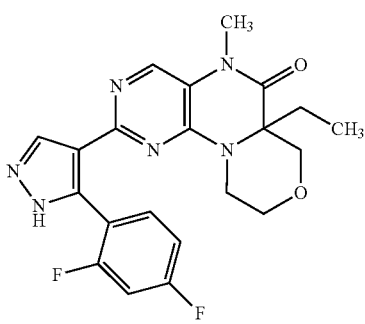 [SMILES: CCC12COCCN1c1nc(-c3cn[nH]c3-c3ccc(F)cc3F)ncc1N(C)C2=O]

The title compounds was prepared similarly to the methods described in Example 134, starting from Intermediate Z-4 instead of Intermediate B-1 (per method of Example 132 to give the analog of Compound I-132). LCMS: 427.2 m/z (M+H)$^+$; ret. Time: 6.21 min (Analytical Method C).

Example 406-408

Synthesis of 7-ethyl-2-(2-(4-fluorophenyl)-1H-imidazol-1-yl)-5-methyl-8-(1-methyl-1H-pyrazol-5-yl)-7,8-dihydropteridin-6(5H)-one (406), (R)-7-ethyl-2-(2-(4-fluorophenyl)-1-imidazol-1-yl)-5-methyl-8-(1-methyl-1H-pyrazol-3-yl)-7,8-dihydropteridin-6(5H)-one (407), and (S)-7-ethyl-2-(2-(4-fluorophenyl)-1H-imidazol-1-yl)-5-methyl-8-(1-methyl-1H-pyrazol-3-yl)-7,8-dihydropteridin-6(5H)-one (408)

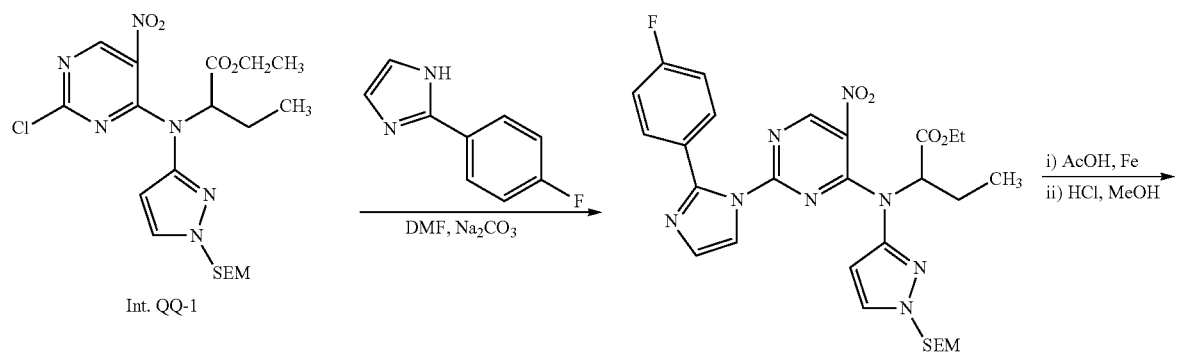

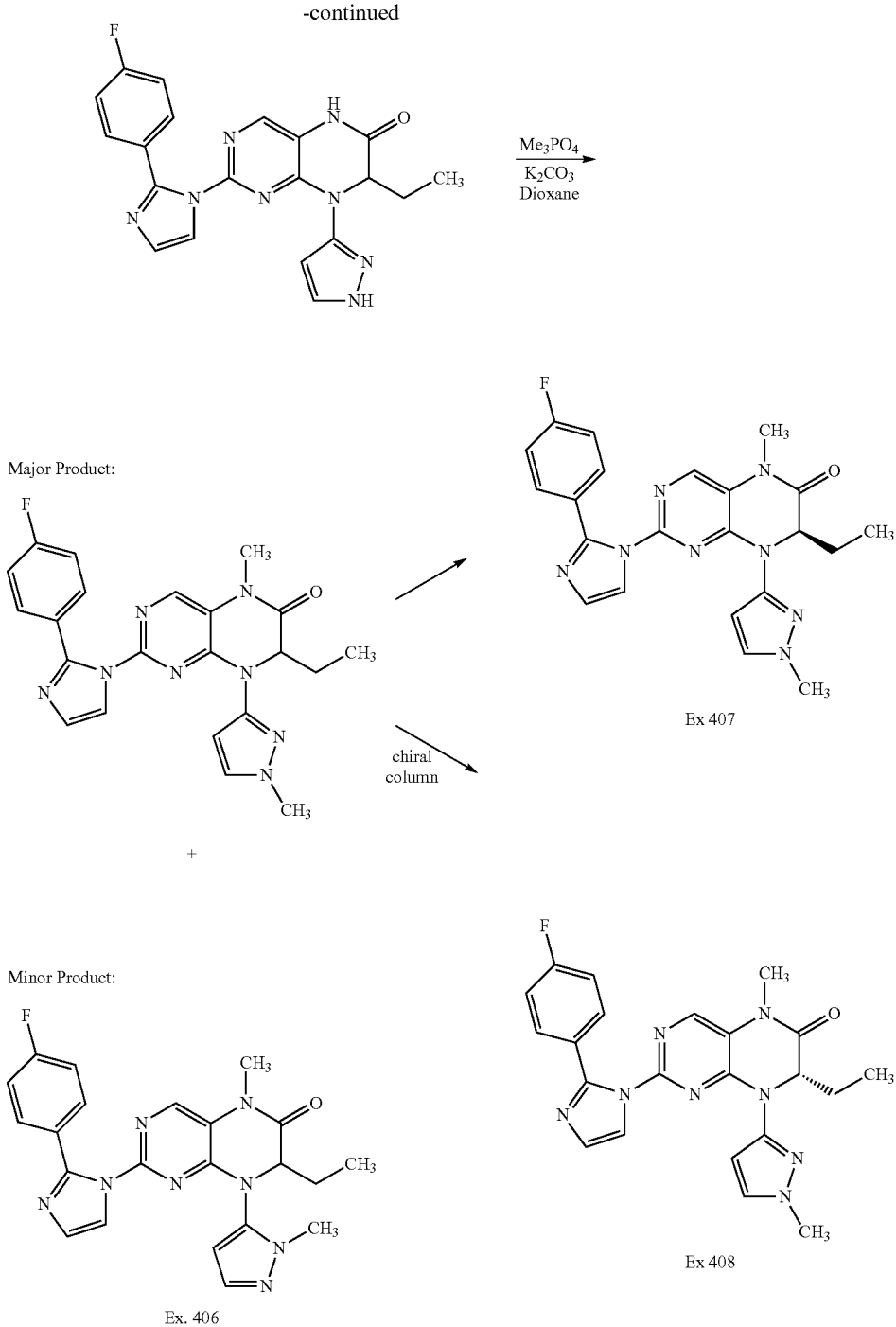

The title compounds were prepared similarly to the methods described herein, for example, the first step is similar to that of Example 3, with Intermediate QQ-1 instead of Intermediate A, and 2-(2-fluorphenyl)-1H-imidazole instead of 1H-imidazole, the next step is similar to the analogous step in the preparation of Intermediate F, with an additional deprotection step as described in Example 331. The deprotected intermediate is then reacted similarly to the last step of Example 3, resulting in a mixture of compounds with methylation at either nitrogen of the pyrazole ring.
Example 406 LCMS: 433.1 m/z (M+H)+; ret. Time: 4.71 min (Analytical Method C). The racemic mixture of the major product was resolved by chiral HPLC using a ChiralPak OH-H (2×25 cm) column with an isocratic mixture of 20:80 ethanol:hexane at 10 mL/min with detection at 220 nm.

Example 407 The (−) rotating enantiomer. LCMS: 433.1 m/z (M+H)+; ret. Time: 5.46 min (Analytical Method C).

Example 408 The (+) rotating enantiomer. LCMS: 433.1 m/z (M+H)+; ret. Time: 5.46 min (Analytical Method C).

The absolute configuration of these compounds has been assigned based on their PLK2 activities, with Example 407 being the more active compound.

Example 409 and Example 410

Synthesis of (R)-7-ethyl-5-methyl-8-(1-methyl-1H-pyrazol-4-yl)-2-(2-phenyl-1H-imidazol-1-yl)-7,8-dihydropteridin-6(5H)-one (409) and (S)-7-ethyl-5-methyl-8-(1-methyl-1-pyrazol-4-yl)-2-(2-phenyl-1H-imidazol-1-yl)-7,8-dihydropteridin-6(5H)-one (410)

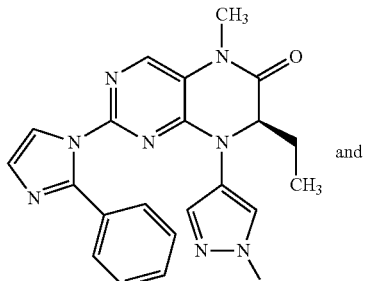

Ex 409 and

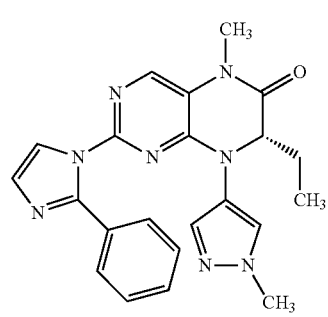

Ex 410

The title compounds were prepared similarly to the methods described in Examples 291, 331 and 362, with Intermediate KK instead of Intermediate CC and with 2-phenyl-1H-imidazole instead of 2-(4-fluorophenyl)-1H-imidazole in the method of Example 291, then deprotected similarly to Example 331 and methylated similarly to Example 362. The resulting racemic mixture was resolved by chiral HPLC using an isocratic mixture of Ethanol:Hexane (33:67, 1 mL/min) eluting from a ChiralPak IA (5×50 cm) column to give the title compounds.

Example 409 LCMS: 415.2 m/z (M+H)$^+$; ret. Time: 4.28 min (Analytical Method C).

Example 410 LCMS: 415.2 m/z (M+H)$^+$; ret. Time: 4.18 min (Analytical Method C).

The absolute configuration of these compounds has been assigned based on their PLK2 activities, with Example 409 being the more active compound.

Example 411 and Example 412

Synthesis of (S)-2-(5-(2,4-difluorophenyl)-1H-pyrazol-4-yl)-6a-ethyl-5-methyl-6a,7,9,10-tetrahydro-[1,4]oxazino[3,4-h]pteridin-6(5H)-one (411) and (R)-2-(5-(2,4-difluorophenyl)-1H-pyrazol-4-yl)-6a-ethyl-5-methyl-6a,7,9,10-tetrahydro-[1,4]oxazino[3,4-h]pteridin-6(5H)-one (412)

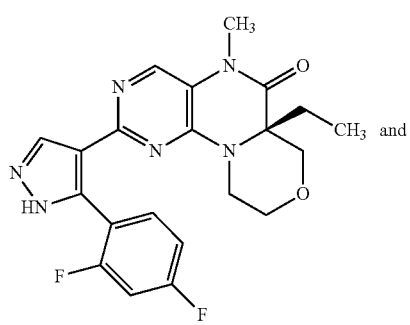

Ex 411 and

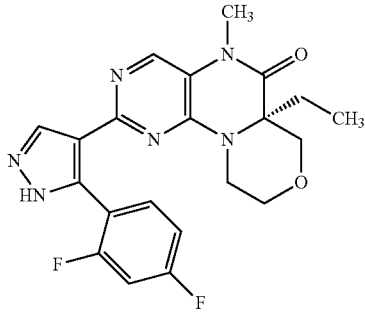

Ex 412

The racemic mixture of Example 405 was resolved by chiral HPLC using an isocratic mixture of EtOH:Hexane (1:4, 1 mL/min) as eluent from a Chiracel IA column to provide the title compounds.

Example 411 The (−) rotating enantiomer. LCMS: 427.2 m/z (M+H)$^+$; ret. Time: 10.45 min (Chiral separation conditions; see above); $^1$H NMR (CD$_3$OD) δ: 8.31-8.13 (m, 1H), 7.87 (s, 1H), 7.50 (q, J=7.8 Hz, 1H), 7.17-6.95 (m, 2H), 4.03 (d, J=11.6 Hz, 1H), 3.74 (dd, J=11.5, 3.7 Hz, 1H), 3.62 (d, J=11.6 Hz, 1H), 3.52-3.35 (m, 2H), 3.33 (s, 3H), 2.76 (t, J=12.7 Hz, 1H), 2.27 (sext, J=7.5 Hz, 1H), 1.89 (sext, J=7.3 Hz, 1H), 0.72 (t, J=7.6 Hz, 3H).

Example 412 The (+) rotating enantiomer. LCMS: 427.2 m/z (M+H)$^+$; ret. Time: 12.90 min (Chiral separation conditions; see above); $^1$H NMR (CD$_3$OD) δ: 8.31-8.13 (m, 1H), 7.87 (s, 1H), 7.50 (q, J=7.8 Hz, 1H), 7.17-6.95 (m, 2H), 4.03 (d, J=11.6 Hz, 1H), 3.74 (dd, J=11.5, 3.7 Hz, 1H), 3.62 (d, J=11.6 Hz, 1H), 3.52-3.35 (m, 2H), 3.33 (s, 3H), 2.76 (t, J=12.7 Hz, 1H), 2.27 (sext, J=7.5 Hz, 1H), 1.89 (sext, J=7.3 Hz, 1H), 0.72 (t, J=7.6 Hz, 3H).

The absolute configuration of these compounds has been assigned based on their PLK2 activities, with Example 411 being the more active compound.

Example 413 and Example 414

Synthesis of (S)-6a-ethyl-5-methyl-2-(5-phenylisoxazol-4-yl)-6a,7,9,10-tetrahydro-[1,4]oxazino[3,4-h]pteridin-6(5H)-one (413) and (R)-6a-ethyl-5-methyl-2-(5-phenylisoxazol-4-yl)-6a,7,9,10-tetrahydro-[1,4]oxazino[3,4-h]pteridin-6(5H)-one (414)

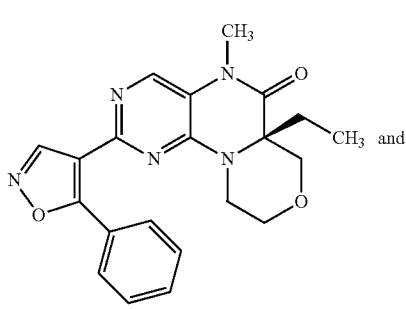

Ex 413 and

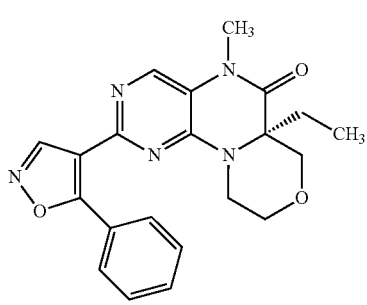

Ex 414

The title compounds were prepared similarly to the methods described in Example 133, starting from Intermediate Z-2 instead of Intermediate B-1 (per method of Example 132 to give the analog of Compound I-132). The resulting racemic mixture was resolved by chiral HPLC using an isocratic mixture of EtOH:Hexane (3:7, 1 mL/min) as eluent from a Chiracel OD-H column (0.46×250 mm) to provide the title compounds.
Example 413 LCMS: 391.2 m/z (M+H)⁺; ret. Time: 4.28 min (Analytical Method A).
Example 414 LCMS: 391.2 m/z (M+H)⁺; ret. Time: 4.27 min (Analytical Method A).
The absolute configuration of these compounds has been assigned based on their PLK2 activities, with Example 413 being the more active compound.

Example 415 and Example 416

Synthesis of (S)-6a-ethyl-2-(4-(5-fluoropyridin-2-yl)-1,2,3-thiadiazol-5-yl)-5-methyl-6a,7,9,10-tetrahydro-[1,4]oxazino[3,4-h]pteridin-6(5H)-one (415) and (R)-6a-ethyl-2-(4-(5-fluoropyridin-2-yl)-1,2,3-thiadiazol-5-yl)-5-methyl-6a,7,9,10-tetrahydro-[1,4]oxazino[3,4-h]pteridin-6(5H)-one (416)

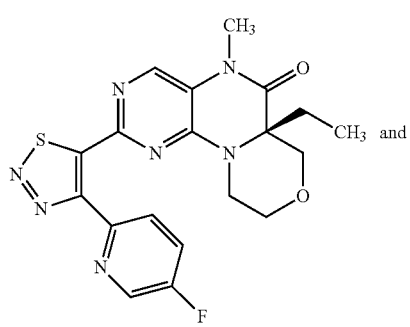

Ex 415

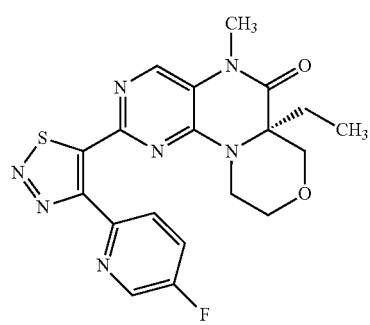

Ex 416

The title compounds were prepared similarly to the methods described in Example 368, with Intermediate Z-5 instead of Intermediate Z-2. The resulting racemic mixture was resolved by chiral HPLC using an isocratic mixture of EtOH: hexane (30:70; 1 mL/min) as eluent with a Chiracel OD-H (4.6×250 mm) column to give the title compounds.
Example 415 LCMS: 427.1 m/z (M+H)⁺; ret. Time: 6.90 min (Analytical Method A).
Example 416 LCMS: 427.1 m/z (M+H)⁺; ret. Time: 6.85 min (Analytical Method A).
The absolute configuration of these compounds has been assigned based on their PLK2 activities, with Example 415 being the more active compound.

Example 417

Synthesis of (R)-7-ethyl-5-methyl-8-(1-methyl-1H-pyrazol-4-yl)-2-(1-methyl-3-(thiazol-2-yl)-1H-pyrazol-4-yl)-7,8-dihydropteridin-6(5H)-one

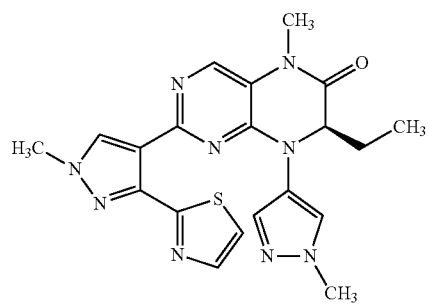 [SMILES: CC[C@@H]1C(=O)N(C)c2cnc(-c3cn(C)nc3-c3nccs3)nc2N1c1cnn(C)c1]

The title compound was prepared similarly to the methods described in Example 5, with Intermediate KK-2 instead of Intermediate B and with 1-methyl-3-(thiazol-2-yl)-1H-pyrazol-4-ylboronic acid instead of pyridin-4-ylboronic acid. LCMS: 436.1 m/z (M+H)⁺; ret. Time: 5.69 min (Analytical Method A).

Example 418

Synthesis of (S)-6a-ethyl-2-(2-phenyl-1H-imidazol-1-yl)-6a,7,9,10-tetrahydro-[1,4]oxazino[3,4-h]pteridin-6(5H)-one

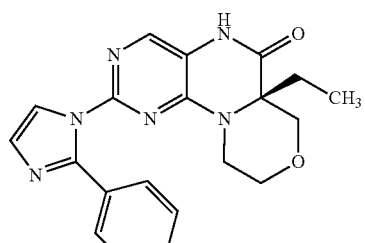

The title compound was prepared similarly to the methods described in Example 3, with Intermediate Z-1 instead of Intermediate A, and 2-phenyl-1H-imidazole instead of 1H-imidazole in the first step, with the title compound isolated prior to the last step. The resulting racemic mixture was resolved by chiral HPLC, where the two isomers were isolated and the absolute configuration of the title compound was assigned based on its PLK2 activity relative to the other isomer, where the title compound is the more active compound.

Example 419

Synthesis of (R)-2-(3-(2,4-difluorophenyl)-1H-pyrazol-4-yl)-7-ethyl-5-methyl-8-(1-methyl-1H-pyrazol-4-yl)-7,8-dihydropteridin-6(5H)-one

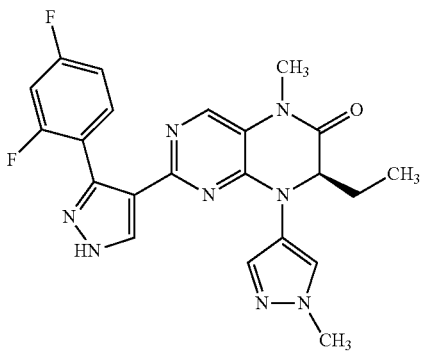 [SMILES: CC[C@@H]1C(=O)N(C)c2cnc(-c3c[nH]nc3-c3ccc(F)cc3F)nc2N1c1cnn(C)c1]

The title compound was prepared similarly to the methods described in Example 5, with Intermediate KK-2 instead of Intermediate B and with 5-(2,4-difluorophenyl)-4-(4,4,5,5-tetramethyl-1,3,2-dioxaborolan-2-yl)-1-((2-(trimethylsilyl)ethoxy)methyl)-1H-pyrazole (Boronic Acid 4) instead of pyridin-4-ylboronic acid. The resulting coupling product is then deprotected by the method described in Example 331 to give the title compound. LCMS: 451.1 m/z (M+H)$^+$; ret. Time: 4.81 min (Analytical Method C).

Example 420

Synthesis of 2-(3-(2,4-difluorophenyl)-1H-pyrazol-4-yl)-7-ethyl-5-methyl-8-(1-methyl-1H-pyrazol-3-yl)-7,8-dihydropteridin-6(5H)-one

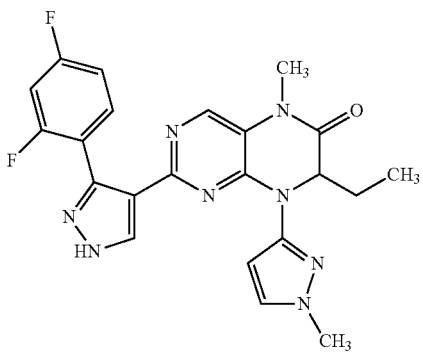 [SMILES: CCC1C(=O)N(C)c2cnc(-c3c[nH]nc3-c3ccc(F)cc3F)nc2N1c1ccn(C)n1]

The title compound was prepared similarly to the methods described in Example 5, with Intermediate QQ-2 instead of Intermediate B and with 5-(2,4-difluorophenyl)-4-(4,4,5,5-tetramethyl-1,3,2-dioxaborolan-2-yl)-1-((2-(trimethylsilyl)ethoxy)methyl)-1H-pyrazole (Boronic Acid 4) instead of pyridin-4-ylboronic acid. The resulting coupling product is then deprotected by the method described in Example 331 to give the title compound. LCMS: 451.1 m/z (M+H)$^+$; ret. Time: 6.02 min (Analytical Method C).

Example 421

Synthesis of (R)-7-ethyl-5-methyl-8-(1-methyl-1H-pyrazol-3-yl)-2-(1-methyl-3-(thiazol-2-yl)-1H-pyrazol-4-yl)-7,8-dihydropteridin-6(5H)-one

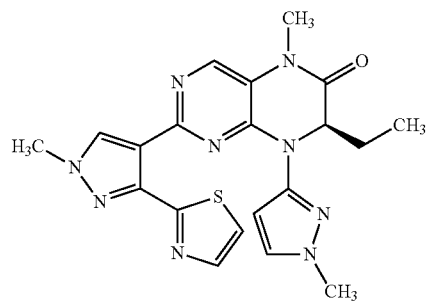 [SMILES: CC[C@@H]1C(=O)N(C)c2cnc(-c3cn(C)nc3-c3nccs3)nc2N1c1ccn(C)n1]

The title compound is prepared similarly to the methods described in Example 5, with Intermediate QQ-2 instead of Intermediate B and with 1-methyl-3-(thiazol-2-yl)-1H-pyrazol-4-ylboronic acid instead of pyridin-4-ylboronic acid.

Example 422

Synthesis of (R)-7-ethyl-5-methyl-8-(1-methyl-1H-pyrazol-3-yl)-2-(1-methyl-5-(thiazol-2-yl)-1H-pyrazol-4-yl)-7,8-dihydropteridin-6(5H)-one

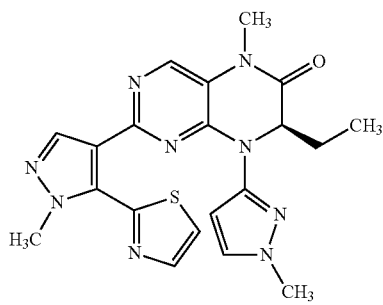 [SMILES: CC[C@@H]1C(=O)N(C)c2cnc(-c3cnn(C)c3-c3nccs3)nc2N1c1ccn(C)n1]

The title compound is prepared similarly to the methods described in Example 5, with Intermediate QQ-2 instead of Intermediate B and with 1-methyl-5-(thiazol-2-yl)-1H-pyrazol-4-ylboronic acid instead of pyridin-4-ylboronic acid.

Example 423

Synthesis of (R)-7-ethyl-5-methyl-8-(1-methyl-1H-pyrazol-4-yl)-2-(5-(thiazol-2-yl)-1H-pyrazol-4-yl)-7,8-dihydropteridin-6(5H)-one

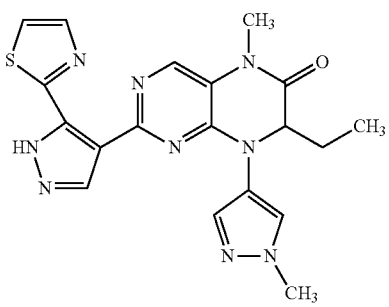 [SMILES: CCC1C(=O)N(C)c2cnc(-c3cn[nH]c3-c3nccs3)nc2N1c1cnn(C)c1]

The title compound is prepared similarly to the methods described in Example 5, with Intermediate KK-3 instead of Intermediate B and with 5-(thiazol-2-yl)-1-((2-(trimethylsilyl)ethoxy)methyl)-1H-pyrazol-4-ylboronic acid (Boronic Acid 1) instead of pyridin-4-ylboronic acid. The resulting coupling product is then deprotected by the method described in Example 331 to give the title compound.

Example 424

Synthesis of (R)-7-ethyl-5-methyl-8-(1-methyl-1H-pyrazol-3-yl)-2-(3-phenylpyridin-4-yl)-7,8-dihydropteridin-6(5H)-one

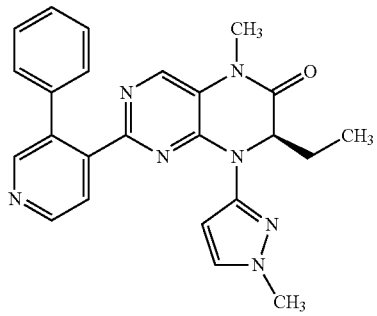 [SMILES: CC[C@@H]1C(=O)N(C)c2cnc(-c3ccncc3-c3ccccc3)nc2N1c1ccn(C)n1]

The title compound is prepared similarly to the methods described in Example 5, with Intermediate QQ-2 instead of Intermediate B and with 3-phenyl-4-(4,4,5,5-tetramethyl-1,3,2-dioxaborolan-2-yl)pyridine (Boronic Acid 2) instead of pyridin-4-ylboronic acid.

Example 425

Synthesis of (R)-7-ethyl-5-methyl-8-(1-methyl-1H-pyrazol-3-yl)-2-(2-phenylpyridin-3-yl)-7,8-dihydropteridin-6(5H)-one

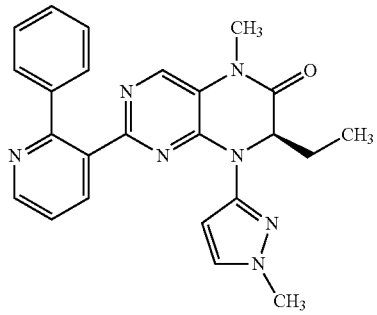 [SMILES: CC[C@@H]1C(=O)N(C)c2cnc(-c3cccnc3-c3ccccc3)nc2N1c1ccn(C)n1]

The title compound is prepared similarly to the methods described in Example 5, with Intermediate QQ-2 instead of Intermediate B and with 2-phenyl-3-(4,4,5,5-tetramethyl-1,3,2-dioxaborolan-2-yl)pyridine (prepared similarly to the methods used for Boronic Acid 2) instead of pyridin-4-yloronic acid.

Example 426

Synthesis of (R)-7-ethyl-5-methyl-8-(1-methyl-1H-pyrazol-4-yl)-2-(2-phenylpyridin-3-yl)-7,8-dihydropteridin-6(5H)-one

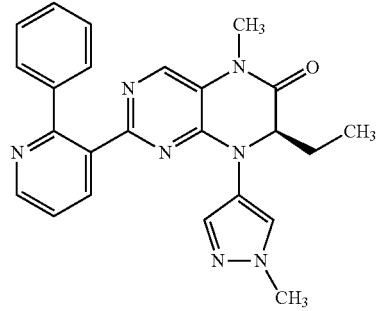 [SMILES: CC[C@@H]1C(=O)N(C)c2cnc(-c3cccnc3-c3ccccc3)nc2N1c1cnn(C)c1]

The title compound is prepared similarly to the methods described in Example 5, with Intermediate KK-2 instead of Intermediate B and with 2-phenyl-3-(4,4,5,5-tetramethyl-1,3,2-dioxaborolan-2-yl)pyridine (prepared similarly to the methods used for Boronic Acid 2) instead of pyridin-4-ylboronic acid.

Example 427

Synthesis of (R)-7-ethyl-5-methyl-8-(1-methyl-1H-pyrazol-4-yl)-2-(3-phenylpyridin-4-yl)-7,8-dihydropteridin-6(5H)-one

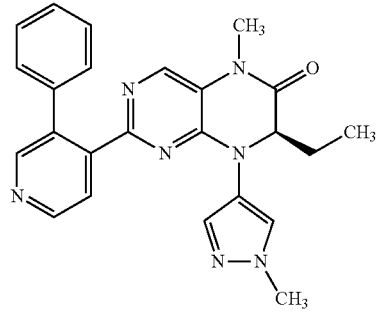 [SMILES: CC[C@@H]1C(=O)N(C)c2cnc(-c3ccncc3-c3ccccc3)nc2N1c1cnn(C)c1]

The title compound is prepared similarly to the methods described in Example 5, with Intermediate KK-2 instead of Intermediate B and with 3-phenyl-4-(4,4,5,5-tetramethyl-1,3,2-dioxaborolan-2-yl)pyridine (Boronic Acid 2) instead of pyridin-4-ylboronic acid.

Example 428

Synthesis of (R)-7-ethyl-5-methyl-8-(1-methyl-1H-pyrazol-3-yl)-2-(2-phenyl-1H-imidazol-1-yl)-7,8-dihydropteridin-6(5H)-one

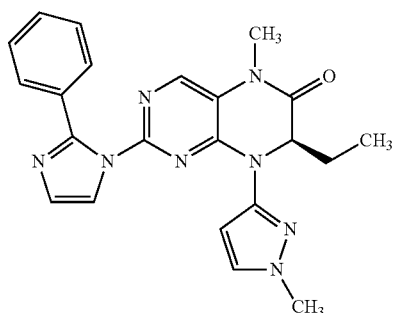

The title compound is prepared similarly to the methods described in Examples 291, 331 and 362, with Intermediate QQ-2 instead of Intermediate CC and with 2-phenyl-1H-imidazole instead of 2-(4-fluorophenyl)-1H-imidazole in the method of Example 291, then deprotected similarly to Example 331 and methylated similarly to Example 362.

Example 429

Synthesis of (S)-6a-ethyl-2-(2-phenyl-1H-imidazol-1-yl)-6a,7,9,10-tetrahydro-[1,4]oxazino[3,4-h]pteridin-6(5H)-one

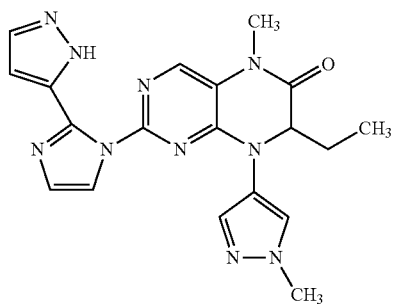 [SMILES: CCC1C(=O)N(C)c2cnc(-n3ccnc3-c3ccn[nH]3)nc2N1c1cnn(C)c1]

The title compound is prepared similarly to the methods described in Examples 291, 331 and 362, with Intermediate KK-3 instead of Intermediate CC and with 5-(1H-imidazol-2-yl)-1H-pyrazole instead of 2-(4-fluorophenyl)-1H-imidazole in the method of Example 291, then deprotected similarly to Example 331 and methylated similarly to Example 362.

Example 430

Synthesis of 2-(4-(1H-pyrazol-5-yl)thiazol-5-yl)-7-ethyl-5-methyl-8-(1-methyl-1H-pyrazol-4-yl)-7,8-dihydropteridin-6(5H)-one

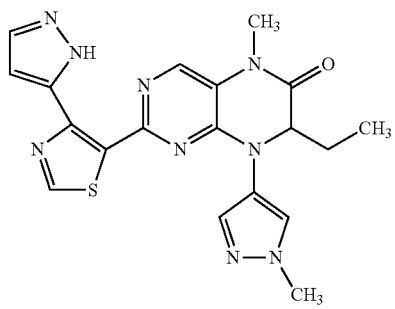 [SMILES: CCC1C(=O)N(C)c2cnc(-c3scnc3-c3ccn[nH]3)nc2N1c1cnn(C)c1]

The title compound is prepared similarly to the methods of Example 337 and Example 348, with Intermediate KK-5 instead of Intermediate C-7 in Example 337, and reacting the resulting analog of compound 2-337 similarly to the method of Example 348.

Example 431

Synthesis of (S)-2-(2-(2,3-difluorophenyl)-1H-imidazol-1-yl)-6a-ethyl-5-methyl-6a,7,9,10-tetrahydro-[1,4]oxazino[3,4-h]pteridin-6(5H)-one

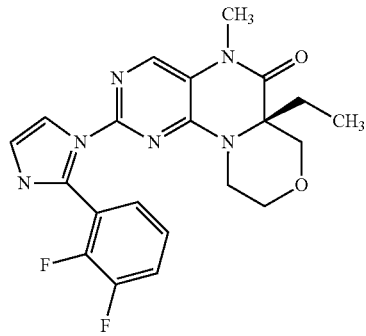

The title compound is prepared similarly to the methods described in Example 3, with Intermediate Z-1 instead of Intermediate A, and 2-(2,4-difluorophenyl)-1H-imidazole instead of 1H-imidazole in the first step. The resulting racemic mixture is resolved by chiral HPLC and the absolute configuration of the title compound is assigned based on its PLK2 activity relative to the other isomer, where the title compound is the more active compound.

Example 432

Synthesis of 4-(7-ethyl-5-methyl-6-oxo-2-(5-(thiazol-2-yl)-1H-pyrazol-4-yl)-6,7-dihydropteridin-8(5H)-yl)benzonitrile

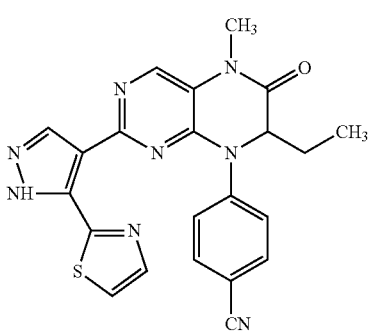 [SMILES: CCC1C(=O)N(C)c2cnc(-c3cn[nH]c3-c3nccs3)nc2N1c1ccc(C#N)cc1]

The title compound is prepared similarly to the methods described in Example 5, with Intermediate PP instead of Intermediate B and with 5-(thiazol-2-yl)-1-((2-(trimethylsilyl)ethoxy)methyl)-1H-pyrazol-4-ylboronic acid (Boronic Acid 1) instead of pyridin-4-ylboronic acid. The resulting coupling product is then deprotected by the method described in Example 331 to give the title compound.

Example 433

Synthesis of 4-(7-ethyl-5-methyl-6-oxo-2-(5-(thiazol-2-yl)-1H-pyrazol-4-yl)-6,7-dihydropteridin-8(5H)-yl)benzamide

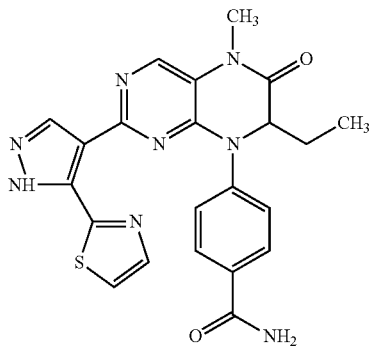 [SMILES: CCC1C(=O)N(C)c2cnc(-c3cn[nH]c3-c3nccs3)nc2N1c1ccc(C(N)=O)cc1]

The title compound is isolated as a side product of Example 432.

Example 434

Synthesis of (7R)-7-ethyl-5-methyl-2-(1-methyl-3-(thiazol-2-yl)-1H-pyrazol-4-yl)-8-(tetrahydrofuran-3-yl)-7,8-dihydropteridin-6(5H)-one

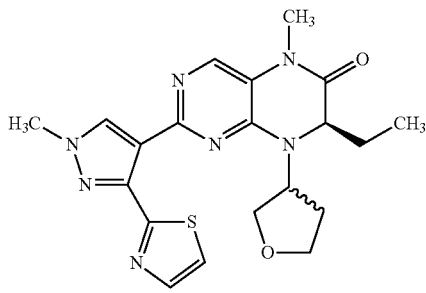 [SMILES: CC[C@@H]1C(=O)N(C)c2cnc(-c3cn(C)nc3-c3nccs3)nc2N1C1CCOC1]

The title compound is prepared similarly to the methods described in Example 5, with Intermediate N instead of Intermediate B and with 1-methyl-3-(thiazol-2-yl)-1H-pyrazol-4-ylboronic acid instead of pyridin-4-ylboronic acid.

Example 435

Synthesis of (7R)-7-ethyl-5-methyl-2-(1-methyl-5-(thiazol-2-yl)-1H-pyrazol-4-yl)-8-(tetrahydrofuran-3-yl)-7,8-dihydropteridin-6(5H)-one

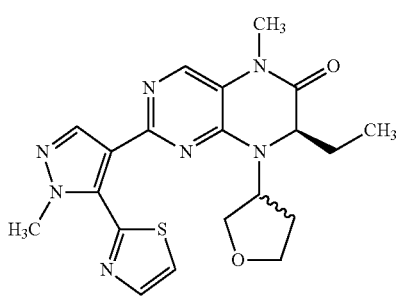 [SMILES: CC[C@@H]1C(=O)N(C)c2cnc(-c3cnn(C)c3-c3nccs3)nc2N1C1CCOC1]

The title compound is prepared similarly to the methods described in Example 5, with Intermediate N instead of Intermediate B and with 1-methyl-5-(thiazol-2-yl)-1H-pyrazol-4-ylboronic acid instead of pyridin-4-ylboronic acid.

Example 436

Additional Synthetic Examples

The methods described herein above can be readily adapted by one skilled in the art to make compounds of Formula I. The following tables indicate compounds made by such adaptation of the above methods, where appropriate starting materials and reagents were used. The tables following a given core structure provide the structure of

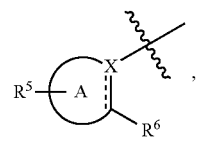

where

represents the point of attachment of ring A to the 7-position of the pteridinone core, with the Example number (in bold) and mass determination $(M^+(\#)=m/z\ (M+H)^+)$ below each structure. Where given, compounds have the stereochemistry as shown in the core structure unless indicated otherwise. The last table provides the entire compound structure along with Example number and mass data.

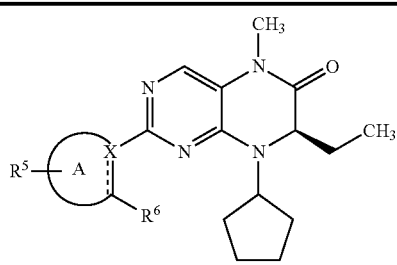

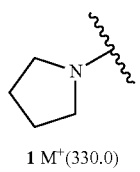

1 $M^+(330.0)$

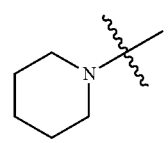

2 $M^+(344.0)$

| 215 -continued | 216 -continued |
|---|---|
| 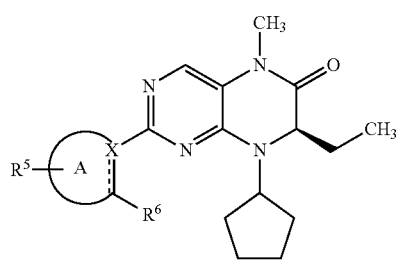 | 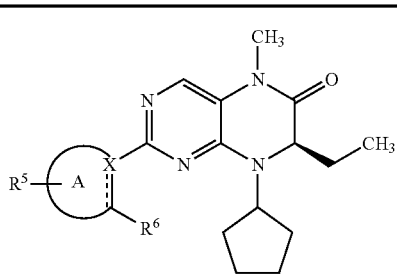 |
| 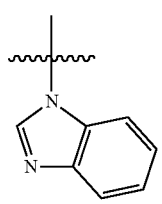<br>4 M⁺(377.0) | 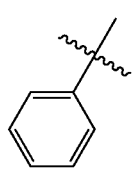<br>12 M⁺(337.0) |
| 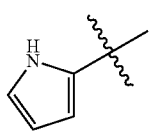<br>6 M⁺(326.0) | 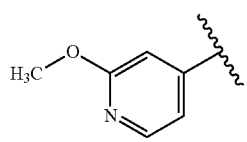<br>15 M⁺(368.2) |
| 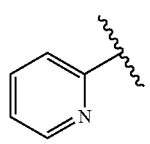<br>8 M⁺(338.0) | 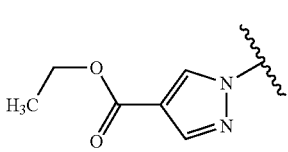<br>18 M⁺(399.2) |
| 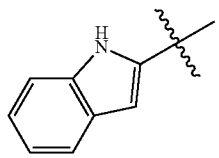<br>9 M⁺(376.0) | 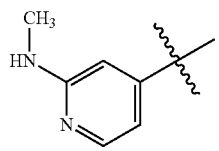<br>20 M⁺(367.2) |
| 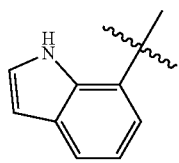<br>10 M⁺(376.0) | 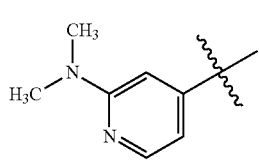<br>21 M⁺(381.3) |
| 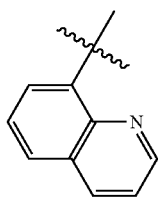<br>11 M⁺(388.0) | 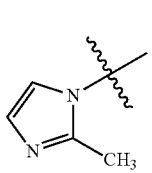<br>27 M⁺(341.2) |

| 217 -continued | 218 -continued |
|---|---|
| 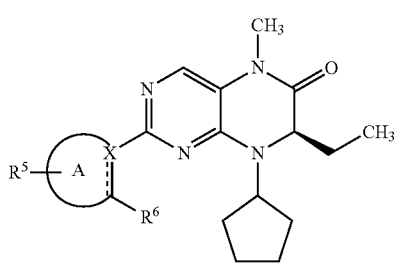 | 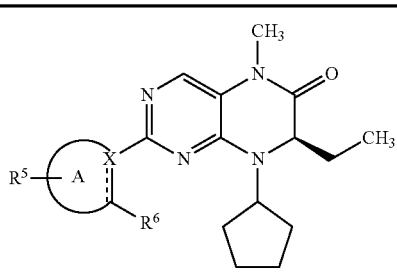 |
| 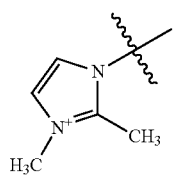
28 M⁺(355.3) | 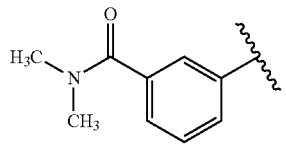
57 M⁺(408.1) |
| 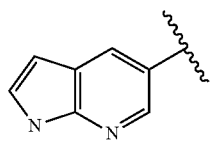
32 M⁺(377.2) | 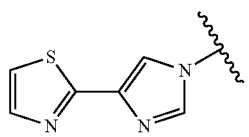
60 M⁺(410.0) |
| 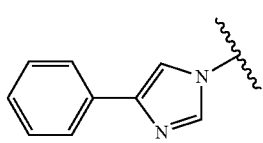
36 M⁺(403.1) | 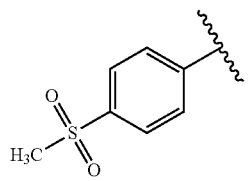
64 M⁺(415.1) |
| 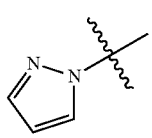
42 M⁺(327.1) | 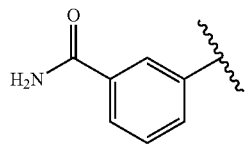
66 M⁺(380.2) |
| 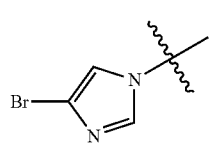
43 M⁺(405.1) | 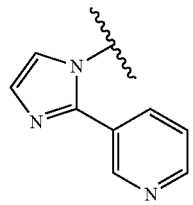
67 M⁺(404.2) |
| 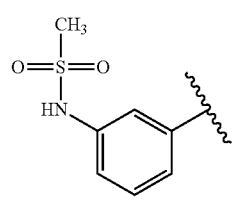
53 M⁺(430.4) | 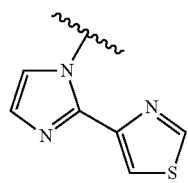
68 M⁺(410.0) |

| 219 -continued | 220 -continued |
|---|---|
| 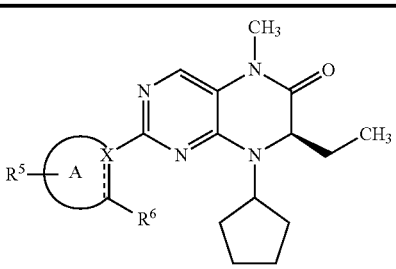 | 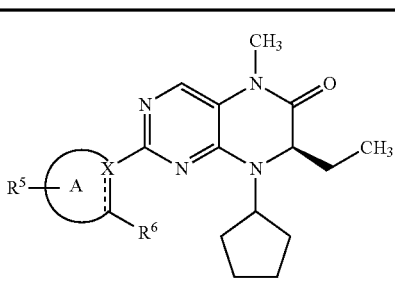 |
| 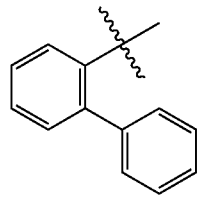 70 M⁺(413.2) | 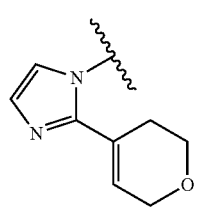 84 M⁺(409.2) |
| 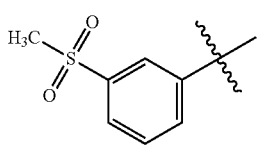 71 M⁺(415.1) | 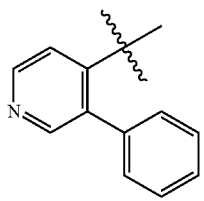 85 M⁺(414.2) |
| 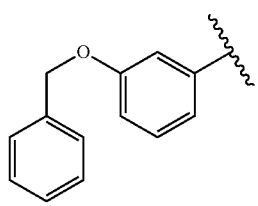 72 M⁺(443.2) | 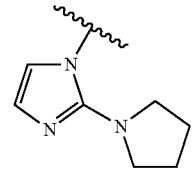 86 M⁺(396.2) |
| 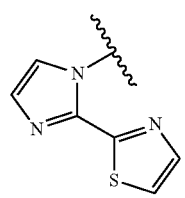 74 M⁺(410.0) | 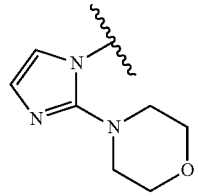 87 M⁺(412.2) |
| 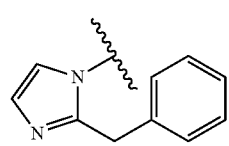 75 M⁺(417.2) | 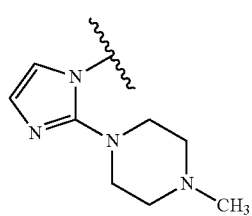 88 M⁺(425.2) |
| 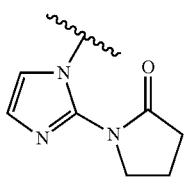 82 M⁺(410.2) | |

221
-continued
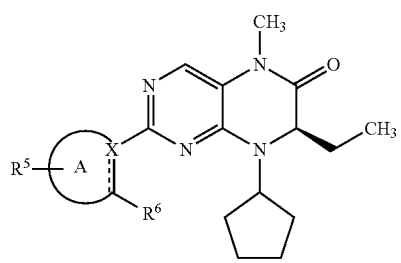
222
-continued
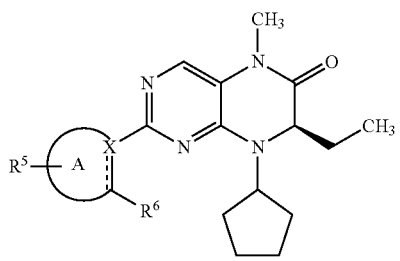
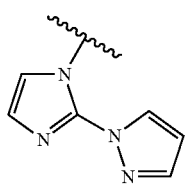
89 M⁺(393.2)
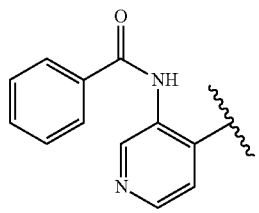
102 M⁺(457.2)
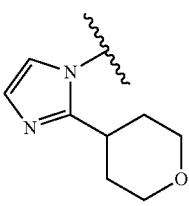
90 M⁺(411.2)
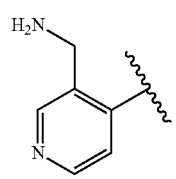
105 M⁺(367.3)
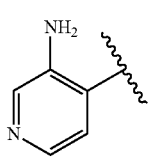
91 M⁺(353.0)
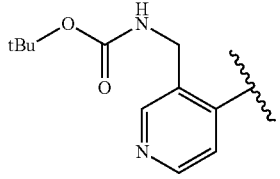
106 M⁺(467.3)
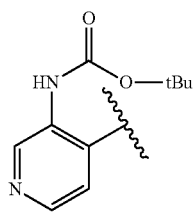
92 M⁺(453.3)
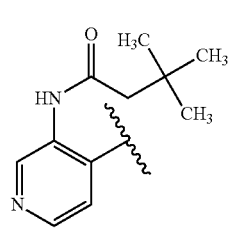
108 M⁺(451.2)
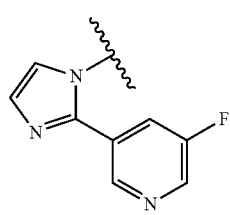
99 M⁺(422.2)
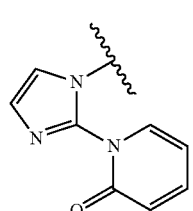
113 M⁺(420.2)

| 223 -continued | 224 -continued |
|---|---|
| 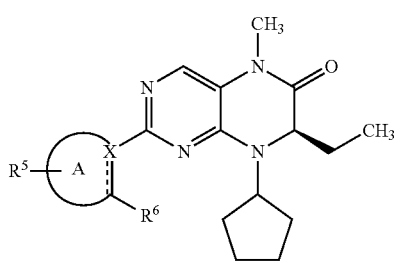 | 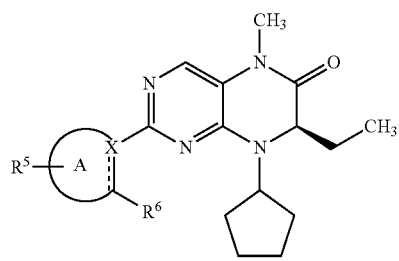 |
| 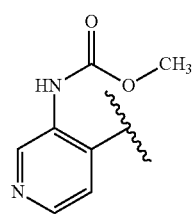<br>114 M⁺(411.1) | 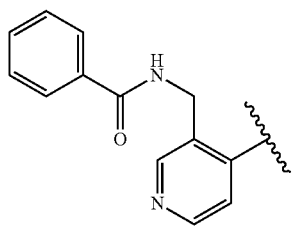<br>123 M⁺(471.3) |
| 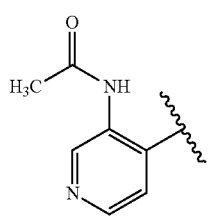<br>115 M⁺(395.2) | 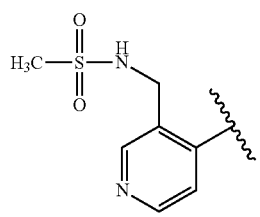<br>124 M⁺(445.2) |
| 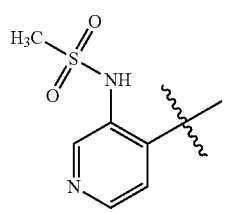<br>116 M⁺(431.2) | 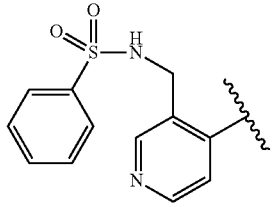<br>125 M⁺(507.2) |
| 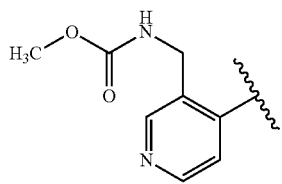<br>121 M⁺(425.2) | 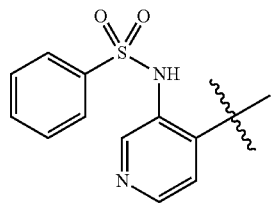<br>127 M⁺(493.2) |
| 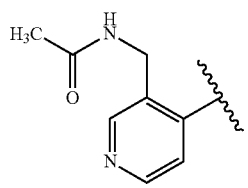<br>122 M⁺(409.2) | 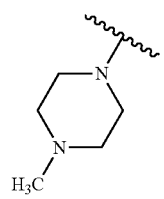<br>210 M⁺(359.2) |

| 225 -continued | 226 -continued |
|---|---|
| 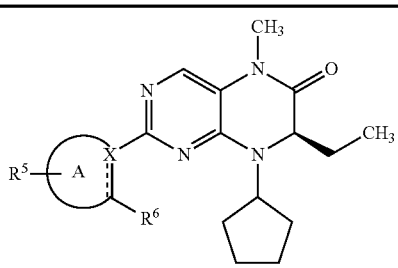 | 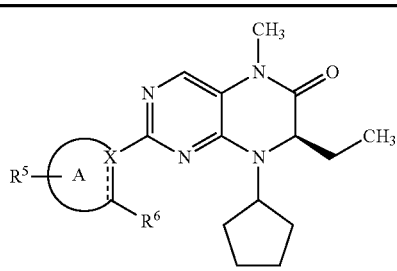 |
| 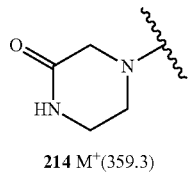 [SMILES: *N1CCNC(=O)C1]
214 M+(359.3) | 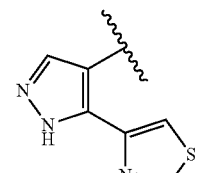
307 M+(410.2) |
| 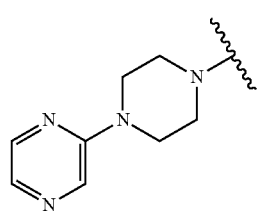
223 M+(423.2) | 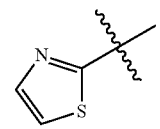
330 M+(344.1) |
| 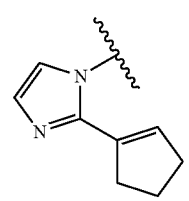
231 M+(393.2) | 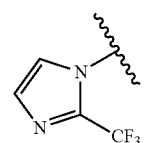
352 M+(395.2) |
| 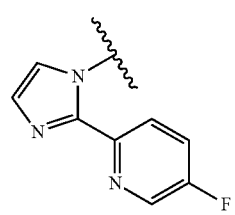
271 M+(422.3) | 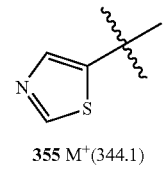 [SMILES: *c1cncs1]
355 M+(344.1) |
| 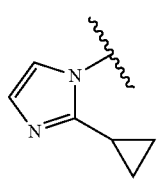
288 M+(367.1) | 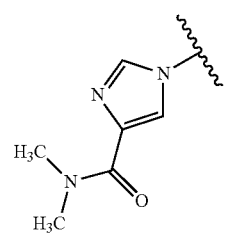
384 M+(398.1) |
| 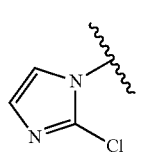
292 M+(361.2) | 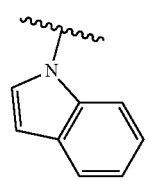
385 M+(376.2) |

| 227 | 228 |
|---|---|
| 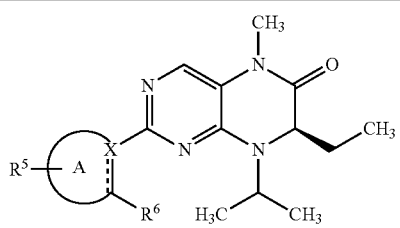 | 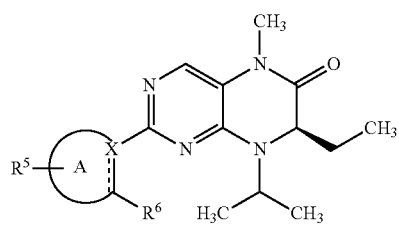 -continued |
| 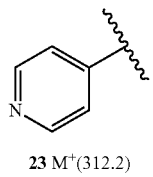  23 M⁺(312.2) | 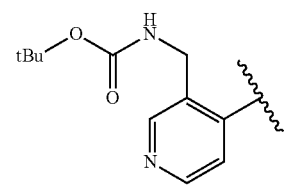  107 M⁺(441.3) |
| 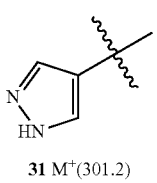  31 M⁺(301.2) | 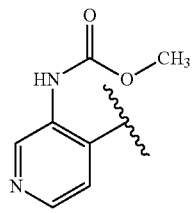  117 M⁺(385.2) |
| 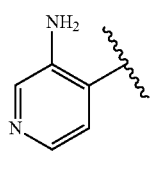  93 M⁺(327.0) | 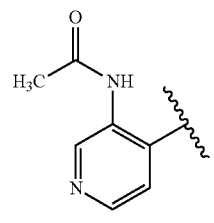  118 M⁺(369.1) |
| 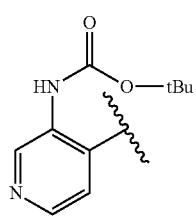  94 M⁺(427.2) | 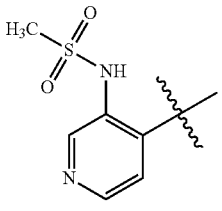  119 M⁺(405.2) |
| 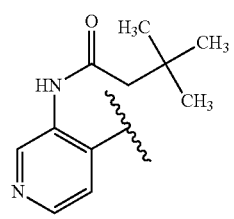  103 M⁺(425.3) | 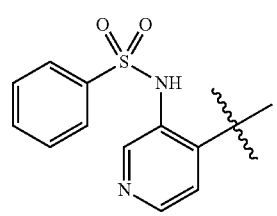  120 M⁺(467.2) |
| 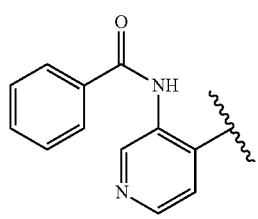  104 M⁺(431.2) | |

| 229 -continued | 230 -continued |
|---|---|
| 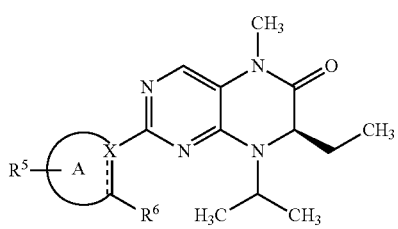 | 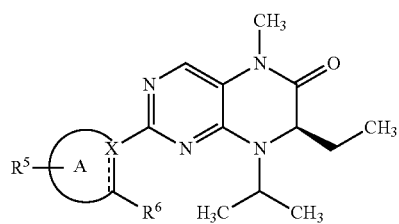 |
| 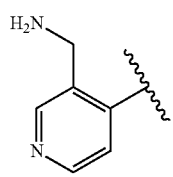<br>126 M⁺(341.2) | 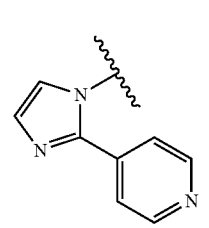<br>136 M⁺(481.2) |
| 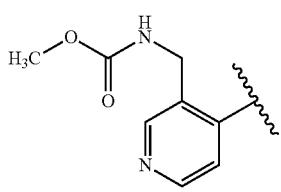<br>128 M⁺(399.2) | 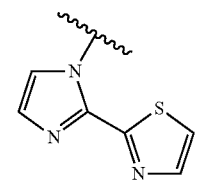<br>150 M⁺(378.2) |
| 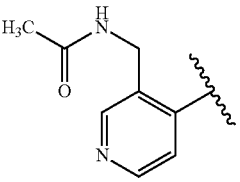<br>129 M⁺(383.2) | 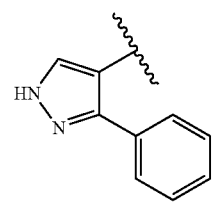<br>151 M⁺(384.1) |
| 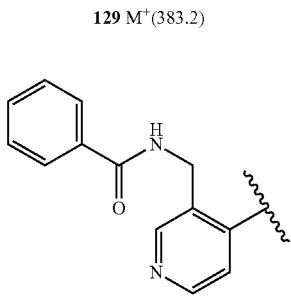<br>130 M⁺(445.2) | |
| | |
| 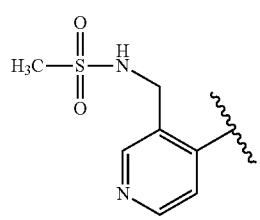<br>131 M⁺(419.2) | 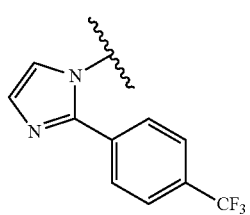<br>166 M⁺(445.2) |
(Between 151 and 166 in column 230: 164 M⁺(377.2))

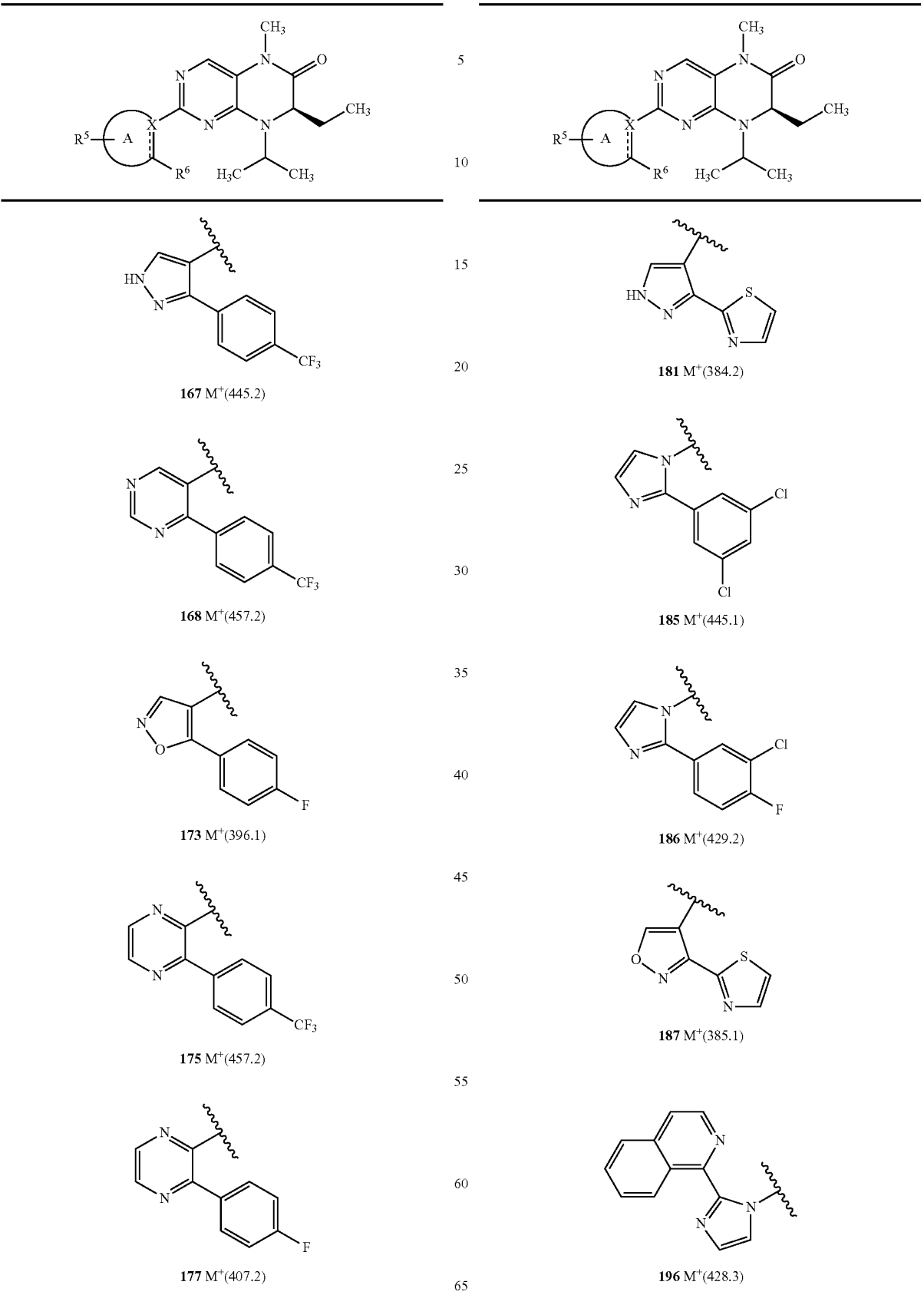

| 233 -continued | 234 -continued |
|---|---|
| 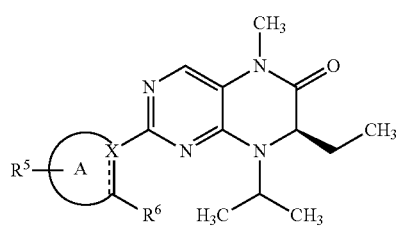 | 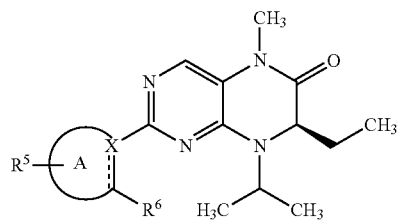 |
| 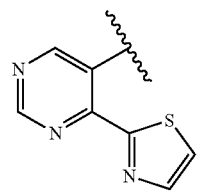
197 M⁺(396.1) | 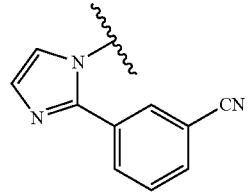
228 M⁺(402.2) |
| 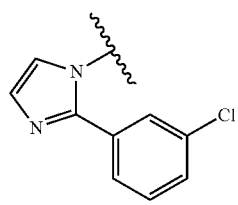
204 M⁺(411.1) | 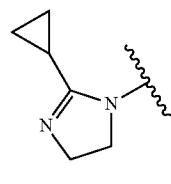
297 M⁺(343.1) |
| 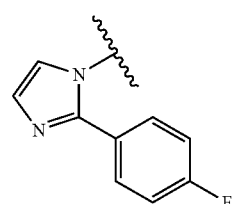
212 M⁺(391.3) | 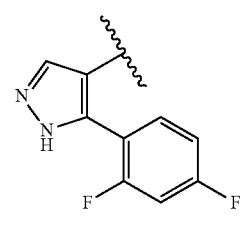
312 M⁺(413.1) |
| 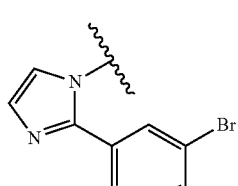
220 M⁺(455.0) | 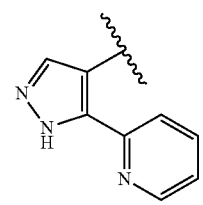
313 M⁺(378.1) |
| 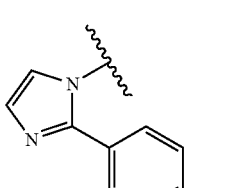
227 M⁺(402.2) | 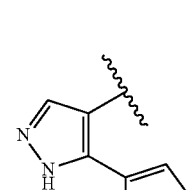
320 M⁺(383.9) |

| 235 -continued | 236 -continued |
|---|---|
| 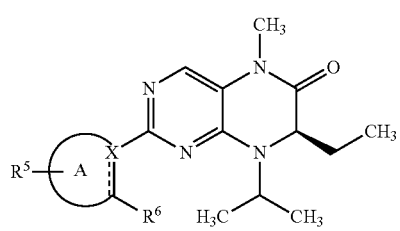 | 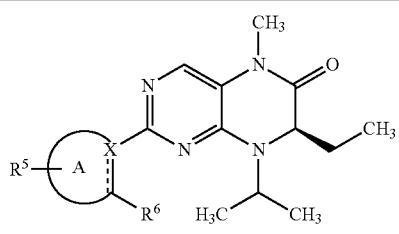 |
| 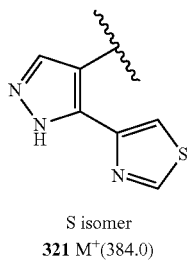 [SMILES: *c1cn[nH]c1-c1cscn1]  S isomer  321 M⁺(384.0) | 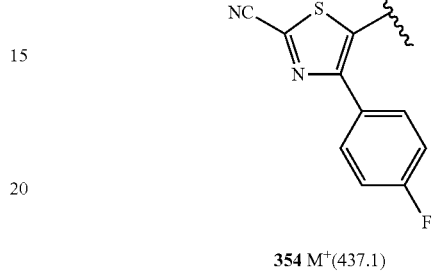  354 M⁺(437.1) |
| 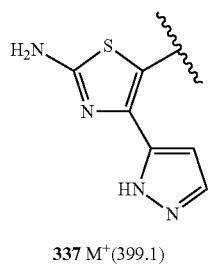 [SMILES: *c1sc(N)nc1-c1ccn[nH]1]  337 M⁺(399.1) | 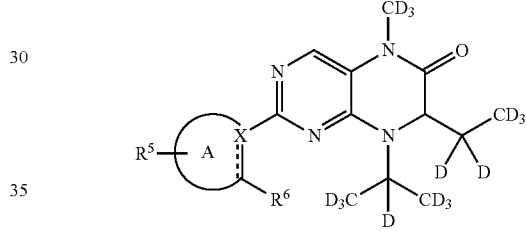 |
| 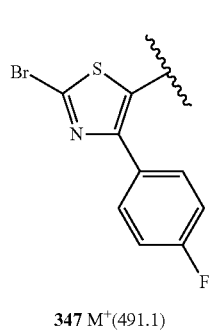 [SMILES: *c1sc(Br)nc1-c1ccc(F)cc1]  347 M⁺(491.1) | 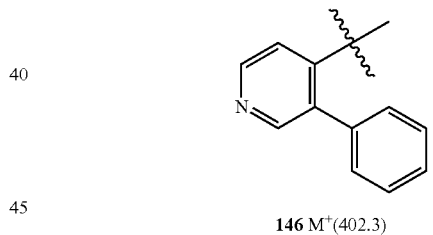  146 M⁺(402.3) |
|  | 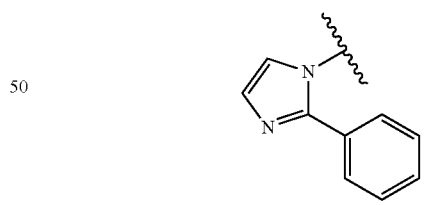  155 M⁺(391.3) |
| 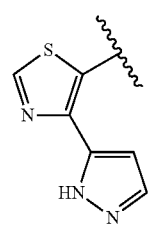  348 M⁺(384.1) | 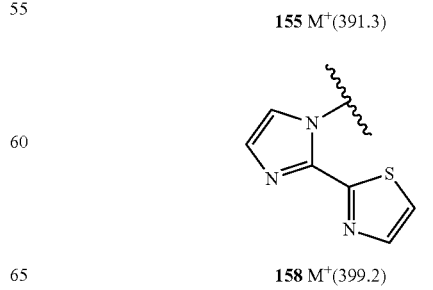  158 M⁺(399.2) |

| 237 -continued | 238 -continued |
|---|---|
| 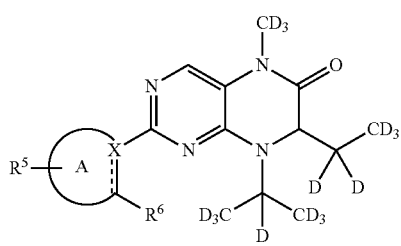 | 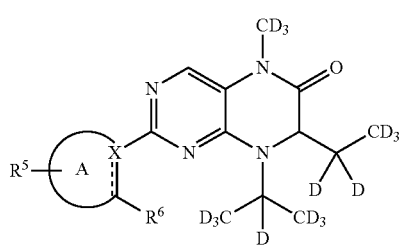 |
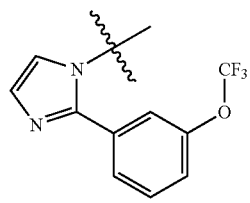
160 M⁺(476.2)
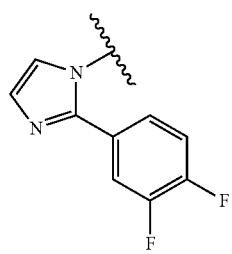
169 M⁺(428.2)
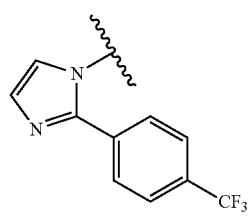
161 M⁺(460.3)
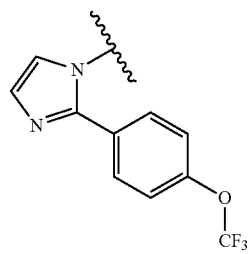
170 M⁺(476.3)
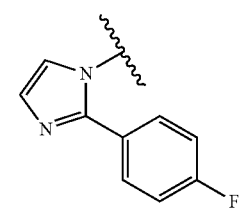
162 M⁺(410.3)
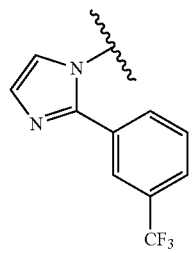
172 M⁺(460.3)
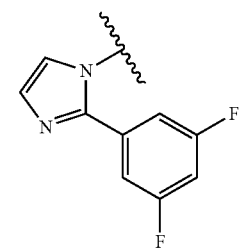
163 M⁺(428.2)
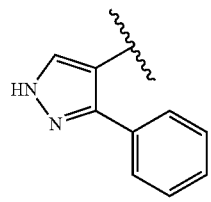
165 M⁺(392.3)
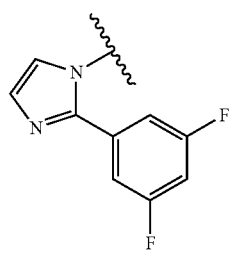
S isomer
178 M⁺(428.2)

239 -continued
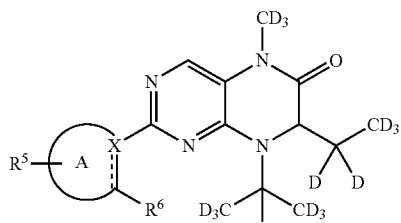
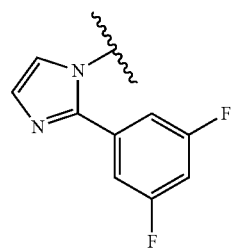
R isomer
179 M+(428.2)
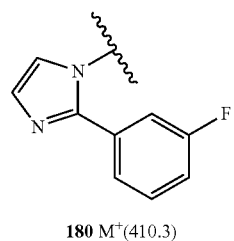 [SMILES: *n1ccnc1-c1cccc(F)c1]
180 M+(410.3)
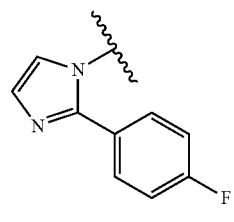
S isomer
199 M+(410.3)
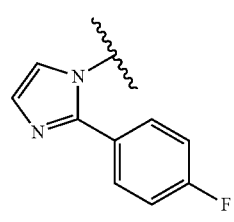
R isomer
200 M+(410.3)
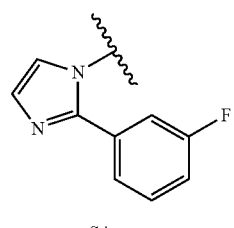
S isomer
201 M+(410.3)
240 -continued
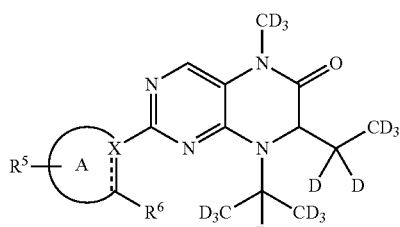
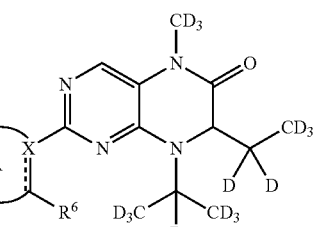
R isomer
202 M+(410.3)
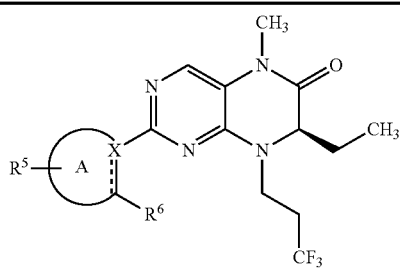
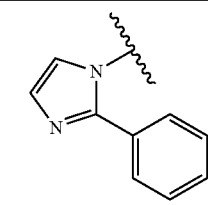
190 M+(431.2)
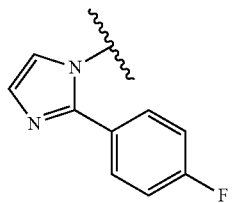
233 M+(449.2)
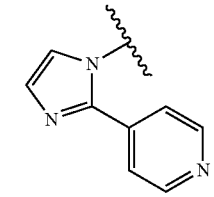
234 M+(432.1)

| 241 -continued | 242 |
|---|---|
| 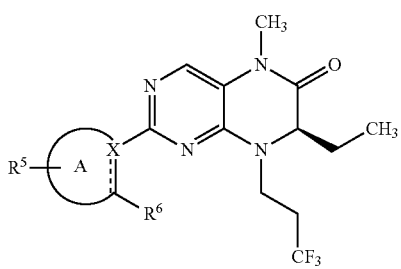 | 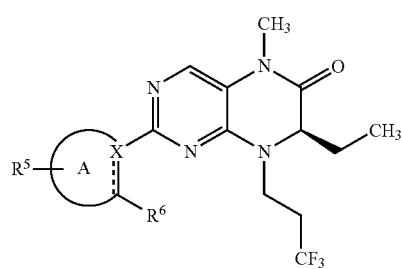 |
| | |
|---|---|
| 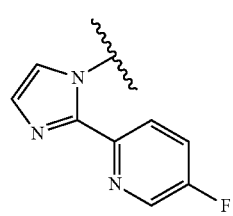
244 M⁺(450.1) | 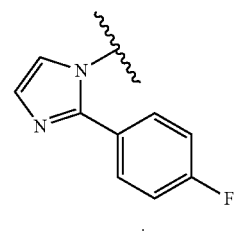
racemic
255 M⁺(503.1) |
| 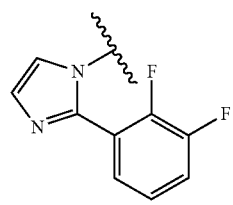
254 M⁺(467.2) | 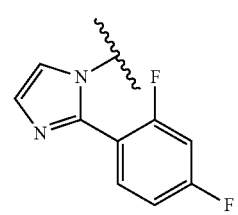
293 M⁺(521.1) |
| 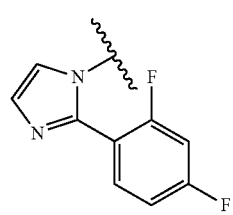
277 M⁺(467.1) | 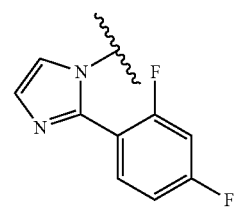
S isomer
294 M⁺(521.1)
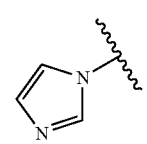
301 M⁺(409.0) |
| 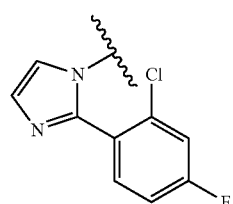
282 M⁺(483.1) | 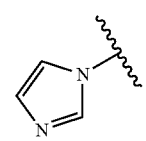
S isomer
302 M⁺(409.0) |

| 243 | 244 |
|---|---|
| 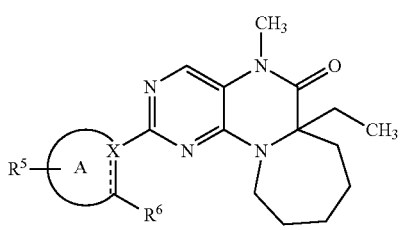 | 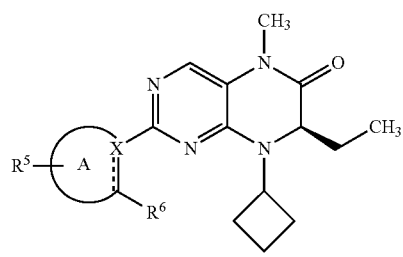 |
| 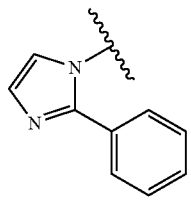<br>205 M⁺(403.2) | 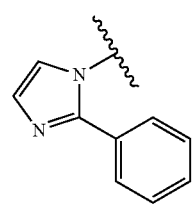<br>47 M⁺(389.2) |
| 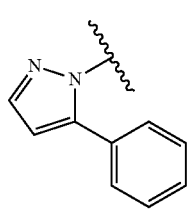<br>209 M⁺(403.2) | 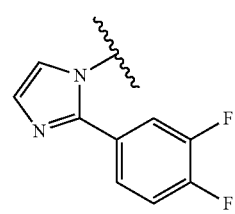<br>48 M⁺(425.1) |
| 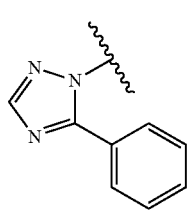<br>216 M⁺(404.2) | 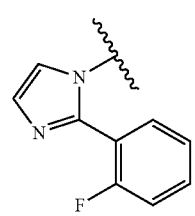<br>49 M⁺(407.2) |
| | 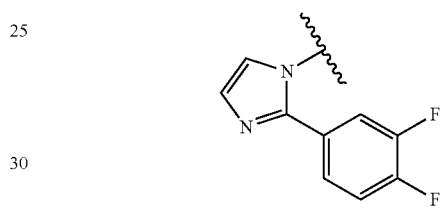<br>50 M⁺(407.2) |
| 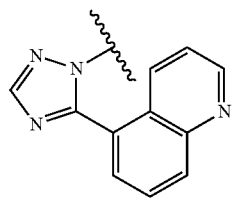<br>217 M⁺(455.2) | 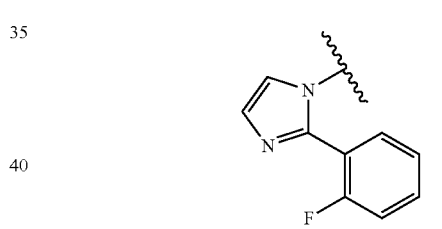<br>51 |

| 245 -continued | 246 -continued |
|---|---|
| 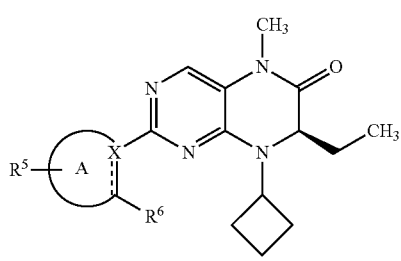 | 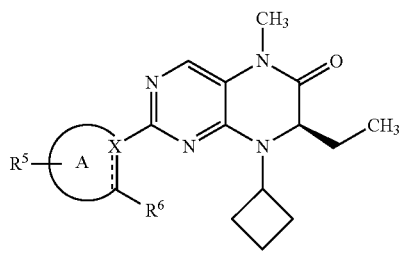 |
| 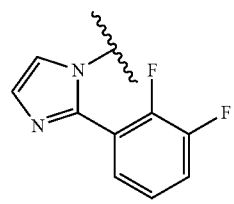<br>52 | 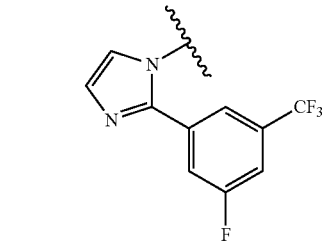<br>171 M⁺(457.2) |
| 96 M⁺(414.2) | 174 M⁺(475.1) |
| 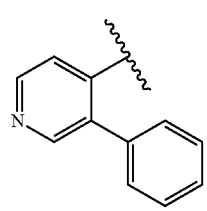<br>98 M⁺(391.1) | 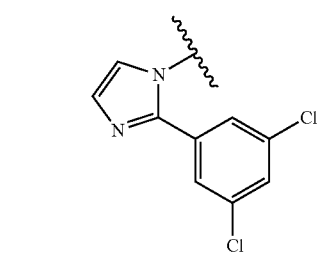<br>198 M⁺(457.1) |
| 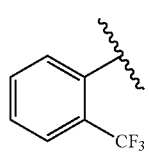<br>112 M⁺(410.2) | 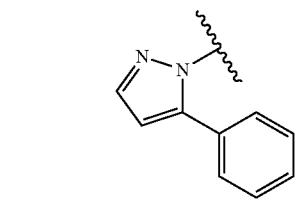<br>207 M⁺(389.2) |
| 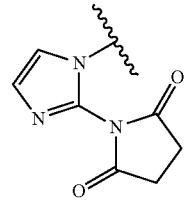<br>156 M⁺(396.1) | 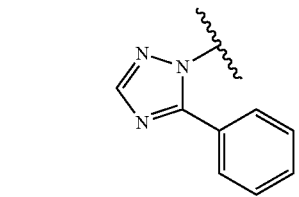<br>208 M⁺(390.2) |

247
-continued
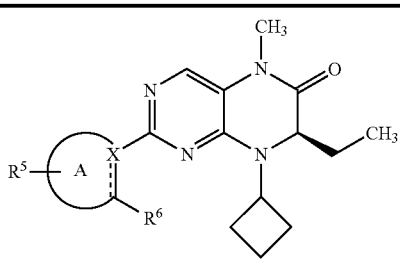
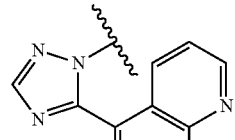
215 M⁺(441.3)
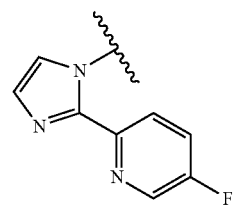
224 M⁺(408.2)
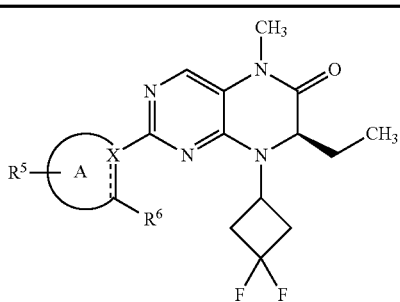
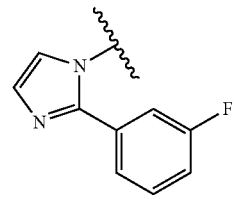
194 M⁺(391.2)
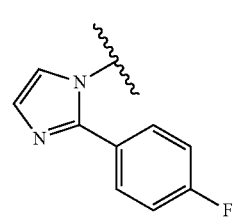
247 M⁺(443.1)
248
-continued
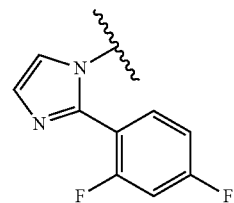
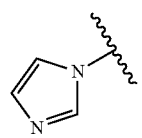
260 M⁺(461.1)
303 M⁺(349.0)
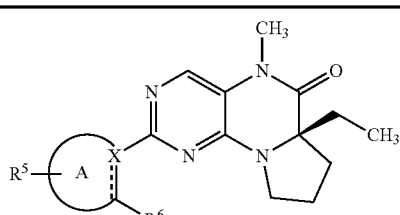
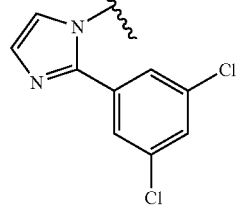
184 M⁺(443.2)
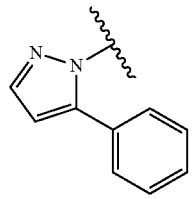
193 M⁺(375.1)

249
-continued
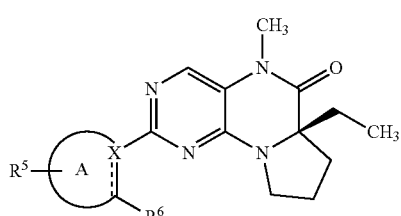
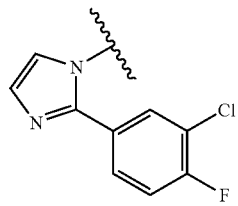
206 M⁺(426.2)
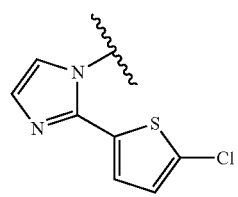
213 M⁺(427.2)
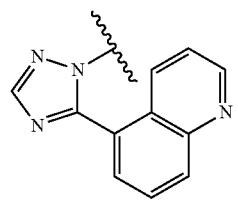
218 M⁺(415.1)
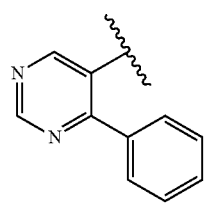
219 M⁺(427.1)
222 M⁺(387.1)
250
-continued
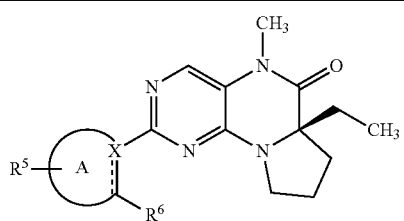
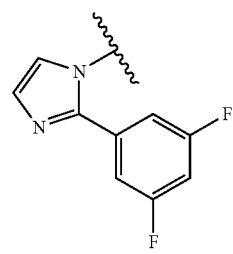
225 M⁺(393.1)
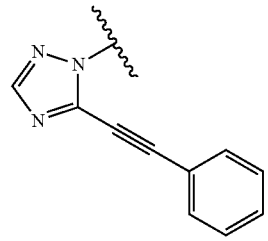
226 M⁺(411.1)
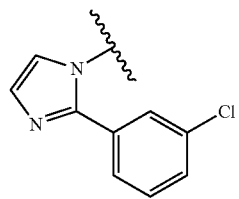
235 M⁺(400.1)
236 M⁺(409.1)
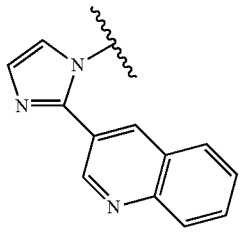
241 M⁺(426.2)

| 251 -continued | 252 -continued |
|---|---|
| 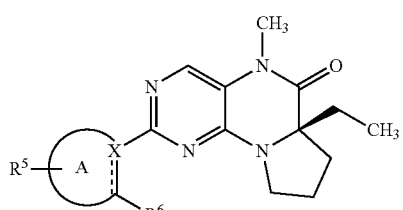 | 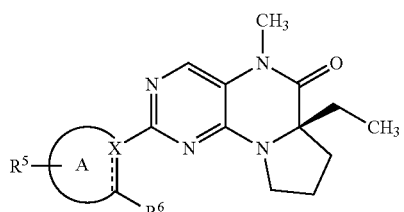 |
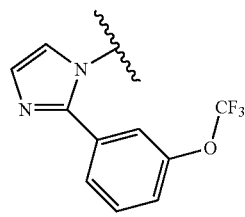
251 M⁺(459.1)
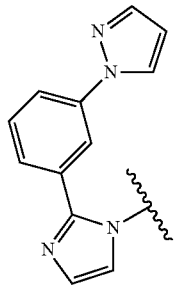
276 M⁺(441.1)
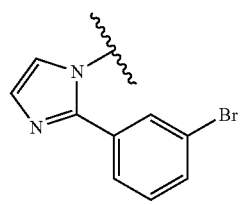
252 M⁺(455.0)
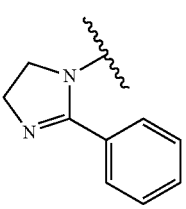
281 M⁺(377.1)
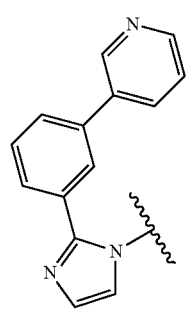
272 M⁺(452.3)
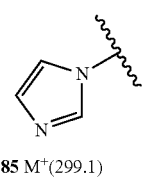
285 M⁺(299.1)
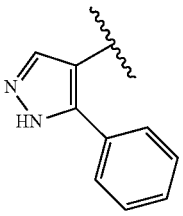
305 M⁺(375.2)
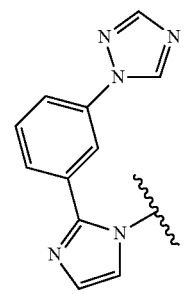
273 M⁺(442.3)
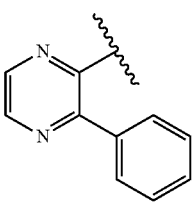
316 M⁺(387.1)

| 253 | 254 |
|---|---|
| -continued | -continued |
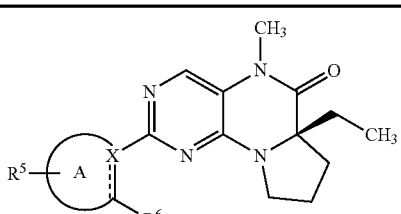
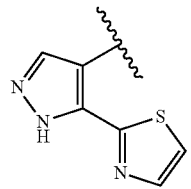
338 M⁺(382.0)
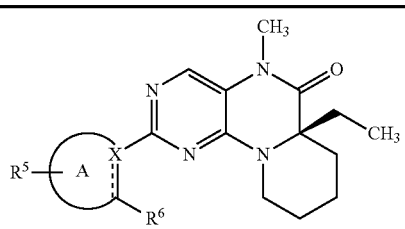
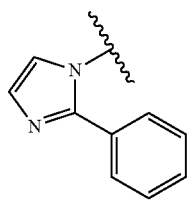
racemic
238 M⁺(389.2)
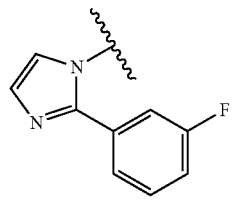
racemic
239 M⁺(407.2)
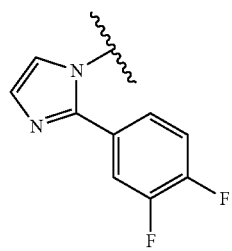
racemic
240 M⁺(425.2)
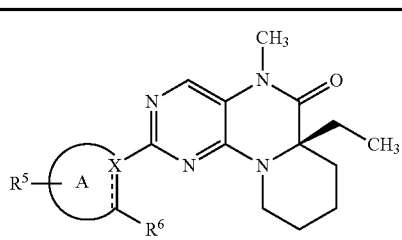
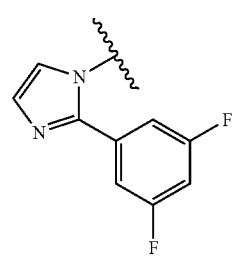
racemic
243 M⁺(425.1)
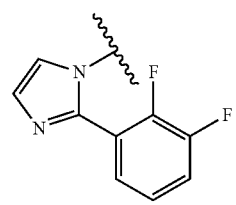
racemic
248 M⁺(425.1)
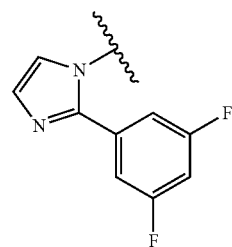
249 M⁺(425.3)
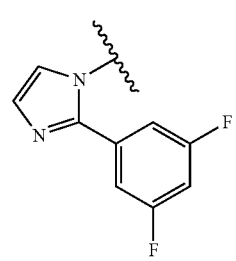
R isomer
250 M⁺(425.2)

| 255 -continued | 256 -continued |
|---|---|
| 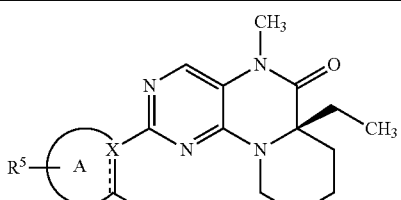 | 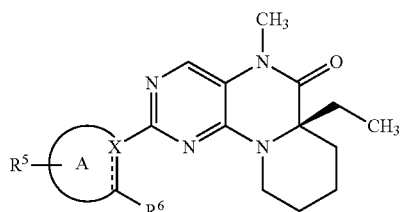 |
| 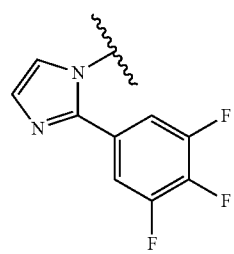  racemic  256 M⁺(443.1) | 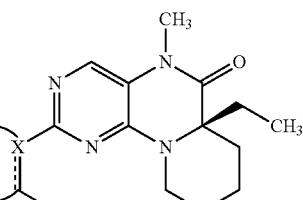  R isomer  263 M⁺(389.3) |
| 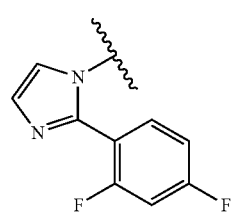  racemic  257 M⁺(425.2) | 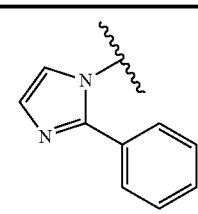  264 M⁺(407.2) |
| 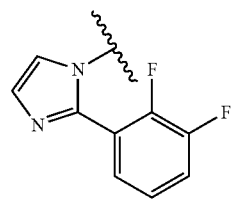  259 M⁺(425.2) | 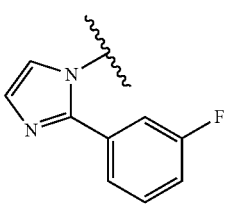  R isomer  265 M⁺(407.3) |
| 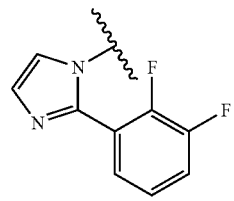  R isomer  261 M⁺(425.2) | 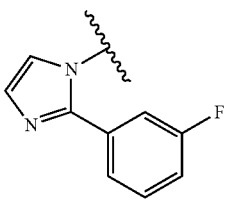  266 M⁺(443.2) |
| 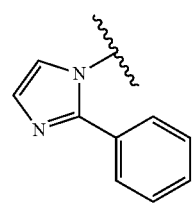  262 M⁺(389.2) | 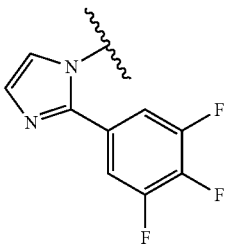  R isomer  267 M⁺(443.2) |

-continued
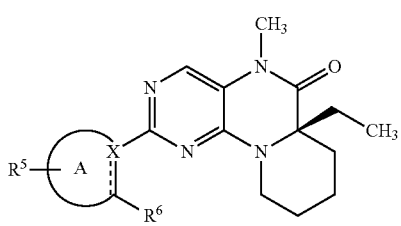
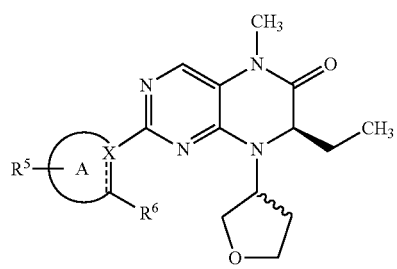
All but 203 are made from Intermediate N-1, compounds are pure diastereomers, but orientation of the tetrahydrofuran 3-carbon is not known.
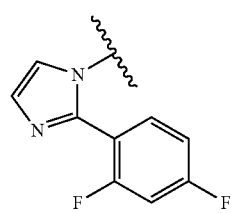
269 M⁺(425.2)
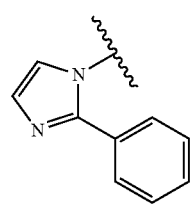
182 M⁺(405.2) and 203 M⁺(405.2)
separate stereoisomers
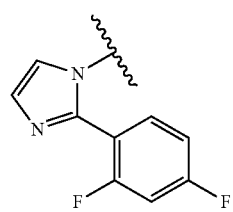
R isomer
270 M⁺(425.2)
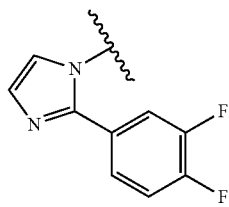
191 M⁺(441.1)
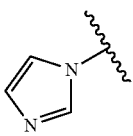
racemic
283 M⁺(313.1)
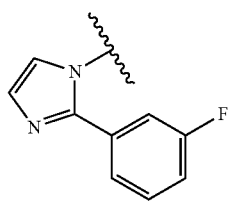
192 M⁺(423.1)
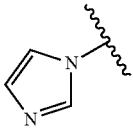
286 M⁺(313.1)
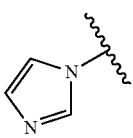
R isomer
287 M⁺(313.1)
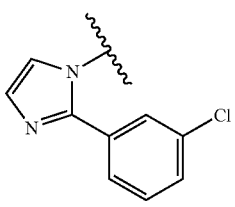
211 M⁺(439.1)

259
-continued
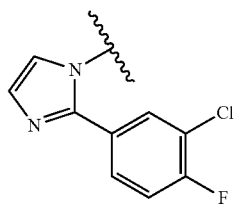
232 M⁺(457.2)
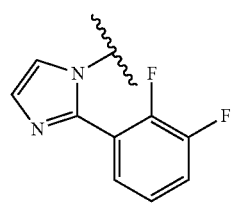
253 M⁺(441.2)
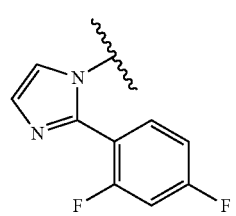
268 M⁺(441.1)
---
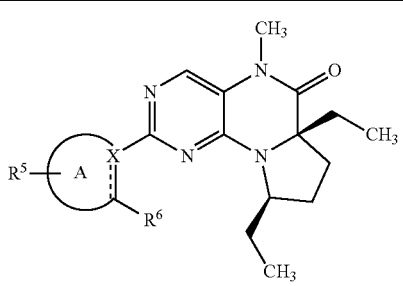
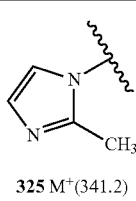
325 M⁺(341.2)
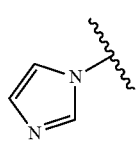
334 M⁺(326.9)
260
-continued
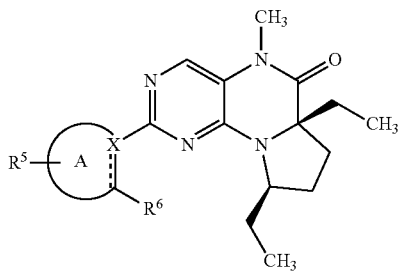
---
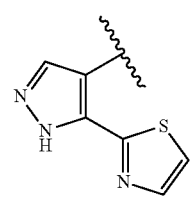
340 M⁺(410.1)
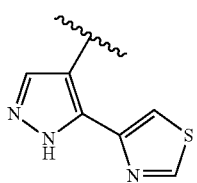
356 M⁺(410.2)
---
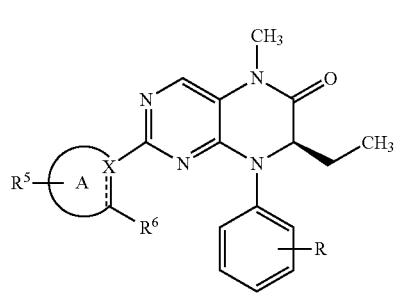
R as indicated in table.
---
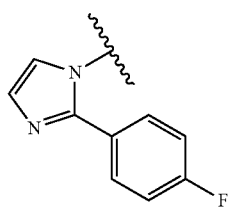
R = 4-F
324 M⁺(447.1)

261
-continued
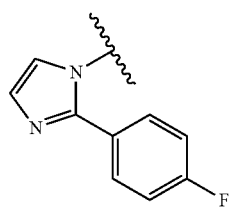
R = 3-CN
racemic
332 M⁺(454.2)
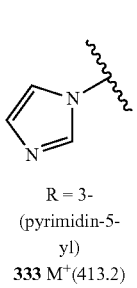
R = 3-
(pyrimidin-5-
yl)
333 M⁺(413.2)
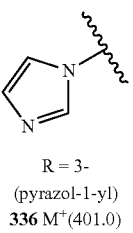
R = 3-
(pyrazol-1-yl)
336 M⁺(401.0)
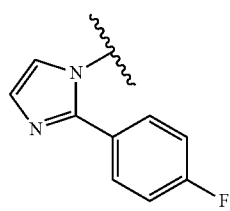
R = 3-
(pyrimidin-5-
yl)
346 M⁺(507.1)
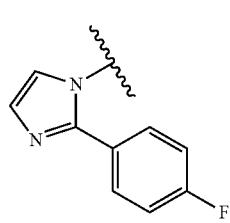
R = 3-CN
358 M⁺(454.1)
262
-continued
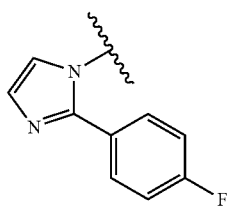
R = 3-CN
S isomer
359 M⁺(454.1)
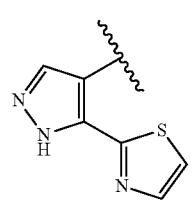
R = 4-F
racemic
370 M⁺(436.1)
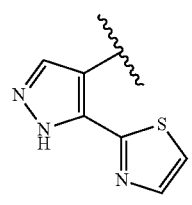
R = 3-CN
racemic
372 M⁺(443.0)
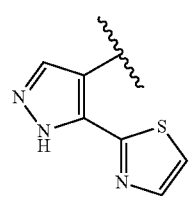
R = 4-Cl
S isomer
383 M⁺(452.1)
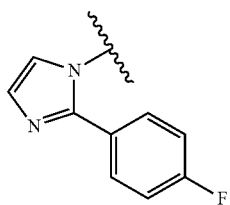
R = 4-Cl
racemic
388 M⁺(463.1)

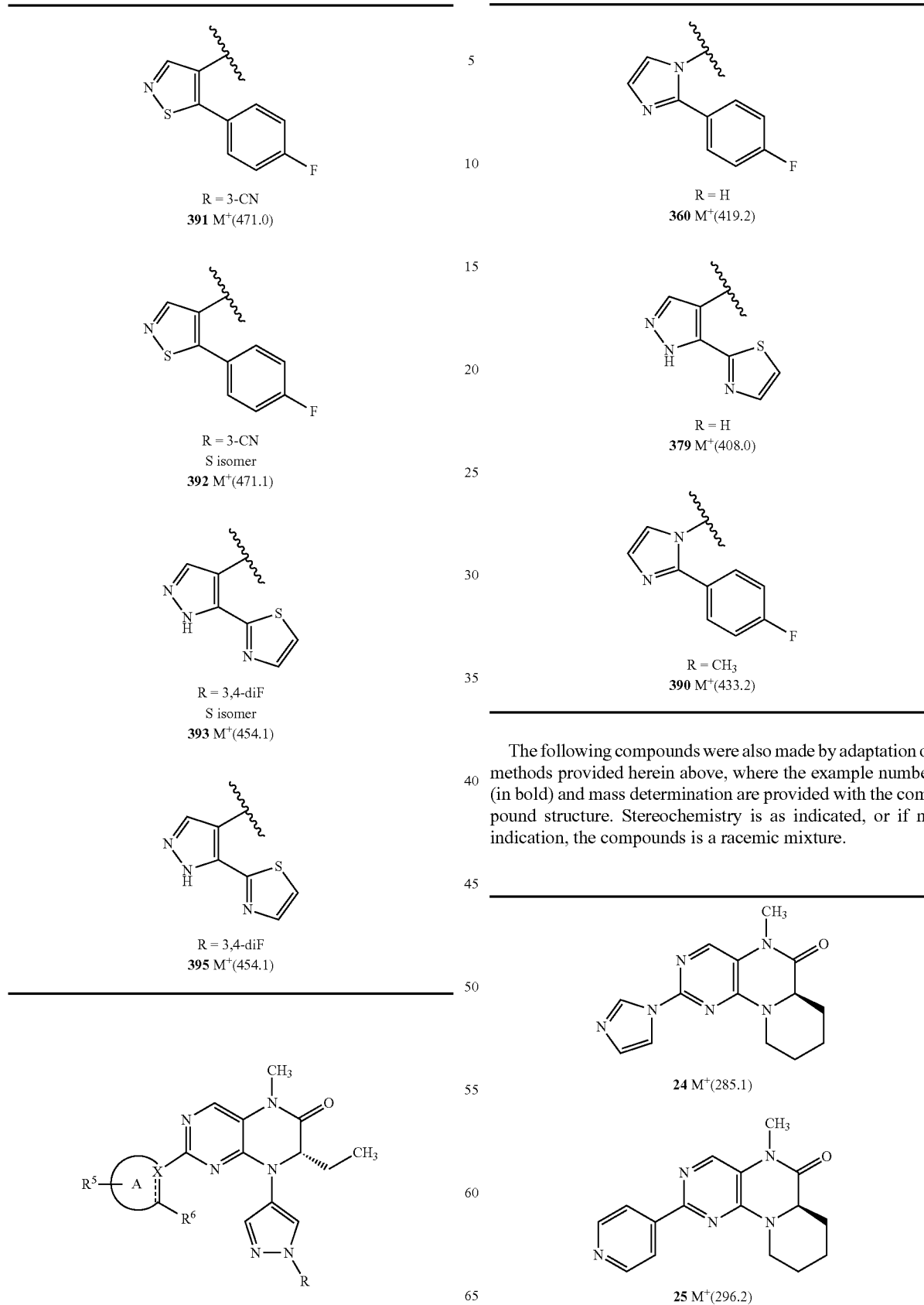
The following compounds were also made by adaptation of methods provided herein above, where the example number (in bold) and mass determination are provided with the compound structure. Stereochemistry is as indicated, or if no indication, the compounds is a racemic mixture.

-continued
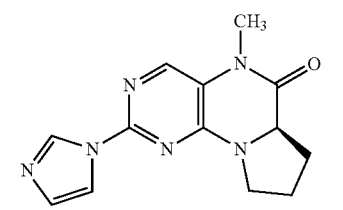
33 M⁺(271.0)
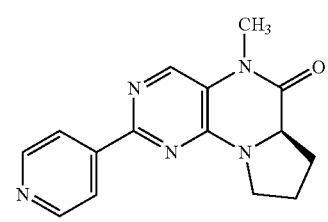
34 M⁺(282.0)
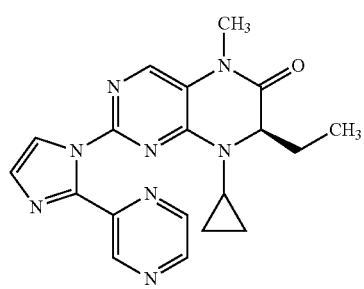
141 M⁺(377.2)
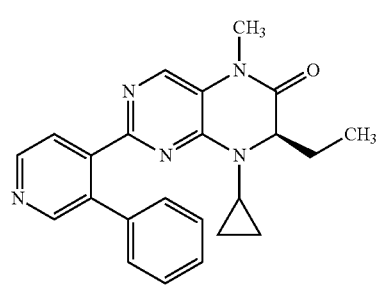
142 M⁺(386.2)
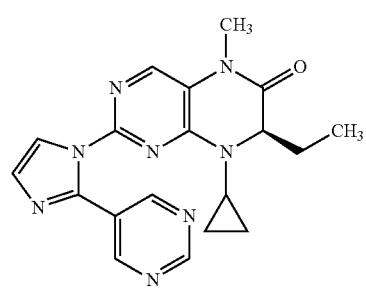
143 M⁺(377.1)
-continued
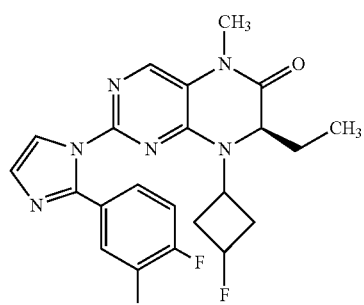
229 M⁺(443.1)
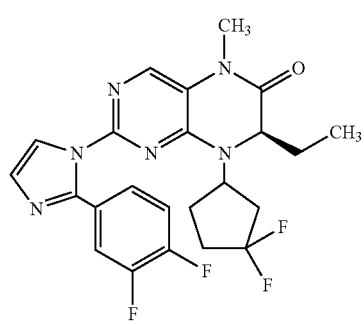
237 M⁺(475.1)
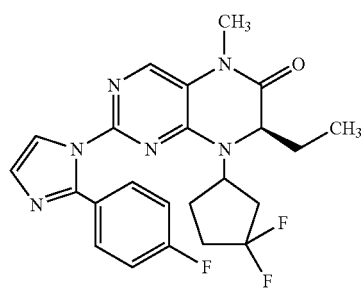
242 M⁺(457.1)
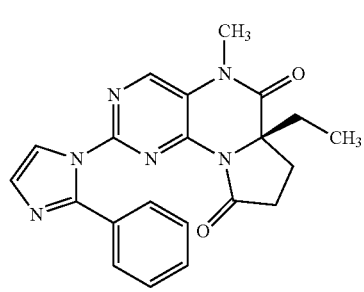
258 M⁺(389.1)

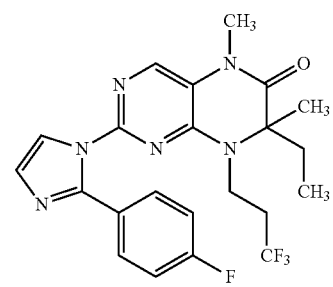
279 M⁺(463.2)
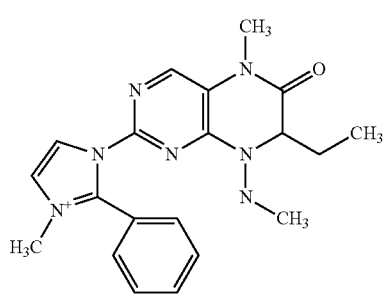
284 M⁺(378.1)
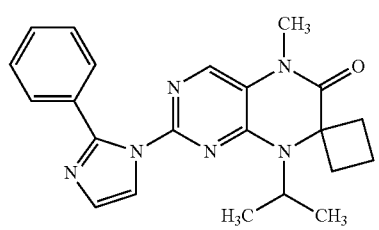
289 M⁺(389.1)
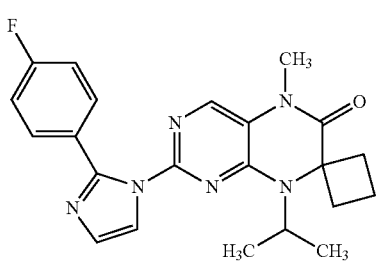
290 M⁺(407.1)
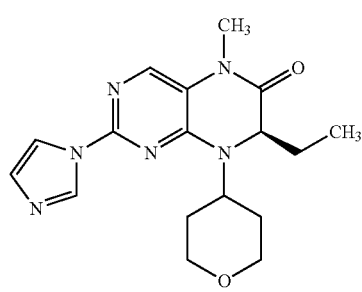
295 M⁺(343.1)
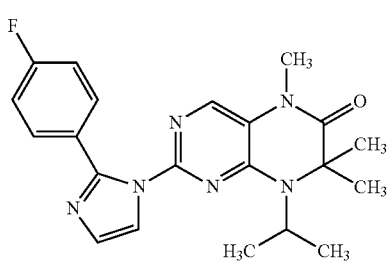
298 M⁺(395.1)
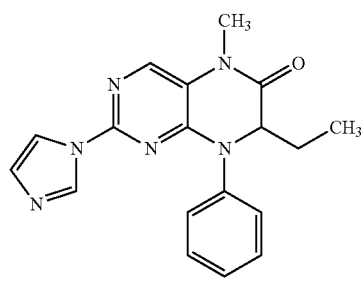
300 M⁺(335.1)
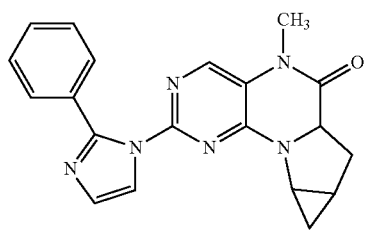
304 M⁺(359.1)
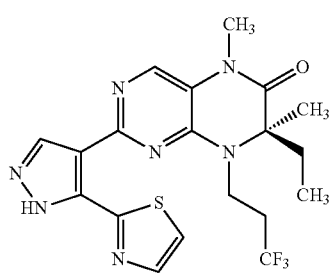
310 M⁺(452.1)
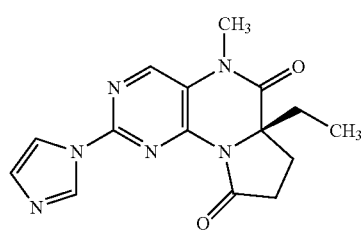
311 M⁺(313.1)

269
-continued
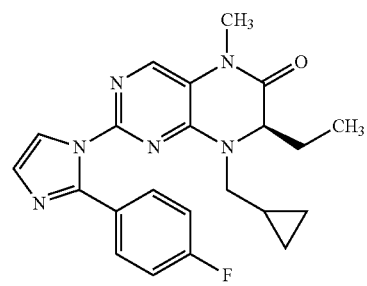
322 M⁺(407.1)
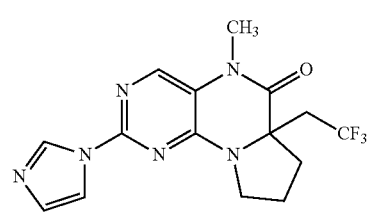
329 M⁺(353.1)
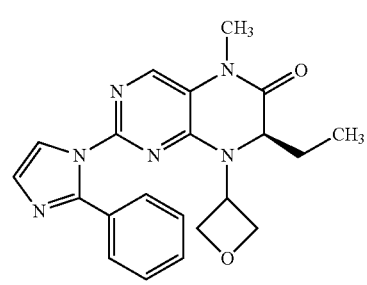
335 M⁺(391.0)
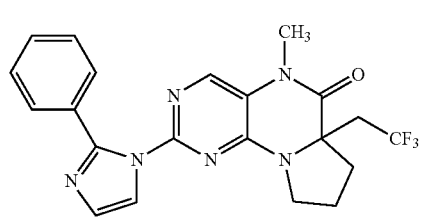
339 M⁺(429.1)
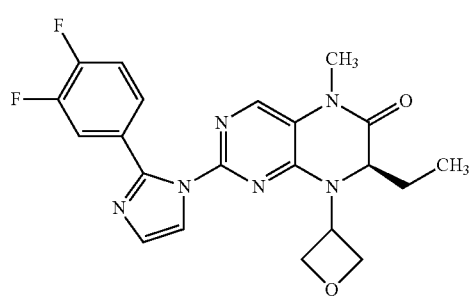
341 M⁺(427.2)
270
-continued
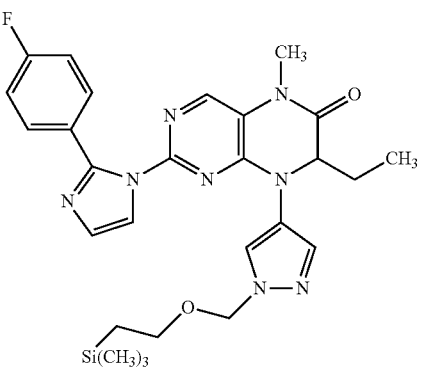
342 M⁺(549.2)
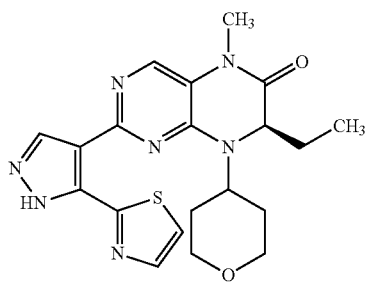
349 M⁺(426.2)
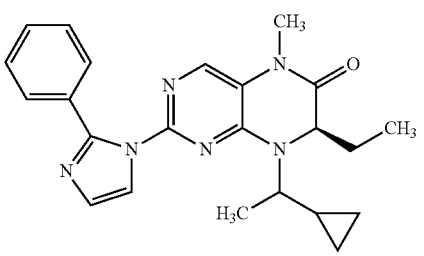
350 M⁺(403.2)
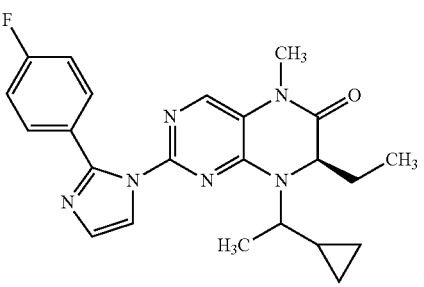
351 M⁺(421.1)

-continued

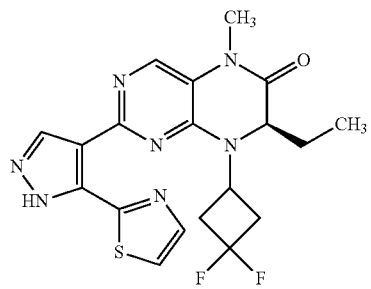

353 M⁺(432.1)

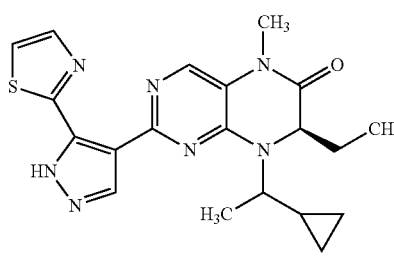

357 M⁺(410.1)

Example A

In Vitro Kinase Activities (PLK TR-FRET Peptide Assay)

Compounds as described herein (compounds of Formula I, e.g., compounds the above Examples) are tested for their in vitro kinase activities using various PLK assays. An exemplary assay procedure is described below.
(1) Test compound solution preparation: prepare 4× compound solution in PLK assay buffer (50 mM HEPES, 10 mM $MgCl_2$, 1 mM EGTA, 0.01% Tween-20, pH7.4). DTT is added to the buffer just before the experiment to a final concentration of 2 mM. Add 2.5 μl/well to a black 384-well low volume plate (4% DMSO at this step).
(2) Kinase preparation: Prepare 2×GST-PLK 1, 2 or 3 (e.g., CarnaBio) solutions in assay buffer (6 nM for PLK1, 6 nM for PLK2 and 0.2 nM for PLK3). Add 5 μl/well, shake the plate, incubate the enzyme with compound at ret. Time for 15 min.
(3) ATP/substrate mixture preparation: Prepare 4× (ATP/ULight-Topo IIα peptide substrate; e.g., Perkin Elmer) mixture in assay buffer (0.4 mM ATP/200 nM peptide). Add 2.5 μl/well, shake the plate and incubate at ret. Time. Reactions time: 60 min for PLK1, 60 min for PLK2 and 15 min for PLK3
(4) EDTA preparation: Dilute 0.5M EDTA to 24 mM with detection buffer. Add 5 μl/well to the plate, shake the plate well for 5 min.
(5) Prepare 4× Eu-anti-P-Topo IIα (T1342) (e.g., Perkin Elmer) solution (8 nM) in detection buffer (50 Tris-HCl, 150 mM NaCl, 0.5% BSA, PH7.5). Add 5 μl/well to the plate, shake the plate and incubate at ret. Time for 1 h before reading on Envision at 665 nm/615 nm. The fluorescent signal as a function of compound concentration was used to determine the compound $IC_{50}$.

The following table summarizes exemplary compounds from the Examples above and their in vitro $IC_{50}$ values as determined using the procedures of Example A. For $IC_{50}$ values in the table, (+++) indicates $IC_{50}$<1 μM, (++) indicates $IC_{50}$ of 1-10 μM, (+) indicates 10 μM<$IC_{50}$<50 μM, and (−) indicates $IC_{50}$>50 μM. For PLK2/PLK1 selectivity, (+++) indicates a ratio of $IC_{50}$(PLK2)/$IC_{50}$(PLK1) of <0.02, (++) indicates a ratio of $IC_{50}$(PLK2)/$IC_{50}$(PLK1) of 0.02 to 0.1, (+) indicates a ratio of $IC_{50}$(PLK2)/$IC_{50}$(PLK1) of 0.1 to 0.5, and (−) indicates a ratio of $IC_{50}$(PLK2)/$IC_{50}$(PLK1) of >0.5.

| Example No. | Plk2 IC$_{50}$ (μM) | Plk1 IC$_{50}$ (μM) | Plk3 IC$_{50}$ (μM) | PLK2/PLK1 |
|---|---|---|---|---|
| 1 | (++) | (+) | | (++) |
| 2 | (+) | (+) | | (−) |
| 3 | (+++) | (+++) | (+) | (+) |
| 4 | (+++) | (+++) | | (−) |
| 5 | (+++) | (+++) | (+) | (+) |
| 6 | (+++) | (+++) | | (+) |
| 7 | (+++) | (+++) | | (+) |
| 8 | (++) | (++) | | (−) |
| 9 | (++) | (+++) | | (−) |
| 10 | (++) | (+) | | (−) |
| 11 | (+) | (−) | | (+) |
| 12 | (++) | (++) | | (+) |
| 13 | (++) | (++) | | (+) |
| 14 | (+++) | (+++) | | (++) |
| 15 | (+++) | (+++) | | (+) |
| 18 | (++) | (+++) | (+) | (−) |
| 19 | (+++) | (+++) | (+) | (+) |
| 20 | (+++) | (+++) | (+) | (+) |
| 21 | (+++) | (+++) | (+) | (+) |
| 22 | (+++) | (++) | (−) | (+) |
| 23 | (+++) | (++) | (−) | (++) |
| 24 | (−) | (−) | | |
| 25 | (+) | (−) | | (+) |
| 26 | (+++) | (+++) | (+++) | (−) |
| 27 | (+++) | (++) | (−) | (+) |
| 28 | (−) | (−) | | |
| 29 | (−) | (−) | (−) | |
| 30 | (−) | (−) | | |
| 31 | (+++) | (++) | (−) | (+) |
| 32 | (+++) | (+++) | (++) | (−) |
| 33 | (+) | (−) | (−) | (+) |
| 34 | (−) | (−) | (−) | |
| 35 | (+++) | (++) | (+) | (+) |
| 36 | (+++) | (+++) | (+) | (−) |
| 37 | (+++) | (+++) | (+++) | (−) |
| 38 | (++) | (+++) | (++) | (−) |
| 39 | (++) | (++) | (+) | (−) |
| 40 | (++) | (+++) | (+) | (−) |
| 41 | (++) | (++) | (+) | (−) |
| 42 | (+++) | (++) | (+) | (++) |
| 43 | (+++) | (+++) | (+) | (+) |
| 44 | (++) | (+++) | (++) | (−) |
| 45 | (+++) | (++) | (+) | (+) |
| 46 | (+++) | (+++) | (++) | (−) |
| 47 | (+++) | (+++) | (++) | (++) |
| 48 | (+++) | (++) | (+) | (+++) |
| 49 | (+++) | (+++) | (++) | (++) |
| 50 | (+++) | (++) | (++) | (+++) |
| 53 | (+++) | (++) | (++) | (+) |
| 54 | (+++) | (+++) | (++) | (−) |
| 55 | (+++) | (+++) | (+) | (+) |
| 56 | (+++) | (++) | (+) | (+) |
| 57 | (++) | (++) | (−) | (+) |
| 58 | (+++) | (++) | (−) | (+) |
| 59 | (+++) | (+++) | (++) | (−) |
| 60 | (+++) | (+++) | (++) | (−) |
| 61 | (++) | (++) | (++) | (+) |
| 62 | (+++) | (+) | (+) | (++) |
| 63 | (+++) | (++) | (++) | (++) |
| 64 | (+++) | (+++) | (++) | (++) |
| 65 | (+++) | (+++) | (+) | (++) |
| 66 | (+++) | (+++) | (++) | (+) |
| 67 | (+++) | (+++) | (+++) | (++) |
| 68 | (+++) | (+++) | (+++) | (++) |
| 69 | (+++) | (+++) | (++) | (−) |
| 70 | (+++) | (+++) | (+++) | (−) |
| 71 | (++) | (++) | (+) | (+) |

-continued

| Example No. | Plk2 IC$_{50}$ (μM) | Plk1 IC$_{50}$ (μM) | Plk3 IC$_{50}$ (μM) | PLK2/PLK1 |
|---|---|---|---|---|
| 72 | (+) | (−) | (−) | (+) |
| 73 | (++) | (+) | (−) | (+) |
| 74 | (+++) | (+++) | (+++) | (++) |
| 75 | (+++) | (++) | (+) | (+) |
| 76 | (+++) | (+) | (++) | (+++) |
| 77 | (+++) | (+++) | (++) | (++) |
| 78 | (+++) | (++) | (+) | (++) |
| 79 | (+++) | (++) | (+) | (++) |
| 80 | (+++) | (+) | (+) | (+++) |
| 81 | (+++) | (++) | (+) | (+++) |
| 82 | (++) | (++) | (+) | (+) |
| 83 | (+++) | (+++) | (+++) | (++) |
| 84 | (+++) | (++) | (+) | (++) |
| 85 | (+++) | (+++) | (+++) | (−) |
| 86 | (++) | (+) | (−) | (+) |
| 87 | (++) | (++) | (−) | (+) |
| 88 | (+) | (+) | (−) | (−) |
| 89 | (+++) | (+++) | (+++) | (++) |
| 90 | (++) | (++) | (+) | (+) |
| 91 | (+++) | (+++) | (++) | (+) |
| 92 | (++) | (+) | (−) | (−) |
| 93 | (+++) | (++) | (−) | (+) |
| 94 | (++) | (+) | (−) | (+) |
| 95 | (+++) | (+++) | (+++) | (++) |
| 96 | (+++) | (+++) | (+++) | (++) |
| 97 | (+++) | (+++) | (+++) | (++) |
| 98 | (++) | (+) | (−) | (+) |
| 99 | (+++) | (+++) | (+++) | (++) |
| 100 | (+++) | (++) | (++) | (++) |
| 101 | (+++) | (+) | (+) | (++) |
| 102 | (+++) | (++) | (++) | (++) |
| 103 | (+) | (+) | (+) | (−) |
| 104 | (+++) | (++) | (++) | (+++) |
| 105 | (+) | (+) | (−) | (−) |
| 106 | (+) | (+) | (−) | (−) |
| 107 | (−) | (−) | (−) | (−) |
| 108 | (+) | (+) | (−) | (−) |
| 109 | (+++) | (++) | (+) | (++) |
| 110 | (+++) | (+++) | (+++) | (++) |
| 111 | (+++) | (++) | (+) | (++) |
| 112 | (+) | (+) | (−) | (−) |
| 113 | (+++) | (++) | (++) | (+) |
| 114 | (+++) | (++) | (+) | (+) |
| 115 | (+++) | (++) | (+) | (+) |
| 116 | (+++) | (++) | (−) | (++) |
| 117 | (++) | (++) | (−) | (+) |
| 118 | (++) | (−) | (−) | (++) |
| 119 | (++) | (−) | (−) | (++) |
| 120 | (++) | (++) | (−) | (−) |
| 121 | (++) | (+) | (+) | (+) |
| 122 | (++) | (+) | (+) | (+) |
| 123 | (+) | (+) | (−) | (−) |
| 124 | (++) | (++) | (+) | (+) |
| 125 | (++) | (+) | (+) | (++) |
| 126 | (+) | (−) | (−) | (−) |
| 127 | (+) | (+) | (−) | (−) |
| 128 | (++) | (+) | (+) | (+) |
| 129 | (+) | (−) | (−) | (+) |
| 130 | (−) | (−) | (−) | (−) |
| 131 | (+) | (−) | (−) | (+) |
| 132 | (+++) | (+++) | (+++) | (−) |
| 133 | (+++) | (+++) | (+++) | (+) |
| 134 | (+++) | (+++) | (+++) | (−) |
| 135 | (+++) | (+++) | (+++) | (−) |
| 136 | (++) | (+) | (−) | (+) |
| 137 | (++) | (−) | (−) | (++) |
| 138 | (+++) | (+++) | (+++) | (−) |
| 139 | (+++) | (+++) | (+++) | (−) |
| 140 | (+++) | (++) | (−) | (+) |
| 141 | (++) | (−) | (−) | (++) |
| 142 | (+++) | (+) | (+) | (++) |
| 143 | (++) | (+) | (+) | (+) |
| 144 | (++) | (−) | (−) | (++) |
| 145 | (++) | (+) | (+) | (++) |
| 146 | (+++) | (+++) | (+++) | (+) |
| 147 | (++) | (−) | (−) | (+++) |
| 148 | (+++) | (++) | (+) | (++) |
| 149 | (+++) | (+) | (+) | (++) |
| 150 | (+++) | (+) | (++) | (+++) |
| 151 | (+++) | (++) | (+) | (+++) |
| 152 | (+++) | (+) | (−) | (+++) |
| 153 | (+++) | (++) | (++) | (++) |
| 154 | (+++) | (++) | (+) | (++) |
| 155 | (+++) | (+++) | (++) | (++) |
| 156 | (+++) | (++) | (++) | (+++) |
| 157 | (+++) | (++) | (+) | (++) |
| 158 | (+++) | (++) | (+) | (+++) |
| 159 | (+++) | (+++) | (++) | (++) |
| 160 | (+++) | (++) | (+) | (++) |
| 161 | (+++) | (++) | (++) | (++) |
| 162 | (+++) | (++) | (++) | (+++) |
| 163 | (+++) | (+++) | (+) | (++) |
| 164 | (+++) | (+++) | (+++) | (+) |
| 165 | (+++) | (+++) | (++) | (+) |
| 166 | (+++) | (++) | (+) | (+) |
| 167 | (+++) | (++) | (+) | (+) |
| 168 | (+) | (+) | (−) | (−) |
| 169 | (+++) | (++) | (+) | (+++) |
| 170 | (+++) | (+) | (−) | (+++) |
| 171 | (+++) | (+) | (−) | (++) |
| 172 | (+++) | (++) | (−) | (++) |
| 173 | (+++) | (++) | (+) | (++) |
| 174 | (+++) | (++) | (+) | (+) |
| 175 | (++) | (++) | (+) | (−) |
| 176 | (+++) | (++) | (−) | (++) |
| 177 | (+++) | (++) | (++) | (+) |
| 178 | (+) | (−) | (−) | (+) |
| 179 | (+++) | (+++) | (++) | (++) |
| 180 | (+++) | (+++) | (++) | (++) |
| 181 | (+++) | (+++) | (++) | (+) |
| 182 | (+++) | (+++) | (+++) | (+++) |
| 183 | (+++) | (++) | (+) | (++) |
| 184 | (+++) | (+) | (+) | (+++) |
| 185 | (+++) | (++) | (++) | (++) |
| 186 | (+++) | (++) | (++) | (+++) |
| 187 | (+) | (+) | (+) | (−) |
| 188 | (+++) | (+++) | (++) | (−) |
| 189 | (+++) | (++) | (++) | (+) |
| 190 | (+++) | (+++) | (++) | (++) |
| 191 | (+++) | (++) | (+) | (+++) |
| 192 | (+++) | (+++) | (++) | (+++) |
| 193 | (++) | (++) | (++) | (+) |
| 194 | (+++) | (+++) | (+) | (++) |
| 195 | (+++) | (+++) | (+++) | (−) |
| 196 | (++) | (+) | (−) | (+) |
| 197 | (++) | (++) | (++) | (−) |
| 198 | (+++) | (++) | (++) | (++) |
| 199 | (++) | (+) | (−) | (+) |
| 200 | (+++) | (++) | (++) | (+++) |
| 201 | (++) | (+) | (−) | (+) |
| 202 | (+++) | (+++) | (++) | (++) |
| 203 | (+++) | (+++) | (++) | (++) |
| 204 | (+++) | (+++) | (++) | (++) |
| 205 | (+++) | (+) | (+) | (+++) |
| 206 | (++) | (−) | (+) | (+++) |
| 207 | (+++) | (+++) | (++) | (−) |
| 208 | (+++) | (+++) | (+++) | (+) |
| 209 | (++) | (+) | (+) | (+) |
| 210 | (−) | (−) | (−) | (−) |
| 211 | (+++) | (+++) | (++) | (+++) |
| 212 | (+++) | (++) | (++) | (+++) |
| 213 | (+++) | (+) | (+) | (+++) |
| 214 | (+) | (++) | (−) | (−) |
| 215 | (++) | (++) | (++) | (−) |
| 216 | (++) | (++) | (+) | (+) |
| 217 | (+) | (−) | (−) | (+) |
| 218 | (+++) | (+) | (+) | (+++) |
| 219 | (++) | (+) | (−) | (+) |
| 220 | (+++) | (+++) | (++) | (++) |
| 221 | (+++) | (++) | (+) | (++) |
| 222 | (++) | (+) | (+) | (++) |
| 223 | (++) | (++) | (−) | (−) |
| 224 | (+++) | (++) | (+) | (+++) |
| 225 | (+++) | (++) | (+) | (+++) |

| Example No. | Plk2 IC$_{50}$ (μM) | Plk1 IC$_{50}$ (μM) | Plk3 IC$_{50}$ (μM) | PLK2/PLK1 |
|---|---|---|---|---|
| 226 | (+++) | (+) | (+) | (+++) |
| 227 | (+++) | (+) | (+) | (+++) |
| 228 | (+++) | (++) | (+) | (++) |
| 229 | (+++) | (++) | (++) | (+++) |
| 230 | (+++) | (++) | (+) | (+++) |
| 231 | (+++) | (++) | (+) | (++) |
| 232 | (+++) | (++) | (++) | (+++) |
| 233 | (+++) | (++) | (+) | (+++) |
| 234 | (+++) | (++) | (+) | (++) |
| 235 | (+) | (−) | (+) | (+) |
| 236 | (+++) | (++) | (+) | (+++) |
| 237 | (+++) | (+++) | (++) | (++) |
| 238 | (+++) | (++) | (+) | (+++) |
| 239 | (+++) | (++) | (+) | (+++) |
| 240 | (+++) | (++) | (+) | (++) |
| 241 | (+++) | (+) | (−) | (++) |
| 242 | (+++) | (+++) | (++) | (++) |
| 243 | (+++) | (+) | (−) | (+++) |
| 244 | (+++) | (+) | (−) | (+++) |
| 245 | (+++) | (+++) | (++) | (−) |
| 246 | (+++) | (+++) | (++) | (+++) |
| 247 | (+++) | (++) | (+) | (+++) |
| 248 | (+++) | (++) | (+) | (+++) |
| 249 | (+++) | (++) | (−) | (+++) |
| 250 | (−) | (−) | (−) | (−) |
| 251 | (+++) | (+) | (−) | (++) |
| 252 | (+++) | (++) | (+) | (+++) |
| 253 | (+++) | (+++) | (++) | (++) |
| 254 | (+++) | (+++) | (++) | (++) |
| 255 | (+++) | (++) | (+) | (++) |
| 256 | (+++) | (−) | (−) | (+++) |
| 257 | (+++) | (+) | (+) | (+++) |
| 258 | (+) | (−) | (−) | (+) |
| 259 | (+++) | (++) | (++) | (+++) |
| 260 | (+++) | (++) | (+) | (+++) |
| 261 | (++) | (−) | (−) | (++) |
| 262 | (+++) | (++) | (++) | (+++) |
| 263 | (+) | (−) | (−) | (+) |
| 264 | (+++) | (++) | (+) | (+++) |
| 265 | (+) | (−) | (−) | (+) |
| 266 | (+++) | (−) | (−) | (+++) |
| 267 | (−) | (−) | (−) | (−) |
| 268 | (+++) | (++) | (++) | (+++) |
| 269 | (+++) | (+) | (+) | (+++) |
| 270 | (+) | (−) | (−) | (+) |
| 271 | (+++) | (+++) | (++) | (++) |
| 272 | (+++) | (+) | (+) | (++) |
| 273 | (+++) | (+) | (−) | (+++) |
| 274 | (−) | (−) | (−) | (−) |
| 275 | (+) | (−) | (−) | (+) |
| 276 | (+++) | (+) | (−) | (+++) |
| 277 | (+++) | (++) | (++) | (+++) |
| 278 | (+++) | (+) | (+) | (+++) |
| 279 | (+++) | (++) | (+) | (+++) |
| 280 | (+++) | (+++) | (+) | (+) |
| 281 | (+++) | (−) | (+) | (++) |
| 282 | (+++) | (+) | (+) | (++) |
| 283 | (+) | (−) | (−) | (+) |
| 284 | (−) | (−) | (−) | (−) |
| 285 | (+) | (−) | (−) | (+) |
| 286 | (++) | (−) | (−) | (++) |
| 287 | (−) | (−) | (−) | (−) |
| 288 | (+++) | (++) | (++) | (++) |
| 289 | (+++) | (++) | (+) | (++) |
| 290 | (++) | (+) | (+) | (++) |
| 291 | (+++) | (++) | (++) | (+++) |
| 292 | (+++) | (++) | (+) | (++) |
| 293 | (+++) | (++) | (+) | (++) |
| 294 | (+) | (−) | (−) | (+) |
| 295 | (++) | (++) | (+) | (−) |
| 296 | (+++) | (+++) | (++) | (+) |
| 297 | (+) | (+) | (+) | (+) |
| 298 | (++) | (−) | (−) | (++) |
| 299 | (+++) | (++) | (+) | (++) |
| 300 | (++) | (++) | (−) | (−) |
| 301 | (+++) | (+) | (+) | (++) |
| 302 | (+) | (−) | (−) | (+) |
| 303 | (++) | (+) | (+) | (++) |
| 304 | (+) | (−) | (−) | (+) |
| 305 | (+++) | (++) | (+) | (++) |
| 306 | (+++) | (+++) | (+++) | (+) |
| 307 | (+++) | (+++) | (+++) | (+) |
| 308 | (++) | (+) | (−) | (++) |
| 309 | (+++) | (+++) | (+++) | (+) |
| 310 | (+++) | (+++) | (−) | (+) |
| 311 | (−) | (−) | (−) | (−) |
| 312 | (+++) | (+++) | (+++) | (+) |
| 313 | (+++) | (++) | (++) | (+) |
| 314 | (+++) | (−) | (++) | (+++) |
| 315 | (+) | (−) | (−) | (+) |
| 316 | (++) | (+) | (++) | (+) |
| 317 | (+++) | (+) | (++) | (+++) |
| 318 | (+++) | (+++) | (+++) | (++) |
| 319 | (+++) | (++) | (++) | (+++) |
| 320 | (+++) | (++) | (++) | (++) |
| 321 | (++) | (−) | (−) | (++) |
| 322 | (+++) | (++) | (++) | (+++) |
| 323 | (+++) | (+++) | (++) | (+) |
| 324 | (+++) | (++) | (++) | (+++) |
| 325 | (++) | (+) | (+) | (++) |
| 326 | (++) | (−) | (−) | (+) |
| 327 | (+++) | (+++) | (++) | (−) |
| 328 | (++) | (−) | (−) | (+++) |
| 329 | (+) | (+) | (+) | (+) |
| 330 | (+++) | (++) | (+) | (++) |
| 331 | (+++) | (+) | (++) | (+++) |
| 332 | (+++) | (+) | (++) | (+++) |
| 333 | (+) | (+) | (−) | (+) |
| 334 | (++) | (++) | (+) | (+) |
| 335 | (+++) | (++) | (+) | (+++) |
| 336 | (+) | (+) | (−) | (−) |
| 337 | (+++) | (++) | (++) | (++) |
| 338 | (+) | (−) | (−) | (+) |
| 339 | (+++) | (+) | (+) | (+++) |
| 340 | (+++) | (+++) | (++) | (++) |
| 341 | (++) | (−) | (−) | (+++) |
| 342 | (+++) | (+) | (++) | (+++) |
| 343 | (++) | (−) | (−) | (++) |
| 344 | (+++) | (−) | (+) | (+++) |
| 345 | (+) | (−) | (−) | (+) |
| 346 | (+++) | (++) | (++) | (+++) |
| 347 | (+++) | (−) | (−) | (+++) |
| 348 | (+++) | (++) | (++) | (++) |
| 349 | (+++) | (+++) | (+++) | (+) |
| 350 | (+++) | (+++) | (+++) | (++) |
| 351 | (+++) | (++) | (++) | (+++) |
| 352 | (+++) | (++) | (++) | (+++) |
| 353 | (+++) | (++) | (++) | (++) |
| 354 | (+++) | (++) | (+++) | (−) |
| 355 | (+++) | (+++) | (++) | (+) |
| 356 | (+++) | (++) | (++) | (+) |
| 357 | (+++) | (+++) | (++) | (+) |
| 358 | (+++) | (++) | (++) | (+++) |
| 359 | (++) | (−) | (+) | (+) |
| 360 | (+) | (−) | (−) | (+) |
| 361 | (+++) | (++) | (++) | (+++) |
| 362 | (+++) | (++) | (++) | (+++) |
| 363 | (+++) | (++) | (++) | (+++) |
| 364 | (+++) | (++) | (++) | (+++) |
| 365 | (+++) | (++) | (++) | (++) |
| 366 | (+++) | (++) | (++) | (+++) |
| 367 | (+++) | (++) | (++) | (+++) |
| 368 | (+++) | (−) | (++) | (+++) |
| 369 | (−) | (−) | (−) | (−) |
| 370 | (+++) | (+++) | (++) | (++) |
| 371 | (+++) | (−) | (−) | (+++) |
| 372 | (+++) | (++) | (++) | (+) |
| 373 | (++) | (+) | (++) | (−) |
| 374 | (+++) | (−) | (+) | (+++) |
| 375 | (+) | (−) | (−) | (+) |
| 376 | (+++) | (+) | (+) | (+++) |
| 377 | (+) | (−) | (−) | (−) |
| 378 | (+++) | (++) | (++) | (++) |
| 379 | (++) | (−) | (−) | (++) |

| Example No. | Plk2 IC$_{50}$ (µM) | Plk1 IC$_{50}$ (µM) | Plk3 IC$_{50}$ (µM) | PLK2/PLK1 |
|---|---|---|---|---|
| 380 | (+++) | (−) | (−) | (+++) |
| 381 | (−) | (−) | (−) | (−) |
| 382 | (+++) | (+++) | (+++) | (+) |
| 383 | (++) | (+) | (−) | (+) |
| 384 | (++) | (++) | (+) | (−) |
| 385 | (++) | (+) | (−) | (+) |
| 386 | (−) | (−) | (−) | (−) |
| 387 | (+++) | (−) | (−) | (+++) |
| 388 | (+++) | (++) | (++) | (+++) |
| 389 | (+++) | (++) | (++) | (+++) |
| 390 | (++) | (−) | (−) | (++) |
| 391 | (+++) | (+++) | (+++) | (+) |
| 392 | (−) | (−) | (−) | (−) |
| 393 | (++) | (+) | (−) | (+) |
| 394 | (+++) | (++) | (++) | (+++) |
| 395 | (+++) | (+++) | (++) | (+) |
| 396 | (−) | (−) | (−) | (−) |
| 397 | (+++) | (+) | (+) | (+++) |
| 398 | (−) | (−) | (−) | (−) |
| 399 | (+++) | (++) | (++) | (+) |
| 400 | (+++) | (++) | (++) | (++) |
| 401 | (+++) | (++) | (++) | (+) |
| 402 | (+++) | (+++) | (+++) | (++) |
| 403 | (+++) | (+) | (++) | (+++) |
| 404 | (−) | (−) | (−) | (−) |
| 405 | (+++) | (+) | (++) | (+++) |
| 406 | (+++) | (+) | (+) | (+++) |
| 407 | (+++) | (++) | (++) | (+++) |
| 408 | (++) | (−) | (−) | (++) |
| 409 | (+++) | (+++) | (++) | (+++) |
| 410 | (−) | (−) | (−) | (−) |
| 411 | (+++) | (+) | (++) | (+++) |
| 412 | (++) | (−) | (−) | (++) |
| 413 | (+++) | (+) | (+) | (+++) |
| 414 | (−) | (−) | (−) | (−) |
| 415 | (++) | (−) | (−) | (+++) |
| 416 | (+) | (−) | (−) | (+) |
| 417 | (+++) | (+) | (−) | (+++) |
| 419 | (+++) | (++) | (++) | (++) |
| 420 | (+++) | (+++) | (+++) | (+) |

Compounds can also be screened in a kinase panel, for example looking at the percent inhibition of a kinase at a given concentration of compound. Compounds were screened at InVitrogen Corporation (Carlsbad, Calif.), which performs kinase screening routinely. The compounds described in Examples 26, 68, 76 and 192 were sent for screening at 10 µM compound in a variety of kinases. These compounds were potent against PLK1, PLK2, and to a lesser extent PLK3 (their relative activities in these kinases based on a calculated IC$_{50}$ can be found in the table above). Compounds 26, 68 and 76 were also screened against ABL1, AKT1, AURKA, CAMK2A, CDK1, CDK2, CDK5, CHEK1, CLK1, CSF1R, DYRK1B, ERBB4, FLT3, GSK3B, INSR, JAK1, LCK, MAPK1, MAPK10, MARK2, PAK4, PDGFRA, PRKACA, PRKCB1, PTK2B, RAF1, RET, ROCK2, STK3, SYK, LRRK2, PIK3R1, RIPK2, STK16 and TTK. None of these showed greater than 30% inhibition, and many were below 10%, demonstrating the high selectivity of these compounds towards PLK. Example 192 was screened against over 300 kinases, with all but 21 of these kinases well below 40% inhibition, including CDK-1, CDK-2, CDK-5, CLK-1, CLK-2, CLK-3, CLK-4, NEK-1, NEK-2, NEK-4, NEK-6, NEK-7, MAP4K4 and STK16, and only four demonstrating greater than 80% inhibition. Two of these were mutant kinases, and the other two, ABL1 and KDR, when titrated, showed an IC$_{50}$ of >10 µM.

Example B

Cell Activities (293-Syn/PLK2 Cell Assay)

Compounds as described herein (compounds of Formula I, e.g., compounds of the above Examples) are tested for their activity in HEK-293 cells expressing α-synuclein and PLK2. An exemplary assay procedure is described below.

(1) Plate HEK-293 cells stably transfected with α-synuclein in 10 cm dishes (Corning) at 1.5e6 cells/cm$_2$ in 10% FCS/DMEM.

(2) Transfect cells with PLK2 (PLK2-pCMV6 (Origene), at a concentration of 24 µg/dish and 72 µl al Fugene6/dish (Roche)).

(3) Trypsinize cells the following day and plate at 30,000 cells/well in PDL coated 96 well tissue culture plates (Becton Dickinson).

(4) Starting with compounds at a concentration of 10 mM solutions, prepare five 1:3 serial dilutions in DMSO.

(5) Dilute test and positive control compound DMSO stocks 1:100 into 10% FCS DMEM.

(6) Change the cell media immediately prior to compound treatment, then add compound+DMEM to cells at 1:10 final dilution (final DMSO concentration is 0.1%).

(7) After 2 hours, place the cells on ice, remove the media and the rinse cells once with cold phosphate buffered saline (PBS). Remove PBS and lyse the cells using a cell extraction buffer (CEB) (10 mM Tris, pH 7.4, 100 mM NaCl, 1 mM EDTA, 1 mM NaF, 1 mM EGTA, 20 mM Na4P$_2$O$_7$, 2 mM Na3VO4, 0.5% Deoxycholate, 1% TritonX-100, 10% Glycerol, 0.1% SDS) with added protease inhibitors (10 µg/ml leupeptin, 20 µg/ml aprotinin)

(8) Freeze plates on dry ice and store at −80°.

Total and p-Ser-129 α-synuclein levels can be quantified with a sandwich ELISA (e.g., using 1H7 as the capture antibody and biotinylated 5C12 and 11A5 as the total and phospho synuclein reporter antibodies respectively; see e.g., *J. Biol. Chem.* 2006, 281:29739-29752, the disclosure of which is incorporated herein in its entirety). Alpha-synuclein phosphorylated at serine 129 (p-Ser-129 α-synuclein) levels are normalized to the total synuclein measured in each lysate and the ratio of phosphorylated synuclein to total synuclein as a function of compound concentration can be used to determine IC$_{50}$ of the compounds.

Example C

In Vivo Activities

Compounds as described herein (Compounds of Formula I, e.g., compounds of the above examples) can be tested for their in vivo activities, e.g., using the test procedures described in *J. Biol. Chem.* 2009, 284(5): 2598-2602 (see, e.g., page 2599, last paragraph), the disclosure of which is incorporated herein in its entirety. For example, mice can be dosed with the compounds of the invention at about 5 mg/kg to about 500 mg/kg (e.g., via tail vein injection) at 5 ml/kg dose volume in 0.9% saline. Mice can be euthanized (e.g., CO$_2$ about 3 h after dosing) and brains can be removed, rinsed in 0.9% saline and separated into left and right hemispheres. The cortex can be dissected from the right hemisphere, frozen on dry ice and stored at −80° C. until used for quantitation of alpha-synuclein levels. Tissue lysates can be prepared and analyzed, e.g., using an ELISA assay (e.g., as described in the above reference; see, e.g., page 2600, first paragraph).

Protein concentrations of lysates can be measured (e.g., using the Micro BCA Kit from Pierce Biotechnology). Total alpha-synuclein and alpha-synuclein phosphorylated at serine 129 (p-Ser-129 α-synuclein) levels can be normalized to the total protein measured in each lysate and a ratio of phosphorylated synuclein to total synuclein can be calculated. Total and p-Ser-129 α-synuclein levels can be quantified using a sandwich ELISA (e.g., using 1H7 as the capture antibody and biotinylated 11A5 as the total or phosphor synuclein reporter antibodies; see e.g., *J. Biol. Chem.* 2006, 281:29739-29752, the disclosure of which is incorporated herein in its entirety).

What is claimed is:

1. A compound having a structure according to Formula (I):

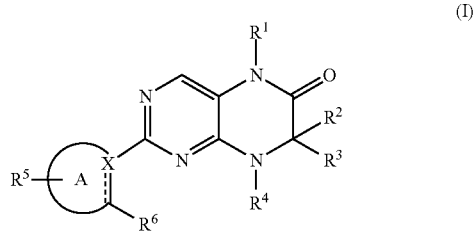

or a salt thereof, wherein:

X is C or N and the dashed line represents a single or double bond;

A is a ring selected from the group consisting of phenyl, pyridine, pyrimidine, pyrazine, pyridazine, pyrrole, pyrazole, imidazole, thiazole, isothiazole, isoxazole, triazole, thiadiazole, benzimidazole, indole, pyrrolo[2,3-b]pyridine, quinoline, pyrrolidine, piperidine, piperazine, and dihydro-imidazole;

$R^1$ is methyl;

$R^2$ is hydrogen, methyl, ethyl, —CH$_2$-cyclopropyl, or —CH$_2$CF$_3$;

$R^4$ and $R^3$, together with the atoms to which they are attached, are optionally joined to form a substituted or unsubstituted heterocyclic ring selected from the group consisting of

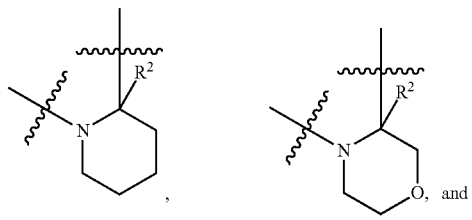

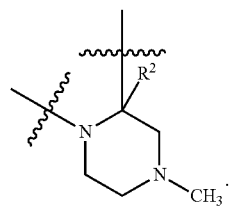

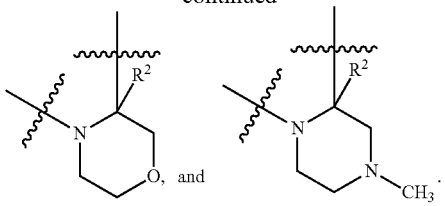

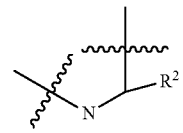

wherein

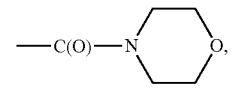

represents the core ring of Formula I, i.e. the N attached to $R^4$ and the C attached to $R^3$;

$R^5$ is hydrogen, —Br, —CN, —CH$_3$, —CH$_2$CN, —CH$_2$CH$_2$NH$_2$, —OH, —O$^-$, =O, —OCH$_3$, —Obenzyl, —C(O)OH, —C(O)OCH$_3$, —C(O)OCH$_2$CH$_3$, —C(O)NH$_2$, —C(O)NHCH$_3$, —C(O)N(CH$_3$)$_2$, $$-C(O)-N\diagup\!\diagdown O,$$

—NH$_2$, =NH, —NHCH$_3$, —N(CH$_3$)$_2$, —NHS(O)$_2$CH$_3$, —S(O)$_2$CH$_3$, phenyl, thiazole, pyridine or pyrazine;

$R^6$ is hydrogen, —Cl, —Br, —CH$_3$, —CF$_3$, —CH$_2$NH$_2$, —NH$_2$, —CH$_2$NHC(O)OCH$_3$, —CH$_2$NHC(O)CH$_3$, —CH$_2$NHC(O)phenyl, —CH$_2$NHS(O)$_2$CH$_3$, —CH$_2$NHS(O)$_2$phenyl, —NHC(O)CH$_3$, —NHC(O)OCH$_3$, —NHC(O)phenyl, —NHS(O)$_2$CH$_3$, —NHS(O)$_2$phenyl, —CH=CHphenyl, cyclopropyl, cyclopentenyl, benzyl, phenyl optionally substituted with 1, 2 or 3 substituents $R^9$, pyridine optionally substituted with 1 fluoro, pyrimidine, pyrazine, pyridazine, pyrazole, thiazole, oxazole, thiophene optionally substituted with 1 chloro, pyrrolidine, oxazolidinone, pyrrolidinone, dihydropyran, tetrahydropyran, morpholine, 4-methyl-piperazine, pyrrolidine-dione, pyridinone, isoquinoline, or quinoline;

$R^7$ at each occurrence is independently —C(O)NH$_2$, fluoro, chloro, cyano, pyrazole, triazole, pyridine or pyrimidine;

$R^8$ is methyl or 2-(trimethylsilyl)ethoxy)methyl, cyclopropyl, or —CH$_2$-cyclopropyl; and $R^9$ at each occurrence is independently selected from the group consisting of fluoro, chloro, bromo, —S(O)$_2$CH$_3$, —OCF$_3$, —CF$_3$, —CN, pyridine, triazole, and pyrazole.

2. The compound of claim 1, wherein:

A is a ring selected from the group consisting of phenyl, pyridin-2-yl, pyridin-3-yl, pyridin-4-yl, pyrimidin-5-yl, pyrazin-2-yl, pyridazin-4-yl, pyridin-2-on-4-yl, pyridin-4-imine, pyrrol-2-yl, pyrazol-1-yl, pyrazol-3-yl, pyrazol-4-yl, imidazol-1-yl; thiazol-5-yl, isothiazol-4-yl, isoxazol-4-yl, 1,2,3-triazol-5-yl, 1,2,4-triazol-1-yl, 1,2,3-thiadiazol-5-yl, benzimidazol-1-yl, indol-1-yl, indol-2-yl, indol-7-yl, pyrrolo[2,3-b]pyridin-5-yl, quinolin-8-yl, pyrrolidin-1-yl, piperidin-1-yl, piperazin-1-yl, and 4,5-dihydro-1H-imidazol-1-yl;
R$^1$ is —CD$_3$ or —CH$_3$;
R$^2$ is hydrogen, —CD$_3$, —CH$_3$, —CD$_2$CD$_3$, —CH$_2$CH$_3$, —CH$_2$-cyclopropyl, or —CH$_2$CF$_3$;
R$^5$ is hydrogen, —Br, —CN, —CH$_3$, —CH$_2$CN, —CH$_2$CH$_2$NH$_2$, —OH, =O, —O$^-$, —OCH$_3$, —Obenzyl, —C(O)OH, —C(O)OCH$_3$, —C(O)OCH$_2$CH$_3$, —C(O)NH$_2$, —C(O)NHCH$_3$, —C(O)N(CH$_3$)$_2$,

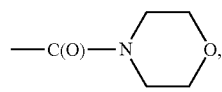

—NH$_2$, —NHCH$_3$, —N(CH$_3$)$_2$, —NHS(O)$_2$CH$_3$, —S(O)$_2$CH$_3$, phenyl, thiazol-2-yl, thiazol-4-yl, pyridin-3-yl, and pyrazin-2-yl;
R$^6$ is hydrogen, —Cl, —Br, —CH$_3$, —CF$_3$, —CH$_2$NH$_2$, —NH$_2$, —CH$_2$NHC(O)OCH$_3$, —CH$_2$NHC(O)CH$_3$, —CH$_2$NHC(O)phenyl, —CH$_2$NHS(O)$_2$CH$_3$, —CH$_2$NHS(O)$_2$-phenyl, —NHC(O)CH$_3$, —NHC(O)OCH$_3$, —NHC(O)phenyl, —NHS(O)$_2$CH$_3$, —NHS(O)$_2$-phenyl, —CH=CHphenyl, cyclopropyl, cyclopent-1-enyl, benzyl, phenyl optionally substituted with 1, 2, or 3 substituents R$^9$, pyridin-2-yl, 5-fluoro-pyridin-2-yl, pyridin-3-yl, 5-fluoro-pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, 5-Cl-thiophen-2-yl, pyrrolidin-1-yl, oxazolidin-2-on-3-yl, 2-oxopyrrolidin-1-yl, 3,6-dihydro-2H-pyran-4-yl, tetrahydro-2H-pyran-4-yl, morpholin-4-yl, 4-methyl-piperazin-1-yl, pyrrolidine-2,5-dion-1-yl, pyridin-2-on-1-yl, isoquinolin-1-yl, quinolin-5-yl, and quinolin-3-yl; and
R$^9$ gives substitution of the phenyl ring selected from the group consisting of 4-S(O)$_2$CH$_3$, 3-OCF$_3$, 4-OCF$_3$, 3-CF$_3$, 4-CF$_3$, 2-F, 3-F, 3-Cl, 3-Br, 4-F, 2,3-diF, 2,4-diF, 2-Cl-4-F, 3,4-diF, 3,5-diF, 3-F-5-CF$_3$, 3-Cl-4-F, 3-CN, 4-CN, 3,4,5-triF, 3-pyridin-3-yl, 3-1,2,4-triazol-1-yl, and 3-pyrazol-1-yl.

3. The compound of claim 1, wherein:
A is a ring selected from the group consisting of phenyl, pyridin-2-yl, pyridin-3-yl, pyridin-4-yl, pyrimidin-5-yl, pyrazin-2-yl, pyridin-2-one, pyridin-4-imine, pyrazol-1-yl, pyrazol-4-yl, imidazol-1-yl, thiazol-5-yl, 1,2,3-triazol-5-yl, 1,2,4-triazol-1-yl, 1,2,3-thiadiazol-5-yl, indol-1-yl, indol-2-yl, indol-7-yl, piperazin-1-yl, 4,5-dihydro-1H-imidazol-1-yl;
R$^1$ is —CD$_3$ or —CH$_3$;
R$^2$ is hydrogen, —CD$_3$, —CH$_3$, —CD$_2$CD$_3$, —CH$_2$CH$_3$ or —CH$_2$CF$_3$;
R$^5$ is hydrogen, —CN, —Br, —CH$_3$, —CH$_2$CN, —CH$_2$CH$_2$NH$_2$, —OH, =O, —O$^-$, —C(O)OH, —C(O)OCH$_3$, —C(O)OCH$_2$CH$_3$, —C(O)NH$_2$, —C(O)NHCH$_3$, —C(O)N(CH$_3$)$_2$,

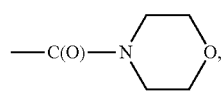

—NH$_2$, —N(CH$_3$)$_2$, —NHS(O)$_2$CH$_3$, phenyl, thiazol-2-yl, thiazol-4-yl, or pyridin-3-yl;
R$^6$ is hydrogen, —Cl, —CH$_3$, —NH$_2$, —CH$_2$NHC(O)OCH$_3$, —CH$_2$NHC(O)CH$_3$, —CH$_2$NHS(O)$_2$CH$_3$, —NHC(O)CH$_3$, —NHC(O)OCH$_3$, —NHS(O)$_2$CH$_3$, cyclopropyl, cyclopent-1-enyl, phenyl optionally substituted with 1, 2, or 3 substituents R$^9$, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, pyrrolidin-1-yl, oxazolidin-2-on-3-yl, 2-oxopyrrolidin-1-yl, tetrahydro-2H-pyran-4-yl, morpholin-4-yl, 4-methyl-piperazin-1-yl, quinolin-5-yl, or quinolin-3-yl; and
R$^9$ gives substitution of the phenyl ring selected from the group consisting of 4-S(O)$_2$CH$_3$, 4-CF$_3$, 3-F, 3-Cl, 3-Br, 4-F, 2,4-diF, 3,4-diF, 3,5-diF, 3-Cl-4-F, 4-CN, 3-1,2,4-triazol-1-yl, and 3-pyrazol-1-yl.

4. The compound of claim 1, wherein:
A is a ring selected from the group consisting of pyridin-3-yl, pyridin-4-yl, pyridin-2-one, pyridin-4-imine, pyrazol-1-yl, pyrazol-4-yl, imidazol-1-yl, thiazol-5-yl, 1,2,4-triazol-1-yl, and 1,2,3-thiadiazol-5-yl;
R$^1$ is —CD$_3$ or —CH$_3$;
R$^2$ is hydrogen, —CD$_3$, —CH$_3$, —CD$_2$CD$_3$, or —CH$_2$CH$_3$;
R$^5$ is hydrogen, —CH$_3$, —CH$_2$CH$_2$NH$_2$, —OH, —O$^-$, —C(O)OH, —C(O)OCH$_2$CH$_3$, —C(O)NH$_2$, —C(O)NHCH$_3$, —C(O)N(CH$_3$)$_2$,

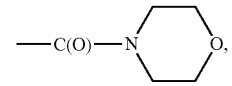

—NHCH$_3$, or pyridin-3-yl; and
R$^6$ is hydrogen, phenyl, 4-methylsulfonyl-phenyl, 4-fluoro-phenyl, 2,3-difluoro-phenyl, 2,4-difluoro-phenyl, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-5-yl, pyrazol-4-yl, thiazol-2-yl, oxazol-2-yl, or oxazolidin-2-on-3-yl.

5. The compound of claim 1, wherein the compound has a structure of Formula (Id)

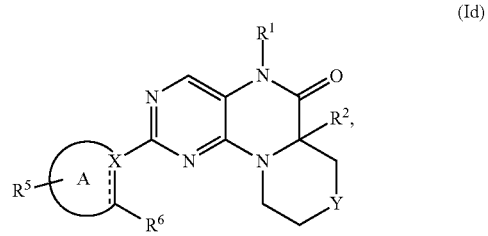

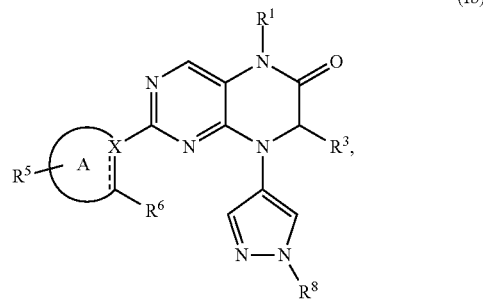

or a salt thereof, wherein:
Y is O or N—CH$_3$; and
X, A, R$^1$, R$^2$, R$^5$, and R$^6$ are as defined for claim 1.

6. The compound of claim 5, wherein the compound has the structure of Formula (Ik):

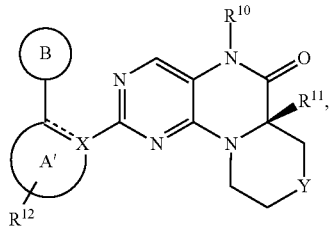
(Ik)

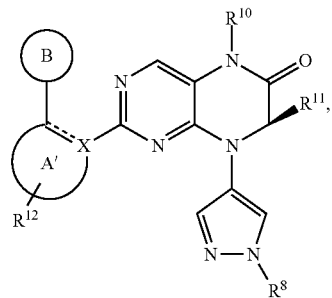
(Ii)

or a salt thereof, wherein:
X is C or N and the dashed line represents a single or double bond;
Y is O or N—CH₃;
A is selected from the group consisting of phenyl, pyridin-2-yl, pyridin-3-yl, pyridin-4-yl, pyrimidin-5-yl, pyrazin-2-yl, pyridin-2-one, pyridin-4-imine, pyrazol-1-yl, pyrazol-4-yl, imidazol-1-yl, thiazol-5-yl, isothiazol-4-yl, isoxazol-4-yl, 1,2,3-triazol-5-yl, 1,2,4-triazol-1-yl, 1,2,3-thiadiazol-5-yl, indol-1-yl, indol-2-yl, indol-7-yl, piperazin-1-yl, 4,5-dihydro-1H-imidazol-1-yl;
B is selected from the group consisting of phenyl optionally substituted with 1, 2, or 3 substituents $R^{16}$, pyridin-2-yl, 5-fluoro-pyridin-2-yl, pyridin-3-yl, pyridin-4-yl, pyrimidin-2-yl, pyrimidin-5-yl, pyrazin-2-yl, pyridazin-3-yl, pyrazol-1-yl, pyrazol-5-yl, pyrazol-4-yl, thiazol-2-yl, thiazol-4-yl, oxazol-2-yl, pyrrolidin-1-yl, oxazolidin-2-on-3-yl, 2-oxopyrrolidin-1-yl, tetrahydro-2H-pyran-4-yl, morpholin-4-yl, 4-methyl-piperazin-1-yl, quinolin-5-yl, and quinolin-3-yl;
$R^{10}$ is —CD₃ or —CH₃;
$R^{11}$ is —CD₂CD₃ or —CH₂CH₃; and
$R^{12}$ is hydrogen, —CH₃, —Br, —CN, or —NH₂.

7. The compound of claim 1, wherein the compound is selected from the group consisting of:
6a-ethyl-5-methyl-2-(2-phenyl-1H-imidazol-1-yl)-6a,7,9,10-tetrahydro-[1,4]oxazino[3,4-h]pteridin-6(5H)-one,
(S)-6a-ethyl-5-methyl-2-(5-(thiazol-2-yl)-1H-pyrazol-4-yl)-6a,7,9,10-tetrahydro-[1,4]oxazino[3,4-h]pteridin-6(5H)-one,
(S)-6a-ethyl-5,8-dimethyl-2-(2-phenyl-1H-imidazol-1-yl)-7,8,9,10-tetrahydro-5H-pyrazino[2,1-h]pteridin-6(6aH)-one,
(S)-2-(2-(2,4-difluorophenyl)-1H-imidazol-1-yl)-6a-ethyl-5-methyl-6a,7,9,10-tetrahydro-[1,4]oxazino[3,4-h]pteridin-6(5H)-one,
(S)-6a-ethyl-2-(2-(5-fluoropyridin-2-yl)-1H-imidazol-1-yl)-5-methyl-6a,7,9,10-tetrahydro-[1,4]oxazino[3,4-h]pteridin-6(5H)-one.
(S)-6a-ethyl-5-methyl-2-(2-(thiazol-2-yl)-1H-imidazol-1-yl)-6a,7,9,10-tetrahydro-[1,4]oxazino[3,4-h]pteridin-6(5H)-one,
(S)-6a-ethyl-5-methyl-2-(3-phenylpyridin-4-yl)-6a,7,9,10-tetrahydro-[1,4]oxazino[3,4-h]pteridin-6(5H)-one,
(S)-6a-ethyl-5-methyl-2-(2-phenylpyridin-3-yl)-6a,7,9,10-tetrahydro-[1,4]oxazino[3,4h]pteridin-6(5H)-one,
(S)-2-(5-(2,4-difluorophenyl)-1H-pyrazol-4-yl)-6a-ethyl-5-methyl-6a,7,9,10-tetrahydro-[1,4]oxazino[3,4-h]pteridin-6(5H)-one, and
(S)-2-(2-(2,3-difluorophenyl)-1H-imidazol-1-yl)-6a-ethyl-5-methyl-6a,7,9,10-tetrahydro-[1,4]oxazino[3,4-h]pteridin-6(5H)-one,
or a salt thereof.

8. A pharmaceutical composition comprising a compound according to claim 1 and a pharmaceutically acceptable carrier.

9. A pharmaceutical composition comprising a compound according to claim 5 and a pharmaceutically acceptable carrier.

* * * * *

UNITED STATES PATENT AND TRADEMARK OFFICE
CERTIFICATE OF CORRECTION

PATENT NO. : 8,445,503 B2
APPLICATION NO. : 12/974401
DATED : May 21, 2013
INVENTOR(S) : Galemmo et al.

It is certified that error appears in the above-identified patent and that said Letters Patent is hereby corrected as shown below:

In the Claims:

Claim 1, col. 280, lines 1-10, delete the two structures above "wherein".

Claim 2, col. 281, line 40, "3,4-diF, 3,5,-diF," should read -- 3,4-diF, 3,5-diCl, 3,5-diF, --.

Claim 5, col. 282, lines 53-65, delete structure labeled "(Ib).".

Claim 6, col. 283, lines 15-26, delete structure labeled "(Ii)".

Claim 6, col. 283, line 32, "A is selected" should read -- A' is selected --.

Signed and Sealed this
Twenty-third Day of July, 2013

Teresa Stanek Rea
*Acting Director of the United States Patent and Trademark Office*